(12) United States Patent
Holcapek et al.

(10) Patent No.: US 12,247,981 B2
(45) Date of Patent: Mar. 11, 2025

(54) METHOD OF DIAGNOSING CANCER BASED ON LIPIDOMIC ANALYSIS OF A BODY FLUID

(71) Applicant: FONS JK GROUP, A.S., Pardubice (CZ)

(72) Inventors: Michal Holcapek, Stare Hradiste (CZ); Eva Cifkova, Krhova (CZ); Miroslav Lisa, Bezdekov (CZ); Robert Jirasko, Pardubice (CZ); Denise Wolrab, Vienna (AT); Tereza Hrnciarova, Prague (CZ)

(73) Assignee: FONS JK Group, a.s., Pardubice (CZ)

( * ) Notice: Subject to any disclaimer, the term of this patent is extended or adjusted under 35 U.S.C. 154(b) by 1055 days.

(21) Appl. No.: 16/962,044

(22) PCT Filed: Nov. 28, 2018

(86) PCT No.: PCT/EP2018/082811
§ 371 (c)(1),
(2) Date: Jul. 14, 2020

(87) PCT Pub. No.: WO2019/141422
PCT Pub. Date: Jul. 25, 2019

(65) Prior Publication Data
US 2020/0363419 A1    Nov. 19, 2020

(30) Foreign Application Priority Data

Jan. 22, 2018 (EP) .................................... 18152687
May 29, 2018 (EP) .................................... 18174963

(51) Int. Cl.
*G01N 33/574* (2006.01)
*G01N 30/72* (2006.01)
(Continued)

(52) U.S. Cl.
CPC ....... *G01N 33/57488* (2013.01); *G01N 33/92* (2013.01); *G01N 2405/02* (2013.01); *G01N 2405/04* (2013.01); *G01N 2405/08* (2013.01)

(58) Field of Classification Search
CPC ............. G01N 33/57488; G01N 33/92; G01N 2405/02; G01N 2405/04; G01N 2405/08
See application file for complete search history.

(56) References Cited

U.S. PATENT DOCUMENTS

| 2012/0202188 A1 | 8/2012 | Pastural et al. |
| 2013/0109592 A1 | 5/2013 | Fan et al. |
| 2013/0140452 A1 | 6/2013 | Kamlage et al. |

FOREIGN PATENT DOCUMENTS

| WO | 2015104113 A1 | 7/2015 |
| WO | 2016164474 A1 | 10/2016 |

(Continued)

OTHER PUBLICATIONS

Nima Patel et al: "A Novel Three Serum Phospholipid Panel Differentiates Normal Individuals from Those with Prostate Cancer", PLOS One, vol. 9, No. 3, Mar. 6, 2014 (Mar. 6, 2014), p. e88841, XP055509802, DOI: 10.1371/journal.pone.0088841 abstract;p. e88842, col. 2;table 7—• fig. 1. • p . e88844-5, https://journals.plos.org/plosone/article?id=10.1371/journal.pone.0088841.

(Continued)

*Primary Examiner* — Rebecca M Fritchman
(74) *Attorney, Agent, or Firm* — NOTORO, MICHALOS & ZACCARIA P.C.

(57) ABSTRACT

A method of diagnosing cancer based on lipidomic analysis of a body fluid taken from the body of a patient is disclosed. The method includes the steps of spiking of the sample with a set of internal standards having at least one internal standard for each lipid class present in the sample, subsequently processing the sample by liquid-liquid lipidomic extraction or by solid phase lipidomic extraction, measure- (Continued)

ment of the processed sample by a mass spectrometry method, determining concentrations for at least 51, more preferably for all lipids present at a level above detection threshold of the mass spectrometry method, statistical evaluation of the determined concentrations of the lipids, the statistical evaluation determining the level of probability of the patient suffering from cancer, or optionally from a specific type of cancer.

16 Claims, 13 Drawing Sheets

(51) Int. Cl.
*G01N 33/92* (2006.01)
*G01N 1/00* (2006.01)

(56) References Cited

FOREIGN PATENT DOCUMENTS

| WO | 2016207391 A1 | 12/2016 |
| WO | 2017155473 A1 | 9/2017 |
| WO | 2017186859 A1 | 11/2017 |

OTHER PUBLICATIONS

Loubna A. Hammad et al: "Elevated levels of hydroxylated phosphocholine lipids in the blood serum of breast cancer patients", Rapid Communications in Mass Spectrometry., vol. 23, No. 6, Mar. 30, 2009 (Mar. 30, 2009), pp. 863-876, XP055509806, GB ISSN: 0951-4198, DOI: 10.1002/rcm.3947 abstract; fig.4, https://onlinelibrary.wiley.com/doi/abs/10.1002/rcm.3947.
International Search Report and Written Opinion for corresponding PCT application No. PCT/EP2018/082811, mailed Jan. 28, 2019.

METHOD OF DIAGNOSING CANCER BASED ON LIPIDOMIC ANALYSIS OF A BODY FLUID

FIELD OF ART

The present invention relates to a method of diagnosing cancer based on lipidomic analysis of a body fluid which is suitable for high throughput screening with a high selectivity and specificity.

BACKGROUND ART

Cancer is one of the most serious human diseases, which results in huge number of deaths worldwide. There are numerous types of cancer, typically classified according to the primary organ, when the tumor cells start to grow. Even the cancer of one particular organ has several disease subtypes resulting in large complexity and heterogeneity of this disease, which requires a personalized treatment to increase the chances for a full or at least a partial recovery of individual patients. Early diagnosis of the cancer is the most critical issue investigated by many research teams throughout the world, because the early cancer diagnosis can significantly increase the chances for survival and recovery. Unfortunately, many cancer types have no or only minor symptoms at early stages, so the common situation is that the patient is diagnosed too late. The prognosis is much better when the disease is recognized earlier, but the currently available diagnostic methods are complex, expensive, and laborious, which is unsuitable for routine population screening. Therefore, there is a need to continuously develop new methods for screening and diagnosing cancer and for distinguishing among various types of cancer, which would be fast, economical, with a limited invasiveness, suitable for routine high-throughput screening, with a sufficient sensitivity and specificity, i.e., low percentage of false positive and false negative results. Various methods based on specific biomarkers are investigated, using samples of body fluids, most commonly blood. These tentative biomarkers are often proteins, glycoproteins, products of protein cleavage, and short RNA, such as miRNA. The diagnosis using these biomarkers usually relies on immunochemical methods or PCR.

Breast cancer is besides skin cancer the most common cancer type for women and includes multiple sub-cancer types. Physical examination, mammography and fine-needle aspiration are common tools for the diagnosis of breast cancer. On the other hand, prostate cancer is the most common cancer type for men. Symptoms may be associated with urinary dysfunction. Another cancer type is kidney cancer. Their main subtypes are renal cell carcinoma, transitional cell cancer and Wilms tumor. Symptoms may involve blood in the urine, a lump in the abdomen and weight loss. The survival rate of all these cancer types strongly depends on the cancer stage and on whether the cancer metastasized to other organs. In case of cancer suspicion, ultrasound, computer tomography, or magnetic resonance imaging are employed. For cancer confirmation needle biopsy is usually performed, whereby a cancer tissue sample is examined under the microscope.

Pancreatic cancer belongs among the most lethal tumors with the lowest survival rate of all cancers. It is expected to become the second leading cause of cancer-related death in the US as well as Europe by the year 2020. Pancreatic cancer is very hard to be diagnosed at early stages. The pancreas is deep inside the body, so early tumors cannot be seen or felt by health care providers during routine physical examinations. People usually have no symptoms until the cancer has already spread to other organs. If people are at an increased risk of pancreatic cancer due to genetic predispositions or show signs and symptoms that can be associated with this disease, specific examinations and tests can be done Imaging tests are most often performed in case of serious suspicion of pancreatic cancer: computed tomography, magnetic resonance imaging, abdominal or endoscopic ultrasound, cholangiopancreatography, somatostatin receptor scintigraphy, positron emission tomography, or angiography. Screening tests or examinations may be used to look for a disease in people who have no symptoms, and who have not had that disease before. However, the imaging tests used for patients with an increased risk or a suspicion of pancreatic cancer are not applicable for large-scale population screening, and moreover imaging tests may have sensitivity limitations in the detection of tumors at an early stage. For a conclusive diagnosis of pancreatic cancer, percutaneous, endoscopic, or surgical biopsy can be done, but again these invasive methods are not applicable for routine population screening.

So far, several types of blood tests have been considered to diagnose pancreatic cancer, such as carbohydrate antigen 19-9 (CA19-9), carcinoembryonic antigen (CEA), or Kirsten-ras (KRAS), but unfortunately low sensitivity and low specificity do not allow their use in the clinical practice for early diagnosis. No screening tests have so far been developed that would allow the detection of sufficiently early stages to lower the risk of dying from pancreatic cancer. Reliable detection of early stage pancreatic cancer is urgently needed, but at this time, no major professional groups recommend any routine screening for pancreatic cancer in people at risk.

It would be desirable to develop diagnostic methods based on other methodologies and other types of biomarkers. These screening methods have to fulfil several requirements, such as available treatment for early diagnosed disease with significantly better prognosis compared to late diagnosis, sufficiently high sample throughput to be able to perform at least a partial population screening of individuals at higher risk, the screening price has to be acceptable for the healthcare system in relation to the benefits obtained by early diagnosis, etc. The blood or urine collection is a common part of the preventative healthcare. For the population screening, a high throughput methodology based on blood analysis is indispensable. Once the blood analysis gives a positive result, further investigations such as imaging methods, i.e. magnetic resonance spectroscopy, have to be done. However, even though such test is urgently needed, there are just limited studies so far for the analysis of cancer from blood mainly based on the analysis of DNA, RNA or proteins. Previous studies showed that lipids play a crucial role in cancer development, as demonstrated in the analysis of tumor tissues and cell lines [E. Cífková, M. Holčapek, M. Lísa, D. Vrána, J. Gatěk, B. Melichar, Anal. Bioanal. Chem. 407 (2015) 991-1002, E. Cífková, M. Lísa, R. Hrstka, D. Vrána, J. Gatěk, B. Melichar, M. Holčapek, Rapid Commun. Mass Spectrom. 31 (2017) 253-263], but not yet for collectable body fluids applicable for high-throughput screening. The first attempts towards the lipidomic analysis of human body fluids have been presented by Metanomics [US 2013/0140452, WO 2016/207391], but unfortunately sensitivities and specificities were too low for real-life applications. The principal problem of body fluid analysis is that early stage tumor may have too small impact on the dysregulation of monitored metabolites and lipids, which may result in the situation that the effect of biological variability is larger than the effect of the studied cancer type, and then no statistically relevant differences can be discovered in body fluids.

The present invention aims at overcoming the problems and challenges of the current state of the art, and to provide a method of diagnosing cancer even in early stages, said method being usable for routine high-throughput population screening.

The notation of lipid compounds in this text is as follows: abbreviation of the class of the compounds, number of carbons: number of double bonds. The abbreviation of the class may be preceded by information about isotopic labeling, if relevant. More details about the description of lipid annotations and abbreviations used in this patent application is given in Table 1.

The principal problem is that early stage tumors as well as different cancer types may have too small impact on the dysregulation of monitored metabolites and lipids in body fluids. This may leads to the fact that the effect of biological variability is larger than the effect on studied cancer types and then no statistically relevant differences can be discovered in body fluids.

The present invention aims at overcoming the problems and challenges of the current state of the art, and to provide a method of diagnosing cancer from the analysis of biological fluids, which is also capable of distinguishing among multiple cancer types even in early stages, said method being usable for routine high-throughput population screening.

TABLE 1

Lipid nomenclature and abbreviations used in this application.

| Lipid category | Lipid class/subclass (abbreviation) | Lipid species | Examples of lipid annotation for particular Fatty acyl/alkyl level[b] | Fatty acyl/alkyl position level |
|---|---|---|---|---|
| Glycerolipids | Monoacylglycerols (MG) | MG 18:0 | MG 18:0 | MG |
|  | Diacylglycerols (DG) | DG 34:1 | DG 18:1_16:0 | DG |
|  | Triacylglycerols (TG) | TG57:3 | TG | TG |
|  | Phosphatidyl- Diacyl[c] | PC 34:1 | PC 16:0_18:1 | PC 16:0/18:1 |
|  | cholines (PC) Alkyl-acyl or plasmalogen[c] | PC O-34:1 or PC P-PA 34:1 | PC O-16:0_18:1 or PC P-PA 16:0_18:1 | PC O-16:0/18:1 or PC P-PA 16:0/18:1 |
| Glycero-phospholipids | Phosphatidic acids (PA) |  |  |  |
|  | Phosphatidylethanolamines | PE 34:1 | PE 16:0_18:1 | PE 16:0/18:1 |
|  | Phosphatidylglycerols (PG) | PG 34:1 | PG 16:0_18:1 | PG 16:0/18:1 |
|  | Phosphatidylinositols (PI) | PI 34:1 | PI 16:0 18:1 | PI 16:0/18:1 |
|  | Phosphatidylserines (PS) | PS 34:1 | PS 16:0 18:1 | PS 16:0/18:1 |
|  | Lysophospholipids (prefix L) | LPC 18:1 | LPC 18:1 | LPC 18:1/0:0 |
|  | Ceramides (Cer) | Cer 34:1 | Cer d18:1/16:0 |  |
|  | Sphingomyelins (SM) | SM 34:1 | SM d18:1/16:0 |  |
| Sphingolipids[d] | Hexosylceramides (HexCer) | HexCer | HexCer d18:1/16:0 |  |
|  | Dihexosylceramides | Hex2Cer | Hex2Cer d18:1/16:0 |  |
|  | Sulfatides (Sul or SHexCer) | SHexCer | SHexCer d18:1/16:0 |  |
|  | Sulfodihexosylceramides | SHexCer | SHexCer d18:1/16:0 |  |
| Sterol Lipids | Cholesteryl esters (CE) |  | CE 16:0 |  |

[a]Information on the total number of carbon atoms and double bonds of present fatty acyls, alkyls, or sphingoid backbone for particular lipid class or subclass.
[b]Particular information about present fatty acyls, alkyls, or sphingoid backbone for particular lipid class or subclass.
[c]Bond type subclasses of PC (applicable for other classes of glycerophospholipids).
[d]Annotation of lipid species level for sphingolipids is based on the common assumption of a sphingoid base with two hydroxyl groups and no hydroxylation of N-acyl. In case of the presence of additional hydroxyl on the ceramide part of sphingolipids without any specification of its position, the OH in parentheses is placed behind the CN:DB number.

SUMMARY OF THE INVENTION

The present invention provides a method using lipidomic analysis for the diagnosis of a plurality of human cancer types. The major advantage of the present invention is that the lipidomic profiling works well for all cancer stages including the most early stages, unlike a previously published work based on the proteomic analysis combined with other methodologies, where the sensitivity for stage 1 was only 40% [J. D. Cohen et al., Science 359 (2018) 926], which is truly not valuable for early diagnosis. The basic and rather simple hypothesis explaining the success of lipidomic analysis for cancer screening is that the tumor cells are so quickly divided that these cells require a large number of building blocks for the preparation of lipid bilayers of new tumor cells. This process is much faster than conventional cell division in the healthy organism, therefore the lipidomic composition of tumor and normal cell must be different as well, and these changes are also reflected in collectable body fluids.

The present invention thus provides a method of diagnosing cancer based on lipidomic analysis of a body fluid taken from the body of a patient, comprising the steps of:
spiking of the sample with a set of internal standards comprising at least one internal standard for each lipid class present in the sample,
subsequently processing the sample by liquid-liquid lipidomic extraction or by solid phase lipidomic extraction,
measurement of the processed sample by a mass spectrometry method,
determining concentrations for at least 51, more preferably for all lipids present at a level above detection threshold of the mass spectrometry method, using the internal standards for the corresponding lipid classes for the quantitation, or using relative concentrations, or using ratios of concentrations and/or signal intensities,
statistical evaluation of the determined concentrations of the lipids, said statistical evaluation determining the level of probability of the patient suffering from cancer, or optionally from a specific type of cancer, based on the determined lipid concentrations compared to a cancerous pattern, or optionally a specific cancerous pattern, and a non-cancerous pattern, wherein the cancerous pattern or the specific cancerous pattern and the non-cancerous pattern are determined by statistical analysis of the lipid concentrations for a group of known cancer samples and non-cancer samples, and wherein the statistical evaluation is done separately for males and females.

The method of the invention allows to distinguish between a healthy person and a person suffering from a cancer, as well as to distinguish between various types of cancer. The cancerous pattern generally indicates that the patient suffers from a cancer, while the specific cancerous pattern indicates that the patient suffers from a specific type of cancer.

In one embodiment of the present invention, a method of diagnosing pancreaticcancer based on lipidomic analysis of a body fluid taken from the body of a patient is provided, comprising the steps of:

spiking of the sample with a set of internal standards comprising at least one internal standard for each lipid class present in the sample, subsequently processing the sample by liquid-liquid lipidomic extraction, measurement of the processed sample by a mass spectrometry method, determining concentrations for at least 31 or for at least 51 lipids, preferably at least 60 or at least 120 lipids or at least 230, more preferably for all lipids present at a level above detection threshold of the mass spectrometry method, using the internal standards for the corresponding lipid classes for the quantitation, or using relative concentrations, or using ratios of concentrations and/or signal intensities, statistical evaluation of the determined concentrations of the lipids, said statistical evaluation determining the level of probability of the patient suffering from pancreatic cancer based on the determined lipid concentrations compared to a pancreatic cancerous pattern and a non-cancerous pattern, wherein the cancerous pattern and the non-cancerous pattern are determined by statistical analysis of the lipid concentrations for a group of known pancreatic cancer samples and non-cancer samples, and wherein the statistical evaluation is done separately for males and females.

In this embodiment, the at least 31 lipids useful in method of diagnosing pancreatic cancer include:

| Lipid |
| --- |
| HexCer d18:1/16:0; HexCer d18:1/15:1 (1OH) |
| SM 34:1 |
| HexCer d18:1/24:1; HexCer d18:1/23:2 (1OH) |
| PE 34:1; PE P-35:0 |
| PC 32:0; PC O-33:0 |
| PE 36:4; PE P-37:3 |
| PC 34:1; PC P-35:0 |
| PE 34:2; PE P-35:1 |
| PC P-34:0; PC 33:1 |
| DG 36:2 |
| Cer d18:1/24:1; Cer d18:1/23:2 (1OH) |
| CE 16:0 |
| SM 41:1 |
| SM 41:2 |
| PC 34:4; PC P-35:3 |
| HexCer d18:1/24:0; HexCer d18:1/23:1 (1OH) |
| PE P-36:3; PE 35:4 |
| PE P-38:4; PE 37:5 |
| PE P-38:5; PE 37:6 |

-continued

| Lipid |
| --- |
| PE P-36:2; PE 35:3 |
| SM 32:1 |
| HexCer d18:1/22:0; HexCer d18:1/21:1 (1OH) |
| PE P-38:3; PE 37:4 |
| PC P-38:2; PC 37:3 |
| PE P-40:5; PE 39:6 |
| PE 36:0; PE P-38:6 |
| PE 38:0; PE P-40:6, PE 0-39:0 |
| PE P-36:3; PE 35:4 |
| PC P-34:1; PC 33:2 |
| PC P-36:2; PC 35:3 |
| DG 34:3 |

The term "body fluid" includes body fluids and components of body fluids. The body fluid for use in this invention is preferably selected from plasma, serum, blood, urine, oncosomes, exosomes, extracellular vesicles. The isolation of exosomes and other extracellular vesicles (EV) from body fluids (onkosomes and microvesicles) or cell-culture media is known in the art and typically performed by differential centrifugation or ultracentrifugation, often combined with sucrose density gradients.

In preferred embodiments, the concentrations of at least 51, or at least 120, or at least 230, or at least 400, or at least 406, or at least 440, or at least 450, or at least 500 lipids are determined.

In one preferred embodiment, the concentrations of at least 51 lipids are determined when the body fluid is blood, plasma or serum.

A particularly preferred set of at least 51 lipids, the concentration of which shall be determined in the methods of the present invention, is shown in Table 2 below. A more preferred set of lipids is shown in Table 3 below. These lipids are particularly useful when the body fluid is blood, plasma or serum.

In another preferred embodiment, the concentrations of at least 75 lipids are determined when the body fluid is urine. A particularly preferred set of at least 75 lipids is shown in Table 4 below.

The patient is a mammal, preferably a human.

The specific types of cancer include kidney, prostate, breast, lungs, stomach, pancreatic, ovarian, head and neck, colon, liver, colorectal, esophagus, small intestine cancer, bladder, brain, cervical, thyroid, laryngeal, skin cancers, etc.

Preferably, the specific types of cancer include kidney, prostate, breast, lungs, pancreatic and stomach cancers.

The internal standards must be lipid-type compounds, structurally close to the relevant lipid class. Typically, the internal standards are compounds having the structure (in particular the polar head structure) typical for the relevant lipid class but containing fatty acyls with shorter chains than naturally occurring lipids (e.g. chains 12:0 or 14:0) or fatty acyls with odd number of carbon atoms (e.g. chains 17:0, 17:1 or 19:1) or isotopically labelled analogues (e.g. D7-Chol, D7-CE 16:0).

The lipid classes are as follows:

| | |
| --- | --- |
| Cholesterylesters (CE) | Lysophosphatidylserines (LPS) |
| Ceramides (Cer) | Monoacylglycerols (MG) |
| Diacylglycerols (DG) | Phosphatidic acids (PA) |
| Dihexosylceramides | Phosphatidylcholines |

| (Hex2Cer) | (PC) |
| Hexosylceramides | Phosphatidylethanolamines |
| (HexCer) | (PE) |
| Cholesterol | Phosphatidylglycerols (PG) |
| Lysophosphatidic acids | Phosphatidylserines |
| (LPA) | (PS) |
| Lysophosphatidylcholines | Sphingomyelins |
| (LPC) | (SM) |
| Lysophosphatidylethanolamines | Sulfohexosylceramides |
| (LPE) | (SulfoHexCer) |
| Lysophosphatidylglycerols | Triacylglycerols |
| (LPG) | (TG) |

An example of a set of internal standards (IS) is the following list:

| D7-CE 16:0 | LPE 14:0 | PG 14:0/14:0 |
| Cer d18:1/12:0 | LPG 14:0 | PS 14:0/14:0 |
| DG 12:1/12:1 | LPA 14:0 | SM d18:1/12:0 |
| Hex2Cer d18:1/12:0 | MG 19:1 | SulfoHexCer d18:1/12:0 |
| HexCer d18:1/12:0 | PA 14:0/14:0 | TG 19:1/19:1/19:1 |
| D7-Chol | PC 14:0/14:0 | LPS 17:1 |
| LPC 17:0 | PE 14:0/14:0 | |

The notation of lipid compounds in this text is as follows: abbreviation of the class of the compounds, number of carbons: number of double bonds. The abbreviation of the class may be preceded by information about isotopic labeling, if relevant.

Due to the addition of the internal standard before sample processing, slight differences due to for instance pipetting errors can be compensated as the internal standard is affected in the same way as the target compounds. This ensures a better reliability of the quantitation of individual lipids.

Liquid-liquid lipidomic extractions are known in the art. Solvents may be used, selected from chlorinated alkanes, dialkyl ethers, alcohols, and water mixtures, which forms bilayer systems containing organic and aqueous phases. Preferably, chloroform, methyl-tert-butyl ether, methanol, ethanol, propanol, and/or butanol are used. Most preferably, chloroform-methanol-water system is used, as described e.g. in E. Cífková, M. Holčapek, M. Lísa, D. Vrána, J. Gatěk, B. Melichar, Anal. Bioanal. Chem. 407 (2015) 991-1002; or in E. Cífková, M. Lísa, R. Hrstka, D. Vrána, J. Gatěk, B. Melichar, M. Holčapek, Rapid Commun. Mass Spectrom. 31 (2017) 253-263. The organic phase of liquid-liquid extraction system containing lipids is collected and used for further processing. As the migration and solubility of the components of the sample are time-dependent, it is highly preferred that the extraction step is always performed in the same way for all the samples measured in one batch, in particular that the extraction is performed over the same period of time for each sample. The organic phase is typically processed by evaporation of the organic solvent and re-dissolving the residue in the solvent for mass spectrometry measurement. Suitable solvents for mass spectrometry measurements include chlorinated alkanes, alkanes and alcohols, preferably chloroform or dichloromethane, hexane and C1-C4 alcohols, most preferably a mixture of chloroform and 2-propanol (e.g., in volume ratio 1:1) or hexane:2-propanol:chloroform 7:1.5:1.5 or chloroform-methanol-2-propanol (1:2:4, v/v/v). Further components may be added, e.g., ammonium acetate, acetic acid, etc. Alkanes, unless defined otherwise, mean C1-C6 alkanes, preferably C1-C4 alkanes.

It is preferred to remove proteins from the sample during or after the liquid-liquid extraction, as proteins may undesirably interfere with the analysis of lipids.

The mass spectrometry method is selected from shotgun mass spectrometry, liquid chromatography—mass spectrometry (LC/MS), ultrahigh-performance liquid chromatography—mass spectrometry (UHPLC/MS), supercritical fluid chromatography—mass spectrometry (SFC/MS), ultra-high-performance supercritical fluid chromatography—mass spectrometry (UHPSFC/MS), and matrix-assisted laser desorption/ionization mass spectrometry (MALDI/MS).

The method of the present invention benefits from the use of a pooled sample. A pooled sample is a sample prepared by mixing identical volumes of several samples, wherein the mixed samples include samples from cancer patients and healthy volunteers. The ratio of samples originating from males to samples originating from females should be approximately the same as in the measured batch of samples. The term "approximately the same" refers to deviation from the ratio of male:female in the measured batch at most by 20%, preferably at most by 10%, more preferably at most by 5%. The pooled sample is preferably obtained by pooling 50-100 samples.

Concentrations of internal standards in the mixture were carefully researched in order to be applicable for all mass spectrometry based methods used in this invention. The concentration of the internal standard should be preferably in the concentration range of naturally occurring lipids. However, as the concentration range varies significantly within the lipid class, it is preferred to use the concentration between 10 and 100% of the concentration of the most abundant naturally occurring lipid species within the respective class, more preferably between 20 and 80%.

The pooled sample, processed in the same way as any other sample, i.e., spiked with internal standard mixture and subjected to liquid-liquid extraction and any other sample processing steps, is used for the full validation and quality control during the mass spectrometry measurements. The order of samples is randomized in sample measurement sequences to avoid measurements of non-cancerous and cancerous samples in a certain portion of the measurement sequence.

The pooled sample may be used for observing intra-day accuracy and intra-day precision, as well as inter-day accuracy and inter-day precision.

Furthermore, it is advantageous to prepare test samples or pooled samples spiked with varying concentrations of the internal standard mixture.

The limit of detection (LOD) of a lipid is preferably determined based on signal to noise ratio, e.g., such as S/N=3.

The pooled sample spiked with varying concentrations of the internal standard mixture is used for determining the lower limit of quantitation (LLOQ) and the upper limit of quantitation (ULOQ), said limits corresponding to the first and the last points of linearity range of the calibration curve. The calibration curve is the dependence of signal on the concentration of a lipid. The linearity range of calibration curve is an interval from LLOQ to ULOQ, where the concentration of lipids can be determined.

The concentrations for all lipids present at a level above LLOQ of the mass spectrometry method are also commonly called "lipidomic profile".

The quantitation (determining concentrations) for all lipids present at a level above LLOQ and below ULOQ of the mass spectrometry method, using the internal standards for the corresponding lipid classes for the quantitation, preferably comprises the following procedures and corrections:

- isotopic correction (deisotoping), i.e., correction of signal intensity of a lipid having due to isotopic contribution M+2 of another lipid with a molecular weight being 2 mass units lower than said lipid (e.g., isotopic interference from the lipid with one additional double bond) or due to isotopic contribution M+1 of another lipid with a molecular weight 1 mass unit lower than said lipid (e.g., interferences between PC and SM subgroups). The correction is done by subtracting calculated M+2 (or M+1) relative intensity based on known intensity in measured spectra.
- zero filling procedure in which the signals of lipid species which are not detected for particular sample, are replaced by 50 to 100%, preferably by 60 to 100%, more preferably by 60 to 70% or by 80 to 90%, or by 70 to 100% or by 67% or by 80%, of the minimum concentration observed for said lipid species in all samples.

The accuracy and reliability of quantitation is ensured or improved by the following features:

- use of at least one exogenous lipid class internal standard for the quantitation of lipid species in each class,
- coelution and coionization of lipid (sub)class internal standards and analytes from the same lipid class using either lipid class separation chromatography method coupled to mass spectrometry (MS) or MS without any chromatographic separation. This co-processing is ensured by the addition of the internal standard before the sample is processed,
- use of the pooled sample spiked with the internal standards as quality control sample injected after a predetermined number of samples,
- measurement control by extracting the signal response of each internal standard in each sample and evaluation of signal response of those over the time period of the measurement sequence daily,
- zero filling procedure,
- isotopic correction.

These features prevent one or more of: low reproducibility, lack of robustness, signal shifts over time, ion suppression/enhancement, carry-over effects, and response change of mass spectrometer due to contamination.

These features thus help to control the quality of measurements by prevention of low reproducibility, lack of robustness, signal shifts over time, ion suppression/enhancement, carry-over effects, and response change of mass spectrometer due to contamination.

When several hundreds of lipids are determined in hundreds of samples, it may happen that the expected signal is not detected for some lipid molecules due to various reasons, and then the concentration should be reported as "below LLOQ" in accordance with established analytical practice. This well-established analytical approach does not work well in case of lipidomic quantitation, and the MDA based on such approach would provide poor resolution of healthy/disease groups, and may not provide acceptable sensitivity and selectivity for the detection of cancer. This approach is adapted to cases in which all missing signals correspond to the situation that the true concentration of the analyte is below LLOQ, for example the determination of low number of analytes well separated by chromatography. However, the situation in lipidomic quantitation is very different, because quantify ca. 150-400 lipids per sample are quantified and many of them (or all in case of shotgun) are co-eluting, which may result in the absence of signal due to other reasons than the concentration below LLOQ, mainly due to ion suppression or other reasons causing the signal drop, including the system contamination, mobile phase impurity, bleeding of chromatographic column, etc. The complexity of lipidomic analysis is enormous, and it is a natural situation that some signals are not properly recorded and processed regardless of the best analytical practice and careful analytical work. Therefore, we have developed a new zero filling approach where the values which are missing for any reason are replaced by 75 to 85%, preferably by 80%, of the minimum concentration observed for this lipid species in all samples. This approach significantly improves the quality of subsequent statistical analysis. Our preliminary results show that when the zero-filling approach is neglected, the quality of cancer detection is significantly worse or impossible. Afterwards the average and the standard deviation of the duplicates are calculated.

The statistical evaluation is preferably performed by multivariate data analysis (MDA). The MDA methods may be non-supervised statistical methods such as principal component analysis (PCA) or supervised statistical methods such as orthogonal projections to latent structures discriminant analysis (OPLS-DA).

The "cancerous pattern" means the pattern of lipid concentrations typical for samples of a body fluid obtained from patients suffering from a cancer. It is usually obtained by statistical analysis of the samples obtained from patients suffering from various types of cancer versus samples obtained from healthy volunteers.

The "specific cancerous pattern" means the pattern of lipid concentrations typical for samples of a body fluid obtained from patients suffering from a specific type of cancer. It is usually obtained by statistical analysis of the samples obtained from patients suffering from the specific type of cancer versus samples obtained from healthy volunteers, and/or versus samples obtained from patients suffering from other specific types of cancer.

The "pancreatic cancerous pattern" means the pattern of lipid concentrations typical for samples of a body fluid obtained from patients suffering from pancreatic cancer. It is usually obtained by statistical analysis of the samples obtained from patients suffering from pancreatic cancer versus samples obtained from healthy volunteers.

The "non-cancerous pattern" means the pattern of lipid concentrations typical for samples of a body fluid obtained from healthy volunteers, i.e., from subjects not suffering from cancer. The term "non-cancerous sample" or "non-cancer sample" refers to a sample of a body fluid obtained from healthy volunteers, i.e., from subjects not suffering from cancer.

Preferably, the statistical evaluation involves

- data pre-processing such as centering, scaling, and/or transformation. The centering correlates the changes relative to the average of the data set. The scaling unifies the impact of different concentration ranges on the model (Unit Variance (UV) and Pareto scaling) so that low concentrations (maybe equally important) are not masked by very abundant concentrations. The logarithmic transformation assembles the data to the normal distribution. A proper pre-processing has a significant influence on the quality of results.
- PCA analysis used for identification of outliers, measurement failures as well as other influential factors. The PCA analysis may also visualize differences between groups as well as cluster the quality control (QC) samples in comparison to other samples.

discrimination analysis (OPLS-DA) for group separation of cancer patients and healthy volunteers. The discrimination analysis is performed for males and females separately.

assignment of the statistical parameters as well as the evaluation of the prediction power.

The statistical methods are first used to build statistical models (cancerous patterns, specific cancerous patterns, and non-cancerous patterns) based on lipidomic profiles of body fluids of healthy volunteers and diagnosed cancer patients. These statistical models are then used for visualization of differences of the cancerous and non-cancerous pattern, as well as for the determination of the level of probability of the patient suffering from cancer or from a specific cancer (such as pancreatic cancer), or being healthy, based on the determined lipid concentrations resulting in a cancerous pattern, a specific cancerous pattern or a non-cancerous pattern, respectively.

Preferably, in the step of evaluation using statistical data, the evaluated sample is first evaluated for the probability of the evaluated patient suffering from cancer or being healthy, and subsequently, provided that the evaluated patient is determined to have a probability of suffering from cancer being above a pre-determined level (e.g., the pre-determined level may be 50%, or 60%, or 70%, or 80%, or 90%), the evaluated sample is evaluated for determining the specific cancer.

The sensitivity and specificity describe the prediction power of the method to correctly assign samples from healthy volunteers or cancer patients groups. The sensitivity and specificity values should be over 70%, preferably over 80% or over 85%, more preferably over 90% for samples of known and unknown classification. In some embodiments, the sensitivity and specificity values achieved are over 95% for samples of known and unknown classification.

Based on the data obtained by the inventors, the sensitivity and selectivity of the method of the invention for pancreatic cancer, for example for OPLS-DA models, is 100% for samples with known classification (292 subjects tested), and 95% for samples with unknown classification (73 subjects tested). Such sensitivity and selectivity is better than selectivity and sensitivity achievable by any other known method for pancreatic cancer diagnosis. Data obtained by the inventors also show that patients with stages 1-2 (early stages) can be identified in the screening using the method of the invention. This represents a significant advantage of the present method. The capability to identify early stage cancers results in identification of patients at a stage when the cancer can be successfully treated.

The sample throughput of the methodology of the invention is at least 4000 samples or preferably at least 10 000 samples per year and one mass spectrometry apparatus at current level of automation of standard mass spectrometry labs. Known methods of multiplexing and higher automation may further increase the sample throughput.

Suitable sets of lipids to be determined for diagnosing the presence of a cancer disease, or for diagnosing a specific type of cancer are usually obtained by an analysis of all detectable lipids for a group of healthy volunteers and cancer patients. The lipids which are present in different amounts in the healthy vs. cancer samples or healthy vs. specific cancer samples or first specific cancer vs. second specific cancer samples are preferred for inclusion into the sets of lipids to be determined.

TABLE 2

The following table shows a minimum list of lipid species the concentrations of which are determined in the present invention (preferably in blood, plasma or serum samples). Optionally, the concentrations of further lipids may be determined.

| Sphingolipids | | | | | |
|---|---|---|---|---|---|
| Cer 34:1 | SM 34:2 | SM 40:1 | SM 42:2 | Sul 40:1 | Sul 42:1 |
| Cer 42:1 | SM 36:1 | SM 40:2 | SM 42:3 | Sul 40:1(OH) | Sul 42:1(2OH) |
| Cer 40:1 | SM 36:2 | SM 41:1 | SM 43:1 | Sul 40:2(OH) | Sul 42:1(OH) |
| Cer 42:2 | SM 38:1 | SM 41:2 | Sul 34:0(OH) | Sul 41:1 | |
| SM 34:1 | SM 39:1 | SM 42:1 | Sul 34:2(OH) | Sul 41:1(OH) | |
| Glycerophospholipids | | | | | |
| LPC 16:0 | LPC 18:2 | PC 34:1 | PC 36:3 | PC O-34:2/P-34:1 | PC O-36:5/P-36:4 |
| LPC 18:0 | PC 32:0 | PC 34:2 | PC 36:4 | PC O-34:3/P-34:2 | PE 34:1 |
| LPC 18:1 | PC 32:2 | PC 36:2 | PC 38:4 | PC O-36:3/P-36:2 | |
| Glycerolipids | | | | | |
| TG 49:1 | TG 50:4 | TG 50:5 | TG 51:4 | TG 53:4 | TG 55:5 |

Minimum list of lipid species listed in Table 2 is particularly suitable for the differentiation of cancer and healthy samples. In general, the prediction power reflected in the sensitivity and specificity of a model is the higher the more species are included to build the statistical model. Therefore, it is advantageous to quantify as many lipids as possible in the biological fluid. It is possible to reduce the variables i.e. by including just statistically relevant species as determined by the P-value and/or the VIP value (p-value<0.05 and VIP value>1). For the generation of the minimum list of lipid, only those species are included which fulfil both criteria when analysing various cancer types. A compromise for all three tested MS based methods was performed, thus the list presented in Table 2 is generally applicable in the method of the present invention.

TABLE 3

The following table shows a preferred set of lipids the concentrations of which are preferably determined in the present invention in blood, plasma or serum samples. Optionally, the concentrations of further lipids may be determined.

Glycerophospholipids

| | | | | | |
|---|---|---|---|---|---|
| LPC 15:0 | PC 36:2 | PC O-36:5 | PE 37:3 | PE O-36:6 | PI 34:2 |
| LPC 16:0 | PC 36:3 | PC O-37:1 | PE 37:5 | PE O-36:7 | PI 34:3 |
| LPC 16:1 | PC 36:4 | PC O-37:2 | PE 37:6 | PE O-37:1 | PI 35:0 |
| LPC 18:0 | PC 36:5 | PC O-37:3 | PE 38:0 | PE O-37:2 | PI 35:1 |
| LPC 18:1 | PC 37:3 | PC O-38:2 | PE 38:1 | PE O-37:3 | PI 36:1 |
| LPC 18:2 | PC 37:4 | PC O-38:3 | PE 38:2 | PE O-38:0 | PI 36:2 |
| LPC 20:3 | PC 37:5 | PC O-38:4 | PE 38:4 | PE O-38:1 | PI 36:3 |
| LPC 20:4 | PC 37:6 | PC O-38:5 | PE 38:5 | PE O-38:2 | PI 36:4 |
| LPC 22:6 | PC 38:2 | PC O-38:6 | PE 38:6 | PE O-38:3 | PI 38:1 |
| LPC O-16:0 | PC 38:3 | PC O-39:2 | PE 38:7 | PE O-38:4 | PI 38:2 |
| LPE 16:0 | PC 38:4 | PC O-39:3 | PE 39:0 | PE O-38:5 | PI 38:3 |
| LPE 18:0 | PC 38:5 | PC O-40:5 | PE 39:4 | PE O-38:6 | PI 38:4 |
| LPE 18:1 | PC 38:6 | PC O-40:6 | PE 39:5 | PE O-39:0 | PI 38:5 |
| LPE 18:2 | PC 39:5 | PC O-40:9 | PE 39:6 | PE O-39:1 | PI 40:0 |
| LPE 20:4 | PC 39:6 | PE 32:1 | PE 40:4 | PE O-39:2 | PI 40:4 |
| LPE 22:5 | PC 40:4 | PE 33:1 | PE 40:5 | PE O-40:0 | PI 40:5 |
| LPE 22:6 | PC 40:5 | PE 33:2 | PE 40:6 | PE O-40:4 | PI 40:6 |
| PC 30:0 | PC 40:6 | PE 34:0 | PE 40:7 | PE O-40:5 | PS 34:0 |
| PC 32:0 | PC O-33:0 | PE 34:1 | PE 41:2 | PE O-40:6 | PS 36:1 |
| PC 32:1 | PC O-33:1 | PE 34:2 | PE 42:9 | PE O-40:7 | PS 36:4 |
| PC 32:2 | PC O-33:2 | PE 34:3 | PE O-33:1 | PE O-40:8 | PS 36:5 |
| PC 34:1 | PC O-34:1 | PE 35:1 | PE O-34:1 | PE O-40:9 | PS 37:0 |
| PC 34:2 | PC O-34:2 | PE 35:2 | PE O-34:2 | PE O-42:2 | PS 38:1 |
| PC 34:3 | PC O-34:3 | PE 35:3 | PE O-35:1 | PG 32:1 | PS 38:2 |
| PC 34:4 | PC O-35:1 | PE 35:5 | PE O-35:2 | PG 36:0 | PS 38:3 |
| PC 35:1 | PC O-35:2 | PE 36:1 | PE O-35:3 | PG 36:4 | PS 38:4 |
| PC 35:2 | PC O-35:3 | PE 36:2 | PE O-36:1 | PI 32:0 | PS 38:6 |
| PC 35:3 | PC O-36:1 | PE 36:3 | PE O-36:2 | PI 32:1 | PS 38:7 |
| PC 35:4 | PC O-36:2 | PE 36:4 | PE O-36:3 | PI 33:0 | PS 42:1 |
| PC 35:5 | PC O-36:3 | PE 36:5 | PE O-36:4 | PI 33:1 | |
| PC 36:1 | PC O-36:4 | PE 37:0 | PE O-36:5 | PI 34:1 | |

Sphingolipids

| | | | | | |
|---|---|---|---|---|---|
| Cer 33:2 (OH) | Hex2Cer 33:2 (OH) | SM 34:0 | SM 41:3 | Sul 38:2 | Sul 42:3 (OH) |
| Cer 34:1 | Hex2Cer 34:1 | SM 34:1 | SM 42:1 | Sul 38:2 (OH) | SulfoHex2Cer 34:1 |
| Cer 34:2 | Hex2Cer 39:1 (OH) | SM 34:2 | SM 42:2 | Sul 40:0 (2OH) | SulfoHex2Cer 40:1 |
| Cer 34:3 | Hex2Cer 39:2 (OH) | SM 35:1 | SM 42:3 | Sul 40:0 (OH) | SulfoHex2Cer 42:1 |
| Cer 35:3 (OH) | Hex2Cer 40:1 | SM 36:0 | SM 42:4 | Sul 40:1 | SulfoHex2Cer 42:2 |
| Cer 36:2 | Hex2Cer 41:3 (OH) | SM 36:1 | SM 43:1 | Sul 40:1 (OH) | GM3 34:1 |
| Cer 36:3 | Hex2Cer 42:2 | SM 36:2 | SM 43:2 | Sul 40:2 | GM3 34:2 |
| Cer 36:4 | HexCer 33:2 (OH) | SM 37:0 | SM 43:3 | Sul 40:2 (OH) | GM3 36:1 |
| Cer 39:2 (OH) | HexCer 34:1 | SM 37:1 | Sul 32:1 (OH) | Sul 41:1 | GM3 36:2 |
| Cer 40:1 | HexCer 39:2 (OH) | SM 38:0 | Sul 34:0 (OH) | Sul 41:1 (OH) | GM3 38:1 |
| Cer 40:2 | HexCer 40:1 | SM 38:1 | Sul 34:1 | Sul 41:2 | GM3 38:2 |
| Cer 40:2 (OH) | HexCer 41:2 (OH) | SM 38:2 | Sul 34:1 (OH) | Sul 41:2 (OH) | GM3 40:2 |
| Cer 41:1 | HexCer 41:3 (OH) | SM 39:1 | Sul 34:2 | Sul 42:0 (2OH) | GM3 40:1 |
| Cer 41:2 (OH) | HexCer 42:1 | SM 39:2 | Sul 34:2 (OH) | Sul 42:1 | GM3 41:1 |
| Cer 41:3 (OH) | HexCer 42:2 | SM 40:0 | Sul 35:1 | Sul 42:1 (2OH) | GM3 41:2 |
| Cer 42:1 | HexCer 42:2 (OH) | SM 40:1 | Sul 36:1 | Sul 42:1 (OH) | GM3 42:3 |
| Cer 42:2 | HexCer 43:1 | SM 40:2 | Sul 36:1 (OH) | Sul 42:2 | GM3 42:2 |
| Cer 42:2 (OH) | SM 32:1 | SM 40:3 | Sul 37:1 | Sul 42:2 (2OH) | GM3 42:1 |
| Cer 42:3 | SM 32:1 | SM 41:1 | Sul 38:1 | Sul 42:2 (OH) | GM3 42:2 (OH) |
| Cer 43:1 | SM 33:1 | SM 41:2 | Sul 38:1 (OH) | Sul 42:3 | GM3 42:1 (OH) |

Glycerolipids

| | | | | | |
|---|---|---|---|---|---|
| MG 16:0 | DG 36:1 | TG 47:2 | TG 50:5 | TG 53:4 | TG 56:4 |
| MG 16:1 | DG 36:2 | TG 48:0 | TG 51:1 | TG 53:5 | TG 56:5 |
| MG 18:0 | DG 36:3 | TG 48:1 | TG 51:2 | TG 54:1 | TG 56:6 |
| MG 18:1 | DG 36:4 | TG 48:2 | TG 51:3 | TG 54:2 | TG 56:7 |
| MG 18:2 | TG 42:2 | TG 48:3 | TG 51:4 | TG 54:3 | TG 56:8 |
| MG 19:0 | TG 44:0 | TG 48:4 | TG 51:5 | TG 54:4 | TG 57:1 |
| DG 30:0 | TG 44:1 | TG 49:0 | TG 51:6 | TG 54:5 | TG 58:0 |
| DG 32:0 | TG 44:2 | TG 49:1 | TG 52:1 | TG 54:6 | TG 58:2 |
| DG 32:1 | TG 45:0 | TG 49:2 | TG 52:2 | TG 54:7 | TG 58:3 |
| DG 32:2 | TG 45:1 | TG 49:3 | TG 52:3 | TG 54:8 | TG 58:4 |
| DG 34:0 | TG 46:0 | TG 50:0 | TG 52:4 | TG 55:4 | TG 58:5 |
| DG 34:1 | TG 46:1 | TG 50:1 | TG 52:5 | TG 55:5 | TG 58:6 |
| DG 34:2 | TG 46:2 | TG 50:2 | TG 52:6 | TG 55:6 | TG 58:7 |
| DG 34:3 | TG 47:0 | TG 50:3 | TG 53:2 | TG 56:1 | TG 58:8 |
| DG 36:0 | TG 47:1 | TG 50:4 | TG 53:3 | TG 56:2 | TG 58:8 |

TABLE 3-continued

The following table shows a preferred set of lipids the concentrations of which are preferably determined in the present invention in blood, plasma or serum samples. Optionally, the concentrations of further lipids may be determined.

| Sterol lipids | | | | | |
|---|---|---|---|---|---|
| CE 14:0 | CE 16:1 | CE 18:2 | CE 20:4 | CE 22:6 | cholesterol sulfate |
| CE 16:0 | CE 18:1 | CE 18:3 | CE 20:5 | cholesterol | cholesterol sulfate (OH) |

TABLE 4

The following table shows a preferred set of lipids the concentrations of which are preferably determined in the present invention for urine samples. Optionally, the concentrations of further lipids may be determined.

| Sterol conjugates | Sulfoglycosphinglolipids | |
|---|---|---|
| hydroxypregnenolone sulfate | Sul 34:1 | Sul 42:1 (2OH) |
| lithocholic acid glycine conjugate | Sul 34:1 (OH) | Sul 42:0 (2OH) |
| cortisol sulfate | Sul 36:1 | Sul 43:1 (2OH) |
| glycochenodeoxycholic acid | Sul 36:1 (OH) | Sul 43:0 (2OH) |
| lithocholic acid sulfate | Sul 38:1 | SulfoHex$_2$Cer 34:1 |
| testosterone glucuronide | Sul 38:1 (OH) | SulfoHex$_2$Cer 34:1 (OH) |
| glycocholic acid | Sul 40:2 | SulfoHex$_2$Cer 36:1 |
| androsterone glucuronide/dihydrotestosterone glucuronide | Sul 40:1 | SulfoHex$_2$Cer 38:1 |
| | Sul 41:2 | SulfoHex$_2$Cer 38:1 (OH) |
| cholesterol sulfate | Sul 40:2 (OH) | SulfoHex$_2$Cer 40:2 |
| glycochenodeoxycholic acid sulfate | Sul 41:1 | SulfoHex$_2$Cer 40:1 |
| hydroxyandrostenedione glucuronide | Sul 40:1 (OH) | SulfoHex$_2$Cer 41:1 |
| 11-oxo-androsterone glucuronide | Sul 40:0 (OH) | SulfoHex$_2$Cer 40:1 (OH) |
| hydroxyandrosterone glucuronide | Sul 42:3 | SulfoHex$_2$Cer 42:3 |
| taurolithocholic acid | Sul 42:2 | SulfoHex$_2$Cer 42:2 |
| sulfocholic acid | Sul 41:2 (OH) | SulfoHex$_2$Cer 42:1 |
| pregnanediol glucuronide | Sul 42:1 | SulfoHex$_2$Cer 41:1 (OH) |
| taurodeoxycholic acid | Sul 41:1 (OH) | SulfoHex$_2$Cer 40:0 (2OH) |
| sulfoglycolithocholic acid | Sul 41:0 (OH) | SulfoHex$_2$Cer 42:2 (OH) |
| taurocholic acid | Sul 40:0 (2OH) | SulfoHex$_2$Cer 42:1 (OH) |
| glycochenodeoxycholic acid sulfate | Sul 42:3 (OH) | SulfoHex$_2$Cer 41:0 (2OH) |
| aldosterone glucuronide | Sul 42:2 (OH) | SulfoHex$_2$Cer 42:0 (2OH) |
| tetrahydroaldosterone glucuronide | Sul 42:1 (OH) | |
| psychosine sulfate | Sul 42:0 (OH) | |
| deoxycholic acid glucuronide | Sul 41:0 (2OH) | |
| cholic acid glucuronide | Sul 43:2 (OH) | |
| glycochenodeoxycholic acid glucuronide | Sul 43:1 (OH) | |

Preferred sets of lipids for individual types of cancers are shown in the following tables.

TABLE 5

Most up- and down-regulated species from S-plot of OPLS-DA model when comparing non-cancerous samples with cancerous samples for both genders and males (M) and various cancer types (N = non-tumor, T = tumor, data about sensitivity and specificity relate to a set of persons whose samples were measured employing UHPSFC/MS).

| S-plot | N-T all cancers both genders | N-T all cancers M | N-T breast cancer M | N-T kidney cancer M | N-T prostate cancer M |
|---|---|---|---|---|---|
| Up-regulated species in cancer | DG 34:0 | DG 34:0 | DG 34:0 | DG 34:0 | TG 49:0 |
| | MG 18:0 | DG 36:0 | DG 36:0 | DG 36:0 | TG 42:2 |
| | TG 49:0 | TG 49:0 | MG 16:0 | MG 18:0 | DG 34:0 |
| | MG 16:0 | MG 18:0 | MG 18:0 | MG 16:0 | DG 36:0 |
| | DG 36:0 | TG 42:2 | TG 50:0 | TG 42:2 | TG 44:0 |
| Down-regulated species in cancer | TG 42:2 | MG 16:0 | TG 48:0 | TG 49:0 | TG 56:1 |
| | TG 44:0 | TG 44:0 | TG 51:1 | Cer 42:3 | TG 45:0 |
| | SM 42:1 | SM 42:1 | SM 42:1 | SM 42:1 | SM 42:1 |
| | SM 41:1 | SM 41:1 | LPC 18:2 | SM 41:1 | SM 41:1 |
| | SM 41:2 | SM 40:1 | LPC 18:0 | TG 58:6 | SM 40:1 |
| | SM 40:1 | LPC 18:2 | LPC 18:1 | LPC 18:2 | LPC 18:2 |
| | SM 38:1 | SM 38:1 | LPC 16:0 | SM 40:1 | LPC 18:0 |
| | SM 40:2 | SM 41:2 | SM 41:1 | SM 38:1 | SM 41:2 |

TABLE 5-continued

Most up- and down-regulated species from S-plot of OPLS-DA model when comparing non-cancerous samples with cancerous samples for both genders and males (M) and various cancer types (N = non-tumor, T = tumor, data about sensitivity and specificity relate to a set of persons whose samples were measured employing UHPSFC/MS).

| S-plot | N-T all cancers both genders | N-T all cancers M | N-T breast cancer M | N-T kidney cancer M | N-T prostate cancer M |
|---|---|---|---|---|---|
|  | Cer 42:1 | SM 40:2 | SM 40:1 | SM 41:2 | SM 40:2 |
|  | LPC 18:2 | LPC 18:0 | PC 32:2 | Cer 42:1 | SM 38:1 |
|  | SM 34:1 | Cer 42:1 | SM 38:1 | SM 40:2 | LPC 16:0 |
|  | LPC 18:0 | SM 34:1 | PC O-36:4 | TG 58:4 | SM 42:2 |
| No.: N/T | 170/282 | 75/157 | 75/9 | 75/81 | 75/67 |
| Sensitivity [%] | 89.4 | 93.0 | 100 | 90.1 | 86.6 |
| Specificity [%] | 80.6 | 81.3 | 100 | 90.7 | 94.7 |

TABLE 6

Most up- and down-regulated species from S-plot of OPLS-DA model when comparing non-cancerous samples with cancerous samples for females (F) and various cancer types (N = non-tumor, T = tumor, data about sensitivity and specificity relate to a set of persons whose samples were measured employing UHPSFC/MS).

| S-plot | N-T all cancers F | N-T breast cancer F | N-T kidney cancer F |
|---|---|---|---|
| Up-regulated species in cancer | MG 18:0 | MG 18:0 | MG 18:0 |
|  | MG 16:0 | MG 16:0 | MG 16:0 |
|  | DG 34:0 | TG 49:0 | DG 34:0 |
|  | TG 49:0 | DG 34:0 | DG 36:0 |
|  | TG 42:2 | TG 42:2 | — |
|  | DG 36:0 | TG 44:0 | — |
|  | — | TG 58:2 | — |
|  | SM 42:1 | SM 42:1 | SM 42:1 |
|  | SM 41:1 | PC 36:1 | SM 41:1 |
|  | SM 41:2 | SM 41:1 | SM 41:2 |
| Down-regulated species in cancer | Cer 42:1 | PC O-34:3 | TG 56:1 |
|  | SM 40:1 | SM 41:2 | PC 32:2 |
|  | PC O-34:3 | PC O-38:6 | SM 40:1 |
|  | SM 38:1 | PC O-36:3 | Cer 42:1 |
|  | PC 36:1 | SM 40:1 | TG 47:1 |
|  | TG 55:5 | Cer 42:1 | TG 49:1 |
|  | SM 40:2 | SM 38:1 | TG 51:4 |
| No.: N/T | 95/125 | 95/94 | 95/31 |
| Sensitivity [%] | 88.0 | 87.2 | 74.2 |
| Specificity [%] | 87.4 | 93.7 | 100 |

TABLE 7

Most up- and down-regulated species from S-plot of OPLS-DA model when comparing cancerous samples with each other (N = non-tumor, T = tumor, data about sensitivity and specificity relate to a set of persons whose samples were measured employing UHPSFC/MS).

| S-plot | T-T 1/kidney vs. 2/prostate M | T-T 1/breast vs. 2/kidney M | T-T 1/breast vs. 2/kidney F |
|---|---|---|---|
| Up-regulated species in cancer 2 | TG 56:1 | SM 42:1 | PC 36:1 |
|  | TG 50:0 | LPC 18:2 | TG 58:6 |
|  | TG 44:1 | PC 32:2 | PC O-38:6 |
|  | TG 44:0 | LPC 18:1 | PC O-38:5 |
|  | TG 46:0 | LPC 18:0 | Cer 42:3 |
|  | TG 44:2 | PC O-38:6 | PC O-36:5 |
|  | TG 46:1 | LPC 16:0 | Cer 40:1 |
|  | TG 45:0 | PC O-36:3 | PC 32:0 |
|  | TG 42:2 | PC O-34:3 | DG 36:2 |
|  | TG 47:0 | PC 36:5 | LPC 18:1 |
| Up-regulated species in cancer 1 | MG 18:0 | TG 50:0 | TG 49:0 |
|  | MG 16:0 | TG 55:5 | TG 56:1 |
|  | DG 36:0 | TG 51:1 | TG 44:1 |
|  | DG 34:0 | TG 58:6 | TG 45:0 |
|  | DG 36:3 | TG 48:0 | TG 45:1 |
|  | DG 34:2 | TG 53:2 | TG 44:2 |
|  | DG 32:0 | TG 52:1 | TG 46:2 |
|  | DG 32:1 | TG 56:1 | TG 44:0 |
|  | DG 36:2 | TG 49:0 | TG 47:1 |
|  | DG 34:1 | TG 54:2 | TG 46:1 |
| No.: T/T | 81/67 | 9/81 | 94/31 |
| Sensitivity [%] | 76.1 | 100 | 74.2 |
| Specificity [%] | 80.3 | 22.2 | 96.8 |

TABLE 8

Most up- and down-regulated species from S-plot of OPLS-DA model when comparing non-cancerous samples with cancerous samples for both genders and males (M) and various cancer types (N = non-tumor, T = tumor, data about sensitivity and specificity relate to a set of persons whose samples were measured employing MALDI-MS).

| S-plot | N-T all cancers both genders | N-T all cancers M | N-T breast cancer M | N-T kidney cancer M | N-T prostate cancer M |
|---|---|---|---|---|---|
| Up-regulated | — | — | — | SulfoHex2Cer 42:2 | — |
| Down-regulated species in cancer | Sul 34:0 (OH) | SM 43:1 | Sul 40:1 | SM 43:1 | Sul 34:0 (OH) |
|  | SM 43:1 | SM 39:1 | Sul 41:1 (OH) | Sul 41:1 (OH) | Sul 40:1 |
|  | SM 39:1 | Sul 41:1 (OH) | Sul 34:0 (OH) | SM 39:1 | SM 43:1 |
|  | Sul 41:1 (OH) | Sul 40:1 | Sul 42:1 | Sul 40:1 (OH) | Sul 42:1 |
|  | Sul 40:1 | Sul 34:0 (OH) | Sul 40:1 (OH) | Sul 34:0 (OH) | SM 39:1 |
|  | SM 41:1 | Sul 40:1 (OH) | Sul 42:1 (OH) | Sul 40:1 | SM 40:3 |
|  | Sul 41:1 | SM 41:1 | Sul 40:2 (OH) | SM 41:1 | Sul 34:2 (OH) |
|  | Sul 34:2 (OH) | Sul 34:2 (OH) | Sul 34:2 (OH) | Sul 42:1 (OH) | Sul 40:2 (OH) |
|  | Sul 42:1 | Sul 40:2 (OH) | Sul 41:1 | SM 32:1 | Sul 41:1 (OH) |

TABLE 8-continued

Most up- and down-regulated species from S-plot of OPLS-DA model when comparing non-cancerous samples with cancerous samples for both genders and males (M) and various cancer types (N = non-tumor, T = tumor, data about sensitivity and specificity relate to a set of persons whose samples were measured employing MALDI-MS).

| S-plot | N-T all cancers both genders | N-T all cancers M | N-T breast cancer M | N-T kidney cancer M | N-T prostate cancer M |
|---|---|---|---|---|---|
|  | SM 33:1 | SM 32:1 | Sul 42:3 (OH) | Sul 34:2 (OH) | Sul 40:1 (OH) |
| No.: N/T | 170/282 | 75/157 | 75/9 | 75/80 | 75/67 |
| Sensitivity [%] | 89.7 | 91.1 | 55.6 | 90.0 | 85.1 |
| Specificity [%] | 82.9 | 81.3 | 100 | 93.3 | 96.0 |

TABLE 9

Most up- and down-regulated species from S-plot of OPLS-DA model when comparing non-cancerous samples with cancerous samples for females (F) and various cancer types (N = non-tumor, T = tumor, data about sensitivity and specificity relate to a set of persons whose samples were measured employing MALDI-MS).

| S-plot | N-T all cancers F | N-T breast cancer F | N-T kidney cancer F |
|---|---|---|---|
| Up-regulated | — | — | SulfoHex2Cer 42:2 |
| Down-regulated species in cancer | Sul 34:0 (OH) | Sul 34:0 (OH) | Sul 41:1 (OH) |
|  | Sul 41:1 (OH) | SM 39:1 | Sul 34:0 (OH) |
|  | SM 43:1 | Sul 41:1 (OH) | SM 39:1 |
|  | SM 39:1 | SM 43:1 | SM 43:1 |
|  | Sul 41:1 | SM 33:1 | Sul 40:1 (OH) |
|  | Sul 40:1 | Sul 42:1 | Sul 42:1 (OH) |
|  | Sul 42:1 | Sul 40:1 | Sul 42:1 (2OH) |
|  | SM 33:1 | Sul 41:1 | Sul 41:1 |
|  | Sul 42:1 (2OH) | SM 43:2 | SM 41:1 |
|  | Sul 34:2 (OH) | SM 32:1 | Sul 40:1 |
| No.: N/T | 95/125 | 95/94 | 95/31 |
| Sensitivity [%] | 88.8 | 86.2 | 83.9 |
| Specificity [%] | 91.6 | 95.8 | 98.9 |

TABLE 10

Most up- and down-regulated species from S-plot of OPLS-DA model when comparing non-cancerous samples with cancerous samples for both genders and males (M) and various cancer types (N = non-tumor, T = tumor, data about sensitivity and specificity relate to a set of persons where result; from MALDI and UHPSFC are combined).

| S-plot | N-T all cancers both genders | N-T all cancers M | N-T breast cancer M | N-T kidney cancer M | N-T prostate cancer M |
|---|---|---|---|---|---|
| Up-regulated species in cancer | DG 34:0 | DG 34:0 | DG 34:0 | DG 34:0 | TG 49:0 |
|  | MG 18:0 | DG 36:0 | DG 36:0 | DG 36:0 | TG 42:2 |
|  | MG 16:0 | MG 18:0 | MG 18:0 | MG 18:0 | TG 44:0 |
|  | DG 36:0 | MG 16:0 | MG 16:0 | MG 16:0 | TG 56:1 |
|  | TG 49:0 | TG 42:2 | TG 50:0 | SulfoHex2Cer 42:2 | DG 36:0 |
|  | TG 42:2 | TG 49:0 | TG 48:0 | TG 49:0 | DG 34:0 |
|  | TG 44:0 | SulfoHex2Cer 42:2 | TG 51:1 | TG 42:2 | TG 45:0 |
|  | — | TG 44:0 | TG 55:5 | PI 38:6 | — |
| Down-regulated species in cancer | SM 42:1 | SM 42:1 | SM 42:1 | SM 42:1 | SM 42:1 |
|  | SM 41:1 | SM 41:1 | LPC 18:2 | TG 58:6 | SM 41:1 |
|  | Sul 34:0 (OH) | SM 40:1 | LPC 18:0 | SM 41:1 | SM 40:1 |
|  | SM 41:2 | Sul 41:1 (OH) | Sul 40:1 | Sul 41:1 (OH) | LPC 18:0 |
|  | SM 40:1 | SM 43:1 | LPC 18:1 | SM 40:1 | LPC 18:2 |
|  | SM 43:1 | LPC 18:2 | LPC 16:0 | SM 43:1 | SM 38:1 |
|  | SM 38:1 | Sul 40:1 | Sul 42:1 | SM 38:1 | SM 41:2 |
|  | SM 40:2 | SM 38:1 | Sul 34:0 (OH) | SM 40:2 | SM 40:2 |
|  | SM 39:1 | Sul 34:0 (OH) | Sul 41:1 (OH) | SM 39:1 | Sul 34:0 (OH) |
|  | Sul 41:1 (OH) | Sul 40:1 (OH) | Sul 40:1 (OH) | SM 41:2 | Sul 40:1 |
| No.: N/T | 170/282 | 75/157 | 75/9 | 75/81 | 75/67 |
| Sensitivity [%] | 92.6 | 94.3 | 100 | 93.8 | 79.1 |
| Specificity [%] | 87.7 | 77.3 | 100 | 93.3 | 97.3 |

TABLE 11

Most up- and down-regulated species from S-plot of OPLS-DA model when comparing non-cancerous samples with cancerous samples for females (F) and various cancer types (N = non-tumor, T = tumor, data about sensitivity and specificity relate to a set of persons where results from MALDI and UHPSFC are combined).

| S-plot | N-T all cancers F | N-T breast cancer F | N-T kidney cancer F |
|---|---|---|---|
| Up-regulated species in cancer | MG 18:0 | MG 18:0 | MG 18:0 |
| | MG 16:0 | MG 16:0 | MG 16:0 |
| | DG 34:0 | TG 49:0 | DG 34:0 |
| | TG 49:0 | DG 34:0 | DG 36:0 |
| | TG 42:2 | TG 42:2 | Cer 42:3 |
| | TG 44:0 | TG 44:0 | SulfoHex2Cer 42:2 |
| | DG 36:0 | TG 58:2 | — |
| | — | TG 58:3 | — |
| Down-regulated species in cancer | SM 42:1 | SM 42:1 | SM 42:1 |
| | SM 41:1 | SM 41:1 | SM 41:1 |
| | SM 41:2 | SM 41:2 | Sul 41:1 (OH) |
| | SM 43:1 | PC O-34:3 | SM 41:2 |
| | TG 55:5 | PC 36:1 | SM 39:1 |
| | SM 40:1 | SM 40:1 | Sul 42:1 (OH) |
| | Cer 42:1 | Sul 42:1 | Sul 40:1 (OH) |
| | Sul 41:1 (OH) | Sul 34:0 (OH) | TG 51:4 |
| | PC O-34:3 | PC O-36:3 | TG 49:2 |
| | SM 39:1 | Sul 41:1 (OH) | PC 32:2 |
| No.: N/T | 95/125 | 95/94 | 95/31 |
| Sensitivity [%] | 89.6 | 91.5 | 83.9 |
| Specificity [%] | 90.5 | 94.7 | 100 |

TABLE 12

Most up- and down-regulated species from S-plot of OPLS-DA model when comparing cancerous samples (cancer types) with each other (N = non-tumor, T = tumor, data about sensitivity and specificity relate to a set of persons where results from MALDI and UHPSFC/MS are combined).

| S-plot | T-T 1/kidney vs. 2/prostate M | T-T 1/breast vs. 2/kidney M | T-T 1/breast vs. 2/kidney F |
|---|---|---|---|
| Up-regulated species in cancer 2 | TG 56:1 | SM 42:1 | PC 36:1 |
| | TG 50:0 | LPC O-38:6 | PC O-38:6 |
| | TG 44:0 | PC 32:2 | PC O-38:5 |
| | TG 45:0 | Sul 42:1 | PC O-36:5 |
| | TG 49:0 | Sul 40:1 | Cer 42:3 |
| | TG 46:0 | LPC 18:1 | SM 36:0 |
| | TG 44:1 | LPC 18:0 | TG 58:6 |
| | TG 47:0 | Sul 40:2 | PC 32:0 |
| | TG 46:1 | Sul 42:1 (OH) | Cer 40:1 |
| | TG 44:2 | Sul 42:2 | DG 36:0 |
| Up-regulated species in cancer 1 | MG 18:0 | TG 55:5 | TG 49:0 |
| | MG 16:0 | TG 58:6 | TG 56:1 |
| | DG 36:0 | TG 53:2 | TG 48:4 |
| | DG 34:0 | TG 56:5 | TG 44:1 |
| | DG 36:3 | TG 51:1 | TG 50:5 |
| | SulfoHex2Cer 42:2 | TG 53:3 | TG 52:6 |
| | DG 34:2 | DG 34:0 | TG 48:3 |
| | Sul 42:3 | TG 55:4 | TG 46:2 |
| | LPC 16:0 | TG 54:2 | TG 50:4 |
| | DG 34:1 | TG 56:6 | TG 44:2 |
| No.: T/T | 81/67 | 9/81 | 94/31 |
| Sensitivity [%] | 91.0 | 100 | 77.4 |
| Specificity [%] | 82.7 | 22.2 | 97.9 |

TABLE 13

Most up- and down-regulated species from S-plot of OPLS-DA model when comparing non-cancerous plasma samples with kidney cancerous plasma samples for males (M) and females (F) (N = non-tumor, T = tumor, data about sensitivity and specificity relate to a set of persons whose samples were measured employing shotgun MS).

| S-plot | N-T kidney F | N-T kidney M |
|---|---|---|
| Up-regulated species in cancer | PE 42:9 | LPC 16:0 |
| | SM 42:2 | SM 42:2 |
| | PC 38:4 | Hex2Cer 34:1 |
| | MG 19:0 | PS 42:1 |
| | LPC O-16:0 | PS 36:5 |
| | TG 56:5 | HexCer 42:2 |
| | PS 32:2 | CE 16:0 |
| | SM 36:0 | PC 34:1 |
| | CE 16:0 | PS 36:4 |
| | LPC 18:0 | MG 18:0 |
| Down-regulated species in cancer | CE 14:0 | LPC 18:2 |
| | PC 32:2 | PE P-36:4 |
| | SM 33:1 | SM 39:1 |
| | SM 32:1 | PC 34:4 |
| | PC 34:4 | SM 41:2 |
| | SM 39:1 | PC O-36:5 |
| | SM 41:1 | PS 38:7 |
| | PC 34:3 | SM 41:1 |
| | HexCer 42:1 | TG 56:6 |
| | LPC 18:2 | SM 40:2 |
| No.: T/N | 28/31 | 71/30 |
| Sensitivity [%] | 100 | 95.8 |
| Specificity [%] | 93.6 | 76.7 |

TABLE 14

Most up- and down-regulated species from S-plot of OPLS-DA model when comparing non-cancerous (N) urine samples with kidney and prostate cancerous (T) urine samples for both genders, males (M) and females (F) (N = non-tumor, T = tumor, data about sensitivity and specificity relate to a set of persons whose samples were measured employing MALDI-MS (absolute quantitation).

| S-plot | N-T both cancers (kidney, prostate) M | N-T prostate cancer M | N-T kidney cancer M |
|---|---|---|---|
| Up-regulated species in cancer | Sul 42:3 | Sul 42:3 | SulfoHex2Cer 40:2 |
| | SulfoHex2Cer 40:2 | SulfoHex2Cer 38:1 (OH) | Sul 42:3 |
| | SulfoHex2Cer 38:1 (OH) | cortisol sulfate | SulfoHex2Cer 38:1 |
| | sulfocholic acid | SulfoHex2Cer 34:1 (OH) | sulfocholic acid |

TABLE 14-continued

Most up- and down-regulated species from S-plot of OPLS-DA model when comparing non-cancerous
(N) urine samples with kidney and prostate cancerous (T) urine samples for both genders, males
(M) and females (F) (N = non-tumor, T = tumor, data about sensitivity and specificity
relate to a set of persons whose samples were measured employing MALDI-MS (absolute quantitation).

|  | | | |
| --- | --- | --- | --- |
| | Sul 43:1 (2OH) | Sul 43:1 (2OH) | SulfoHex2Cer 42:2 |
| | SulfoHex2Cer 34:1 (OH) | SulfoHex2Cer 40:2 | SulfoHex2Cer 38:1 (OH) |
| | Sul 42:3 (OH) | SulfoHex2Cer 41:1 (OH) | SulfoHex2Cer 34:1 |
| | SulfoHex2Cer 41:1 (OH) | sulfocholic acid | SulfoHex2Cer 42:1 |
| | cortisol sulfate | Sul 42:3 (OH) | SulfoHex2Cer 34:1 (OH) |
| | SulfoHex2Cer 38:1 | Sul 41:2 | Sul 43:1 (2OH) |
| Down-regulated | Sul 38:1 (OH) | hydroxypregnenolone sulfate | Sul 40:0 (2OH) |
| species in | Sul 34:1 (OH) | Sul 38:1 (OH) | Sul 41:0 (2OH) |
| cancer | SulfoHex2Cer 40:1 (OH) | Sul 40:2 | Sul 41:0 (OH) |
| | Sul 40:0 (2OH) | SulfoHex2Cer 40:1 (OH) | Sul 38:1 (OH) |
| | Sul 40:1 (OH) | Sul 38:1 | Sul 40:0 (OH) |
| | SulfoHex2Cer 40:0 (2OH) | SulfoHex2Cer 40:0 (2OH) | Sul 40:1 (OH) |
| | Sul 41:0 (OH) | Sul 34:1 (OH) | Sul 42:0 (2OH) |
| | Sul 41:1 | Sul 42:1 (2OH) | Sul 42:1 (2OH) |
| | Sul 41:0 (2OH) | Sul 40:1 (OH) | Sul 41:1 (OH) |
| | taurolithocholic acid | | Sul 41:1 |
| No.: N/T | 34/137 | 34/67 | 34/72 |
| Sensitivity [%] | 93.5 | 91.0 | 91.7 |
| Specificity [%] | 58.8 | 76.5 | 76.5 |

| S-plot | N-T kidney cancer both genders | N-T kidney cancer F |
| --- | --- | --- |
| Up-regulated species in cancer | SulfoHex2Cer 42:2<br>Sul 42:3<br>SulfoHex2Cer 40:2<br>SulfoHex2Cer 38:1<br>SulfoHex2Cer 42:1<br>cortisol sulfate<br>SulfoHex2Cer 40:1<br>SulfoHex2Cer 34:1<br>SulfoHex2Cer 38:1 (OH)<br>sulfocholic acid | Sul 42:3<br>SulfoHex2Cer 40:2<br>SulfoHex2Cer 42:2<br>SulfoHex2Cer 38:1 (OH)<br>SulfoHex2Cer 42:1<br>Sul 43:1 (2OH)<br>Sul 42:3 (OH)<br>SulfoHex2Cer 40:1<br>Sul 42:2<br>SulfoHex2Cer 41:1 (OH) |
| Down-regulated species in cancer | taurolithocholic acid<br>Sul 40:0 (2OH)<br>Sul 41:0 (2OH)<br>Sul 38:1 (OH)<br>cholesterol sulfate<br>Sul 41:0 (OH)<br>Sul 40:0 (OH)<br>SulfoHex2Cer 40:0 (2OH)<br>Sul 42:0 (2OH)<br>Sul 40:1 (OH) | taurolithocholic acid<br>taurocholic acid<br>taurodeoxycholic acid<br>sulfoglycolithocholic acid<br>Sul 40:0 (2OH)<br>Sul 34:1 (OH)<br>Sul 41:0 (2OH)<br>Sul 38:1 (OH)<br>Sul 40:0 (OH)<br>Sul 42:1 (2OH) |
| No.: N/T | 70/101 | 36/29 |
| Sensitivity [%] | 87.1 | 86.2 |
| Specificity [%] | 87.1 | 86.1 |

For diagnosing pancreatic cancer, the lipidomic profile comprising at least 51, preferably at least 120, lipids is used in the present method. In one preferred embodiment, the lipids to be detected in order to build a very reliable statistical model are preferably at least the sets shown in Table 15, or the sets listed in the Tables 28, 29, 30 or 31.

TABLE 15

| | Set 1 (particularly suitable for shotgun MS) | Set 2 (particularly suitable for UHPSFC/MS) |
| --- | --- | --- |
| CE 14:0 | PE 32:0; PE O-33:0 | CE 16:1 |
| CE 16:0 | PE 32:1; PE P-33:0 | CE 16:0 |
| CE 16:1 | PE 34:0; PE P-36:6 | CE 18:3 |
| CE 18:1 | PE 34:1; PE P-35:0 | CE 18:2 |
| CE 18:2 | PE 34:2; PE P-35:1 | CE 18:1 |
| CE 18:3 | PE 34:3; PE P-35:2 | CE 20:5 |
| CE 20:4 | PE 36:0; PE P-38:6 | CE 20:4 |
| CE 20:5 | PE 36:1; PE P-37:0 | CE 20:3 |
| CE 22:4 | PE 36:2; PE P-37:1 | CE 20:2 |
| CE 22:5 | PE 36:3; PE P-37:2 | CE 22:6 |
| CE 22:6 | PE 36:4; PE P-37:3 | Cer d42:2 |
| Cer d18:0/16:1; Cer d18:0/15:2 (1OH) | PE 36:5; PE P-37:4 | Cer d42:1 |
| Cer d18:0/16:2 | PE 38:0; PE P-40:6, PE O-39:0 | DG 34:2 |

TABLE 15-continued

| Set 1 (particularly suitable for shotgun MS) | | Set 2 (particularly suitable for UHPSFC/MS) |
|---|---|---|
| Cer d18:0/18:2 | PE 38:1; PE P-40:7; PE P-39:0 | DG 34:1 |
| Cer d18:0/24:0; Cer d18:0/23:1 (1OH) | PE 38:2; PE P-40:8; PE P-39:1 | DG 36:3 |
| Cer d18:0/24:1; Cer d18:0/23:2 (1OH) | PE 38:3; PE P-40:9; PE P-39:2 | DG 36:2 |
| Cer d18:1/16:0; Cer d18:1/15:1 (1OH) | PE 38:4; PE P-40:10; PE P-29:3 | DG 36:0 |
| Cer d18:1/16:1; Cer d18:1/15:2 (1OH) | PE 38:5; PE P-39:4 | DG 37:4 |
| Cer d18:1/16:2 | PE 38:6; PE P-39:5 | Coenzyme Q10 |
| Cer d18:1/18:0; Cer d18:1/17:1 (1OH) | PE 38:7; PE O-38:0; PE 37:0 | MG 16:0 |
| Cer d18:1/18:2 | PE 40:1; PE P-42:7; PE P-41:0 | MG 18:1 |
| Cer d18:1/18:3 | PE 40:2; PE P-42:8; PE P-41:1 | MG 18:0 |
| Cer d18:1/20:0; Cer d18:1/19:1 (1OH) | PE 40:3; PE P-42:9; PE P-41:2 | PC O-32:1/P-32:0 |
| Cer d18:1/22:0; Cer d18:1/21:1 (1OH) | PE 40:4; PE P-42:10; PE P-41:3 | PC 32:2 |
| Cer d18:1/23:0; Cer d18:1/22:1 (1OH) | PE 40:5; PE P-41:4 | PC 32:1 |
| Cer d18:1/24:0; Cer d18:1/23:1 (1OH) | PE 40:6; PE P-41:5 | PC 32:0 |
| Cer d18:1/24:1; Cer d18:1/23:2 (1OH) | PE 40:7; PE O-40:0; PE 39:0 | PC O-34:3/P-34:2 |
| Cer d18:1/25:0; Cer d18:1/24:1 (1OH) | PE 40:8; PE P-40:0; PE 39:1 | PC 34:3 |
| DG 30:0 | PE 42:9; PE P-42:1; PE 41:2 | PC 34:2 |
| DG 31:0 | PEP-34:0; PE 33:1 | PC 34:1 |
| DG 32:0 | PE P-34:1; PE 33:2 | PC O-36:5/P-36:4 |
| DG 32:1 | PE P-36:0; PE 35:1 | PC O-36:4/P-36:3 |
| DG 32:2 | PE P-36:1; PE 35:2 | PC O-36:3/P-36:2 |
| DG 34:0 | PE P-36:2; PE 35:3 | PC 35:2 |
| DG 34:1 | PE P-36:3; PE 35:4 | PC 35:1 |
| DG 34:2 | PE P-36:4; PE 35:5 | PC 36:5 |
| DG 34:3 | PE P-38:2; PE 37:3 | PC 36:4 |
| DG 36:0 | PE P-38:3; PE 37:4 | PC 36:3 |
| DG 36:1 | PE P-38:4; PE 37:5 | PC 36:2 |
| DG 36:2 | PE P-38:5; PE 37:6 | PC 36:1 |
| DG 36:3 | PE P-40:4; PE 39:5 | PC O-38:6/P-38:5 |
| DG 36:4 | PE P-40:5; PE 39:6 | PC O-38:5/P-38:4 |
| DG 38:2 | PG 32:0; PG O-33:0 | PC 37:3 |
| DG 38:3 | PG 32:1; PG P-33:0 | PC 38:7 |
| DG 38:4 | PG 34:0; PG P-36:6 | PC 38:6 |
| DG 38:5 | PG 34:1; PG P-35:0 | PC 38:5 |
| DG 38:6 | PG 34:2; PG P-35:1 | PC 38:4 |
| Hex2Cer d18:1/16:0; Hex2Cer d18:1/15:1 (1OH) | PG 36:1; PG P-37:0 | PC 38:3 |
| Hex2Cer d18:1/20:0; Hex2Cer d18:1/19:1 (1OH) | PG 36:2; PG P-37:1 | PC 38:2 |
| Hex2Cer d18:1/21:0 (1OH) | PG 36:3; PG P-37:2 | PC 40:6 |
| Hex2Cer d18:1/22:0; Hex2Cer d18:1/21:1 (1OH) | PG 36:4; PG P-37:3 | PC 40:5 |
| Hex2Cer d18:1/24:1; Hex2Cer d18:1/23:2 (1OH) | PI 32:0; PI O-33:0 | PC 40:4 |
| HexCer d18:1/16:0; HexCer d18:1/15:1 (1OH) | PI 32:1; PI P-33:0 | PC O-44:5/P-44:4 |
| HexCer d18:1/20:0; HexCer d18:1/19:1 (1OH) | PI 34:0; PI P-36:6 | SM d34:2 |
| HexCer d18:1/22:0; HexCer d18:1/21:1 (1OH) | PI 34:1; PI P-35:0 | SM d34:1 |
| HexCer d18:1/24:0; HexCer d18:1/23:1 (1OH) | PI 34:2; PI P-35:1 | SM d36:2 |
| HexCer d18:1/24:1; HexCer d18:1/23:2 (1OH) | PI 36:0; PI P-38:6 | SM d36:1 |
| HexCer d18:1/25:0; HexCer d18:1/24:1 (1OH) | PI 36:1; PI P-37:0 | SM d38:2 |
| LPC 16:0 | PI 36:2; PI P-37:1 | SM d38:1 |
| LPC 16:1 | PI 36:3; PI P-37:2 | SM d39:1 |
| LPC 18:0 | PI 36:4; PI P-37:3 | SM d40:2 |
| LPC 18:1 | PI 38:2; PI P-40:8; PI P-39:1 | SM d40:1 |
| LPC 18:2 | PI 38:3; PI P-40:9; PI P-39:2 | SM d41:2 |
| LPC 20:1 | PI 38:4; PI P-40:10; PI P-29:3 | SM d41:1 |
| LPC 20:3 | PI 38:5; PI P-39:4 | SM d42:3 |
| LPC 20:4 | PI 38:6; PI P-39:5 | SM d42:2 |
| LPC 22:6 | PI 40:0; PI P-42:6, PI O-41:0 | SM d42:1 |
| LPE 16:0 | PI 40:4; PI P-42:10; PI P-4L3 | TG 46:1 |
| LPE 18:0 | PI 40:5; PI P-41:4 | TG 46:0 |
| LPE 18:1 | PI 40:6; PI P-41:5 | TG 47:1 |
| LPE 18:2 | PI 42:3; PI P-43:2 | TG 47:0 |
| LPE 20:4 | PI P-36:0; PI 35:1 | TG 48:3 |
| LPE 22:6 | PI P-36:1; PI 35:2 | TG 48:2 |
| LPG 20:0 | PI P-38:3; PI 37:4 | TG 48:1 |
| LPG O-18:0; LPG 17:0 | PS 34:0; PS P-36:6 | TG 48:0 |
| LPG O-20:0; LPG 19:0 | PS 34:2; PS P-35:1 | TG 49:2 |
| LPG O-22:0; LPG 21:0 | PS 36:1; PS P-37:0 | TG 49:1 |
| MG 16:0 | PS 38:4; PS P-40:10; PS P-29:3 | TG 50:4 |
| MG 17:0 | PS 38:6; PS P-39:5 | TG 50:3 |

TABLE 15-continued

| Set 1 (particularly suitable for shotgun MS) | | Set 2 (particularly suitable for UHPSFC/MS) |
|---|---|---|
| MG 18:0 | PS 42:1; PS P-43:0 | TG 50:2 |
| MG 18:1 | PS P-32:0; PS-31:1 | TG 50:1 |
| MG 22:0 | SM 32:1 | TG 51:6 |
| PC 30:0 | SM 33:1 | TG 51:5 |
| PC 32:0; PC O-33:0 | SM 34:0 | TG 51:4 |
| PC 32:1; PC P-33:0 | SM 34:1 | TG 51:3 |
| PC 32:2; PC P-33:1 | SM 34:2 | TG 51:2 |
| PC 34:1; PC P-35:0 | SM 35:1 | TG 51:1 |
| PC 34:2; PC P-35:1 | SM 36:0 | TG 52:6 |
| PC 34:3; PC P-35:2 | SM 36:1 | TG 52:5 |
| PC 34:4; PC P-35:3 | SM 36:2 | TG 52:4 |
| PC 36:0; PC P-38:6 | SM 37:0 | TG 52:3 |
| PC 36:1; PC P-37:0 | SM 39:1 | TG 52:2 |
| PC 36:2; PC P-37:1 | SM 40:0 | TG 52:1 |
| PC 36:3; PC P-37:2 | SM 40:1 | TG 53:4 |
| PC 36:4; PC P-37:3 | SM 41:1 | TG 53:3 |
| PC 36:5; PC P-37:4 | SM 41:2 | TG 53:2 |
| PC 38:2; PC P-40:8; PC P-39:1 | SM 42:2 | TG 53:1 |
| PC 38:3; PC P-40:9; PC P-39:2 | SM 43:1 | TG 54:7 |
| PC 38:4; PC P-40:10; PC P-29:3 | SM 44:2 | TG 54:6 |
| PC 38:5; PC P-39:4 | Sulfatide 41:0; Sulfatide 40:1 (1OH) | TG 54:5 |
| PC 38:6; PC P-39:5 | Sulfatide 41:1; Sulfatide 40:2 (1OH) | TG 54:4 |
| PC 40:4; PC P-42:10; PC P-41:3 | Sulfatide 43:0; Sulfatide 42:1 (1OH) | TG 54:3 |
| PC 40:5; PC P-41:4 | Sulfatide 43:1; Sulfatide 42:2 (1OH) | TG 54:2 |
| PC 40:6; PC P-41:5 | Sulfatide 43:2; Sulfatide 42:3 (1OH) | TG 55:6 |
| PC O-32:0; PC-31:0 | TG 56:3 | TG 55:4 |
| PC O-34:0; PC 33:0 | TG 56:4 | TG 55:3 |
| PC P-32:0; PC-31:1 | TG 56:5 | TG 56:9 |
| PC P-34:0; PC 33:1 | TG 56:6 | TG 56:8 |
| PC P-34:1; PC 33:2 | TG 58:6 | TG 56:7 |
| PC P-36:0; PC 35:1 | | TG 56:6 |
| PC P-36:1; PC 35:2 | | TG 56:5 |
| PC P-36:2; PC 35:3 | | TG 56:4 |
| PC P-36:3; PC 35:4 | | TG 56:3 |
| PC P-36:4; PC 35:5 | | TG 56:1 |
| PC P-38:2; PC 37:3 | | TG 58:10 |
| PC P-38:3; PC 37:4 | | TG 58:9 |
| PC P-38:4; PC 37:5 | | TG 58:8 |
| PC P-38:5; PC 37:6 | | TG 58:7 |
| PC P-40:3; PC 39:4 | | TG 58:6 |
| PC P-40:4; PC 39:5 | | TG 60:11 |
| PC P-40:5; PC 39:6 | | TG 60:10 |
| 230 | | 121 |

BRIEF DESCRIPTION OF DRAWINGS

In the following descriptions, T1, T2, T3, T4, Tis, and Tx are stages of cancer (primary tumor) according to TNM classification. T1 is a very early stage of cancer, Tis means carcinoma insitu, and Tx means that tumour cannot be assessed.

DETAILED DESCRIPTION OF THE INVENTION

Figure 1:
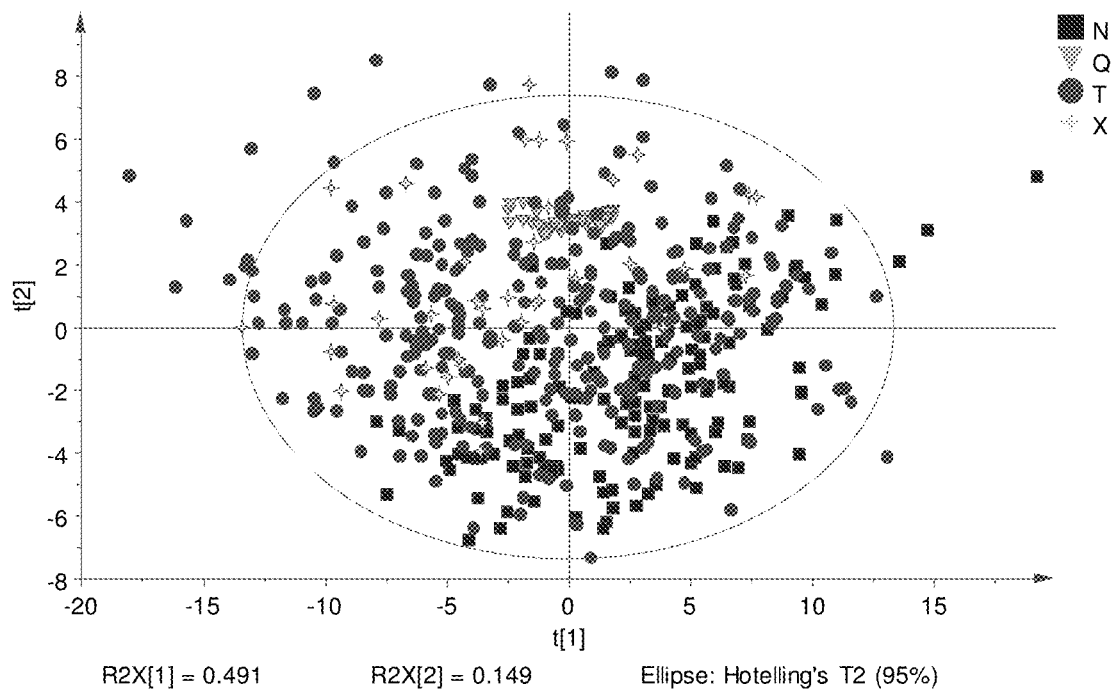
FIG. 1: PCA statistical model of 170 plasma samples of healthy controls (N), 282 plasma samples of patients suffering from cancer (T), 38 plasma samples of unknown classification (X) and quality control (Q) for both genders (generated from UHPSFC/MS data).

Sample Collection:

Human body fluid samples of cancer patients and healthy volunteers are collected in the hospital, typically blood or urine. Other samples types are isolated from blood, such as plasma, serum, oncosomes, exosomes, extracellular vesicles, etc. The blood of human subjects is collected in the standard and well established way used in hospitals into anticoagulant-containing tubes, such as EDTA, heparin, citrate tubes, then serum or plasma is isolated using standardized protocols well known to a person skilled in the art, storage at −80° C. at the clinic, transport from the clinic to the analytical laboratory using biological transport bags with dry ice (−20° C.), storage again at −80° C. until the analysis.

Preparation of a Set of Internal Standards (Mixture of Internal Standards):

Generally, an internal standard mixture is used for quantitation of lipid species. The internal standard for each lipid class behaves in the same way as the target compounds belonging to this lipid class. Due to the addition of the internal standard before sample processing, slight differences due to for instance pipetting errors can be compensated as the internal standard is affected in the same way as the target compounds.

In a particular embodiment, 2-4 mg of each standard is weighed into 2 mL HPLC glass vials using an analytical balance and dissolved in corresponding volume (chloroform:2-propanol—2:8) in order to obtain a final concentration of 2, 2.1, 1 or 0.25 μg/μL. Standards for each lipid class are mixed together to form internal standard mixtures as described in Table 16 for all herein shown types of MS analysis.

Preferably, one mixture of internal standards is prepared in a sufficient amount for the whole experiment, in order to avoid variances in quantitation due to slight differences in concentration of the internal standards when the mixture is prepared in several batches. Aliquots may be prepared of this internal standard mixture and stored at −80° C.

TABLE 16

Preparation of internal standards mixture.

| Internal standards | MW | Stock concentration [μg/μL] | Volume [μL] | Concentration in plasma [nmol/mL] |
| --- | --- | --- | --- | --- |
| CE d7 16:0 | 631.6285 | 2 | 200 | 443.3 |
| Cer d18:1/12:0 | 481.4495 | 2 | 4 | 11.6 |
| DG 12:1/12:1 | 452.3502 | 2 | 15 | 46.4 |
| Hex2Cer d18:1/12:0 | 805.5551 | 2 | 4 | 7.0 |
| HexCer d18:1/12:0 | 643.5023 | 2.1 | 3 | 6.9 |
| Chol d7 | 393.6988 | 2 | 300 | 1066.8 |
| PI 33:1 d7 | 846.596 | 1 | 16 | 13.2 |
| LPC 17:0 | 509.3481 | 2.1 | 20 | 57.7 |
| LPE 14:0 | 425.2542 | 2 | 4 | 13.2 |
| LPG 14:0 | 478.2308 | 2.1 | 14 | 43.0 |
| MG 19:1 | 370.3083 | 2 | 30 | 113.4 |
| PA 14:0/14:0 | 614.3924 | 2 | 4 | 9.1 |
| PC 14:0/14:0 | 677.4996 | 2 | 60 | 124.0 |
| PE 14:0/14:0 | 635.4526 | 2 | 4 | 8.8 |
| PG 14:0/14:0 | 688.4291 | 2 | 2 | 4.1 |

TABLE 16-continued

Preparation of internal standards mixture.

| Internal standards | MW | Stock concentration [µg/µL] | Volume [µL] | Concentration in plasma [nmol/mL] |
|---|---|---|---|---|
| PS 14:0/14:0 | 701.4244 | 2 | 4 | 8.0 |
| SM d18:1/12:0 | 646.505 | 2 | 20 | 43.3 |
| SulfoHexCer d18:1/12:0 | 740.4857 | 0.25 | 0.28 | 0.1 |
| TG 19:1/19:1/19:1 | 926.8302 | 2 | 75 | 113.3 |
| PC 44:2 | 897.719 | 2 | 80 | 124.8 |
| Solvent | | CHCl$_3$:IPA 2:8 | 140.72 | |
| Total Volume | | | 1000 | |

Sample Processing:

All samples are spiked before the extraction with the appropriate internal standard mixture (depending on which body fluid and which mass spectrometry method is used).

The lipidomic extractions were preferably performed by well-established procedures using chloroform-methanol-water extraction systems as published in our previous works [E. Cífková, M. Holčapek, M. Lísa, D. Vrána, J. Gatěk, B. Melichar, Anal. Bioanal. Chem. 407 (2015) 991-1002; E. Cífková, M. Lísa, R. Hrstka, D. Vrána, J. Gatěk, B. Melichar, M. Holčapek, Rapid Commun. Mass Spectrom. 31 (2017) 253-263]. The order of samples for extractions is randomized. 25 µL of serum or plasma and 17.5 µL of internal standard mixture and 2 mL chloroform (2×1 mL) and 1 mL methanol are transferred into a glass vial (4 mL). Biological samples contain also proteins, which may lead to sticky and slimy samples. It must be ensured that the pipette draws the 25 µL of serum or plasma and is not blocked with the slimy components during drawing. The glass vials are closed and put for 10 min into the ultrasonic bath at 40° C. for homogenization. Afterwards, the samples are allowed to reach room temperature in order to ensure no evaporation of the organic solvents when opening the vials. 600 µL of water are added to each sample. The samples are closed and vortexed for 1 min. It is important to do the extraction step always in the same way for all samples of one batch (one study). The target lipids for mass spectrometry are better soluble in the organic layer (bottom layer). Afterwards, the samples are centrifuged for 3 min at 3000 rpm in order to separate the organic and aqueous layer (in between these two layers a protein layer in the form of white precipitate is formed). The aqueous layer (upper layer) is removed via a glass pipette. The organic solvent containing the target compounds is evaporated under a stream of nitrogen at 30° C. and the glass vials containing the residue (target compounds) are stored at −80° C.

Before analysis, the samples are allowed to reach ambient temperature (so that they cannot draw water from the air when opening the vials) and then the residue from the extraction and evaporation (previous step) is dissolved in 500 µL chloroform:2-propanol (1:1, v/v). It is advisable to prepare enough solvent mixture of chloroform:2-propanol (1:1, v/v) mixture for all samples to avoid variations between individual batches of the solvent mixture. The samples are vortexed carefully for 1 min to ensure that the target compounds are dissolved. The solution is filtered using a 0.2 µm syringe filter in order to get rid of undissolved components, which may compromise the MS analysis. The vials are closed with PTFE caps and stored at −80° C.

For urine samples, reversed-phase solid phase extraction is performed. 2 mL of human urine together with 3 µL of mixture of internal standards dissolved in methanol (Sufo-HexCer d18:1/12:0 of concentration 1.7 µg/mL and D4 taurocholic acid of concentration 16.7 µg/mL) are loaded on 200 mg tC18 cartridge (Sep-Pak Vac, 37-55 µm particle size) (Waters, Milford, MA, USA) previously primed with 3 mL of methanol followed by 3 mL of water. Columns are washed with 3 mL of water, and studied lipids are further eluted with 3 mL of methanol. The eluates are collected, then evaporated by the gentle stream of nitrogen and redissolved in the mixture of 300 µL of methanol before the measurement.

Sample Preparation for UHPSFC/MS Analysis

The filtrate is diluted 5 times or 20 times with a mixture of hexane:2-propanol:chloroform 7:1.5:1.5 and transferred into an HPLC vial. The vials containing the diluted filtrate are closed with slit caps for analysis with UHPSFC/MS and placed in the autosampler.

Sample Preparation for Shotgun MS Analysis

The filtrates are diluted 10 times depending on the samples by chloroform-methanol-2-propanol (1:2:4, v/v/v) mixture containing 7.5 mmol/L of ammonium acetate and 1% of acetic acid.

Sample Preparation for MALDI-MS Analysis

MALDI matrix 9-aminoacridine (Sigma-Aldrich, St. Louis, MO, USA) is dissolved in methanol-water mixture (4:1, v/v) to provide the concentration of 5 mg/ml or 10 mg/ml and mixed with particular lipid extracts (1:1, v/v)—less preferably lipid extracts can be diluted with methanol (1:1, 1:2, or 1:3, v/v) before mixing with matrix. The deposited amount of extract/matrix mixture is 1 µl and the dried droplet crystallization is used for the sample deposition on the target plate. The deposition of small aliquot of chloroform on MALDI plate spots before the application of diluted extract/matrix mixture is applied to avoid the drop spreading.

Mass Spectrometry (MS) Method Development and Validation

Three major MS based methods for lipidomic quantitation were developed in particular, which are described in more detail here. The method benefits from the use of pooled sample, which is a mixture of identical volumes of all samples for smaller studies with less than 100 subjects. In this study, the pooled sample is prepared from equal volumes of randomly selected cancer patients and healthy volunteers samples, keeping the ratio of males and females in the same proportion as in the sample set. The pooled sample is used for the method development and optimization. The pooled sample with added internal standard mixture per each lipid class to be quantified is used for the full validation and QC during the measurements. The order of samples is always randomized in sample sequences to avoid measurements of non-cancerous and cancerous samples in certain portion of sequence.

The system suitability test was carried out before the validation procedure at three concentration levels typically reported as low, medium and high concentration levels. All concentration levels must be within the linear dynamic range. The low concentration level is close to the lower limit of quantitation (LLOQ), the middle concentration level is in the middle of the linear dynamic range, and the high concentration level is close to the upper limit of quantitation (ULOQ). In a particular embodiment, we use 5, 17.5, and 30 µl of IS mixture prepared according to Table 16 for low, medium and high concentration levels, respectively. Validation parameters such as selectivity, accuracy, precision, calibration curve, limits of detection and quantitation, matrix effect, carry-over and stability were determined. Individual parameters were determined for IS representing properties of the lipid class. The selectivity was determined using 3 extracts of the pooled serum sample spiked before extraction with the IS mixture at low, middle and high concentration level and 3-6 extracts of appropriate non-spiked serum samples. The accuracy and precision were studied using the pooled serum sample spiked after the extraction at low, medium and high concentration levels. The intra-day accuracy and intra-day precision were studied using three samples per concentration level. The inter-day accuracy and inter-day precision were evaluated among three independent runs on two different days using three samples at the low, medium and high concentration level. The LLOQ and ULOQ corresponded to the first and the last points of linearity range, respectively. The limit of detection (LOD) was determined based on signal to noise ratio (S/N=3) observed from reconstructed ion chromatogram or neutral loss (NL) and precursor ion (PI) mass spectra (shotgun MS) of internal standard mixture. The extraction recovery was determined by calculating the ratio of the signal response of samples spiked before and after extraction for low, medium and high concentration. The process efficiency was determined by calculating the ratio of the signal response of the spiked samples before extraction and the neat standard at different concentrations. The matrix effect was calculated from the ratio of the signal response of samples spiked after extraction and the neat standard. The carry-over was evaluated for each IS by the injection of blank sample with the pure solvent after the calibration sample at high concentration level (dilution factor of 10). The reliability of results obtained within analysis of large sample sets was evaluated by on-instrument and freeze-and-thaw stability tests. The stability of spiked plasma extract at middle concentration level was measured in autosampler at certain time intervals: 0, 4, 8, 12, 16, and 24 hours. Sample for freeze-and-thaw experiment was analyzed immediately after complete unassisted thawing in autosampler.

TABLE 17

Dilution scheme for calibration with pooled sample for UHPSFC/MS (volumes in µl) for plasma samples.

| Mixture of IS | Pooled sample | Hexane: 2-propanol: chloroform (7:1.5:1.5, v/v/v) |
|---|---|---|
| 150 | 100 | 250 |
| 100 | 100 | 300 |
| 50 | 100 | 350 |
| 20 | 100 | 380 |
| 15 | 100 | 385 |
| 10 | 100 | 390 |
| 5 | 100 | 395 |
| 3.5 | 100 | 396.5 |
| 2 | 100 | 398 |
| IS mixture 1: 50 diluted | | |
| 75 | 100 | 325 |
| 50 | 100 | 350 |
| 25 | 100 | 375 |
| 10 | 100 | 390 |
| 7.5 | 100 | 392.5 |
| 5 | 100 | 395 |
| 2.5 | 100 | 397.5 |
| 1 | 100 | 399 |

For calibration, the optimized mixture of IS for all methods in several dilutions were used in order to calibrate in the concentration ranges relevant for individual lipid classes. Depending on the dilution factor of the corresponding mass spectrometric method, the corresponding amounts of matrix were used. For instance, UHPSFC/MS uses 1:5 dilution of sample extracts. Therefore, 1/5 of blank plasma of a pooled sample were added (see Table 17 for more details).

UHPSFC/MS

Supercritical fluid chromatography is a tool for the separation of compounds of different polarity employing supercritical carbon dioxide (mobile phase) as main component for removing the compounds from an adsorbent (column-stationary phase). The addition of an organic solvent (typically methanol) to the supercritical carbon dioxide broadens the application range of UHPSFC and allows the removal of more polar compounds from the column. Generally, compounds can be differentiated if they are better soluble in water or alcohols, than they are of polar nature or if they are better soluble for instance in hexane than they are of nonpolar nature. Depending on the nature of the stationary phase, the mobile phase and the target compounds, like polar or nonpolar, interactions can be forced. For instance, polar compounds prefer to interact with polar stationary phases and in order to remove those from the stationary phase, a polar mobile phase can be used to remove the compounds from the stationary phase. A careful adjustment of these interactions by optimization of the mobile phase properties using a certain stationary phase allows the separation of compounds. The optimization of dimensions and properties of the stationary phase, such as smaller particle size and spherical particles of the sorbents, allows for a higher efficiency and is therefore called ultrahigh performance supercritical fluid chromatography (UHPSFC).

The chromatographic separation can be optimized for the separation of lipid classes, taking into account in particular the following. A lipid class has a dominant structural moiety (polar head group) in common which is mainly responsible for the interaction governing the retention mechanism. A lipid class can comprise numerous lipid species varying in the hydrocarbon chain length and structure (e.g., double bonds). Internal standards are added for each lipid (sub) class, therefore it is possible to identify and quantify all lipid species within a particular lipid (sub)class by comparing it to the class internal standard. MS-Analysis: Using a high-resolution, accurate-mass spectrometer as a detector allows the identification and quantification of lipids, as each lipid species has a defined m/z value and gives a signal response depending on the concentration in the sample. In order to improve ionization and therefore the signal response of the target compounds, additives like acids and buffers are added to the sample or to the mobile phase. In case of UHPSFC/MS, the use of a make-up solvent like acidified methanol further improves the sensitivity.

In one particular embodiment, a detailed description of all parameters applied for the UHPSFC/MS method to obtain the results presented herein below is as follows: Instrument—Acquity Ultra Performance Convergence Chromatography (UPC$^2$) System hyphenated to the hybrid quadrupole-traveling wave ion mobility-time of flight mass spectrometer Synapt G2 Si from Waters. Chromatographic settings—stationary phase: Acquity BEH UPC$^2$ column (100×3 mm, 1.7 μm, Waters), the flow rate was 1.9 mL/min, the injection volume 1 μL, the column temperature 60° C., the active back pressure regulator (ABPR) was set to 1800 psi, gradient mode:$CO_2$ and methanol with 30 mM ammonium acetate and 1% water. The gradient started at 1% modifier and increased to 51% in 5 mM, afterwards kept constant for 1 mM and flushed back to starting conditions with a total run time of 7.5 mM. injection needle wash: a mixture of hexane-2-propanol-water (1:2:0.5, v/v) column wash after each biological sample injection: a blank was injected using a fast gradient: 0 mM-1%, 1.4 mM-51%, 1.6 mM-51%, 1.8 mM-1%, and 4.8 mM-1% modifier, make-up effluent: HPLC 515 pump (Waters), make-up flow rate 0.25 mL/min methanol with 1% water, and optionally 0.1% formic acid.

ESI-MS settings: a capillary voltage of 3 kV, a sampling cone of 20 V, the source offset of 90 V, a source temperature of 150° C., a drying temperature of 500° C., the cone gas flow of 50 L h$^{-1}$, the drying gas flow of 1000 L h$^{-1}$ and the nebulizer gas of 4 bar. Resolution mode or sensitivity mode in positive ion mode and a mass range of m/z 50-1200. The scan time was 0.15 s, and measurements were performed in continuum mode. The peptide leucine enkephaline was used as the lock mass with a scan time of 0.1 s and interval of 30 s.

During the analysis, the samples in the sequence should be randomized so that not the same type of samples, such as only healthy (non-cancerous) samples, are measured in a row. This guarantees that in case of an error at a certain time not only one type of sample is affected. Furthermore, it is important to measure QC samples after a predetermined amount of samples in order to verify the instrument performance.

Before measuring biological samples, no injection, blank and QC samples are measured to check the instrument performance and afterwards it is continued with biological samples. All samples are measured in duplicates and after 20 samples or 40+40 injections (sample+wash) respectively, QC and blank samples are measured. During the whole study, measurement and sample preparation control is performed by evaluating the peak areas of each internal standard of each sample and exporting results in the Microsoft Excel file. The QC samples are aliquots of an extract of a mixture of serum or plasma samples. The lock mass is continuously measured during analysis, however the lock mass correction is not applied online, as preliminary results showed that the mass accuracy is worse using online correction. Furthermore, continuum mode is applied so that it is possible to monitor the resolution of the instrument. After measurements, the raw data get noise reduced using the MassLynx software from Waters. This improves the mass spectra as well as significantly reduces the file size, which allows easier handling of the files for further processing. The files are further processed by applying the lock mass correction and converting the files from profile to centroid mode, which enhances the mass accuracy and further reduces the file size. (The file size is important for data processing. The processing software can only hardly deal with huge file sizes and sample numbers, resulting in continuous errors making the processing time-consuming and cumbersome.)

All investigations regarding measurement control, profile mode and offline lock mass correction as well as the noise reduction improved data quality.

Shotgun MS

Experiments as presented herein below were performed on a quadrupole-linear ion trap mass spectrometer 6500 QTRAP (Sciex, Concord, ON, Canada) equipped by ESI probe with the following setting of tuning parameters: the ionspray voltage 5200 V, the curtain gas 20 psi, the source temperature 50° C., the ion source gas(1) 15 psi, and the ion source gas(2) 10 psi. MS/MS scans are measured with the scan rate 1000 Da/s, the declustering potential 80 V, the entrance potential 10 V, and the collision energy specified in the Table 18. Samples are introduced by a flow injection using a liquid chromatograph Agilent 1290 Series (Agilent Technologies) consisted of Agilent 1290 binary pump and Agilent 1260 autosampler. 50 μL of sample was injected into the flow rate 3 μL/min of chloroform-methanol-2-propanol (1:2:4, v/v/v) mixture containing 7.5 mmol/L of ammonium acetate and 1% of acetic acid with the analysis time 12 min, and the autosampler temperature 20° C. LC/MS system is washed after each analysis with methanol-2-propanol-water (2:2:1, v/v/v) mixture containing 7.5 mmol/L of ammonium acetate and 1% of acetic acid. Measured data experiments are extracted using LipidView software with the mass tolerance 0.3 Da, the minimum S/N=5 and the minimum intensity 1%. Raw data characterized by type of scans, m/z values and peak intensities are exported as .txt data and further processed using our Microsoft Excel macro script for the detection and quantitation of lipids. Lipid classes are characterized using type of scans, and individual lipid species in selected MS/MS scan are detected according to m/z values with the mass tolerance 0.3 Da based on the database compiled from identified lipids in the pooled sample followed by the isotopic correction of ion intensities. Concentration of lipid species are calculated from corrected ion intensity related to the intensity of lipid class internal standards.

TABLE 18

Characterization of shotgun MS/MS scans and their parameters for individual lipid classes. PI—precursor ion scan and NL—neutral loss scan.

| Lipid class | Type of MS/MS scan | Collision energy | Observed ions |
| --- | --- | --- | --- |
| CE | PI 369; PI 376 | 12 | $[M + NH_4]^+$ |
| Cer | PI 264; PI 266 | 35 | $[M + H]^+$ |
| DG | NL 35 | 20 | $[M + NH_4]^+$ |
| Hex2Cer | PI 264; PI 266 | 35 | $[M + H]^+$ |
| HexCer | PI 264; PI 266 | 35 | $[M + H]^+$ |
| Cholesterol | PI 369; PI 376 | 12 | $[M + NH_4]^+$ |
| LPA | NL 115 | 25 | $[M + NH_4]^+$ |
| LPC | PI 184 | 35 | $[M + H]^+$ |
| LPE | NL 141 | 30 | $[M + H]^+$ |

TABLE 18-continued

Characterization of shotgun MS/MS scans and their parameters for individual lipid classes. PI—precursor ion scan and NL—neutral loss scan.

| Lipid class | Type of MS/MS scan | Collision energy | Observed ions |
|---|---|---|---|
| LPG | NL 189 | 30 | $[M + NH_4]^+$ |
| LPS | NL 185 | 30 | $[M + H]^+$ |
| MG | NL 35 | 20 | $[M + NH_4]^+$ |
| PA | NL 115 | 25 | $[M + NH_4]^+$ |
| PC | PI 184 | 35 | $[M + H]^+$ |
| PE | NL 141 | 30 | $[M + H]^+$ |
| PG | NL 189 | 30 | $[M + NH_4]^+$ |
| PS | NL 185 | 30 | $[M + H]^+$ |
| SM | PI 184 | 35 | $[M + H]^+$ |
| SulfoHexCer | NL 98 | 25 | $[M + H]^+$ |
| TG | NL 17 | 30 | $[M + NH_4]^+$ |

MALDI Mass Spectrometry

Mass spectra were measured using ultrahigh-resolution MALDI mass spectrometer LTQ Orbitrap XL (Thermo Fisher Scientific, Waltham, MA, USA) equipped with the nitrogen UV laser (337 nm, 60 Hz) with a beam diameter of about 80 μm×100 μm. The LTQ Orbitrap instrument is operated in the negative-ion mode over a normal mass range m/z 400-2000 and the mass resolution is set to R=100,000 (full width at half maximum definition, at m/z 400). The zig-zag (or spiral outwards) sample movement with 250 μm step size is used during the individual data acquisition. The laser energy corresponds to 15% of maximum and 2 microscans/scan with 2 laser shots per microscan at 36 different positions are accumulated for each measurement to achieve a reproducible signal. Each sample (spotted matrix and body fluid extract mixture) is spotted five times. The total acquisition time of one sample including five consecutive spots is around ten minutes. Each measurement is represented by one average MALDI-MS spectrum with thousands of m/z values. The automatic peak assignment is subsequently performed and particular m/z peaks are matched with deprotonated molecules from a database created during the identification procedure using the Excel macro script. This peak assignment results in the generation of the list of present m/z of studied lipids with the average intensities in particular spectra for each samples that is used for further statistical evaluation.

Data Processing and Quantitation

The data processing starts with the data export from MS vendor software (e.g., Waters, Sciex or Thermo Scientific) into a data-processing software which may be Microsoft Excel for further steps to be done semi-automatically using e.g. advanced Excel script, in particular isotopic correction (Tables 19 and 20) and zero-filling. Quality control (QC) samples should be regularly injected to check the right and constant response of mass spectrometer. The typical QC sample is a pooled sample containing internal standards for all lipid classes to be quantified, which is injected after every 20 injections, and responses of individual internal standards are plotted versus the time. If responses of the internal standards are reduced too much, then it is the indication of an instrumental problem, typically the mass spectrometer requires cleaning due to the injection of too many samples. The typical cleaning interval is about several hundreds of samples, but it may strongly depend on the quality of prepared sample extracts, geometry of ion source, and system configuration.

The following example describes the example of UHPSFC/MS measurement on Synapt G2Si instrument from Waters, but similar approach is also applicable for other MS methods and different MS platforms from any instrumental vendor. The noise reduced, lock mass corrected and converted files are further processed with the MarkerLynx software. The reduced sequence table only including serum or plasma samples and QC samples has to be prepared in MassLynx with the corresponding suffix in the sample name (sample_nr20_AFAMM). Then the time scan range for each lipid class over the whole sequence has to be determined (for example m/z 250-350 is used for CE). For each lipid class, the method is created in MarkerLynx with the corresponding scan range, which will be combined, the mass peak separation of 50 mDa and marker intensity threshold of 3000. The method for each lipid class is applied for the sequence and MarkerLynx table with m/z values against the combined intensities is created. This table is exported into a text file and imported into a homemade database for the identification and quantitation of lipid species using Microsoft Excel. The m/z values obtained from MarkerLynx are compared to the accurate m/z values deposited as database for hundreds of lipid species for the identification. The database was created by evaluating present species in tissue and plasma samples. The identified lipid species are isotopically corrected and quantified by calculating the concentration in relation to the intensity and concentration of the (sub)class IS obtaining the table of lipid species concentrations vs. individual samples. Zero-filling procedure is performed. The average of the multiple injected samples for individual lipid species is calculated. The final data matrix, where the columns are individual subjects and lines are individual lipids, are used for further MDA statistical evaluation for absolute quantification. For relative quantification, the concentration of individual species within a class is related to the sum of concentrations of this lipid class in one sample. The resulting table is then used for statistical evaluation equally as for the absolute quantification.

TABLE 19

Database of lipid species monitored during the identification step in the positive-ion mode together with the calculation of isotopic correction for M + 1 and M + 2 isotopic peaks (so called deisotoping).

| | | Isotopic correction | |
|---|---|---|---|
| Lipid | m/z | M + 2 | M + 1 |
| CE 16:0 D7 (IS) | 376.3955 | 0.00% | 0.00% |
| CE 10:0 | 558.5244 | 0.00% | 0.00% |
| CE 12:0 | 586.5557 | 0.00% | 0.00% |
| CE 14:1 | 612.5714 | 0.00% | 0.00% |
| CE 14:0 | 614.5870 | 10.59% | 0.00% |
| CE 15:1 | 626.5532 | 0.00% | 0.00% |

TABLE 19-continued

Database of lipid species monitored during the identification step in the positive-ion mode together with the calculation of isotopic correction for M + 1 and M + 2 isotopic peaks (so called deisotoping).

| Lipid | m/z | Isotopic correction | |
|---|---|---|---|
| | | M + 2 | M + 1 |
| CE 15:0 | 628.6027 | 11.09% | 0.00% |
| CE 16:1 | 640.6027 | 0.00% | 0.00% |
| CE 16:0 | 642.6184 | 11.61% | 0.00% |
| CE 16:0 D7 (IS) | 649.6623 | 0.00% | 0.00% |
| CE 17:1 | 654.6183 | 0.00% | 0.00% |
| CE 17:0 | 656.6340 | 12.14% | 0.00% |
| CE 18:4 | 662.5870 | 0.00% | 0.00% |
| CE 18:3 | 664.6027 | 12.64% | 0.00% |
| CE 18:2 | 666.6184 | 12.65% | 0.00% |
| CE 18:1 | 668.6340 | 12.67% | 0.00% |
| CE 18:0 | 670.6497 | 12.68% | 0.00% |
| CE 19:1 | 682.6497 | 0.00% | 0.00% |
| CE 19:0 | 684.6653 | 13.23% | 0.00% |
| CE 20:5 | 688.6027 | 0.00% | 0.00% |
| CE 20:4 | 690.6184 | 13.75% | 0.00% |
| CE 20:3 | 692.6340 | 13.76% | 0.00% |
| CE 20:2 | 694.6497 | 13.77% | 0.00% |
| CE 20:1 | 696.6653 | 13.78% | 0.00% |
| CE 20:0 | 698.6810 | 13.80% | 0.00% |
| CE 21:1 | 710.6809 | 0.00% | 0.00% |
| CE 21:0 | 712.6966 | 14.37% | 0.00% |
| CE 22:6 | 714.6184 | 14.39% | 0.00% |
| CE 22:5 | 716.6340 | 14.90% | 0.00% |
| CE 22:4 | 718.6496 | 14.91% | 0.00% |
| CE 22:3 | 720.6653 | 14.93% | 0.00% |
| CE 22:2 | 722.6810 | 14.94% | 0.00% |
| CE 22:1 | 724.6966 | 14.95% | 0.00% |
| CE 22:0 | 726.7123 | 14.96% | 0.00% |
| CE 23:1 | 738.7122 | 0.00% | 0.00% |
| CE 23:0 | 740.7279 | 15.57% | 0.00% |
| CE 24:5 | 744.6653 | 0.00% | 0.00% |
| CE 24:4 | 746.6809 | 16.13% | 0.00% |
| CE 24:3 | 748.6966 | 16.14% | 0.00% |
| CE 24:2 | 750.7122 | 16.15% | 0.00% |
| CE 24:1 | 752.7279 | 0.00% | 0.00% |
| CE 24:0 | 754.7436 | 16.18% | 0.00% |
| CE 25:0 | 768.7592 | 0.00% | 0.00% |
| CE 26:5 | 772.6966 | 0.00% | 0.00% |
| CE 26:4 | 774.7122 | 17.39% | 0.00% |
| CE 26:3 | 776.7279 | 17.40% | 0.00% |
| CE 26:0 | 782.7748 | 0.00% | 0.00% |
| CE 27:0 | 796.7905 | 0.00% | 0.00% |
| CE 28:0 | 810.8061 | 0.00% | 0.00% |
| TG 35:0 | 642.5667 | 0.00% | 0.00% |
| TG 36:1 | 654.5667 | 0.00% | 0.00% |
| TG 36:0 | 656.5823 | 10.53% | 0.00% |
| TG 38:3 | 678.5667 | 0.00% | 0.00% |
| TG 38:2 | 680.5823 | 11.49% | 0.00% |
| TG 38:1 | 682.5980 | 11.50% | 0.00% |
| TG 38:0 | 684.6136 | 11.51% | 0.00% |
| TG 40:4 | 704.5823 | 0.00% | 0.00% |
| TG 40:3 | 706.5980 | 12.50% | 0.00% |
| TG 40:2 | 708.6136 | 12.51% | 0.00% |
| TG 40:1 | 710.6293 | 12.52% | 0.00% |
| TG 40:0 | 712.6449 | 12.54% | 0.00% |
| TG 41:1 | 724.6449 | 0.00% | 0.00% |
| TG 41:0 | 726.6606 | 13.07% | 0.00% |
| TG 42:4 | 732.6136 | 0.00% | 0.00% |
| TG 42:3 | 734.6293 | 0.00% | 0.00% |
| TG 42:2 | 736.6449 | 13.59% | 0.00% |
| TG 42:1 | 738.6606 | 13.60% | 0.00% |
| TG 42:0 | 740.6763 | 13.61% | 0.00% |
| TG 43:1 | 752.6763 | 0.00% | 0.00% |
| TG 43:0 | 754.6919 | 14.17% | 0.00% |
| TG 44:4 | 760.6449 | 0.00% | 0.00% |
| TG 44:3 | 762.6606 | 0.00% | 0.00% |
| TG 44:2 | 764.6763 | 14.71% | 0.00% |
| TG 44:1 | 766.6919 | 14.72% | 0.00% |
| TG 44:0 | 768.7076 | 14.73% | 0.00% |
| TG O-46:5/P-46:4 | 772.6813 | 0.00% | 0.00% |
| TG O-46:4/P-46:3 | 774.6970 | 15.64% | 0.00% |
| TG 45:3 | 776.6762 | 0.00% | 0.00% |

TABLE 19-continued

Database of lipid species monitored during the identification step in the positive-ion mode together with the calculation of isotopic correction for M + 1 and M + 2 isotopic peaks (so called deisotoping).

| Lipid | m/z | Isotopic correction M + 2 | Isotopic correction M + 1 |
|---|---|---|---|
| TG 45:2 | 778.6919 | 15.29% | 0.00% |
| TG 45:1 | 780.7076 | 15.30% | 0.00% |
| TG 45:0 | 782.7232 | 15.31% | 0.00% |
| TG 46:4 | 788.6763 | 0.00% | 0.00% |
| TG 46:3 | 790.6919 | 15.87% | 0.00% |
| TG 46:2 | 792.7076 | 15.58% | 0.00% |
| TG 46:1 | 794.7232 | 15.89% | 0.00% |
| TG 46:0 | 796.7389 | 15.91% | 0.00% |
| TG 47:3 | 804.7076 | 0.00% | 0.00% |
| TG 47:2 | 806.7232 | 16.48% | 0.00% |
| TG 47:1 | 808.7389 | 16.50% | 0.00% |
| TG 47:0 | 810.7545 | 16.51% | 0.00% |
| TG 48:5 | 814.6919 | 0.00% | 0.00% |
| TG 48:4 | 816.7076 | 0.00% | 0.00% |
| TG 48:3 | 818.7232 | 17.09% | 0.00% |
| TG 48:2 | 820.7389 | 17.10% | 0.00% |
| TG 48:1 | 822.7545 | 17.11% | 0.00% |
| TG 48:0 | 824.7702 | 17.13% | 0.00% |
| TG 49:3 | 832.7389 | 0.00% | 0.00% |
| TG 49:2 | 834.7545 | 17.73% | 0.00% |
| TG 49:1 | 836.7702 | 17.74% | 0.00% |
| TG 49:0 | 838.7858 | 17.76% | 0.00% |
| TG 50:6 | 840.7076 | 18.32% | 0.00% |
| TG 50:5 | 842.7232 | 18.33% | 0.00% |
| TG 50:4 | 844.7389 | 18.34% | 0.00% |
| TG 50:3 | 846.7545 | 18.36% | 0.00% |
| TG 50:2 | 848.7702 | 18.37% | 0.00% |
| TG 50:1 | 850.7858 | 18.38% | 0.00% |
| TG 50:0 | 852.8015 | 18.40% | 0.00% |
| TG 51:6 | 854.7232 | 18.41% | 0.00% |
| TG 51:5 | 856.7389 | 18.98% | 0.00% |
| TG 51:4 | 858.7545 | 18.99% | 0.00% |
| TG 51:3 | 860.7702 | 19.01% | 0.00% |
| TG 51:2 | 862.7858 | 19.02% | 0.00% |
| TG 51:1; TG 52:8 | 864.8015 | 19.04% | 0.00% |
| TG 52:7 | 866.7232 | 0.00% | 0.00% |
| TG 51:0 | 866.8171 | 19.04% | 0.00% |
| TG 52:6 | 868.7389 | 19.06% | 0.00% |
| TG 52:5 | 870.7545 | 19.65% | 0.00% |
| TG 52:4 | 872.7702 | 19.66% | 0.00% |
| TG 52:3 | 874.7858 | 19.67% | 0.00% |
| TG 52:2 | 876.8015 | 19.69% | 0.00% |
| TG 52:1 | 878.8171 | 19.70% | 0.00% |
| TG 52:0 | 880.8328 | 19.72% | 0.00% |
| TG 53:6 | 882.7545 | 19.73% | 0.00% |
| TG 53:5 | 884.7702 | 20.32% | 0.00% |
| TG 53:4 | 886.7858 | 20.34% | 0.00% |
| TG 53:3; TG 54:10 | 888.8015 | 20.35% | 0.00% |
| TG 53:2; TG 54:9 | 890.8171 | 20.36% | 0.00% |
| TG 54:8 | 892.7388 | 0.00% | 0.00% |
| TG 53:1 | 892.8327 | 20.38% | 0.00% |
| TG 54:7 | 894.7545 | 20.98% | 0.00% |
| TG 53:0 | 894.8484 | 20.39% | 0.00% |
| TG 54:6 | 896.7702 | 20.41% | 0.00% |
| TG 54:5 | 898.7858 | 21.01% | 0.00% |
| TG 54:4 | 900.8015 | 21.02% | 0.00% |
| TG 54:3 | 902.8171 | 21.04% | 0.00% |
| TG 54:2 | 904.8328 | 21.05% | 0.00% |
| TG 54:1 | 906.8484 | 21.07% | 0.00% |
| TG 54:0 | 908.8641 | 21.08% | 0.00% |
| TG 55:6 | 910.7858 | 21.10% | 0.00% |
| TG 55:5 | 912.8015 | 21.71% | 0.00% |
| TG 55:4 | 914.8171 | 21.73% | 0.00% |
| TG 55:3; TG 56:10 | 916.8328 | 21.74% | 0.00% |
| TG 56:9 | 918.7545 | 0.00% | 0.00% |
| TG 55:2 | 918.8484 | 21.75% | 0.00% |
| TG 56:8 | 920.7701 | 22.38% | 0.00% |
| TG 55:1 | 920.8640 | 21.76% | 0.00% |
| TG 56:7 | 922.7858 | 22.39% | 0.00% |
| TG 55:0; TG 56:7 | 922.8797 | 21.79% | 0.00% |
| TG 56:6 | 924.8015 | 21.80% | 0.00% |
| TG 56:5 | 926.8171 | 22.42% | 0.00% |

TABLE 19-continued

Database of lipid species monitored during the identification step in
the positive-ion mode together with the calculation of isotopic correction
for M + 1 and M + 2 isotopic peaks (so called deisotoping).

|  |  | Isotopic correction ||
| --- | --- | --- | --- |
| Lipid | m/z | M + 2 | M + 1 |
| TG 56:4 | 928.8328 | 22.44% | 0.00% |
| TG 56:3 | 930.8484 | 22.45% | 0.00% |
| TG 56:2 | 932.8641 | 22.47% | 0.00% |
| TG 56:1 | 934.8797 | 22.48% | 0.00% |
| TG 57:7 | 936.8014 | 0.00% | 0.00% |
| TG 56:0 | 936.8954 | 22.50% | 0.00% |
| TG 57:6 | 938.8171 | 22.51% | 0.00% |
| TG 58:12 | 940.7388 | 0.00% | 0.00% |
| TG 57:5 | 940.8328 | 23.15% | 0.00% |
| TG 58:11 | 942.7545 | 23.79% | 0.00% |
| TG 57:4 | 942.8484 | 23.16% | 0.00% |
| TG 58:10 | 944.7701 | 23.81% | 0.00% |
| TG 57:3 (IS) | 944.8640 | 23.18% | 0.00% |
| TG 58:9 | 946.7858 | 23.82% | 0.00% |
| TG 57:2 | 946.8797 | 23.20% | 0.00% |
| TG 58:8 | 948.8014 | 23.84% | 0.00% |
| TG 57:1; TG 58:8 | 948.8954 | 23.21% | 0.00% |
| TG 58:7 | 950.8171 | 23.86% | 0.00% |
| TG 57:0; TG 58:7 | 950.9110 | 23.23% | 0.00% |
| TG 58:6 | 952.8328 | 23.24% | 0.00% |
| TG 58:5 | 954.8484 | 23.89% | 0.00% |
| TG 58:4 | 956.8641 | 23.90% | 0.00% |
| TG 58:3 | 958.8797 | 23.92% | 0.00% |
| TG 58:2 | 960.8954 | 23.93% | 0.00% |
| TG 59:8 | 962.8171 | 0.00% | 0.00% |
| TG 58:1 | 962.9110 | 23.95% | 0.00% |
| TG 59:7 | 964.8327 | 24.60% | 0.00% |
| TG 58:0 | 964.9267 | 23.96% | 0.00% |
| TG 60:13 | 966.7545 | 0.00% | 0.00% |
| TG 59:6 | 966.8484 | 23.98% | 0.00% |
| TG 60:12 | 968.7701 | 25.29% | 0.00% |
| TG 59:5 | 968.8641 | 24.64% | 0.00% |
| TG 60:11 | 970.7858 | 25.30% | 0.00% |
| TG 59:4 | 970.8797 | 24.65% | 0.00% |
| TG 60:10 | 972.8014 | 25.32% | 0.00% |
| TG 59:3 | 972.8953 | 24.67% | 0.00% |
| TG 60:9 | 974.8171 | 25.33% | 0.00% |
| TG 59:2 | 974.9110 | 24.68% | 0.00% |
| TG 60:8 | 976.8327 | 25.35% | 0.00% |
| TG 59:1 | 976.9266 | 24.70% | 0.00% |
| TG 59:1; TG 60:8 | 976.9267 | 24.70% | 0.00% |
| TG 60:7 | 978.8484 | 25.37% | 0.00% |
| TG 59:0; TG 60:7 | 978.9423 | 24.72% | 0.00% |
| TG 60:6 | 980.8641 | 24.73% | 0.00% |
| TG 60:5 | 982.8797 | 25.40% | 0.00% |
| TG 60:4 | 984.8954 | 25.41% | 0.00% |
| TG 60:3 | 986.9110 | 25.43% | 0.00% |
| TG 60:2 | 988.9267 | 25.45% | 0.00% |
| TG 60:1 | 990.9423 | 25.46% | 0.00% |
| TG 60:0 | 992.9580 | 25.48% | 0.00% |
| TG 62:12 | 996.8014 | 0.00% | 0.00% |
| TG 62:11 | 998.8171 | 26.86% | 0.00% |
| TG 61:4 | 998.9110 | 0.00% | 0.00% |
| TG 62:10 | 1000.8327 | 26.88% | 0.00% |
| TG 61:3 | 1000.9266 | 26.20% | 0.00% |
| TG 62:9 | 1002.8484 | 26.89% | 0.00% |
| TG 61:2 | 1002.9423 | 26.22% | 0.00% |
| TG 62:8 | 1004.8640 | 26.91% | 0.00% |
| TG 62:7 | 1006.8797 | 26.92% | 0.00% |
| TG 62:6 | 1008.8953 | 26.94% | 0.00% |
| TG 62:5 | 1010.9110 | 26.96% | 0.00% |
| TG 62:4 | 1012.9266 | 26.97% | 0.00% |
| TG 62:3 | 1014.9423 | 26.99% | 0.00% |
| TG 62:2 | 1016.9579 | 27.01% | 0.00% |
| TG 62:1 | 1018.9736 | 27.02% | 0.00% |
| TG 64:12 | 1024.8327 | 0.00% | 0.00% |
| TG 64:11 | 1026.8484 | 28.46% | 0.00% |
| TG 63:4 | 1026.9423 | 0.00% | 0.00% |
| TG 64:10 | 1028.8640 | 28.48% | 0.00% |
| TG 63:3 | 1028.9579 | 27.79% | 0.00% |
| TG 64:9 | 1030.8797 | 28.50% | 0.00% |
| TG 64:8 | 1032.8953 | 28.52% | 0.00% |

TABLE 19-continued

Database of lipid species monitored during the identification step in the positive-ion mode together with the calculation of isotopic correction for M + 1 and M + 2 isotopic peaks (so called deisotoping).

| Lipid | m/z | Isotopic correction M + 2 | M + 1 |
|---|---|---|---|
| TG 64:7 | 1034.9110 | 28.53% | 0.00% |
| TG 64:6 | 1036.9266 | 28.55% | 0.00% |
| TG 64:5 | 1038.9423 | 28.57% | 0.00% |
| TG 64:4 | 1040.9579 | 28.58% | 0.00% |
| TG 66:12 | 1052.8640 | 0.00% | 0.00% |
| TG 66:11 | 1054.8797 | 30.12% | 0.00% |
| TG 66:10 | 1056.8953 | 30.14% | 0.00% |
| TG 66:9 | 1058.9110 | 30.15% | 0.00% |
| TG 66:8 | 1060.9266 | 30.17% | 0.00% |
| TG 66:7 | 1062.9423 | 30.19% | 0.00% |
| TG 66:6 | 1064.9579 | 30.21% | 0.00% |
| MG 10:0 | 264.2169 | 0.00% | 0.00% |
| MG 12:0 | 292.2482 | 0.00% | 0.00% |
| MG 14:1 | 318.2639 | 0.00% | 0.00% |
| MG 14:0 | 320.2795 | 2.59% | 0.00% |
| MG 15:1 | 332.2795 | 0.00% | 0.00% |
| MG 15:0 | 334.2952 | 2.80% | 0.00% |
| MG 16:1 | 346.2952 | 0.00% | 0.00% |
| MG 16:0 | 348.3108 | 3.03% | 0.00% |
| MG 16:0 | 353.2662 | 0.00% | 0.00% |
| MG 17:1 | 360.3108 | 0.00% | 0.00% |
| MG 17:0 | 362.3265 | 3.27% | 0.00% |
| MG 17:0 | 367.2819 | 0.00% | 0.00% |
| MG 18:4 | 368.2795 | 0.00% | 0.00% |
| Chol | 369.3516 | 0.00% | 0.00% |
| Chol D7 (IS) | 376.3955 | 0.00% | 0.00% |
| Chol | 404.3887 | 0.00% | 0.00% |
| Chol D7 (IS) | 411.4326 | 0.00% | 0.00% |
| MG 18:3 | 370.2952 | 3.50% | 0.00% |
| MG 18:2 | 372.3108 | 3.51% | 0.00% |
| MG 18:1 | 374.3265 | 3.51% | 0.00% |
| MG 18:0 | 376.3421 | 3.52% | 0.00% |
| MG 18:1 | 379.2819 | 0.00% | 0.00% |
| MG 18:0 | 381.2975 | 3.42% | 0.00% |
| MG 19:1 (IS) | 388.3421 | 0.00% | 0.00% |
| MG 19:0 | 390.3578 | 3.78% | 0.00% |
| MG 19:1 (IS) | 393.2975 | 0.00% | 0.00% |
| MG 20:5 | 394.2952 | 0.00% | 0.00% |
| MG 20:4 | 396.3108 | 4.03% | 0.00% |
| MG 20:3 | 398.3265 | 4.04% | 0.00% |
| MG 20:2 | 400.3421 | 4.04% | 0.00% |
| MG 20:1 | 402.3578 | 4.05% | 0.00% |
| MG 21:1 | 416.3734 | 0.00% | 0.00% |
| MG 21:0 | 418.3891 | 4.34% | 0.00% |
| MG 22:6 | 420.3108 | 4.35% | 0.00% |
| MG 22:5 | 422.3265 | 4.61% | 0.00% |
| MG 22:4 | 424.3421 | 4.61% | 0.00% |
| MG 22:3 | 426.3587 | 4.62% | 0.00% |
| MG 22:2 | 428.3734 | 4.63% | 0.00% |
| MG 22:1 | 430.3891 | 4.63% | 0.00% |
| MG 22:0 | 432.4047 | 4.64% | 0.00% |
| DG 24:2 (IS) | 435.3469 | 0.00% | 0.00% |
| MG 23:1 | 444.4047 | 0.00% | 0.00% |
| MG 23:0 | 446.4204 | 4.95% | 0.00% |
| MG 24:1 | 458.4204 | 0.00% | 0.00% |
| MG 24:0 | 460.4360 | 5.27% | 0.00% |
| DG 24:2 (IS) | 470.3840 | 0.00% | 0.00% |
| DG 28:0 | 530.4779 | 0.00% | 0.00% |
| DG 29:0 | 544.4935 | 0.00% | 0.00% |
| DG 30:2 | 554.4779 | 0.00% | 0.00% |
| DG 30:1 | 556.4935 | 7.67% | 0.00% |
| DG 30:0 | 558.5092 | 7.68% | 0.00% |
| DG 31:2 | 568.4935 | 0.00% | 0.00% |
| DG 31:1 | 570.5092 | 8.08% | 0.00% |
| DG 31:0 | 572.5248 | 8.09% | 0.00% |
| DG 32:3 | 580.4936 | 0.00% | 0.00% |
| DG 32:2 | 582.5092 | 8.50% | 0.00% |
| DG 32:1 | 584.5249 | 8.50% | 0.00% |
| DG 32:0 | 586.5405 | 8.51% | 0.00% |
| DG 33:3 | 594.5092 | 0.00% | 0.00% |
| DG 33:2 | 596.5248 | 8.93% | 0.00% |
| DG 33:1 | 598.5405 | 8.94% | 0.00% |

TABLE 19-continued

Database of lipid species monitored during the identification step in
the positive-ion mode together with the calculation of isotopic correction
for M + 1 and M + 2 isotopic peaks (so called deisotoping).

| Lipid | m/z | Isotopic correction | |
|---|---|---|---|
| | | M + 2 | M + 1 |
| DG 33:0 | 600.5561 | 8.95% | 0.00% |
| DG 34:4 | 606.5092 | 0.00% | 0.00% |
| DG 34:3 | 608.5249 | 9.36% | 0.00% |
| DG 34:2 | 610.5405 | 9.37% | 0.00% |
| DG 34:1 | 612.5562 | 9.38% | 0.00% |
| DG 34:0 | 614.5718 | 9.39% | 0.00% |
| DG 35:4 | 620.5248 | 0.00% | 0.00% |
| DG 35:3 | 622.5405 | 9.82% | 0.00% |
| DG 35:2 | 624.5561 | 9.83% | 0.00% |
| DG 35:1 | 626.5718 | 9.84% | 0.00% |
| DG 35:0 | 628.5875 | 9.85% | 0.00% |
| DG 36:5 | 632.5249 | 0.00% | 0.00% |
| DG 36:4 | 634.5405 | 10.28% | 0.00% |
| DG 36:3 | 636.5561 | 10.29% | 0.00% |
| DG 36:2 | 638.5718 | 10.30% | 0.00% |
| DG 36:1 | 640.5874 | 10.31% | 0.00% |
| DG 37:7 | 642.5092 | 0.00% | 0.00% |
| DG 36:0 | 642.6031 | 10.32% | 0.00% |
| DG 37:5 | 646.5405 | 0.00% | 0.00% |
| DG 37:4 | 648.5561 | 0.00% | 0.00% |
| DG 37:3 | 650.5718 | 10.77% | 0.00% |
| DG 37:2 | 652.5874 | 10.78% | 0.00% |
| DG 37:1 | 654.6031 | 10.79% | 0.00% |
| DG 38:7 | 656.5248 | 0.00% | 0.00% |
| DG 37:0 | 656.6188 | 10.80% | 0.00% |
| DG 38:6 | 658.5405 | 11.23% | 0.00% |
| DG 38:5 | 660.5561 | 11.24% | 0.00% |
| DG 38:4 | 662.5718 | 11.26% | 0.00% |
| DG 38:3 | 664.5874 | 11.27% | 0.00% |
| DG 38:2 | 666.6031 | 11.28% | 0.00% |
| DG 38:1 | 668.6187 | 11.29% | 0.00% |
| DG 38:0 | 670.6344 | 11.30% | 0.00% |
| DG 39:6 | 672.5562 | 11.31% | 0.00% |
| DG 39:5 | 674.5718 | 11.75% | 0.00% |
| DG 39:4 | 676.5875 | 11.76% | 0.00% |
| DG 40:10; DG 39:3 | 678.5092 | 11.77% | 0.00% |
| DG 40:9; DG 39:2 | 680.5249 | 12.223% | 0.000% |
| DG 40:8; DG 39:1 | 682.5405 | 12.23% | 0.00% |
| DG 40:7; DG 39:0 | 684.5562 | 12.25% | 0.00% |
| DG 40:6 | 686.5718 | 12.26% | 0.00% |
| DG 40:5 | 688.5874 | 12.27% | 0.00% |
| DG 40:4 | 690.6031 | 12.28% | 0.00% |
| DG 40:3 | 692.6187 | 12.29% | 0.00% |
| DG 40:2 | 694.6344 | 12.30% | 0.00% |
| DG 40:1 | 696.6500 | 12.31% | 0.00% |
| DG 40:0 | 698.6657 | 12.32% | 0.00% |
| DG 41:6 | 700.5675 | 12.33% | 0.00% |
| DG 41:5 | 702.3603 | 12.80% | 0.00% |
| DG 41:4 | 704.6188 | 12.81% | 0.00% |
| DG 42:10; DG 41:3 | 706.5405 | 12.82% | 0.00% |
| DG 42:9; DG 41:2 | 708.5562 | 13.29% | 0.00% |
| DG 42:8; DG 41:1 | 710.5718 | 13.30% | 0.00% |
| DG 42:7; DG 41:0 | 712.5875 | 13.32% | 0.00% |
| DG 42:6 | 714.6031 | 13.33% | 0.00% |
| DG 42:5 | 716.6188 | 13.34% | 0.00% |
| DG 42:4 | 718.6344 | 13.35% | 0.00% |
| DG 42:3 | 720.6501 | 13.36% | 0.00% |
| DG 42:2 | 722.6657 | 13.37% | 0.00% |
| DG 42:1 | 724.6814 | 13.39% | 0.00% |
| DG 42:0 | 726.6970 | 13.40% | 0.00% |
| DG 44:0 | 754.7283 | 0.00% | 0.00% |
| Coenzyme Q10 | 880.7177 | 0.00% | 0.00% |
| Cer d30:1 (IS) | 464.4462 | 0.00% | 0.00% |
| Cer d18:1/12:2 | 478.4255 | 0.00% | 0.00% |
| Cer d18:1/12:1 | 480.4411 | 6.08% | 0.00% |
| Cer d18:0/12:2 | 480.4412 | 0.00% | 0.00% |
| Cer d18:1/12:0 (IS) | 482.4568 | 6.08% | 0.00% |
| Cer d18:0/12:1 (IS) | 482.4568 | 6.08% | 0.00% |
| Cer d18:0/12:0 | 484.4725 | 6.09% | 0.00% |
| Cer d18:1/13:2 | 492.4411 | 0.00% | 0.00% |
| Cer d32:1 | 492.4775 | 0.00% | 0.00% |
| Cer d18:1/13:1; Cer d18:1/12:2 (1OH) | 494.4568 | 6.45% | 0.00% |

TABLE 19-continued

Database of lipid species monitored during the identification step in
the positive-ion mode together with the calculation of isotopic correction
for M + 1 and M + 2 isotopic peaks (so called deisotoping).

| Lipid | m/z | Isotopic correction M + 2 | Isotopic correction M + 1 |
|---|---|---|---|
| Cer d18:0/13:2 | 494.4568 | 0.00% | 0.00% |
| Cer d18:1/13:0; Cer d18:1/12:1 (1OH) | 496.4724 | 6.46% | 0.00% |
| Cer d18:0/13:1; Cer d18:0/12:2 (1OH) | 496.4725 | 6.46% | 0.00% |
| Cer d18:1/12:0 (1OH) | 498.4517 | 6.46% | 0.00% |
| Cer d18:0/13:0; Cer d18:0/12:1 (1OH) | 498.4881 | 6.46% | 0.00% |
| Cer d18:0/12:0 (1OH) | 500.4674 | 6.47% | 0.00% |
| Cer d18:1/14:2 | 506.4568 | 0.00% | 0.00% |
| Cer d18:1/14:1; Cer d18:1/13:2 (1OH) | 508.4724 | 6.83% | 0.00% |
| Cer d18:0/14:2 | 508.4725 | 0.00% | 0.00% |
| Cer d18:1/14:0; Cer d18:1/13:0 (1OH) | 510.4808 | 6.84% | 0.00% |
| Cer d18:0/14:1; Cer d18:0/13:2 (1OH) | 510.4881 | 6.84% | 0.00% |
| Cer d18:1/13:0 (1OH) | 512.4674 | 6.85% | 0.00% |
| Cer d18:0/14:0; Cer d18:0/13:0 (1OH) | 512.4965 | 6.85% | 0.00% |
| Cer d18:0/13:0 (1OH) | 514.4831 | 6.86% | 0.00% |
| Cer d34:2 | 518.4932 | 0.00% | 0.00% |
| Cer d18:1/15:2 | 520.4724 | 0.00% | 0.00% |
| Cer d34:1 | 520.5088 | 7.41% | 0.00% |
| Cer d18:0/15:2 | 522.4881 | 0.00% | 0.00% |
| Cer d18:1/15:1; Cer d18:1/14:2 (1OH) | 522.4881 | 7.23% | 0.00% |
| Cer d34:0 | 522.5245 | 7.42% | 0.00% |
| Cer d18:1/15:0; Cer d18:1/14:1 (1OH) | 524.5037 | 7.24% | 0.00% |
| Cer d18:0/15:1; Cer d18:0/14:2 (1OH) | 524.5038 | 7.24% | 0.00% |
| Cer d18:1/14:0 (1OH) | 526.4830 | 7.24% | 0.00% |
| Cer d18:0/15:0; Cer d18:0/14:1 (1OH) | 526.5194 | 7.24% | 0.00% |
| Cer d18:0/14:0 (1OH) | 528.4987 | 7.25% | 0.00% |
| Cer d18:1/16:2 | 534.4881 | 0.00% | 0.00% |
| Cer d35:1 | 534.5245 | 0.00% | 0.00% |
| Cer d18:1/16:1; Cer d18:1/15:2 (1OH) | 536.5037 | 7.63% | 0.00% |
| Cer d18:0/16:2 | 536.5038 | 0.00% | 0.00% |
| Cer d18:0/16:1; Cer d18:0/15:2 (1OH) | 538.5194 | 7.64% | 0.00% |
| Cer d18:1/16:0; Cer d18:1/15:1 (1OH) | 538.5194 | 7.64% | 0.00% |
| Cer d18:1/15:0 (1OH) | 540.4987 | 7.65% | 0.00% |
| Cer d18:0/16:0; Cer d18:0/15:1 (1OH) | 540.5351 | 7.65% | 0.00% |
| Cer d18:0/15:0 (1OH) | 542.5144 | 7.66% | 0.00% |
| Cer d36:2 | 546.5245 | 0.00% | 0.00% |
| Cer d18:1/17:2 | 548.5037 | 0.00% | 0.00% |
| Cer d36:1 | 548.5401 | 8.27% | 0.00% |
| Cer d18:0/17:2 | 550.5194 | 0.00% | 0.00% |
| Cer d18:1/17:1; Cer d18:1/16:2 (1OH) | 550.5194 | 8.05% | 0.00% |
| Cer d36:0 | 550.5558 | 8.28% | 0.00% |
| Cer d18:1/17:0; Cer d18:1/16:1 (1OH) | 552.5350 | 8.06% | 0.00% |
| Cer d18:0/17:1; Cer d18:0/16:2 (1OH) | 552.5351 | 8.06% | 0.00% |
| Cer d18:1/16:0 (1OH) | 554.5143 | 8.07% | 0.00% |
| Cer d18:0/17:0; Cer d18:0/16:1 (1OH) | 554.5507 | 8.07% | 0.00% |
| Cer d18:0/16:0 (1OH) | 556.5300 | 8.08% | 0.00% |
| Cer d18:1/18:3 | 560.5037 | 0.00% | 0.00% |
| Cer d18:1/18:2 | 562.5193 | 8.48% | 0.00% |
| Cer d37:1 | 562.5558 | 0.00% | 0.00% |
| Cer d18:0/18:2 | 564.5350 | 0.00% | 0.00% |
| Cer d18:1/18:1; Cer d18:1/17:2 (1OH) | 564.5350 | 8.49% | 0.00% |
| Cer d18:1/18:0; Cer d18:1/17:1 (1OH) | 566.5506 | 8.50% | 0.00% |
| Cer d18:0/18:1; Cer d18:0/17:2 (1OH) | 566.5507 | 8.50% | 0.00% |
| Cer d18:1/17:0 (1OH) | 568.5300 | 8.51% | 0.00% |
| Cer d18:0/18:0; Cer d18:0/17:1 (1OH) | 568.5663 | 8.51% | 0.00% |
| Cer d18:0/17:0 (1OH) | 570.5457 | 8.51% | 0.00% |
| Cer d38:2 | 574.5558 | 0.00% | 0.00% |
| Cer d18:1/19:2 | 576.5349 | 0.00% | 0.00% |
| Cer d38:1 | 576.5714 | 9.17% | 0.00% |
| Cer d18:0/19:2 | 578.5506 | 0.00% | 0.00% |
| Cer d18:1/19:1; Cer d18:1/18:2 (1OH) | 578.5506 | 8.93% | 0.00% |
| Cer d38:0 | 578.5871 | 9.18% | 0.00% |
| Cer d18:1/19:0; Cer d18:1/18:1 (1OH) | 580.5662 | 8.94% | 0.00% |
| Cer d18:0/19:1; Cer d18:0/18:2 (1OH) | 580.5663 | 8.94% | 0.00% |
| Cer d18:1/18:0 (1OH) | 582.5383 | 8.95% | 0.00% |
| Cer d18:0/19:0; Cer d18:0/18:1 (1OH) | 582.5819 | 8.95% | 0.00% |
| Cer d18:0/18:0 (1OH) | 584.5540 | 8.96% | 0.00% |
| Cer d18:1/20:2 | 590.5506 | 0.00% | 0.00% |
| Cer d39:1 | 590.5871 | 0.00% | 0.00% |
| Cer d18:1/20:1; Cer d18:1/19:2 (1OH) | 592.5662 | 9.39% | 0.00% |
| Cer d18:0/20:2 | 592.5663 | 0.00% | 0.00% |
| Cer d18:0/20:1; Cer d18:0/19:2 (1OH) | 594.5819 | 9.40% | 0.00% |
| Cer d18:1/20:0; Cer d18:1/19:1 (1OH) | 594.5819 | 9.40% | 0.00% |

TABLE 19-continued

Database of lipid species monitored during the identification step in the positive-ion mode together with the calculation of isotopic correction for M + 1 and M + 2 isotopic peaks (so called deisotoping).

| Lipid | m/z | Isotopic correction M + 2 | Isotopic correction M + 1 |
|---|---|---|---|
| Cer d18:1/19:0 (1OH) | 596.5613 | 9.41% | 0.00% |
| Cer d18:0/20:0; Cer d18:0/19:1 (1OH) | 596.5976 | 9.41% | 0.00% |
| Cer d18:0/19:0 (1OH) | 598.5770 | 9.42% | 0.00% |
| Cer d40:2 | 602.5871 | 0.00% | 0.00% |
| Cer d18:1/21:2 | 604.5662 | 0.00% | 0.00% |
| Cer d40:1 | 604.6027 | 10.11% | 0.00% |
| Cer d18:0/21:2 | 606.5819 | 0.00% | 0.00% |
| Cer d18:1/21:1; Cer d18:1/20:2 (1OH) | 606.5819 | 9.86% | 0.00% |
| Cer d40:0 | 606.6184 | 10.13% | 0.00% |
| Cer d18:1/21:0; Cer d18:1/20:1 (1OH) | 608.5975 | 9.87% | 0.00% |
| Cer d18:0/21:1; Cer d18:0/20:2 (1OH) | 608.5976 | 9.87% | 0.00% |
| Cer d18:1/20:0 (OH) | 610.5769 | 9.88% | 0.00% |
| Cer d18:0/21:0; Cer d18:0/20:1 (1OH) | 610.6132 | 9.88% | 0.00% |
| Cer d18:0/20:0 (1OH) | 612.5926 | 9.89% | 0.00% |
| Cer d18:1/22:2 | 618.5818 | 0.00% | 0.00% |
| Cer d41:1 | 618.6184 | 0.00% | 0.00% |
| Cer d18:0/22:2 | 620.5975 | 0.00% | 0.00% |
| Cer d18:1/22:1; Cer d18:1/21:2 (1OH) | 620.5975 | 10.34% | 0.00% |
| Cer d41:0 | 620.6340 | 10.62% | 0.00% |
| Cer d18:1/22:0; Cer d18:1/21:1 (1OH) | 622.6131 | 10.35% | 0.00% |
| Cer d18:0/22:1; Cer d18:0/21:2 (1OH) | 622.6132 | 10.35% | 0.00% |
| Cer d18:1/21:0 (1OH) | 624.5926 | 10.36% | 0.00% |
| Cer d18:0/22:0; Cer d18:0/21:1 (1OH) | 624.6288 | 10.36% | 0.00% |
| Cer d18:0/21:0 (1OH) | 626.6083 | 10.37% | 0.00% |
| Cer d42:3 | 628.6027 | 0.00% | 0.00% |
| Cer d42:2 | 630.6184 | 11.10% | 0.00% |
| Cer d18:1/23:2 | 632.5974 | 0.00% | 0.00% |
| Cer d42:1 | 632.6340 | 11.11% | 0.00% |
| Cer d18:0/23:2 | 634.6131 | 0.00% | 0.00% |
| Cer d18:1/23:1; Cer d18:1/22:2 (1OH) | 634.6131 | 10.83% | 0.00% |
| Cer d42:0 | 634.6497 | 11.12% | 0.00% |
| Cer d18:1/23:0; Cer d18:1/22:1 (1OH) | 636.6287 | 10.84% | 0.00% |
| Cer d18:0/23:1; Cer d18:0/22:2 (1OH) | 636.6288 | 10.84% | 0.00% |
| Cer d18:1/22:0 (1OH) | 638.6082 | 10.85% | 0.00% |
| Cer d18:0/23:0; Cer d18:0/22:1 (1OH) | 638.6444 | 10.85% | 0.00% |
| HexCer d18:1/12:2 | 640.4784 | 10.86% | 0.00% |
| Cer d18:0/22:0 (1OH) | 640.6239 | 10.86% | 0.00% |
| HexCer d18:1/12:1 | 642.4940 | 9.58% | 0.00% |
| HexCer d18:0/12:2 | 642.4941 | 10.87% | 0.00% |
| HexCer d18:1/12:0 (IS) | 644.5097 | 9.59% | 0.00% |
| HexCer d18:0/12:1 (IS) | 644.5097 | 9.59% | 0.00% |
| Cer d43:2 | 644.6340 | 0.00% | 0.00% |
| HexCer d18:0/12:0 | 646.5254 | 9.60% | 0.00% |
| Cer d18:1/24:2 | 646.6131 | 9.60% | 0.00% |
| Cer d43:1 | 646.6497 | 11.63% | 0.00% |
| Cer d18:1/24:1; Cer d18:1/23:2 (1OH) | 648.6287 | 11.34% | 0.00% |
| Cer d18:0/24:2 | 648.6288 | 9.61% | 0.00% |
| Cer d43:0 | 648.6653 | 11.64% | 0.00% |
| Cer d18:0/24:1; Cer d18:0/23:2 (1OH) | 650.6444 | 11.35% | 0.00% |
| Cer d18:1/24:0; Cer d18:1/23:1 (1OH) | 650.6444 | 11.35% | 0.00% |
| Cer d18:1/23:0 (1OH) | 652.6239 | 11.36% | 0.00% |
| Cer d18:0/24:0; Cer d18:0/23:1 (1OH) | 652.6601 | 11.36% | 0.00% |
| HexCer d18:1/13:2 | 654.4940 | 11.07% | 0.00% |
| Cer d18:0/23:0 (1OH) | 654.6396 | 11.07% | 0.00% |
| HexCer d18:1/13:1; HexCer d18:1/12:2 (1OH) | 656.5097 | 10.03% | 0.00% |
| HexCer d18:0/13:2 | 656.5097 | 11.08% | 0.00% |
| Cer d44:3 | 656.6340 | 0.00% | 0.00% |
| HexCer d18:1/13:0; HexCer d18:1/12:1 (1OH) | 658.5253 | 10.04% | 0.00% |
| HexCer d18:0/13:1; HexCer d18:0/12:2 (1OH) | 658.5254 | 10.04% | 0.00% |
| Cer d44:2 | 658.6497 | 12.15% | 0.00% |
| HexCer d18:1/12:0 (1OH); HexCer d18:1/25:2 | 660.5046 | 10.05% | 0.00% |
| HexCer d18:0/13:0; HexCer d18:0/12:1 (1OH) | 660.5410 | 10.05% | 0.00% |
| Cer d44:1 | 660.6653 | 12.16% | 0.00% |
| HexCer d18:0/12:0 (1OH); Cer d18:0/25:2 | 662.5203 | 10.06% | 0.00% |
| Cer d18:1/25:1; Cer d18:1/24:2 (1OH) | 662.6444 | 10.06% | 0.00% |
| Cer d44:0 | 662.6810 | 12.17% | 0.00% |
| Cer d18:1/25:0; Cer d18:1/24:1 (1OH) | 664.6600 | 11.86% | 0.00% |
| Cer d18:0/25:1; Cer d18:0/24:2 (1OH) | 664.6601 | 11.86% | 0.00% |
| Cer d18:1/24:0 (1OH) | 666.6395 | 11.88% | 0.00% |
| Cer d18:0/25:0; Cer d18:0/24:1 (1OH) | 666.6757 | 11.88% | 0.00% |
| HexCer d18:1/14:2 | 668.5097 | 11.58% | 0.00% |
| Cer d18:0/24:0 (1OH) | 668.6552 | 11.89% | 0.00% |

TABLE 19-continued

Database of lipid species monitored during the identification step in the positive-ion mode together with the calculation of isotopic correction for M + 1 and M + 2 isotopic peaks (so called deisotoping).

| Lipid | m/z | Isotopic correction M + 2 | Isotopic correction M + 1 |
|---|---|---|---|
| HexCer d18:1/14:1; HexCer d18:1/13:2 (1OH) | 670.5253 | 10.49% | 0.00% |
| HexCer d18:0/14:2 | 670.5254 | 11.59% | 0.00% |
| HexCer d18:1/14:0; HexCer d18:1/13:0 (1OH) | 672.5337 | 10.50% | 0.00% |
| HexCer d18:0/14:1; HexCer d18:0/13:2 (1OH) | 672.5410 | 10.50% | 0.00% |
| HexCer d18:0/14:0; HexCer d18:0/13:0 (1OH) | 674.5494 | 10.51% | 0.00% |
| Cer d18:1/26:2; HexCer d18:1/13:0 (1OH) | 674.6443 | 10.51% | 0.00% |
| Cer d18:0/26:2; HexCer d18:0/13:0 (1OH) | 676.6600 | 10.52% | 0.00% |
| Cer d18:1/26:1; Cer d18:1/25:2 (1OH) | 676.6600 | 12.38% | 0.00% |
| Cer d18:1/26:0; Cer d18:1/25:1 (1OH) | 678.6756 | 12.39% | 0.00% |
| Cer d18:0/26:1; Cer d18:0/25:2 (1OH) | 678.6757 | 12.39% | 0.00% |
| Cer d18:1/25:0 (1OH) | 680.6552 | 12.41% | 0.00% |
| Cer d18:0/26:0; Cer d18:0/25:1 (1OH) | 680.6913 | 12.41% | 0.00% |
| HexCer d18:1/15:2 | 682.5253 | 12.11% | 0.00% |
| Cer d18:0/25:0 (1OH) | 682.6709 | 12.42% | 0.00% |
| HexCer d18:0/15:2 | 684.5410 | 12.11% | 0.00% |
| HexCer d18:1/15:1; HexCer d18:1/14:2 (1OH) | 684.5410 | 10.96% | 0.00% |
| HexCer d18:1/15:0; HexCer d18:1/14:1 (1OH) | 686.5566 | 10.97% | 0.00% |
| HexCer d18:0/15:1; HexCer d18:0/14:2 (1OH) | 686.5567 | 10.97% | 0.00% |
| HexCer d18:1/14:0 (1OH); Cer d18:1/27:2 | 688.5359 | 10.98% | 0.00% |
| HexCer d18:0/15:0; HexCer d18:0/14:1 (1OH) | 688.5723 | 10.98% | 0.00% |
| HexCer d18:0/14:0 (1OH); Cer d18:0/27:2 | 690.5516 | 10.99% | 0.00% |
| Cer d18:1/27:1; Cer d18:1/26:2 (1OH) | 690.6756 | 10.90% | 0.00% |
| Cer d18:1/27:0; Cer d18:1/26:1 (1OH) | 692.6912 | 12.94% | 0.00% |
| Cer d18:0/27:1; Cer d18:0/26:2 (1OH) | 692.6913 | 11.00% | 0.00% |
| Cer d18:1/26:0 (1OH) | 694.6708 | 12.95% | 0.00% |
| Cer d18:0/27:0; Cer d18:0/26:1 (1OH) | 694.7069 | 12.95% | 0.00% |
| HexCer d18:1/16:2 | 696.5410 | 12.63% | 0.00% |
| Cer d18:0/26:0 (1OH) | 696.6865 | 12.96% | 0.00% |
| HexCer d18:1/16:1; HexCer d18:1/15:2 (1OH) | 698.5566 | 11.44% | 0.00% |
| HexCer d18:0/16:2 | 698.5567 | 12.64% | 0.00% |
| HexCer d18:0/16:1; HexCer d18:0/15:2 (1OH) | 700.5723 | 11.45% | 0.00% |
| HexCer d18:1/16:0; HexCer d18:1/15:1 (1OH) | 700.5723 | 11.45% | 0.00% |
| HexCer d18:0/16:0; HexCer d18:0/15:1 (1OH) | 702.5880 | 11.46% | 0.00% |
| Cer d18:1/28:2; HexCer d18:1/15:0 (1OH) | 702.6756 | 11.46% | 0.00% |
| Cer d18:1/28:1; Cer d18:1/27:2 (1OH) | 704.6912 | 13.48% | 0.00% |
| Cer d18:0/28:2; HexCer d18:0/15:0 (1OH) | 704.6913 | 11.47% | 0.00% |
| Cer d18:0/28:1; Cer d18:0/27:2 (1OH) | 706.7069 | 13.49% | 0.00% |
| Cer d18:1/28:0; Cer d18:1/27:1 (1OH) | 706.7069 | 13.49% | 0.00% |
| Cer d18:1/27:0 (1OH) | 708.6865 | 13.50% | 0.00% |
| Cer d18:0/28:0; Cer d18:0/27:1 (1OH) | 708.7226 | 13.50% | 0.00% |
| HexCer d18:1/17:2 | 710.5566 | 13.17% | 0.00% |
| Cer d18:0/27:0 (1OH) | 710.7022 | 13.51% | 0.00% |
| HexCer d18:0/17:2 | 712.5723 | 13.18% | 0.00% |
| HexCer d18:1/17:1; HexCer d18:1/16:2 (1OH) | 712.5723 | 11.93% | 0.00% |
| HexCer d18:1/17:0; HexCer d18:1/16:1 (1OH) | 714.5879 | 11.95% | 0.00% |
| HexCer d18:0/17:1; HexCer d18:0/16:2 (1OH) | 714.5880 | 11.95% | 0.00% |
| HexCer d18:1/16:0 (1OH) | 716.5672 | 11.96% | 0.00% |
| HexCer d18:0/17:0; HexCer d18:0/16:1 (1OH) | 716.6036 | 11.96% | 0.00% |
| HexCer d18:0/16:0 (1OH) | 718.5829 | 11.97% | 0.00% |
| Cer d18:1/29:1; Cer d18:1/28:2 (1OH) | 718.7069 | 11.97% | 0.00% |
| Cer d18:1/29:0; Cer d18:1/28:1 (1OH) | 720.7225 | 14.06% | 0.00% |
| Cer d18:0/29:1; Cer d18:0/28:2 (1OH) | 720.7226 | 11.98% | 0.00% |
| Cer d18:1/28:0 (1OH) | 722.7201 | 14.07% | 0.00% |
| Cer d18:0/29:0; Cer d18:0/28:1 (1OH) | 722.7382 | 14.07% | 0.00% |
| HexCer d18:1/18:2 | 724.5722 | 13.73% | 0.00% |
| Cer d18:0/28:0 (1OH) | 724.7358 | 14.08% | 0.00% |
| HexCer d18:0/18:2 | 726.5879 | 13.74% | 0.00% |
| HexCer d18:1/18:1; HexCer d18:1/17:2 (1OH) | 726.5879 | 12.44% | 0.00% |
| HexCer d18:1/18:0; HexCer d18:1/17:1 (1OH) | 728.6035 | 12.45% | 0.00% |
| HexCer d18:0/18:1; HexCer d18:0/17:2 (1OH) | 728.6036 | 12.45% | 0.00% |
| HexCer d18:1/17:0 (1OH) | 730.5829 | 12.46% | 0.00% |
| HexCer d18:0/18:0; HexCer d18:0/17:1 (1OH) | 730.6192 | 12.46% | 0.00% |
| HexCer d18:0/17:0 (1OH) | 732.5986 | 12.47% | 0.00% |
| Cer d18:1/30:1; Cer d18:1/29:2 (1OH) | 732.7228 | 12.47% | 0.00% |
| Cer d18:1/30:0; Cer d18:1/29:1 (1OH) | 734.7381 | 14.64% | 0.00% |
| Cer d18:0/30:1; Cer d18:0/29:2 (1OH) | 734.7385 | 12.49% | 0.00% |
| Cer d18:1/29:0 (1OH) | 736.7178 | 14.65% | 0.00% |
| Cer d18:0/30:0; Cer d18:0/29:1 (1OH) | 736.7538 | 14.65% | 0.00% |
| HexCer d18:1/19:2 | 738.5878 | 14.29% | 0.00% |
| Cer d18:0/29:0 (1OH) | 738.7335 | 14.66% | 0.00% |
| HexCer d18:0/19:2 | 740.6035 | 14.31% | 0.00% |
| HexCer d18:1/19:1; HexCer d18:1/18:2 (1OH) | 740.6035 | 12.96% | 0.00% |

TABLE 19-continued

Database of lipid species monitored during the identification step in the positive-ion mode together with the calculation of isotopic correction for M + 1 and M + 2 isotopic peaks (so called deisotoping).

| | | Isotopic correction | |
|---|---|---|---|
| Lipid | m/z | M + 2 | M + 1 |
| HexCer d18:1/19:0; HexCer d18:1/18:1 (1OH) | 742.6191 | 12.97% | 0.00% |
| HexCer d18:0/19:1; HexCer d18:0/18:2 (1OH) | 742.6192 | 12.97% | 0.00% |
| HexCer d18:1/18:0 (1OH) | 744.5912 | 12.98% | 0.00% |
| HexCer d18:0/19:0; HexCer d18:0/18:1 (1OH) | 744.6348 | 12.98% | 0.00% |
| HexCer d18:0/18:0 (1OH) | 746.6069 | 12.99% | 0.00% |
| HexCer d18:1/20:2 | 752.6035 | 12.99% | 0.00% |
| HexCer d18:1/20:1; HexCer d18:1/19:2 (1OH) | 754.6191 | 13.49% | 0.00% |
| HexCer d18:0/20:2 | 754.6192 | 13.01% | 0.00% |
| HexCer d18:0/20:1; HexCer d18:0/19:2 (1OH) | 756.6348 | 13.50% | 0.00% |
| HexCer d18:1/20:0; HexCer d18:1/19:1 (1OH) | 756.6348 | 13.50% | 0.00% |
| HexCer d18:1/19:0 (1OH) | 758.6142 | 13.52% | 0.00% |
| HexCer d18:0/20:0; HexCer d18:0/19:1 (1OH) | 758.6505 | 13.52% | 0.00% |
| HexCer d18:0/19:0 (1OH) | 760.6299 | 13.53% | 0.00% |
| HexCer d18:1/21:2 | 766.6191 | 0.00% | 0.00% |
| HexCer d18:0/21:2 | 768.6348 | 0.00% | 0.00% |
| HexCer d18:1/21:1; HexCer d18:1/20:2 (1OH) | 768.6348 | 14.04% | 0.00% |
| HexCer d18:1/21:0; HexCer d18:1/20:1 (1OH) | 770.6504 | 14.05% | 0.00% |
| HexCer d18:0/21:1; HexCer d18:0/20:2 (1OH) | 770.6505 | 14.05% | 0.00% |
| HexCer d18:1/20:0 (OH) | 772.6298 | 14.06% | 0.00% |
| HexCer d18:0/21:0; HexCer d18:0/20:1 (1OH) | 772.6661 | 14.06% | 0.00% |
| HexCer d18:0/20:0 (OH) | 774.6455 | 14.07% | 0.00% |
| HexCer d18:1/22:2 | 780.6347 | 0.00% | 0.00% |
| HexCer d18:0/22:2 | 782.6504 | 0.00% | 0.00% |
| HexCer d18:1/22:1; HexCer d18:1/21:2 (1OH) | 782.6504 | 14.59% | 0.00% |
| HexCer d18:1/22:0; HexCer d18:1/21:1 (1OH) | 784.6660 | 14.60% | 0.00% |
| HexCer d18:0/22:1; HexCer d18:0/21:2 (1OH) | 784.6661 | 14.60% | 0.00% |
| HexCer d18:1/21:0 (1OH) | 786.6455 | 14.62% | 0.00% |
| HexCer d18:0/22:0; HexCer d18:0/21:1 (1OH) | 786.6817 | 14.62% | 0.00% |
| HexCer d18:0/21:0 (1OH) | 788.6612 | 14.63% | 0.00% |
| HexCer d18:1/23:2 | 794.6503 | 0.00% | 0.00% |
| HexCer d18:0/23:2 | 796.6660 | 0.00% | 0.00% |
| HexCer d18:1/23:1; HexCer d18:1/22:2 (1OH) | 796.6660 | 15.16% | 0.00% |
| HexCer d18:1/23:0; HexCer d18:1/22:1 (1OH) | 798.6816 | 15.17% | 0.00% |
| HexCer d18:0/23:1; HexCer d18:0/22:2 (1OH) | 798.6817 | 15.17% | 0.00% |
| HexCer d18:1/22:0 (1OH) | 800.6611 | 15.18% | 0.00% |
| HexCer d18:0/23:0; HexCer d18:0/22:1 (1OH) | 800.6973 | 15.18% | 0.00% |
| Hex2Cer d18:1/12:2 | 802.5314 | 14.84% | 0.00% |
| HexCer d18:0/22:0 (1OH) | 802.6768 | 15.20% | 0.00% |
| Hex2Cer d18:1/12:1 | 804.5470 | 13.55% | 0.00% |
| Hex2Cer d18:0/12:2 | 804.5471 | 14.85% | 0.00% |
| Hex2Cer d18:0/12:1 (IS) | 806.5627 | 13.56% | 0.00% |
| Hex2Cer d18:1/12:0 (IS) | 806.5627 | 13.56% | 0.00% |
| Hex2Cer d18:0/12:0 | 808.5784 | 13.57% | 0.00% |
| HexCer d18:1/24:2 | 808.6660 | 13.57% | 0.00% |
| HexCer d18:1/24:1; HexCer d18:1/23:2 (1OH) | 810.6816 | 15.74% | 0.00% |
| HexCer d18:0/24:2 | 810.6817 | 13.58% | 0.00% |
| HexCer d18:0/24:1; HexCer d18:0/23:2 (1OH) | 812.6973 | 15.75% | 0.00% |
| HexCer d18:1/24:0; HexCer d18:1/23:1 (1OH) | 812.6973 | 15.75% | 0.00% |
| HexCer d18:1/23:0 (1OH) | 814.6768 | 15.77% | 0.00% |
| HexCer d18:0/24:0; HexCer d18:0/23:1 (1OH) | 814.7130 | 15.77% | 0.00% |
| Hex2Cer d18:1/13:2 | 816.5470 | 15.41% | 0.00% |
| HexCer d18:0/23:0 (1OH) | 816.6925 | 15.78% | 0.00% |
| Hex2Cer d18:0/13:2 | 818.5627 | 15.42% | 0.00% |
| Hex2Cer d18:1/13:1; Hex2Cer d18:1/12:2 (1OH) | 818.5627 | 14.07% | 0.00% |
| Hex2Cer d18:1/13:0; Hex2Cer d18:1/12:1 (1OH) | 820.5783 | 14.08% | 0.00% |
| Hex2Cer d18:0/13:1; Hex2Cer d18:0/12:2 (1OH) | 820.5784 | 14.08% | 0.00% |
| Hex2Cer d18:1/12:0 (1OH); HexCer d18:1/25:2 | 822.5576 | 14.09% | 0.00% |
| Hex2Cer d18:0/13:0; Hex2Cer d18:0/12:1 (1OH) | 822.5940 | 14.09% | 0.00% |
| Hex2Cer d18:0/12:0 (1OH); HexCer d18:0/25:2 | 824.5733 | 14.10% | 0.00% |
| HexCer d18:1/25:1; HexCer d18:1/24:2 (1OH) | 824.6973 | 13.79% | 0.00% |
| HexCer d18:1/25:0; HexCer d18:1/24:1 (1OH) | 826.7129 | 16.35% | 0.00% |
| HexCer d18:0/25:1; HexCer d18:0/24:2 (1OH) | 826.7130 | 13.80% | 0.00% |
| HexCer d18:1/24:0 (1OH) | 828.6924 | 16.36% | 0.00% |
| HexCer d18:0/25:0; HexCer d18:0/24:1 (1OH) | 828.7286 | 16.36% | 0.00% |
| Hex2Cer d18:1/14:2 | 830.5627 | 15.99% | 0.00% |
| HexCer d18:0/24:0 (1OH) | 830.7081 | 16.37% | 0.00% |
| Hex2Cer d18:1/14:1; Hex2Cer d18:1/13:2 (1OH) | 832.5783 | 14.60% | 0.00% |
| Hex2Cer d18:0/14:2 | 832.5784 | 16.00% | 0.00% |
| Hex2Cer d18:1/14:0; Hex2Cer d18:1/13:1 (1OH) | 834.5867 | 14.61% | 0.00% |
| Hex2Cer d18:0/14:1; Hex2Cer d18:0/13:2 (1OH) | 834.5940 | 14.61% | 0.00% |
| Hex2Cer d18:0/14:0; Hex2Cer d18:0/13:1 (1OH) | 836.6024 | 14.63% | 0.00% |
| HexCer d18:1/26:2; Hex2Cer d18:1/13:0 (1OH) | 836.6972 | 14.63% | 0.00% |

TABLE 19-continued

Database of lipid species monitored during the identification step in the positive-ion mode together with the calculation of isotopic correction for M + 1 and M + 2 isotopic peaks (so called deisotoping).

| Lipid | m/z | Isotopic correction M + 2 | Isotopic correction M + 1 |
|---|---|---|---|
| HexCer d18:0/26:2; Hex2Cer d18:0/13:0 (1OH) | 838.7129 | 14.64% | 0.00% |
| HexCer d18:1/26:1; HexCer d18:1/25:2 (1OH) | 838.7129 | 16.94% | 0.00% |
| HexCer d18:1/26:0; HexCer d18:1/25:1 (1OH) | 840.7285 | 16.95% | 0.00% |
| HexCer d18:0/26:1; HexCer d18:0/25:2 (1OH) | 840.7286 | 16.95% | 0.00% |
| HexCer d18:1/25:0 (1OH) | 842.7081 | 16.96% | 0.00% |
| HexCer d18:0/26:0; HexCer d18:0/25:1 (1OH) | 842.7442 | 16.96% | 0.00% |
| Hex2Cer d18:1/15:2 | 844.5783 | 16.59% | 0.00% |
| HexCer d18:0/25:0 (1OH) | 844.7238 | 16.98% | 0.00% |
| Hex2Cer d18:0/15:2 | 846.5940 | 16.60% | 0.00% |
| Hex2Cer d18:1/15:1; Hex2Cer d18:1/14:2 (1OH) | 846.5940 | 15.15% | 0.00% |
| Hex2Cer d18:1/15:0; Hex2Cer d18:1/14:1 (1OH) | 848.6096 | 15.16% | 0.00% |
| Hex2Cer d18:0/15:1; Hex2Cer d18:0/14:2 (1OH) | 848.6097 | 15.16% | 0.00% |
| Hex2Cer d18:1/14:0 (1OH); HexCer d18:1/27:2 | 850.5889 | 15.17% | 0.00% |
| Hex2Cer d18:0/15:0; Hex2Cer d18:0/14:1 (1OH) | 850.6253 | 15.17% | 0.00% |
| Hex2Cer d18:0/14:0 (1OH); HexCer d18:0/27:2 | 852.6046 | 15.18% | 0.00% |
| HexCer d18:1/27:1; HexCer d18:1/26:2 (1OH) | 852.7285 | 14.85% | 0.00% |
| HexCer d18:1/27:0; HexCer d18:1/26:1 (1OH) | 854.7441 | 17.57% | 0.00% |
| HexCer d18:0/27:1; HexCer d18:0/26:2 (1OH) | 854.7442 | 14.86% | 0.00% |
| HexCer d18:1/26:0 (1OH) | 856.7237 | 17.58% | 0.00% |
| HexCer d18:0/27:0; HexCer d18:0/26:1 (1OH) | 856.7598 | 17.58% | 0.00% |
| Hex2Cer d18:1/16:2 | 858.5940 | 17.19% | 0.00% |
| HexCer d18:0/26:0 (1OH) | 858.7394 | 17.59% | 0.00% |
| Hex2Cer d18:1/16:1; Hex2Cer d18:1/15:2 (1OH) | 860.6096 | 15.71% | 0.00% |
| Hex2Cer d18:0/16:2 | 860.6097 | 17.20% | 0.00% |
| Hex2Cer d18:0/16:1; Hex2Cer d18:0/15:2 (1OH) | 862.6253 | 15.72% | 0.00% |
| Hex2Cer d18:1/16:0; Hex2Cer d18:1/15:1 (1OH) | 862.6253 | 15.72% | 0.00% |
| Hex2Cer d18:0/16:0; Hex2Cer d18:0/15:1 (1OH) | 864.6410 | 15.73% | 0.00% |
| HexCer d18:1/28:2; Hex2Cer d18:1/15:0 (1OH) | 864.7285 | 15.73% | 0.00% |
| HexCer d18:1/28:1; HexCer d18:1/27:2 (1OH) | 866.7441 | 18.18% | 0.00% |
| HexCer d18:0/28:2; Hex2Cer d18:0/15:0 (1OH) | 866.7442 | 15.74% | 0.00% |
| HexCer d18:0/28:1; HexCer d18:0/27:2 (1OH) | 868.7598 | 18.20% | 0.00% |
| HexCer d18:1/28:0; HexCer d18:1/27:1 (1OH) | 868.7598 | 18.20% | 0.00% |
| HexCer d18:1/27:0 (1OH) | 870.7394 | 18.21% | 0.00% |
| HexCer d18:0/28:0; HexCer d18:0/27:1 (1OH) | 870.7755 | 18.21% | 0.00% |
| Hex2Cer d18:1/17:2 | 872.6096 | 17.81% | 0.00% |
| HexCer d18:0/27:0 (1OH) | 872.7551 | 18.22% | 0.00% |
| Hex2Cer d18:0/17:2 | 874.6253 | 17.82% | 0.00% |
| Hex2Cer d18:1/17:1; Hex2Cer d18:1/16:2 (1OH) | 874.6253 | 16.28% | 0.00% |
| Hex2Cer d18:1/17:0; Hex2Cer d18:1/16:1 (1OH) | 876.6409 | 16.29% | 0.00% |
| Hex2Cer d18:0/17:1; Hex2Cer d18:0/16:2 (1OH) | 876.6410 | 16.29% | 0.00% |
| Hex2Cer d18:1/16:0 (1OH) | 878.6202 | 16.30% | 0.00% |
| Hex2Cer d18:0/17:0; Hex2Cer d18:0/16:1 (1OH) | 878.6566 | 16.30% | 0.00% |
| Hex2Cer d18:0/16:0 (1OH) | 880.6359 | 16.31% | 0.00% |
| HexCer d18:1/29:1; HexCer d18:1/28:2 (1OH) | 880.7598 | 15.96% | 0.00% |
| HexCer d18:1/29:0; HexCer d18:1/28:1 (1OH) | 882.7754 | 18.84% | 0.00% |
| HexCer d18:0/29:1; HexCer d18:0/28:2 (1OH) | 882.7755 | 15.97% | 0.00% |
| HexCer d18:1/28:0 (1OH) | 884.7730 | 18.85% | 0.00% |
| HexCer d18:0/29:0; HexCer d18:0/28:1 (1OH) | 884.7911 | 18.85% | 0.00% |
| Hex2Cer d18:1/18:2 | 886.6252 | 18.44% | 0.00% |
| HexCer d18:0/28:0 (1OH) | 886.7887 | 18.87% | 0.00% |
| Hex2Cer d18:0/18:2 | 888.6409 | 18.45% | 0.00% |
| Hex2Cer d18:1/18:1; Hex2Cer d18:1/17:2 (1OH) | 888.6409 | 16.86% | 0.00% |
| Hex2Cer d18:1/18:0; Hex2Cer d18:1/17:1 (1OH) | 890.6565 | 16.87% | 0.00% |
| Hex2Cer d18:0/18:1; Hex2Cer d18:0/17:2 (1OH) | 890.6566 | 16.87% | 0.00% |
| Hex2Cer d18:1/17:0 (1OH) | 892.6359 | 16.88% | 0.00% |
| Hex2Cer d18:0/18:0; Hex2Cer d18:0/17:1 (1OH) | 892.6722 | 16.88% | 0.00% |
| Hex2Cer d18:0/17:0 (1OH) | 894.6516 | 16.90% | 0.00% |
| HexCer d18:1/30:1; HexCer d18:1/29:2 (1OH) | 894.7757 | 16.53% | 0.00% |
| HexCer d18:1/30:0; HexCer d18:1/29:1 (1OH) | 896.7910 | 19.49% | 0.00% |
| HexCer d18:0/30:1; HexCer d18:0/29:2 (1OH) | 896.7914 | 16.54% | 0.00% |
| HexCer d18:1/29:0 (1OH) | 898.7707 | 19.51% | 0.00% |
| HexCer d18:0/30:0; HexCer d18:0/29:1 (1OH) | 898.8067 | 19.51% | 0.00% |
| Hex2Cer d18:1/19:2 | 900.6408 | 19.08% | 0.00% |
| HexCer d18:0/29:0 (1OH) | 900.7864 | 19.52% | 0.00% |
| Hex2Cer d18:0/19:2 | 902.6565 | 19.09% | 0.00% |
| Hex2Cer d18:1/19:1; Hex2Cer d18:1/18:2 (1OH) | 902.6565 | 17.45% | 0.00% |
| Hex2Cer d18:1/19:0; Hex2Cer d18:1/18:1 (1OH) | 904.6721 | 17.47% | 0.00% |
| Hex2Cer d18:0/19:1; Hex2Cer d18:0/18:2 (1OH) | 904.6722 | 17.47% | 0.00% |
| Hex2Cer d18:1/18:0 (1OH) | 906.6442 | 17.48% | 0.00% |
| Hex2Cer d18:0/19:0; Hex2Cer d18:0/18:1 (1OH) | 906.6878 | 17.48% | 0.00% |
| Hex2Cer d18:0/18:0 (1OH) | 908.6599 | 17.49% | 0.00% |
| Hex2Cer d18:1/20:2 | 914.6565 | 0.00% | 0.00% |

TABLE 19-continued

Database of lipid species monitored during the identification step in
the positive-ion mode together with the calculation of isotopic correction
for M + 1 and M + 2 isotopic peaks (so called deisotoping).

| Lipid | m/z | Isotopic correction | |
|---|---|---|---|
| | | M + 2 | M + 1 |
| Hex2Cer d18:1/20:1; Hex2Cer d18:1/19:2 (1OH) | 916.6721 | 18.06% | 0.00% |
| Hex2Cer d18:0/20:2 | 916.6722 | 0.00% | 0.00% |
| Hex2Cer d18:0/20:1; Hex2Cer d18:0/19:2 (1OH) | 918.6878 | 18.07% | 0.00% |
| Hex2Cer d18:1/20:0; Hex2Cer d18:1/19:1 (1OH) | 918.6878 | 18.07% | 0.00% |
| Hex2Cer d18:1/19:0 (1OH) | 920.6672 | 18.09% | 0.00% |
| Hex2Cer d18:0/20:0; Hex2Cer d18:0/19:1 (1OH) | 920.7035 | 18.09% | 0.00% |
| Hex2Cer d18:0/19:0 (1OH) | 922.6829 | 18.10% | 0.00% |
| Hex2Cer d18:1/21:2 | 928.6721 | 0.00% | 0.00% |
| Hex2Cer d18:0/21:2 | 930.6878 | 0.00% | 0.00% |
| Hex2Cer d18:1/21:1; Hex2Cer d18:1/20:2 (1OH) | 930.6878 | 18.68% | 0.00% |
| Hex2Cer d18:1/21:0; Hex2Cer d18:1/20:1 (1OH) | 932.7034 | 18.69% | 0.00% |
| Hex2Cer d18:0/21:1; Hex2Cer d18:0/20:2 (1OH) | 932.7035 | 18.69% | 0.00% |
| Hex2Cer d18:1/20:0 (OH) | 934.6828 | 18.70% | 0.00% |
| Hex2Cer d18:0/21:0; Hex2Cer d18:0/20:1 (1OH) | 934.7191 | 18.70% | 0.00% |
| Hex2Cer d18:0/20:0 (OH) | 936.6985 | 18.72% | 0.00% |
| Hex2Cer d18:1/22:2 | 942.6877 | 0.00% | 0.00% |
| Hex2Cer d18:0/22:2 | 944.7034 | 0.00% | 0.00% |
| Hex2Cer d18:1/22:1; Hex2Cer d18:1/21:2 (1OH) | 944.7034 | 19.31% | 0.00% |
| Hex2Cer d18:1/22:0; Hex2Cer d18:1/21:1 (1OH) | 946.7190 | 19.32% | 0.00% |
| Hex2Cer d18:0/22:1; Hex2Cer d18:0/21:2 (1OH) | 946.7191 | 19.32% | 0.00% |
| Hex2Cer d18:1/21:0 (1OH) | 948.6985 | 19.34% | 0.00% |
| Hex2Cer d18:0/22:0; Hex2Cer d18:0/21:1 (1OH) | 948.7347 | 19.34% | 0.00% |
| Hex2Cer d18:0/21:0 (1OH) | 950.7142 | 19.35% | 0.00% |
| Hex2Cer d18:1/23:2 | 956.7033 | 0.00% | 0.00% |
| Hex2Cer d18:0/23:2 | 958.7190 | 0.00% | 0.00% |
| Hex2Cer d18:1/23:1; Hex2Cer d18:1/22:2 (1OH) | 958.7190 | 19.95% | 0.00% |
| Hex2Cer d18:1/23:0; Hex2Cer d18:1/22:1 (1OH) | 960.7346 | 19.97% | 0.00% |
| Hex2Cer d18:0/23:1; Hex2Cer d18:0/22:2 (1OH) | 960.7347 | 19.97% | 0.00% |
| Hex2Cer d18:1/22:0 (1OH) | 962.7141 | 19.98% | 0.00% |
| Hex2Cer d18:0/23:0; Hex2Cer d18:0/22:1 (1OH) | 962.7503 | 19.98% | 0.00% |
| Hex2Cer d18:0/22:0 (1OH) | 964.7298 | 19.99% | 0.00% |
| Hex2Cer d18:1/24:2 | 970.7190 | 0.00% | 0.00% |
| Hex2Cer d18:1/24:1; Hex2Cer d18:1/23:2 (1OH) | 972.7346 | 20.61% | 0.00% |
| Hex2Cer d18:0/24:2 | 972.7347 | 0.00% | 0.00% |
| Hex2Cer d18:0/24:1; Hex2Cer d18:0/23:2 (1OH) | 974.7503 | 20.62% | 0.00% |
| Hex2Cer d18:1/24:0; Hex2Cer d18:1/23:1 (1OH) | 974.7503 | 20.62% | 0.00% |
| Hex2Cer d18:1/23:0 (1OH) | 976.7298 | 20.64% | 0.00% |
| Hex2Cer d18:0/24:0; Hex2Cer d18:0/23:1 (1OH) | 976.7660 | 20.64% | 0.00% |
| Hex2Cer d18:0/23:0 (1OH) | 978.7455 | 20.65% | 0.00% |
| Hex2Cer d18:1/25:2 | 984.7346 | 0.00% | 0.00% |
| Hex2Cer d18:0/25:2 | 986.7503 | 0.00% | 0.00% |
| Hex2Cer d18:1/25:1; Hex2Cer d18:1/24:2 (1OH) | 986.7503 | 21.28% | 0.00% |
| Hex2Cer d18:1/25:0; Hex2Cer d18:1/24:1 (1OH) | 988.7659 | 21.29% | 0.00% |
| Hex2Cer d18:0/25:1; Hex2Cer d18:0/24:2 (1OH) | 988.7660 | 21.29% | 0.00% |
| Hex2Cer d18:1/24:0 (1OH) | 990.7454 | 21.30% | 0.00% |
| Hex2Cer d18:0/25:0; Hex2Cer d18:0/24:1 (1OH) | 990.7816 | 21.30% | 0.00% |
| Hex2Cer d18:0/24:0 (1OH) | 992.7611 | 21.32% | 0.00% |
| Hex2Cer d18:1/26:2 | 998.7502 | 0.00% | 0.00% |
| Hex2Cer d18:0/26:2 | 1000.7659 | 0.00% | 0.00% |
| Hex2Cer d18:1/26:1; Hex2Cer d18:1/25:2 (1OH) | 1000.7659 | 21.96% | 0.00% |
| Hex2Cer d18:1/26:0; Hex2Cer d18:1/25:1 (1OH) | 1002.7815 | 21.97% | 0.00% |
| Hex2Cer d18:0/26:1; Hex2Cer d18:0/25:2 (1OH) | 1002.7816 | 21.97% | 0.00% |
| Hex2Cer d18:1/25:0 (1OH) | 1004.7611 | 21.98% | 0.00% |
| Hex2Cer d18:0/26:0; Hex2Cer d18:0/25:1 (1OH) | 1004.7972 | 21.98% | 0.00% |
| Hex2Cer d18:0/25:0 (1OH) | 1006.7768 | 22.00% | 0.00% |
| Hex2Cer d18:1/27:2 | 1012.7658 | 0.00% | 0.00% |
| Hex2Cer d18:0/27:2 | 1014.7815 | 0.00% | 0.00% |
| Hex2Cer d18:1/27:1; Hex2Cer d18:1/26:2 (1OH) | 1014.7815 | 22.65% | 0.00% |
| Hex2Cer d18:1/27:0; Hex2Cer d18:1/26:1 (1OH) | 1016.7971 | 22.66% | 0.00% |
| Hex2Cer d18:0/27:1; Hex2Cer d18:0/26:2 (1OH) | 1016.7972 | 22.66% | 0.00% |
| Hex2Cer d18:1/26:0 (1OH) | 1018.7767 | 22.68% | 0.00% |
| Hex2Cer d18:0/27:0; Hex2Cer d18:0/26:1 (1OH) | 1018.8128 | 22.68% | 0.00% |
| Hex2Cer d18:0/26:0 (1OH) | 1020.7924 | 22.69% | 0.00% |
| Hex2Cer d18:1/28:2 | 1026.7815 | 0.00% | 0.00% |
| Hex2Cer d18:1/28:1; Hex2Cer d18:1/27:2 (1OH) | 1028.7971 | 23.35% | 0.00% |
| Hex2Cer d18:0/28:2 | 1028.7972 | 0.00% | 0.00% |
| Hex2Cer d18:0/28:1; Hex2Cer d18:0/27:2 (1OH) | 1030.8128 | 23.37% | 0.00% |
| Hex2Cer d18:1/28:0; Hex2Cer d18:1/27:1 (1OH) | 1030.8128 | 23.37% | 0.00% |
| Hex2Cer d18:1/27:0 (1OH) | 1032.7924 | 23.38% | 0.00% |
| Hex2Cer d18:0/28:0; Hex2Cer d18:0/27:1 (1OH) | 1032.8285 | 23.38% | 0.00% |
| Hex2Cer d18:0/27:0 (1OH) | 1034.8081 | 23.40% | 0.00% |
| Hex2Cer d18:1/29:1; Hex2Cer d18:1/28:2 (1OH) | 1042.8128 | 0.00% | 0.00% |

TABLE 19-continued

Database of lipid species monitored during the identification step in
the positive-ion mode together with the calculation of isotopic correction
for M + 1 and M + 2 isotopic peaks (so called deisotoping).

| Lipid | m/z | Isotopic correction M + 2 | Isotopic correction M + 1 |
| --- | --- | --- | --- |
| Hex2Cer d18:1/29:0; Hex2Cer d18:1/28:1 (1OH) | 1044.8284 | 24.08% | 0.00% |
| Hex2Cer d18:0/29:1; Hex2Cer d18:0/28:2 (1OH) | 1044.8285 | 0.00% | 0.00% |
| Hex2Cer d18:1/28:0 (1OH) | 1046.8260 | 24.10% | 0.00% |
| Hex2Cer d18:0/29:0; Hex2Cer d18:0/28:1 (1OH) | 1046.8441 | 24.09% | 0.00% |
| Hex2Cer d18:0/28:0 (1OH) | 1048.8417 | 24.11% | 0.00% |
| Hex2Cer d18:1/30:1; Hex2Cer d18:1/29:2 (1OH) | 1056.8287 | 0.00% | 0.00% |
| Hex2Cer d18:1/30:0; Hex2Cer d18:1/29:1 (1OH) | 1058.8440 | 24.81% | 0.00% |
| Hex2Cer d18:0/30:1; Hex2Cer d18:0/29:2 (1OH) | 1058.8444 | 0.00% | 0.00% |
| Hex2Cer d18:1/29:0 (1OH) | 1060.8237 | 24.83% | 0.00% |
| Hex2Cer d18:0/30:0; Hex2Cer d18:0/29:1 (1OH) | 1060.8597 | 24.83% | 0.00% |
| Hex2Cer d18:0/29:0 (1OH) | 1062.8394 | 24.84% | 0.00% |
| LPE 6:0 | 314.1363 | 0.00% | 0.00% |
| LPE 8:0 | 342.1676 | 0.00% | 0.00% |
| LPE 10:0 | 370.1989 | 0.00% | 0.00% |
| LPE 12:0 | 398.2302 | 0.00% | 0.00% |
| LPE 14:0 (IS) | 426.2615 | 0.00% | 0.00% |
| LPE P-16:0; LPE O-16:1 | 438.2979 | 0.00% | 0.00% |
| LPE O-16:0; LPE 15:0 | 440.2772 | 3.95% | 0.00% |
| LPE 16:2 | 450.2615 | 0.00% | 0.00% |
| LPE 16:1 | 452.2772 | 4.15% | 0.00% |
| LPE 16:0 | 454.2928 | 4.16% | 0.00% |
| LPE P-18:0; LPE O-18:1; LPE 17:1 | 466.3298 | 0.00% | 0.00% |
| LPE O-18:0; LPE 17:0 | 468.3085 | 4.49% | 0.00% |
| LPE 18:4 | 474.2615 | 0.00% | 0.00% |
| LPE 18:3 | 476.2772 | 4.68% | 0.00% |
| LPE 18:2 | 478.2928 | 4.69% | 0.00% |
| LPE 18:1 | 480.3085 | 4.69% | 0.00% |
| LPE 18:0 | 482.3241 | 4.70% | 0.00% |
| LPE P-20:0; LPE O-20:1 | 494.3605 | 0.00% | 0.00% |
| LPE O-20:0; LPE 19:0 | 496.3398 | 5.08% | 0.00% |
| LPE 20:5 | 500.2766 | 0.00% | 0.00% |
| LPE 20:4 | 502.2923 | 5.26% | 0.00% |
| LPE 20:3 | 504.3079 | 5.27% | 0.00% |
| LPE 20:2 | 506.3241 | 5.27% | 0.00% |
| LPE 20:1 | 508.3398 | 5.28% | 0.00% |
| LPE 20:0 | 510.3554 | 5.29% | 0.00% |
| LPE P-22:0; LPE O-22:1 | 522.3918 | 0.00% | 0.00% |
| LPE O-22:0; LPE 21:0 | 524.3711 | 5.71% | 0.00% |
| LPE 22:6 | 526.2928 | 5.72% | 0.00% |
| LPE 22:5 | 528.3079 | 5.89% | 0.00% |
| LPE 22:4 | 530.3235 | 5.89% | 0.00% |
| LPE 22:1 | 536.3711 | 0.00% | 0.00% |
| LPE 22:0 | 538.3867 | 5.92% | 0.00% |
| LPE P-24:0; LPE O-24:1 | 550.4231 | 0.00% | 0.00% |
| LPE O-24:0; LPE 23:0 | 552.4024 | 6.40% | 0.00% |
| LPE 24:1 | 564.4024 | 0.00% | 0.00% |
| LPE 24:0 | 566.4180 | 6.61% | 0.00% |
| LPE 25:0 | 580.4337 | 0.00% | 0.00% |
| LPE 26:0 | 594.4493 | 0.00% | 0.00% |
| LPE 27:0 | 608.4650 | 0.00% | 0.00% |
| LPE 28:0 | 622.4806 | 0.00% | 0.00% |
| PE 28:0 | 636.4599 | 0.00% | 0.00% |
| PE 29:0 | 650.4755 | 0.00% | 0.00% |
| PE 30:1 | 662.4755 | 0.00% | 0.00% |
| PE 30:0 | 664.4912 | 9.17% | 0.00% |
| PE P-32:1; PE-3L2 | 674.5119 | 0.00% | 0.00% |
| PE P-32:0; PE-31:1 | 676.4912 | 9.83% | 0.00% |
| PE O-32:0; PE-31:0 | 678.5068 | 9.84% | 0.00% |
| PE 32:3; PE P-33:2 | 686.4755 | 0.00% | 0.00% |
| PE 32:2; PE P-33:1 | 688.4912 | 10.03% | 0.00% |
| PE 32:1; PE P-33:0 | 690.5068 | 10.04% | 0.00% |
| PE 32:0; PE O-33:0 | 692.5225 | 10.05% | 0.00% |
| PE 32:0 | 692.5225 | 10.05% | 0.00% |
| PE O-34:3/P-34:2 | 700.5276 | 0.00% | 0.00% |
| PE P-34:1; PE 33:2 | 702.5068 | 0.00% | 0.00% |
| PE O-34:2/P-34:1 | 702.5432 | 10.75% | 0.00% |
| PE P-34:0; PE 33:1 | 704.5225 | 10.76% | 0.00% |
| PE O-34:1/P-34:0 | 704.5589 | 10.76% | 0.00% |
| PE O-34:0;PE 33:0 | 706.5381 | 10.77% | 0.00% |
| PE 34:4; PE P-35:3 | 712.4912 | 0.00% | 0.00% |
| PE 34:3; PE P-35:2 | 714.5068 | 10.95% | 0.00% |
| PE 34:2; PE P-35:1 | 716.5225 | 10.96% | 0.00% |

TABLE 19-continued

Database of lipid species monitored during the identification step in
the positive-ion mode together with the calculation of isotopic correction
for M + 1 and M + 2 isotopic peaks (so called deisotoping).

| Lipid | m/z | Isotopic correction | |
|---|---|---|---|
| | | M + 2 | M + 1 |
| PE 34:1; PE P-35:0 | 718.5381 | 10.97% | 0.00% |
| PE 34:0; PE P-36:6 | 720.5538 | 10.98% | 0.00% |
| PE P-36:5; PE 35:6 | 722.4756 | 11.69% | 0.00% |
| PE O-36:6/P-36:5 | 722.5119 | 0.00% | 0.00% |
| PE P-36:4; PE 35:5 | 724.4912 | 11.70% | 0.00% |
| PE O-36:5/P-36:4 | 724.5276 | 11.70% | 0.00% |
| PE P-36:3; PE 35:4 | 726.5068 | 11.71% | 0.00% |
| PE O-36:4/P-36:3 | 726.5432 | 11.71% | 0.00% |
| PE P-36:2; PE 35:3 | 728.5225 | 11.72% | 0.00% |
| PE O-36:3/P-36:2 | 728.5589 | 11.72% | 0.00% |
| PE P-36:1; PE 35:2 | 730.5381 | 11.73% | 0.00% |
| PE O-36:2/P-36:1 | 730.5745 | 11.73% | 0.00% |
| PE P-36:0; PE 35:1 | 732.5538 | 11.74% | 0.00% |
| PE 36:7; PE O-36:0; PE 35:0 | 734.5694 | 11.75% | 0.00% |
| PE 36:6; PE P-37:5 | 736.4912 | 11.90% | 0.00% |
| PE 36:5; PE P-37:4 | 738.5068 | 11.91% | 0.00% |
| PE 36:4; PE P-37:3 | 740.5225 | 11.92% | 0.00% |
| PE 36:3; PE P-37:2 | 742.5381 | 11.93% | 0.00% |
| PE 36:2; PE P-37:1 | 744.5538 | 11.94% | 0.00% |
| PE 36:1; PE P-37:0 | 746.5694 | 11.95% | 0.00% |
| PE O-38:7/P-38:6 | 748.5276 | 0.00% | 0.00% |
| PE 36:0; PE P-38:6 | 748.5851 | 11.96% | 0.00% |
| PE P-38:5; PE 37:6 | 750.5063 | 12.71% | 0.00% |
| PE O-38:6/P-38:5 | 750.5432 | 12.71% | 0.00% |
| PE P-38:4; PE 37:5 | 752.5220 | 14.35% | 0.00% |
| PE O-38:5/P-38:4 | 752.5589 | 12.72% | 0.00% |
| PE P-38:3; PE 37:4 | 754.5376 | 14.36% | 0.00% |
| PE O-38:4/P-38:3 | 754.5745 | 12.73% | 0.00% |
| PE P-38:2; PE 37:3 | 756.5538 | 14.37% | 0.00% |
| PE O-38:3/P-38:2 | 756.5902 | 12.74% | 0.00% |
| PE P-38:1; PE 37:2 | 758.5694 | 14.39% | 0.00% |
| PE P-38:0; PE 37:1 | 760.5851 | 14.40% | 0.00% |
| PE 38:7; PE O-38:0; PE 37:0 | 762.6007 | 14.41% | 0.00% |
| PE 38:6; PE P-39:5 | 764.5225 | 14.55% | 0.00% |
| PE 38:5; PE P-39:4 | 766.5382 | 14.56% | 0.00% |
| PE 38:4; PE P-40:10; PE P-29:3 | 768.5538 | 14.57% | 0.00% |
| PE 38:3; PE P-40:9; PE P-39:2 | 770.5694 | 14.586% | 0.00% |
| PE 38:2; PE P-40:8; PE P-39:1 | 772.5851 | 14.60% | 0.00% |
| PE 38:1; PE P-40:7; PE P-39:0 | 774.6007 | 14.61% | 0.00% |
| PE O-40:7/P-40:6 | 776.5589 | 0.00% | 0.00% |
| PE 38:0; PE P-40:6, PE O-39:0 | 776.6164 | 14.62% | 0.00% |
| PE P-40:5; PE 39:6 | 778.5382 | 13.78% | 0.00% |
| PE O-40:6/P-40:5 | 778.5745 | 13.78% | 0.00% |
| PE P-40:4; PE 39:5 | 780.5538 | 13.79% | 0.00% |
| PE O-40:5/P-40:4 | 780.5902 | 13.79% | 0.00% |
| PE P-40:3; PE 39:4 | 782.5694 | 15.51% | 0.00% |
| PE 40:10; PE P-40:2; PE 39:3 | 784.4912 | 15.52% | 0.00% |
| PE 40:9; PE P-40:1; PE 39:2 | 786.5069 | 15.66% | 0.00% |
| PE 40:8; PE P-40:0; PE 39:1 | 788.5225 | 15.67% | 0.00% |
| PE 40:7; PE O-40:0; PE 39:0 | 790.5381 | 15.69% | 0.00% |
| PE 40:6; PE P-41:5 | 792.5538 | 15.70% | 0.00% |
| PE 40:5; PE P-41:4 | 794.5695 | 15.71% | 0.00% |
| PE 40:4; PE P-42:10; PE P-41:3 | 796.5851 | 15.72% | 0.00% |
| PE 40:3; PE P-42:9; PE P-41:2 | 798.6008 | 15.73% | 0.00% |
| PE 40:2; PE P-42:8; PE P-41:1 | 800.6164 | 15.75% | 0.00% |
| PE 40:1; PE P-42:7; PE P-41:0 | 802.6320 | 15.76% | 0.00% |
| PE 40:0; PE P-42:6, PE O-41:0 | 804.6477 | 15.77% | 0.00% |
| PE P-42:5; PE 41:6 | 806.5694 | 14.90% | 0.00% |
| PE O-42:6/P-42:5 | 806.6058 | 0.00% | 0.00% |
| PE P-42:4; PE 41:5 | 808.5851 | 16.69% | 0.00% |
| PE P-42:3; PE 41:4 | 810.6007 | 16.71% | 0.00% |
| PE 42:10; PE P-42:2; PE 41:3 | 812.5225 | 16.72% | 0.00% |
| PE 42:9; PE P-42:1; PE 41:2 | 814.5382 | 16.85% | 0.00% |
| PE 42:8; PE P-42:0; PE 41:1 | 816.5538 | 16.87% | 0.00% |
| PE 42:7; PE O-42:0 | 818.5694 | 16.88% | 0.00% |
| PE 42:6; PE P-43:5 | 820.5851 | 16.89% | 0.00% |
| PE 42:5; PE P-43:4 | 822.6007 | 16.91% | 0.00% |
| PE 42:4; PE P-43:3 | 824.6164 | 16.92% | 0.00% |
| PE 42:3; PE P-43:2 | 826.6320 | 16.93% | 0.00% |
| PE 42:2; PE P-43:1 | 828.6477 | 16.94% | 0.00% |
| PE 42:1; PE P-43:0 | 830.6633 | 16.96% | 0.00% |
| PE 42:0; PE O-43:0 | 832.6790 | 16.97% | 0.00% |

TABLE 19-continued

Database of lipid species monitored during the identification step in the positive-ion mode together with the calculation of isotopic correction for M + 1 and M + 2 isotopic peaks (so called deisotoping).

| Lipid | m/z | Isotopic correction M + 2 | Isotopic correction M + 1 |
|---|---|---|---|
| PE 44:0 | 860.7103 | 0.00% | 0.00% |
| LPI 6:0 | 450.1734 | 0.00% | 0.00% |
| LPI 8:0 | 478.2047 | 0.00% | 0.00% |
| LPI 10:0 | 506.2360 | 0.00% | 0.00% |
| LPI 12:0 | 534.2673 | 0.00% | 0.00% |
| LPI 14:0 | 562.2986 | 0.00% | 0.00% |
| LPI P-16:0; LPI O-16:1 | 574.3350 | 0.00% | 0.00% |
| LPI O-16:0; LPI 15:0 | 576.3143 | 6.16% | 0.00% |
| LPI 16:2 | 586.2986 | 0.00% | 0.00% |
| PI 16:0 | 587.2827 | 0.00% | 0.00% |
| LPI 16:1 | 588.3143 | 6.36% | 0.00% |
| LPI 16:0 | 590.3299 | 6.37% | 0.00% |
| LPI P-18:0; LPI O-18:1; LPI 17:1 | 602.3669 | 0.00% | 0.00% |
| PI 16:0; LPI O-18:0; LPI 17:0 (IS) | 604.3456 | 6.80% | 0.00% |
| LPI 18:4 | 610.2986 | 0.00% | 0.00% |
| LPI 18:3 | 612.3143 | 6.99% | 0.00% |
| LPI 18:2 | 614.3299 | 6.99% | 0.00% |
| LPI 18:1 | 616.3456 | 7.00% | 0.00% |
| LPI 18:0 | 618.3612 | 7.01% | 0.00% |
| LPI P-20:0; LPI O-20:1 | 630.3976 | 0.00% | 0.00% |
| LPI O-20:0; LPI 19:0 | 632.3769 | 7.49% | 0.00% |
| LPI 20:5 | 636.3137 | 0.00% | 0.00% |
| LPI 20:4 | 638.3294 | 7.67% | 0.00% |
| LPI 20:3 | 640.3450 | 7.68% | 0.00% |
| LPI 20:2 | 642.3612 | 7.68% | 0.00% |
| LPI 20:1 | 644.3769 | 7.69% | 0.00% |
| LPI 20:0 | 646.3925 | 7.70% | 0.00% |
| LPI P-22:0; LPI O-22:1 | 658.4289 | 0.00% | 0.00% |
| LPI O-22:0; LPI 21:0 | 660.4082 | 8.23% | 0.00% |
| LPI 22:6 | 662.3299 | 8.23% | 0.00% |
| LPI 22:5 | 664.3450 | 8.40% | 0.00% |
| LPI 22:4 | 666.3606 | 8.41% | 0.00% |
| LPI 22:1 | 672.4082 | 0.00% | 0.00% |
| LPI 22:0 | 674.4238 | 8.44% | 0.00% |
| LPI P-24:0; LPI O-24:1 | 686.4602 | 0.00% | 0.00% |
| LPI O-24:0; LPI 23:0 | 688.4395 | 9.01% | 0.00% |
| LPI 24:1 | 700.4395 | 0.00% | 0.00% |
| LPI 24:0 | 702.4551 | 9.22% | 0.00% |
| LPI 25:0 | 716.4708 | 0.00% | 0.00% |
| LPI 26:0 | 730.4864 | 0.00% | 0.00% |
| LPI 27:0 | 744.5021 | 0.00% | 0.00% |
| LPI 28:0 | 758.5177 | 0.00% | 0.00% |
| PI 28:0 | 772.4970 | 0.00% | 0.00% |
| PI 29:0 | 786.5126 | 0.00% | 0.00% |
| PI 30:1 | 798.5126 | 0.00% | 0.00% |
| PI 30:0 | 800.5283 | 10.04% | 0.00% |
| PI P-32:1; PI-31:2 | 810.5490 | 0.00% | 0.00% |
| PI P-32:0; PI-31:1 | 812.5283 | 12.85% | 0.00% |
| PI O-32:0; PI-31:0 | 814.5440 | 12.86% | 0.00% |
| PI 32:3; PI P-33:2 | 822.5126 | 0.00% | 0.00% |
| PI 32:2; PI P-33:1 | 824.5283 | 13.05% | 0.00% |
| PI 32:1; PI P-33:0 | 826.5440 | 13.07% | 0.00% |
| PI 32:0; PI O-33:0 | 828.5596 | 13.08% | 0.00% |
| PI P-34:1; PI 33:2 | 838.5440 | 0.00% | 0.00% |
| PI P-34:0; PI 33:1 | 840.5596 | 13.88% | 0.00% |
| PI O-34:0; PI 33:0 | 842.5753 | 13.90% | 0.00% |
| PI 34:4; PI P-35:3 | 848.5283 | 0.00% | 0.00% |
| PI 34:3; PI P-35:2 | 850.5440 | 14.08% | 0.00% |
| PI 34:2; PI P-35:1 | 852.5596 | 14.09% | 0.00% |
| PI 34:1; PI P-35:0 | 854.5753 | 14.10% | 0.00% |
| PI 34:0; PI P-36:6 | 856.5909 | 14.11% | 0.00% |
| PI P-36:5; PI 35:6 | 858.5127 | 14.91% | 0.00% |
| PI 36:4 | 859.5331 | 0.00% | 0.00% |
| PI P-36:4; PI 35:5 | 860.5283 | 14.92% | 0.00% |
| PI P-36:3; PI 35:4 | 862.5440 | 14.93% | 0.00% |
| PI P-36:2; PI 35:3 | 864.5596 | 14.94% | 0.00% |
| PI P-36:1; PI 35:2 | 866.5753 | 14.95% | 0.00% |
| PI P-36:0; PI 35:1 | 868.5909 | 14.96% | 0.00% |
| PI 36:7; PI O-36:0; PI 35:0 | 870.6066 | 14.97% | 0.00% |
| PI 36:6; PI P-37:5 | 872.5283 | 15.12% | 0.00% |
| PI 36:5; PI P-37:4 | 874.5440 | 15.13% | 0.00% |
| PI 36:4; PI P-37:3 | 876.5596 | 15.14% | 0.00% |

TABLE 19-continued

Database of lipid species monitored during the identification step in
the positive-ion mode together with the calculation of isotopic correction
for M + 1 and M + 2 isotopic peaks (so called deisotoping).

| Lipid | m/z | Isotopic correction M + 2 | Isotopic correction M + 1 |
|---|---|---|---|
| PI 36:3; PI P-37:2 | 878.5753 | 15.15% | 0.00% |
| PI 36:2; PI P-37:1 | 880.5909 | 15.16% | 0.00% |
| PI 36:1; PI P-37:0 | 882.6066 | 15.18% | 0.00% |
| PI 36:0; PI P-38:6 | 884.6222 | 15.19% | 0.00% |
| PI 38:5 | 885.5488 | 0.00% | 0.00% |
| PI P-38:5; PI 37:6 | 886.5434 | 16.03% | 0.00% |
| PI 38:4 | 887.5644 | 0.00% | 0.00% |
| PI P-38:4; PI 37:5 | 888.5591 | 16.04% | 0.00% |
| PI 38:3 | 889.5801 | 0.00% | 0.00% |
| PI P-38:3; PI 37:4 | 890.5747 | 16.06% | 0.00% |
| PI P-38:2; PI 37:3 | 892.5909 | 16.07% | 0.00% |
| PI P-38:1; PI 37:2 | 894.6066 | 16.08% | 0.00% |
| PI P-38:0; PI 37:1 | 896.6222 | 16.09% | 0.00% |
| PI 38:7; PI O-38:0; PI 37:0 | 898.6379 | 16.10% | 0.00% |
| PI 38:6; PI P-39:5 | 900.5596 | 16.25% | 0.00% |
| PI 38:5; PI P-39:4 | 902.5753 | 16.26% | 0.00% |
| PI 38:4; PI P-40:10; PI P-29:3 | 904.5909 | 16.27% | 0.00% |
| PI 38:3; PI P-40:9; PI P-39:2 | 906.6066 | 16.28% | 0.00% |
| PI 38:2; PI P-40:8; PI P-39:1 | 908.6222 | 16.29% | 0.00% |
| PI 40:7 | 909.5488 | 0.00% | 0.00% |
| PI 38:1; PI P-40:7; PI P-39:0 | 910.6379 | 16.31% | 0.00% |
| PI 40:6 | 911.5644 | 0.00% | 0.00% |
| PI 38:0; PI P-40:6, PI O-39:0 | 912.6535 | 16.32% | 0.00% |
| PI P-40:5; PI 39:6 | 914.5753 | 17.21% | 0.00% |
| PI P-40:4; PI 39:5 | 916.5909 | 17.22% | 0.00% |
| PI P-40:3; PI 39:4 | 918.6066 | 17.23% | 0.00% |
| PI 40:10; PI P-40:2; PI 39:3 | 920.5283 | 17.25% | 0.00% |
| PI 40:9; PI P-40:1; PI 39:2 | 922.5440 | 17.38% | 0.00% |
| PI 40:8; PIP-40:0; PI 39:1 | 924.5596 | 17.40% | 0.00% |
| PI 40:7; PI O-40:0; PI 39:0 | 926.5753 | 17.41% | 0.00% |
| PI 40:6; PI P-41:5 | 928.5909 | 17.42% | 0.00% |
| PI 40:5; PI P-41:4 | 930.6066 | 17.43% | 0.00% |
| PI 40:4; PI P-42:10; PI P-41:3 | 932.6222 | 17.45% | 0.00% |
| PI 40:3; PI P-42:9; PI P-41:2 | 934.6379 | 17.46% | 0.00% |
| PI 40:2; PI P-42:8; PI P-41:1 | 936.6535 | 17.47% | 0.00% |
| PI 40:1; PI P-42:7; PI P-41:0 | 938.6692 | 17.48% | 0.00% |
| PI 40:0; PI P-42:6, PI O-41:0 | 940.6848 | 17.50% | 0.00% |
| PI P-42:5; PI 41:6 | 942.6066 | 18.43% | 0.00% |
| PI P-42:4; PI 41:5 | 944.6222 | 18.44% | 0.00% |
| PI P-42:3; PI 41:4 | 946.6379 | 18.46% | 0.00% |
| PI 42:10; PI P-42:2; PI 41:3 | 948.5596 | 18.47% | 0.00% |
| PI 42:9; PIP-42:1; PI 41:2 | 950.5753 | 18.61% | 0.00% |
| PI 42:8; PI P-42:0; PI 41:1 | 952.5909 | 18.62% | 0.00% |
| PI 42:7; PI O-42:0 | 954.6066 | 18.63% | 0.00% |
| PI 42:6; PI P-43:5 | 956.6222 | 18.65% | 0.00% |
| PI 42:5; PI P-43:4 | 958.6379 | 18.66% | 0.00% |
| PI 42:4; PI P-43:3 | 960.6535 | 18.67% | 0.00% |
| PI 42:3; PI P-43:2 | 962.6692 | 18.68% | 0.00% |
| PI 42:2; PI P-43:1 | 964.6848 | 18.70% | 0.00% |
| PI 42:1; PI P-43:0 | 966.7005 | 18.71% | 0.00% |
| PI 42:0; PI O-43:0 | 968.7161 | 18.72% | 0.00% |
| PI 44:0 | 996.7474 | 0.00% | 0.00% |
| LPC 6:0 | 356.1833 | 0.00% | 0.00% |
| LPC 8:0 | 384.2146 | 0.00% | 0.00% |
| LPC 10:0 | 412.2459 | 0.00% | 0.00% |
| LPC 12:0 | 440.2772 | 0.00% | 0.00% |
| LPC 14:0 | 468.3085 | 0.00% | 0.00% |
| LPC P-16:0; LPC O-16:1 | 480.3449 | 0.00% | 0.00% |
| LPC O-16:0; LPC 15:0 | 482.3241 | 4.78% | 0.00% |
| LPC 16:2 | 492.3085 | 0.00% | 0.00% |
| LPC 16:1 | 494.3241 | 4.98% | 0.00% |
| LPC 16:0 | 496.3398 | 4.99% | 0.00% |
| LPC P-18:0; LPC O-18:1; LPC 17:1 | 508.3767 | 0.00% | 0.00% |
| LPC O-18:0; LPC 17:0 (IS) | 510.3554 | 5.39% | 0.00% |
| LPC O-18:0 | 510.3918 | 0.00% | 0.00% |
| LPC 18:4 | 516.3085 | 0.00% | 0.00% |
| LPC 18:3 | 518.3241 | 5.58% | 0.00% |
| LPC 18:2 | 520.3398 | 5.58% | 0.00% |
| LPC 18:1 | 522.3554 | 5.59% | 0.00% |
| LPC 18:1 | 522.3554 | 5.59% | 0.00% |
| LPC 18:0 | 524.3711 | 5.60% | 0.00% |
| LPC P-20:0; LPC O-20:1 | 536.4075 | 0.00% | 0.00% |

TABLE 19-continued

Database of lipid species monitored during the identification step in the positive-ion mode together with the calculation of isotopic correction for M + 1 and M + 2 isotopic peaks (so called deisotoping).

| Lipid | m/z | Isotopic correction M + 2 | Isotopic correction M + 1 |
|---|---|---|---|
| LPC O-20:0; LPC 19:0 | 538.3867 | 6.05% | 0.00% |
| LPC 20:5 | 542.3235 | 0.00% | 0.00% |
| LPC 20:4 | 544.3392 | 6.23% | 0.00% |
| LPC 20:3 | 546.3548 | 6.24% | 0.00% |
| LPC 20:2 | 548.3711 | 6.25% | 0.00% |
| LPC 20:1 | 550.3867 | 6.25% | 0.00% |
| LPC 20:0 | 552.4024 | 6.26% | 0.00% |
| LPC P-22:0; LPC O-22:1 | 564.4388 | 0.00% | 0.00% |
| LPC O-22:0; LPC 21:0 | 566.4180 | 6.76% | 0.00% |
| LPC 22:6 | 568.3398 | 6.77% | 0.00% |
| LPC 22:5 | 570.3548 | 6.93% | 0.00% |
| LPC 22:4 | 572.3704 | 6.94% | 0.00% |
| LPC 22:1 | 578.4180 | 0.00% | 0.00% |
| LPC 22:0 | 580.4337 | 6.97% | 0.00% |
| LPC P-24:0; LPC O-24:1 | 592.4701 | 0.00% | 0.00% |
| LPC O-24:0; LPC 23:0 | 594.4493 | 7.52% | 0.00% |
| LPC 24:1 | 606.4493 | 0.00% | 0.00% |
| LPC 24:0 | 608.4650 | 7.73% | 0.00% |
| SM 28:2 | 617.4653 | 0.00% | 0.00% |
| SM 28:1 | 619.4809 | 8.04% | 0.00% |
| SM 28:0 | 621.4966 | 8.05% | 0.00% |
| LPC 25:0 | 622.4806 | 0.00% | 37.46% |
| SM 29:2 | 631.4809 | 0.00% | 0.00% |
| SM 29:1 | 633.4966 | 8.45% | 0.00% |
| SM 29:0 | 635.5123 | 8.46% | 0.00% |
| LPC 26:0 | 636.4963 | 0.00% | 38.57% |
| SM 30:2 | 645.4966 | 0.00% | 0.00% |
| SM 30:1 | 647.5123 | 8.88% | 0.00% |
| SM 30:0 | 649.5279 | 8.89% | 0.00% |
| LPC 27:0 | 650.5119 | 0.00% | 39.67% |
| SM 31:2 | 659.5123 | 0.00% | 0.00% |
| SM 31:1 | 661.5279 | 9.32% | 0.00% |
| SM 31:0 | 663.5436 | 9.33% | 0.00% |
| LPC 28:0 | 664.5276 | 0.00% | 40.78% |
| SM 32:2 | 673.5279 | 0.00% | 0.00% |
| SM 32:1 | 675.5436 | 9.77% | 0.00% |
| SM d32:1 | 675.5436 | 0.00% | 0.00% |
| SM 32:0 | 677.5592 | 9.78% | 0.00% |
| PC 28:0 | 678.5068 | 0.00% | 41.88% |
| SM 33:2 | 687.5436 | 0.00% | 0.00% |
| SM 33:1 | 689.5592 | 10.23% | 0.00% |
| PC O-30:1/P-30:0 | 690.5432 | 0.00% | 0.00% |
| SM 33:0 | 691.5749 | 10.24% | 0.00% |
| PC 29:0 | 692.5225 | 0.00% | 42.99% |
| PC O-30:0 | 692.5589 | 10.30% | 0.00% |
| SM 34:2 | 701.5592 | 0.00% | 0.00% |
| SM 34:1 | 703.5749 | 10.70% | 0.00% |
| PC 30:1 | 704.5225 | 0.00% | 44.07% |
| SM 34:0 | 705.5905 | 10.71% | 42.64% |
| PC 30:0 | 706.5381 | 10.51% | 44.09% |
| SM 35:2 | 715.5749 | 0.00% | 0.00% |
| PC P-32:1; PC-31:2 | 716.5589 | 0.00% | 45.15% |
| PC O-32:2/P-32:1 | 716.5589 | 0.00% | 0.00% |
| SM 35:1 | 717.5905 | 11.19% | 44.81% |
| PC P-32:0; PC-31:1 | 718.5381 | 11.24% | 45.17% |
| PC O-32:1/P-32:0 | 718.5745 | 11.24% | 0.00% |
| SM 35:0 | 719.6062 | 11.20% | 44.83% |
| PC O-32:0; PC-31:0 | 720.5538 | 11.25% | 45.20% |
| PC O-32:0 | 720.5902 | 11.25% | 0.00% |
| PC 32:3; PC P-33:2 | 728.5225 | 0.00% | 0.00% |
| SM 36:2 | 729.5905 | 0.00% | 44.80% |
| PC 32:2; PC P-33:1 | 730.5381 | 11.44% | 46.26% |
| SM 36:1 | 731.6062 | 11.69% | 44.82% |
| PC 32:1; PC P-33:0 | 732.5538 | 11.46% | 46.28% |
| SM 36:0 | 733.6218 | 11.70% | 44.85% |
| PC 32:0; PC O-33:0 | 734.5694 | 11.47% | 46.30% |
| PC O-34:3/P-34:2 | 742.5745 | 0.00% | 0.00% |
| SM 37:2 | 743.6062 | 0.00% | 0.00% |
| PC P-34:1; PC 33:2 | 744.5538 | 0.00% | 47.36% |
| PC O-34:2/P-34:1 | 744.5902 | 12.23% | 0.00% |
| SM 37:1 | 745.6218 | 12.20% | 47.02% |
| PC P-34:0; PC 33:1 | 746.5694 | 12.25% | 47.38% |

TABLE 19-continued

Database of lipid species monitored during the identification step in the positive-ion mode together with the calculation of isotopic correction for M + 1 and M + 2 isotopic peaks (so called deisotoping).

| Lipid | m/z | Isotopic correction M + 2 | Isotopic correction M + 1 |
|---|---|---|---|
| PC O-34:1/P-34:0 | 746.6058 | 12.25% | 0.00% |
| SM 37:0 | 747.6375 | 12.21% | 47.04% |
| PC O-34:0; PC 33:0 | 748.5851 | 12.26% | 47.41% |
| PC 34:4; PC P-35:3 | 754.5382 | 0.00% | 0.00% |
| PC 34:3; PC P-35:2 | 756.5538 | 12.44% | 0.00% |
| SM 38:2 | 757.6218 | 0.00% | 47.01% |
| PC 34:2; PC P-35:1 | 758.5694 | 12.45% | 48.46% |
| SM 38:1 | 759.6375 | 12.72% | 47.03% |
| PC 34:1; PC P-35:0 | 760.5851 | 12.46% | 48.49% |
| SM 38:0 | 761.6531 | 12.74% | 47.06% |
| PC 34:0; PC P-36:6 | 762.6007 | 12.47% | 48.51% |
| PC P-36:5; PC 35:6 | 764.5226 | 13.24% | 0.00% |
| PC P-36:4; PC 35:5 | 766.5382 | 13.25% | 0.00% |
| PC O-36:5/P-36:4 | 766.5745 | 0.00% | 0.00% |
| PC P-36:3; PC 35:4 | 768.5538 | 13.26% | 0.00% |
| PC O-36:4/P-36:3 | 768.5902 | 13.26% | 0.00% |
| PC P-36:2; PC 35:3 | 770.5694 | 13.27% | 0.00% |
| PC O-36:3/P-36:2 | 770.6058 | 13.27% | 0.00% |
| SM 39:2 | 771.6375 | 0.00% | 49.20% |
| PC P-36:1; PC 35:2 | 772.5851 | 13.29% | 49.57% |
| SM 39:1 | 773.6531 | 13.26% | 49.23% |
| PC P-36:0; PC 35:1 | 774.6007 | 13.30% | 49.59% |
| SM 39:0 | 775.6688 | 13.27% | 49.25% |
| PC 36:7; PC O-36:0; PC 35:0 | 776.6164 | 13.31% | 49.62% |
| PC 36:6; PC P-37:5 | 778.5381 | 13.45% | 0.00% |
| PC 36:5; PC P-37:4 | 780.5538 | 13.46% | 0.00% |
| PC 36:4; PC P-37:3 | 782.5694 | 13.48% | 0.00% |
| SM 40:3 | 783.6375 | 0.00% | 49.20% |
| PC 36:3; PC P-37:2 | 784.5851 | 13.49% | 50.65% |
| SM 40:2 | 785.6531 | 13.80% | 49.22% |
| PC 36:2; PC P-37:1 | 786.6007 | 13.50% | 50.67% |
| SM 40:1 | 787.6688 | 13.81% | 49.24% |
| PC 36:1; PC P-37:0 | 788.6164 | 13.51% | 50.70% |
| SM 40:0 | 789.6844 | 13.82% | 49.26% |
| PC 36:0; PC P-38:6 | 790.6320 | 13.52% | 50.72% |
| PC P-38:5; PC 37:6 | 792.5532 | 14.34% | 0.00% |
| PC O-38:6/P-38:5 | 792.5902 | 0.00% | 0.00% |
| PC P-38:4; PC 37:5 | 794.5689 | 14.35% | 0.00% |
| PC O-38:5/P-38:4 | 794.6058 | 14.35% | 0.00% |
| PC P-38:3; PC 37:4 | 796.5845 | 14.36% | 0.00% |
| PC O-38:4/P-38:3 | 796.6215 | 14.36% | 0.00% |
| PC P-38:2; PC 37:3 | 798.6007 | 14.37% | 0.00% |
| SM 41:2 | 799.6688 | 0.00% | 51.41% |
| PC P-38:1; PC 37:2 | 800.6164 | 14.39% | 51.78% |
| SM41:1 | 801.6844 | 14.37% | 51.44% |
| PC P-38:0; PC 37:1 | 802.6320 | 14.40% | 51.80% |
| SM 41:0 | 803.7001 | 14.38% | 51.46% |
| PC 38:7 | 804.5538 | 0.00% | 0.00% |
| PC 38:7; PC O-38:0; PC 37:0 | 804.6477 | 14.41% | 51.82% |
| PC 38:6; PC P-39:5 | 806.5695 | 14.55% | 0.00% |
| PC 38:5; PC P-39:4 | 808.5852 | 14.56% | 0.00% |
| PC 38:4; PC P-40:10; PC P-29:3 | 810.6007 | 14.57% | 0.00% |
| SM d42:3 | 811.6688 | 0.00% | 0.00% |
| PC 38:3; PC P-40:9; PC P-39:2 | 812.6164 | 14.59% | 0.00% |
| SM 42:2 | 813.6844 | 0.00% | 51.43% |
| PC 38:2; PC P-40:8; PC P-39:1 | 814.6320 | 14.60% | 52.88% |
| SM 42:1 | 815.7001 | 14.94% | 51.45% |
| PC 38:1; PC P-40:7; PC P-39:0 | 816.6477 | 14.61% | 52.91% |
| SM 42:0 | 817.7157 | 14.95% | 51.47% |
| PC O-40:7/P-40:6 | 818.6058 | 0.00% | 0.00% |
| PC 38:0; PC P-40:6, PC O-39:0 | 818.6633 | 14.62% | 52.93% |
| PC P-40:5; PC 39:6 | 820.5852 | 15.48% | 0.00% |
| PC O-40:6/P-40:5 | 820.6215 | 15.48% | 0.00% |
| PC P-40:4; PC 39:5 | 822.6008 | 15.50% | 0.00% |
| PC O-40:5/P-40:4 | 822.6371 | 15.50% | 0.00% |
| PC P-40:3; PC 39:4 | 824.6164 | 15.51% | 0.00% |
| PC O-40:4/P-40:3 | 824.6528 | 15.51% | 0.00% |
| PC 40:10; PC P-40:2; PC 39:3 | 826.5382 | 15.52% | 0.00% |
| PC O-40:3/P-40:2 | 826.6684 | 15.52% | 0.00% |
| SM 43:2 | 827.7001 | 0.00% | 53.48% |
| PC 40:9; PC P-40:1; PC 39:2 | 828.5539 | 15.66% | 53.99% |
| PC O-40:2/P-40:1 | 828.6841 | 15.53% | 0.00% |

TABLE 19-continued

Database of lipid species monitored during the identification step in the positive-ion mode together with the calculation of isotopic correction for M + 1 and M + 2 isotopic peaks (so called deisotoping).

| Lipid | m/z | Isotopic correction M + 2 | Isotopic correction M + 1 |
|---|---|---|---|
| SM 43:1 | 829.7157 | 15.52% | 53.50% |
| PC 40:8; PC P-40:0; PC 39:1 | 830.5695 | 15.67% | 54.01% |
| PC O-40:1/P-40:0 | 830.6997 | 15.55% | 0.00% |
| SM 43:0 | 831.7314 | 15.54% | 53.52% |
| PC 40:7; PC O-40:0; PC 39:0 | 832.5851 | 15.69% | 54.03% |
| PC 40:6; PC P-41:5 | 834.6007 | 15.70% | 0.00% |
| PC 40:5; PC P-41:4 | 836.6165 | 15.71% | 0.00% |
| PC 40:4; PC P-42:10; PC P-41:3 | 838.6321 | 15.72% | 0.00% |
| SM d44:3 | 839.7001 | 0.00% | 0.00% |
| PC 40:3; PC P-42:9; PC P-41:2 | 840.6478 | 15.73% | 0.00% |
| SM 44:2 | 841.7157 | 0.00% | 55.67% |
| PC 40:2; PC P-42:8; PC P-41:1 | 842.6633 | 15.75% | 55.09% |
| SM 44:1 | 843.7314 | 16.12% | 55.69% |
| PC 40:1; PC P-42:7; PC P-41:0 | 844.6790 | 15.76% | 55.11% |
| SM 44:0 | 845.7470 | 16.13% | 55.72% |
| PC 40:0; PC P-42:6, PC O-41:0 | 846.6946 | 15.77% | 55.14% |
| PC P-42:5; PC 41:6 | 848.6164 | 16.68% | 0.00% |
| PC O-42:6/P-42:5 | 848.6528 | 0.00% | 0.00% |
| PC P-42:4; PC 41:5 | 850.6321 | 16.69% | 0.00% |
| PC O-42:5/P-42:4 | 850.6684 | 16.69% | 0.00% |
| PC P-42:3; PC 41:4 | 852.6477 | 16.71% | 0.00% |
| PC O-42:4/P-42:3 | 852.6841 | 16.71% | 0.00% |
| PC 42:10; PC P-42:2; PC 41:3 | 854.5695 | 16.72% | 0.00% |
| PC O-42:3/P-42:2 | 854.6997 | 16.72% | 0.00% |
| PC 42:9; PC P-42:1; PC 41:2 | 856.5852 | 16.85% | 0.00% |
| PC O-42:2/P-42:1 | 856.7154 | 16.73% | 0.00% |
| PC 42:8; PC P-42:0; PC 41:1 | 858.6008 | 16.87% | 0.00% |
| PC 42:7; PC O-42:0 | 860.6164 | 16.88% | 0.00% |
| PC 42:6; PC P-43:5 | 862.6320 | 16.89% | 0.00% |
| PC 42:5; PC P-43:4 | 864.6477 | 16.91% | 0.00% |
| PC 42:4; PC P-43:3 | 866.6633 | 16.92% | 0.00% |
| PC 42:3; PC P-43:2 | 868.6790 | 16.93% | 0.00% |
| PC 42:2; PC P-43:1 | 870.6946 | 16.94% | 0.00% |
| PC 42:1; PC P-43:0 | 872.7103 | 16.96% | 0.00% |
| PC 42:0; PC O-43:0 | 874.7259 | 16.97% | 0.00% |
| PC O-44:6/P-44:5 | 876.6841 | 0.00% | 0.00% |
| PC O-44:5/P-44:4 | 878.6997 | 17.94% | 0.00% |
| PC O-44:4/P-44:3 | 880.7154 | 17.95% | 0.00% |
| PC 44:0 | 902.7573 | 0.00% | 0.00% |
| Sulfatide 30:2 | 722.4473 | 0.00% | 0.00% |
| Sulfatide 30:1 | 724.4630 | 15.10% | 0.00% |
| Sulfatide 30:0 | 726.4786 | 15.11% | 0.00% |
| Sulfatide 31:2 | 736.4630 | 0.00% | 0.00% |
| Sulfatide 31:1; Sulfatide 30:2 (1OH) | 738.4786 | 15.55% | 0.00% |
| Sulfatide 31:0; Sulfatide 30:1 (1OH) | 740.4943 | 15.56% | 0.00% |
| Sulfatide 30:0 (1OH) | 742.4735 | 15.57% | 0.00% |
| Sulfatide 32:2 | 750.4786 | 0.00% | 0.00% |
| Sulfatide 32:1; Sulfatide 31:2 (1OH) | 752.4946 | 16.02% | 0.00% |
| Sulfatide 32:0; Sulfatide 31:1 (1OH) | 754.5099 | 16.03% | 0.00% |
| Sulfatide 31:0 (1OH) | 756.4892 | 16.04% | 0.00% |
| Sulfatide 33:2 | 764.4943 | 0.00% | 0.00% |
| Sulfatide 33:1; Sulfatide 32:2 (1OH) | 766.5099 | 16.50% | 0.00% |
| Sulfatide 33:0; Sulfatide 32:1 (1OH) | 768.5255 | 16.51% | 0.00% |
| Sulfatide 32:0 (1OH) | 770.5048 | 16.52% | 0.00% |
| Sulfatide 34:2 | 778.5099 | 0.00% | 0.00% |
| Sulfatide 34:1; Sulfatide 33:2 (1OH) | 780.5255 | 17.00% | 0.00% |
| Sulfatide 34:0; Sulfatide 33:1 (1OH) | 782.5412 | 17.01% | 0.00% |
| Sulfatide 33:0 (1OH) | 784.5205 | 17.02% | 0.00% |
| Sulfatide 35:2 | 792.5255 | 0.00% | 0.00% |
| Sulfatide 35:1; Sulfatide 34:2 (1OH) | 794.5412 | 17.50% | 0.00% |
| Sulfatide 35:0; Sulfatide 34:1 (1OH) | 796.5569 | 17.51% | 0.00% |
| Sulfatide 34:0 (1OH) | 798.5361 | 17.52% | 0.00% |
| Sulfatide 36:2 | 806.5412 | 0.00% | 0.00% |
| Sulfatide 36:1; Sulfatide 35:2 (1OH) | 808.5569 | 18.02% | 0.00% |
| Sulfatide 36:0; Sulfatide 35:1 (1OH) | 810.5725 | 18.03% | 0.00% |
| Sulfatide 35:0 (1OH) | 812.5518 | 18.05% | 0.00% |
| Sulfatide 37:2 | 820.5569 | 0.00% | 0.00% |
| Sulfatide 37:1; Sulfatide 36:2 (1OH) | 822.5725 | 18.55% | 0.00% |
| Sulfatide 37:0; Sulfatide 36:1 (1OH) | 824.5882 | 18.56% | 0.00% |
| Sulfatide 36:0 (1OH) | 826.5674 | 18.57% | 0.00% |
| Sulfatide 38:3 | 832.5569 | 0.00% | 0.00% |
| Sulfatide 38:2 | 834.5725 | 19.08% | 0.00% |

TABLE 19-continued

Database of lipid species monitored during the identification step in the positive-ion mode together with the calculation of isotopic correction for M + 1 and M + 2 isotopic peaks (so called deisotoping).

| Lipid | m/z | Isotopic correction M + 2 | Isotopic correction M + 1 |
|---|---|---|---|
| Sulfatide 38:1; Sulfatide 37:2 (1OH) | 836.5882 | 19.09% | 0.00% |
| Sulfatide 38:0; Sulfatide 37:1 (1OH) | 838.6038 | 19.10% | 0.00% |
| Sulfatide 37:0 (1OH) | 840.5831 | 19.11% | 0.00% |
| Sulfatide 39:2; Sulfatide 38:3 (1OH) | 848.5882 | 0.00% | 0.00% |
| Sulfatide 39:1; Sulfatide 38:2 (1OH) | 850.6038 | 19.65% | 0.00% |
| Sulfatide 39:0; Sulfatide 38:1 (1OH) | 852.6195 | 19.66% | 0.00% |
| Sulfatide 38:0 (1OH) | 854.5987 | 19.67% | 0.00% |
| Sulfatide 40:3 | 860.5881 | 0.00% | 0.00% |
| Sulfatide 40:2 | 862.6038 | 20.20% | 0.00% |
| Sulfatide 40:1; Sulfatide 39:2 (1OH) | 864.6195 | 20.22% | 0.00% |
| Sulfatide 40:0; Sulfatide 39:1 (1OH) | 866.6351 | 20.23% | 0.00% |
| Sulfatide 39:0 (1OH) | 868.6144 | 20.24% | 0.00% |
| Sulfatide 41:2; Sulfatide 40:3 (1OH) | 876.6195 | 0.00% | 0.00% |
| Sulfatide 41:1; Sulfatide 40:2 (1OH) | 878.6351 | 20.79% | 0.00% |
| Sulfatide 41:0; Sulfatide 40:1 (1OH) | 880.6508 | 20.80% | 0.00% |
| Sulfatide 40:0 (1OH) | 882.6300 | 20.81% | 0.00% |
| Sulfatide 42:3 | 888.6195 | 0.00% | 0.00% |
| Sulfatide 42:2 | 890.6351 | 21.37% | 0.00% |
| Sulfatide 42:1; Sulfatide 41:2 (1OH) | 892.6508 | 21.38% | 0.00% |
| Sulfatide 42:0; Sulfatide 41:1 (1OH) | 894.6664 | 21.40% | 0.00% |
| Sulfatide 41:0 (1OH) | 896.6457 | 21.41% | 0.00% |
| Sulfatide 43:2; Sulfatide 42:3 (1OH) | 904.6508 | 0.00% | 0.00% |
| Sulfatide 43:1; Sulfatide 42:2 (1OH) | 906.6664 | 21.98% | 0.00% |
| Sulfatide 43:0; Sulfatide 42:1 (1OH) | 908.6821 | 22.00% | 0.00% |
| Sulfatide 42:0 (1OH) | 910.6613 | 22.01% | 0.00% |
| Sulfatide 44:3 | 916.6508 | 0.00% | 0.00% |
| Sulfatide 44:2 | 918.6664 | 22.59% | 0.00% |
| Sulfatide 44:1; Sulfatide 43:2 (1OH) | 920.6821 | 22.60% | 0.00% |
| Sulfatide 44:0; Sulfatide 43:1 (1OH) | 922.6977 | 22.62% | 0.00% |
| Sulfatide 43:0 (1OH) | 924.6770 | 22.63% | 0.00% |
| LPA 6:0 | 288.1206 | 0.00% | 0.00% |
| LPA 8:0 | 316.1519 | 0.00% | 0.00% |
| LPA 10:0 | 344.1832 | 0.00% | 0.00% |
| LPA 12:0 | 372.2145 | 0.00% | 0.00% |
| LPA 14:0 (IS) | 400.2458 | 0.00% | 0.00% |
| LPAP-16:0; LPA O-16:1 | 412.2822 | 0.00% | 0.00% |
| LPA O-16:0; LPA 15:0 | 414.2615 | 3.46% | 0.00% |
| LPA 16:2 | 424.2458 | 0.00% | 0.00% |
| LPA 16:1 | 426.2615 | 3.67% | 0.00% |
| LPA 16:0 | 428.2771 | 3.67% | 0.00% |
| LPA P-18:0; LPA O-18:1; LPA 17:1 | 440.3140 | 0.00% | 0.00% |
| LPA O-18:0; LPA 17:0 | 442.2928 | 3.95% | 0.00% |
| LPA 18:4 | 448.2458 | 0.00% | 0.00% |
| LPA 18:3 | 450.2615 | 4.15% | 0.00% |
| LPA 18:2 | 452.2771 | 4.15% | 0.00% |
| LPA 18:1 | 454.2928 | 4.16% | 0.00% |
| LPA 18:0 | 456.3084 | 4.16% | 0.00% |
| LPA P-20:0; LPA O-20:1 | 468.3448 | 0.00% | 0.00% |
| LPA O-20:0; LPA 19:0 | 470.3241 | 4.49% | 0.00% |
| LPA 20:5 | 474.2609 | 0.00% | 0.00% |
| LPA 20:4 | 476.2766 | 4.68% | 0.00% |
| LPA 20:3 | 478.2922 | 4.69% | 0.00% |
| LPA 20:2 | 480.3084 | 4.69% | 0.00% |
| LPA 20:1 | 482.3241 | 4.70% | 0.00% |
| LPA 20:0 | 484.3397 | 4.70% | 0.00% |
| LPA P-22:0; LPA O-22:1 | 496.3761 | 0.00% | 0.00% |
| LPA O-22:0; LPA 21:0 | 498.3554 | 5.08% | 0.00% |
| LPA 22:6 | 500.2771 | 5.09% | 0.00% |
| LPA 22:5 | 502.2922 | 5.26% | 0.00% |
| LPA 22:4 | 504.3078 | 5.27% | 0.00% |
| LPA 22:1 | 510.3554 | 0.00% | 0.00% |
| LPA 22:0 | 512.3710 | 5.29% | 0.00% |
| LPA P-24:0; LPA O-24:1 | 524.4074 | 0.00% | 0.00% |
| LPA O-24:0; LPA 23:0 | 526.3867 | 5.72% | 0.00% |
| LPA 24:1 | 538.3867 | 0.00% | 0.00% |
| LPA 24:0 | 540.4023 | 5.93% | 0.00% |
| LPA 25:0 | 554.4180 | 0.00% | 0.00% |
| LPA 26:0 | 568.4336 | 0.00% | 0.00% |
| LPA 27:0 | 582.4493 | 0.00% | 0.00% |
| LPA 28:0 | 596.4649 | 0.00% | 0.00% |
| PA 28:0 (IS) | 610.4442 | 0.00% | 0.00% |
| PA 29:0 | 624.4598 | 0.00% | 0.00% |

TABLE 19-continued

Database of lipid species monitored during the identification step in
the positive-ion mode together with the calculation of isotopic correction
for M + 1 and M + 2 isotopic peaks (so called deisotoping).

| Lipid | m/z | Isotopic correction M + 2 | Isotopic correction M + 1 |
| --- | --- | --- | --- |
| PA 30:1 | 636.4598 | 0.00% | 0.00% |
| PA 30:0 | 638.4755 | 8.35% | 0.00% |
| PA P-32:1; PA-31:2 | 648.4962 | 0.00% | 0.00% |
| PA P-32:0; PA-31:1 | 650.4755 | 8.96% | 0.00% |
| PA O-32:0; PA-31:0 | 652.4911 | 8.97% | 0.00% |
| PA 32:3; PA P-33:2 | 660.4598 | 0.00% | 0.00% |
| PA 32:2; PA P-33:1 | 662.4755 | 9.16% | 0.00% |
| PA 32:1; PA P-33:0 | 664.4911 | 9.17% | 0.00% |
| PA 32:0; PA O-33:0 | 666.5068 | 9.18% | 0.00% |
| PA P-34:1; PA 33:2 | 676.4911 | 0.00% | 0.00% |
| PA P-34:0; PA 33:1 | 678.5068 | 9.84% | 0.00% |
| PA O-34:0; PA 33:0 | 680.5224 | 9.85% | 0.00% |
| PA 34:4; PA P-35:3 | 686.4755 | 0.00% | 0.00% |
| PA 34:3; PA P-35:2 | 688.4911 | 10.03% | 0.00% |
| PA 34:2; PA P-35:1 | 690.5068 | 10.04% | 0.00% |
| PA 34:1; PA P-35:0 | 692.5224 | 10.05% | 0.00% |
| PA 34:0; PA P-36:6 | 694.5381 | 10.06% | 0.00% |
| PA P-36:5; PA 35:6 | 696.4599 | 10.72% | 0.00% |
| PA P-36:4; PA 35:5 | 698.4755 | 10.73% | 0.00% |
| PA P-36:3; PA 35:4 | 700.4911 | 10.74% | 0.00% |
| PA P-36:2; PA 35:3 | 702.5068 | 10.75% | 0.00% |
| PA P-36:1; PA 35:2 | 704.5224 | 10.76% | 0.00% |
| PA P-36:0; PA 35:1 | 706.5381 | 10.77% | 0.00% |
| PA 36:7; PA O-36:0; PA 35:0 | 708.5537 | 10.79% | 0.00% |
| PA 36:6; PA P-37:5 | 710.4755 | 10.93% | 0.00% |
| PA 36:5; PA P-37:4 | 712.4911 | 10.94% | 0.00% |
| PA 36:4; PA P-37:3 | 714.5068 | 10.95% | 0.00% |
| PA 36:3; PA P-37:2 | 716.5224 | 10.97% | 0.00% |
| PA 36:2; PA P-37:1 | 718.5381 | 10.98% | 0.00% |
| PA 36:1; PA P-37:0 | 720.5537 | 10.99% | 0.00% |
| PA 36:0; PA P-38:6 | 722.5694 | 11.00% | 0.00% |
| PA P-38:5; PA 37:6 | 724.4905 | 11.70% | 0.00% |
| PA P-38:4; PA 37:5 | 726.5062 | 11.71% | 0.00% |
| PA P-38:3; PA 37:4 | 728.5218 | 11.72% | 0.00% |
| PA P-38:2; PA 37:3 | 730.5381 | 11.73% | 0.00% |
| PA P-38:1; PA 37:2 | 732.5537 | 11.74% | 0.00% |
| PA P-38:0; PA 37:1 | 734.5694 | 11.75% | 0.00% |
| PA 38:7; PA O-38:0; PA 37:0 | 736.5850 | 11.76% | 0.00% |
| PA 38:6; PA P-39:5 | 738.5068 | 11.91% | 0.00% |
| PA 38:5; PA P-39:4 | 740.5225 | 11.92% | 0.00% |
| PA 38:4; PA P-40:10; PA P-29:3 | 742.5381 | 11.93% | 0.00% |
| PA 38:3; PA P-40:9; PA P-39:2 | 744.5537 | 11.941% | 0.00% |
| PA 38:2; PA P-40:8; PA P-39:1 | 746.5694 | 11.95% | 0.00% |
| PA 38:1; PA P-40:7; PA P-39:0 | 748.5850 | 11.97% | 0.00% |
| PA 38:0; PA P-40:6; PA O-39:0 | 750.6007 | 11.98% | 0.00% |
| PA P-40:5; PA 39:6 | 752.5225 | 12.72% | 0.00% |
| PA P-40:4; PA 39:5 | 754.5381 | 12.73% | 0.00% |
| PA P-40:3; PA 39:4 | 756.5537 | 12.74% | 0.00% |
| PA 40:10; PA P-40:2; PA 39:3 | 758.4755 | 12.76% | 0.00% |
| PA 40:9; PA P-40:1; PA 39:2 | 760.4912 | 12.90% | 0.00% |
| PA 40:8; PA P-40:0; PA 39:1 | 762.5068 | 12.91% | 0.00% |
| PA 40:7; PA O-40:0; PA 39:0 | 764.5224 | 12.92% | 0.00% |
| PA 40:6; PA P-41:5 | 766.5381 | 12.93% | 0.00% |
| PA 40:5; PA P-41:4 | 768.5538 | 12.95% | 0.00% |
| PA 40:4; PA P-42:10; PA P-41:3 | 770.5694 | 12.96% | 0.00% |
| PA 40:3; PA P-42:9; PA P-41:2 | 772.5851 | 12.97% | 0.00% |
| PA 40:2; PA P-42:8; PA P-41:1 | 774.6007 | 12.98% | 0.00% |
| PA 40:1; PA P-42:7; PA P-41:0 | 776.6163 | 12.99% | 0.00% |
| PA 40:0; PA P-42:6; PA O-41:0 | 778.6320 | 13.01% | 0.00% |
| PA P-42:5; PA 41:6 | 780.5537 | 13.79% | 0.00% |
| PA P-42:4; PA 41:5 | 782.5694 | 13.81% | 0.00% |
| PA P-42:3; PA 41:4 | 784.5850 | 13.82% | 0.00% |
| PA 42:10; PA P-42:2; PA 41:3 | 786.5068 | 13.83% | 0.00% |
| PA 42:9; PA P-42:1; PA 41:2 | 788.5225 | 13.97% | 0.00% |
| PA 42:8; PA P-42:0; PA 41:1 | 790.5381 | 13.98% | 0.00% |
| PA 42:7; PA O-42:0 | 792.5537 | 13.99% | 0.00% |
| PA 42:6; PA P-43:5 | 794.5694 | 14.01% | 0.00% |
| PA 42:5; PA P-43:4 | 796.5850 | 14.02% | 0.00% |
| PA 42:4; PA P-43:3 | 798.6007 | 14.03% | 0.00% |
| PA 42:3; PA P-43:2 | 800.6163 | 14.05% | 0.00% |
| PA 42:2; PA P-43:1 | 802.6320 | 14.06% | 0.00% |
| PA 42:1; PA P-43:0 | 804.6476 | 14.07% | 0.00% |

TABLE 19-continued

Database of lipid species monitored during the identification step in
the positive-ion mode together with the calculation of isotopic correction
for M + 1 and M + 2 isotopic peaks (so called deisotoping).

| | | Isotopic correction | |
|---|---|---|---|
| Lipid | m/z | M + 2 | M + 1 |
| PA 42:0; PA O-43:0 | 806.6633 | 14.08% | 0.00% |
| PA 44:0 | 834.6946 | 0.00% | 0.00% |
| S1P d16:1 | 374.2067 | 0.00% | 0.00% |
| S1P d16:0 | 376.2223 | 2.60% | 0.00% |
| S1P d17:0 | 386.2067 | 0.00% | 0.00% |
| S1P d17:1 | 388.2223 | 2.80% | 0.00% |
| S1P d18:2 | 400.2223 | 0.00% | 0.00% |
| S1P d18:1 | 402.2380 | 3.01% | 0.00% |
| S1P d18:0 | 404.2536 | 3.02% | 0.00% |
| S1P d19:1 | 414.2380 | 0.00% | 0.00% |
| S1P d19:0 | 416.2531 | 3.24% | 0.00% |
| S1P d20:1 | 430.2693 | 0.00% | 0.00% |
| S1P d20:0 | 432.2849 | 3.48% | 0.00% |
| LPS 6:0 | 358.1261 | 0.00% | 0.00% |
| LPS 8:0 | 386.1574 | 0.00% | 0.00% |
| LPS 10:0 | 414.1887 | 0.00% | 0.00% |
| LPS 12:0 | 442.2200 | 0.00% | 0.00% |
| LPS 14:0 | 470.2513 | 0.00% | 0.00% |
| LPS P-16:0; LPS O-16:1 | 482.2877 | 0.00% | 0.00% |
| LPS O-16:0; LPS 15:0 | 484.2670 | 4.64% | 0.00% |
| LPS 16:2 | 494.2513 | 0.00% | 0.00% |
| LPS 16:1 | 496.2670 | 4.84% | 0.00% |
| LPS 16:0 | 498.2826 | 4.85% | 0.00% |
| LPS P-18:0; LPS O-18:1; LPS 17:1 (IS) | 510.3196 | 0.00% | 0.00% |
| LPS O-18:0; LPS 17:0 | 512.2983 | 5.20% | 0.00% |
| LPS 18:4 | 518.2513 | 0.00% | 0.00% |
| LPS 18:3 | 520.2670 | 5.39% | 0.00% |
| LPS 18:2 | 522.2826 | 5.40% | 0.00% |
| LPS 18:1 | 524.2983 | 5.40% | 0.00% |
| LPS 18:0 | 526.3139 | 5.41% | 0.00% |
| LPS P-20:0; LPS O-20:1 | 538.3503 | 0.00% | 0.00% |
| LPS O-20:0; LPS 19:0 | 540.3296 | 5.81% | 0.00% |
| LPS 20:5 | 544.2664 | 0.00% | 0.00% |
| LPS 20:4 | 546.2821 | 6.00% | 0.00% |
| LPS 20:3 | 548.2977 | 6.00% | 0.00% |
| LPS 20:2 | 550.3139 | 6.01% | 0.00% |
| LPS 20:1 | 552.3296 | 6.02% | 0.00% |
| LPS 20:0 | 554.3452 | 6.02% | 0.00% |
| LPS P-22:0; LPS O-22:1 | 566.3816 | 0.00% | 0.00% |
| LPS O-22:0; LPS 21:0 | 568.3609 | 6.48% | 0.00% |
| LPS 22:6 | 570.2826 | 6.48% | 0.00% |
| LPS 22:5 | 572.2977 | 6.65% | 0.00% |
| LPS 22:4 | 574.3133 | 6.66% | 0.00% |
| LPS 22:1 | 580.3609 | 0.00% | 0.00% |
| LPS 22:0 | 582.3765 | 6.69% | 0.00% |
| LPS P-24:0; LPS O-24:1 | 594.4129 | 0.00% | 0.00% |
| LPS O-24:0; LPS 23:0 | 596.3922 | 7.19% | 0.00% |
| LPS 24:1 | 608.3922 | 0.00% | 0.00% |
| LPS 24:0 | 610.4078 | 7.40% | 0.00% |
| LPS 25:0 | 624.4235 | 0.00% | 0.00% |
| LPS 26:0 | 638.4391 | 0.00% | 0.00% |
| LPS 27:0 | 652.4548 | 0.00% | 0.00% |
| LPS 28:0 | 666.4704 | 0.00% | 0.00% |
| PS 28:0 (IS) | 680.4497 | 0.00% | 0.00% |
| PS 29:0 | 694.4653 | 0.00% | 0.00% |
| PS 30:1 | 706.4653 | 0.00% | 0.00% |
| PS 30:0 | 708.4810 | 10.04% | 0.00% |
| PS P-32:1; PS-31:2 | 718.5017 | 0.00% | 0.00% |
| PS P-32:0; PS-31:1 | 720.4810 | 10.72% | 0.00% |
| PS O-32:0; PS-3L0 | 722.4966 | 10.73% | 0.00% |
| PS 32:3; PS P-33:2 | 730.4653 | 0.00% | 0.00% |
| PS 32:2; PS P-33:1 | 732.4810 | 10.92% | 0.00% |
| PS 32:1; PS P-33:0 | 734.4966 | 10.93% | 0.00% |
| PS 32:0; PS O-33:0 | 736.5123 | 10.94% | 0.00% |
| PS P-34:1; PS 33:2 | 746.4966 | 0.00% | 0.00% |
| PS P-34:0; PS 33:1 | 748.5123 | 11.68% | 0.00% |
| PS O-34:0; PS 33:0 | 750.5279 | 11.69% | 0.00% |
| PS 34:4; PS P-35:3 | 756.4810 | 0.00% | 0.00% |
| PS 34:3; PS P-35:2 | 758.4966 | 11.87% | 0.00% |
| PS 34:2; PS P-35:1 | 760.5123 | 11.88% | 0.00% |
| PS 34:1; PS P-35:0 | 762.5279 | 11.89% | 0.00% |
| PS 34:0; PS P-36:6 | 764.5436 | 11.90% | 0.00% |

TABLE 19-continued

Database of lipid species monitored during the identification step in
the positive-ion mode together with the calculation of isotopic correction
for M + 1 and M + 2 isotopic peaks (so called deisotoping).

| Lipid | m/z | Isotopic correction M + 2 | Isotopic correction M + 1 |
|---|---|---|---|
| PS P-36:5; PS 35:6 | 766.4654 | 12.67% | 0.00% |
| PS P-36:4; PS 35:5 | 768.4810 | 12.64% | 0.00% |
| PS P-36:3; PS 35:4 | 770.4966 | 12.65% | 0.00% |
| PS P-36:2; PS 35:3 | 772.5123 | 12.66% | 0.00% |
| PS P-36:1; PS 35:2 | 774.5279 | 12.67% | 0.00% |
| PS P-36:0; PS 35:1 | 776.5436 | 12.68% | 0.00% |
| PS 36:7; PS O-36:0; PS 35:0 | 778.5593 | 12.69% | 0.00% |
| PS 36:6; PS P-37:5 | 780.4810 | 12.84% | 0.00% |
| PS 36:5; PS P-37:4 | 782.4966 | 12.85% | 0.00% |
| PS 36:4; PS P-37:3 | 784.5123 | 12.86% | 0.00% |
| PS 36:3; PS P-37:2 | 786.5279 | 12.87% | 0.00% |
| PS 36:2; PS P-37:1 | 788.5436 | 12.88% | 0.00% |
| PS 36:1; PS P-37:0 | 790.5593 | 12.90% | 0.00% |
| PS 36:0; PS P-38:6 | 792.5749 | 12.91% | 0.00% |
| PS P-38:5; PS 37:6 | 794.4961 | 13.68% | 0.00% |
| PS P-38:4; PS 37:5 | 796.5118 | 13.69% | 0.00% |
| PS P-38:3; PS 37:4 | 798.5274 | 13.70% | 0.00% |
| PS P-38:2; PS 37:3 | 800.5436 | 13.71% | 0.00% |
| PS P-38:1; PS 37:2 | 802.5593 | 13.72% | 0.00% |
| PS P-38:0; PS 37:1 | 804.5749 | 13.74% | 0.00% |
| PS 38:7; PS O-38:0; PS 37:0 | 806.5906 | 13.75% | 0.00% |
| PS 38:6; PS P-39:5 | 808.5123 | 13.89% | 0.00% |
| PS 38:5; PS P-39:4 | 810.5280 | 13.90% | 0.00% |
| PS 38:4; PS P-40:10; PS P-29:3 | 812.5436 | 13.91% | 0.00% |
| PS 38:3; PS P-40:9; PS P-39:2 | 814.5593 | 13.925% | 0.00% |
| PS 38:2; PS P-40:8; PS P-39:1 | 816.5749 | 13.94% | 0.00% |
| PS 38:1; PS P-40:7; PS P-39:0 | 818.5906 | 13.95% | 0.00% |
| PS 38:0; PS P-40:6, PS O-39:0 | 820.6062 | 13.96% | 0.00% |
| PS P-40:5; PS 39:6 | 822.5280 | 14.78% | 0.00% |
| PS P-40:4; PS 39:5 | 824.5436 | 14.79% | 0.00% |
| PS P-40:3; PS 39:4 | 826.5593 | 14.80% | 0.00% |
| PS 40:10; PS P-40:2; PS 39:3 | 828.4810 | 14.81% | 0.00% |
| PS 40:9; PS P-40:1; PS 39:2 | 830.4967 | 14.95% | 0.00% |
| PS 40:8; PS P-40:0; PS 39:1 | 832.5123 | 14.96% | 0.00% |
| PS 40:7; PS O-40:0; PS 39:0 | 834.5279 | 14.98% | 0.00% |
| PS 40:6; PS P-41:5 | 836.5436 | 14.99% | 0.00% |
| PS 40:5; PS P-41:4 | 838.5593 | 15.00% | 0.00% |
| PS 40:4; PS P-42:10; PS P-41:3 | 840.5749 | 15.01% | 0.00% |
| PS 40:3; PS P-42:9; PS P-41:2 | 842.5906 | 15.03% | 0.00% |
| PS 40:2; PS P-42:8; PS P-41:1 | 844.6062 | 15.04% | 0.00% |
| PS 40:1; PS P-42:7; PS P-41:0 | 846.6219 | 15.05% | 0.00% |
| PS 40:0; PS P-42:6, PS O-41:0 | 848.6375 | 15.06% | 0.00% |
| PS P-42:5; PS 41:6 | 850.5593 | 15.92% | 0.00% |
| PS P-42:4; PS 41:5 | 852.5749 | 15.94% | 0.00% |
| PS P-42:3; PS 41:4 | 854.5906 | 15.95% | 0.00% |
| PS 42:10; PS P-42:2; PS 41:3 | 856.5123 | 15.96% | 0.00% |
| PS 42:9; PS P-42:1; PS 41:2 | 858.5280 | 16.10% | 0.00% |
| PS 42:8; PS P-42:0; PS 41:1 | 860.5436 | 16.11% | 0.00% |
| PS 42:7; PS O-42:0 | 862.5593 | 16.12% | 0.00% |
| PS 42:6; PS P-43:5 | 864.5749 | 16.14% | 0.00% |
| PS 42:5; PS P-43:4 | 866.5906 | 16.15% | 0.00% |
| PS 42:4; PS P-43:3 | 868.6062 | 16.16% | 0.00% |
| PS 42:3; PS P-43:2 | 870.6219 | 16.18% | 0.00% |
| PS 42:2; PS P-43:1 | 872.6375 | 16.19% | 0.00% |
| PS 42:1; PS P-43:0 | 874.6532 | 16.20% | 0.00% |
| PS 42:0; PS O-43:0 | 876.6688 | 16.21% | 0.00% |
| PS 44:0 | 904.7001 | 0.00% | 0.00% |
| LPG 6:0 | 362.1574 | 0.00% | 0.00% |
| LPG 8:0 | 390.1887 | 0.00% | 0.00% |
| LPG 10:0 | 418.2200 | 0.00% | 0.00% |
| LPG 12:0 | 446.2513 | 0.00% | 0.00% |
| LPG 14:0 (IS) | 474.2826 | 0.00% | 0.00% |
| LPGP-16:0; LPG O-16:1 | 486.3190 | 0.00% | 0.00% |
| LPG O-16:0; LPG 15:0 | 488.2983 | 4.65% | 0.00% |
| LPG 16:2 | 498.2826 | 0.00% | 0.00% |
| LPG 16:1 | 500.2983 | 4.85% | 0.00% |
| LPG 16:0 | 502.3139 | 4.86% | 0.00% |
| LPG P-18:0; LPG O-18:1; LPG 17:1 | 514.3508 | 0.00% | 0.00% |
| LPG O-18:0; LPG 17:0 | 516.3296 | 5.21% | 0.00% |
| LPG 18:4 | 522.2826 | 0.00% | 0.00% |
| LPG 18:3 | 524.2983 | 5.40% | 0.00% |
| LPG 18:2 | 526.3139 | 5.41% | 0.00% |

TABLE 19-continued

Database of lipid species monitored during the identification step in the positive-ion mode together with the calculation of isotopic correction for M + 1 and M + 2 isotopic peaks (so called deisotoping).

| Lipid | m/z | Isotopic correction M + 2 | Isotopic correction M + 1 |
|---|---|---|---|
| LPG 18:1 | 528.3296 | 5.42% | 0.00% |
| LPG 18:0 | 530.3452 | 5.42% | 0.00% |
| LPG P-20:0; LPG O-20:1 | 542.3816 | 0.00% | 0.00% |
| LPG O-20:0; LPG 19:0 | 544.3609 | 5.83% | 0.00% |
| LPG 20:5 | 548.2977 | 0.00% | 0.00% |
| LPG 20:4 | 550.3134 | 6.01% | 0.00% |
| LPG 20:3 | 552.3290 | 6.02% | 0.00% |
| LPG 20:2 | 554.3452 | 6.02% | 0.00% |
| LPG 20:1 | 556.3609 | 6.03% | 0.00% |
| LPG 20:0 | 558.3765 | 6.04% | 0.00% |
| LPGP-22:0; LPG O-22:1 | 570.4129 | 0.00% | 0.00% |
| LPG O-22:0; LPG 21:0 | 572.3922 | 6.49% | 0.00% |
| LPG 22:6 | 574.3139 | 6.50% | 0.00% |
| LPG 22:5 | 576.3290 | 6.67% | 0.00% |
| LPG 22:4 | 578.3446 | 6.67% | 0.00% |
| LPG 22:1 | 584.3922 | 0.00% | 0.00% |
| LPG 22:0 | 586.4078 | 6.70% | 0.00% |
| LPG P-24:0; LPG O-24:1 | 598.4442 | 0.00% | 0.00% |
| LPG O-24:0; LPG 23:0 | 600.4235 | 7.20% | 0.00% |
| LPG 24:1 | 612.4235 | 0.00% | 0.00% |
| LPG 24:0 | 614.4391 | 7.41% | 0.00% |
| LPG 25:0 | 628.4548 | 0.00% | 0.00% |
| LPG 26:0 | 642.4704 | 0.00% | 0.00% |
| LPG 27:0 | 656.4861 | 0.00% | 0.00% |
| LPG 28:0 | 670.5017 | 0.00% | 0.00% |
| PG 28:0 | 684.4810 | 0.00% | 0.00% |
| PG 29:0 | 698.4966 | 0.00% | 0.00% |
| PG 30:1 | 710.4966 | 0.00% | 0.00% |
| PG 30:0 | 712.5123 | 10.06% | 0.00% |
| PG P-32:1; PG-31:2 | 722.5330 | 0.00% | 0.00% |
| PG P-32:0; PG-31:1 | 724.5123 | 10.74% | 0.00% |
| PG O-32:0; PG-31:0 | 726.5279 | 10.75% | 0.00% |
| PG 32:3; PG P-33:2 | 734.4966 | 0.00% | 0.00% |
| PG 32:2; PG P-33:1 | 736.5123 | 10.94% | 0.00% |
| PG 32:1; PG P-33:0 | 738.5279 | 10.96% | 0.00% |
| PG 32:0; PG O-33:0 | 740.5436 | 10.97% | 0.00% |
| PG P-34:1; PG 33:2 | 750.5279 | 0.00% | 0.00% |
| PG P-34:0; PG 33:1 | 752.5436 | 11.70% | 0.00% |
| PG O-34:0; PG 33:0 | 754.5592 | 11.71% | 0.00% |
| PG 34:4; PG P-35:3 | 760.5123 | 0.00% | 0.00% |
| PG 34:3; PG P-35:2 | 762.5279 | 11.89% | 0.00% |
| PG 34:2; PG P-35:1 | 764.5436 | 11.90% | 0.00% |
| PG 34:1; PG P-35:0 | 766.5592 | 11.91% | 0.00% |
| PG 34:0; PG P-36:6 | 768.5749 | 11.92% | 0.00% |
| PG P-36:5; PG 35:6 | 770.4967 | 12.65% | 0.00% |
| PG P-36:4; PG 35:5 | 772.5123 | 12.66% | 0.00% |
| PG P-36:3; PG 35:4 | 774.5279 | 12.67% | 0.00% |
| PG P-36:2; PG 35:3 | 776.5436 | 12.68% | 0.00% |
| PG P-36:1; PG 35:2 | 778.5592 | 12.69% | 0.00% |
| PG P-36:0; PG 35:1 | 780.5749 | 12.70% | 0.00% |
| PG 36:7; PG O-36:0; PG 35:0 | 782.5905 | 12.72% | 0.00% |
| PG 36:6; PG P-37:5 | 784.5123 | 12.86% | 0.00% |
| PG 36:5; PG P-37:4 | 786.5279 | 12.87% | 0.00% |
| PG 36:4; PG P-37:3 | 788.5436 | 12.88% | 0.00% |
| PG 36:3; PG P-37:2 | 790.5592 | 12.90% | 0.00% |
| PG 36:2; PG P-37:1 | 792.5749 | 12.91% | 0.00% |
| PG 36:1; PG P-37:0 | 794.5905 | 12.92% | 0.00% |
| PG 36:0; PG P-38:6 | 796.6062 | 12.93% | 0.00% |
| PG P-38:5; PG 37:6 | 798.5273 | 13.70% | 0.00% |
| PG P-38:4; PG 37:5 | 800.5430 | 13.71% | 0.00% |
| PG P-38:3; PG 37:4 | 802.5586 | 13.72% | 0.00% |
| PG P-38:2; PG 37:3 | 804.5749 | 13.73% | 0.00% |
| PG P-38:1; PG 37:2 | 806.5905 | 13.75% | 0.00% |
| PG P-38:0; PG 37:1 | 808.6062 | 13.76% | 0.00% |
| PG 38:7; PG O-38:0; PG 37:0 | 810.6218 | 13.77% | 0.00% |
| PG 38:6; PG P-39:5 | 812.5436 | 13.91% | 0.00% |
| PG 38:5; PG P-39:4 | 814.5593 | 13.92% | 0.00% |
| PG 38:4; PG P-40:10; PG P-29:3 | 816.5749 | 13.94% | 0.00% |
| PG 38:3; PG P-40:9; PG P-39:2 | 818.5905 | 13.95% | 0.00% |
| PG 38:2; PG P-40:8; PG P-39:1 | 820.6062 | 13.96% | 0.00% |
| PG 38:1; PG P-40:7; PG P-39:0 | 822.6218 | 13.97% | 0.00% |
| PG 38:0; PG P-40:6, PG O-39:0 | 824.6375 | 13.98% | 0.00% |

TABLE 19-continued

Database of lipid species monitored during the identification step in the positive-ion mode together with the calculation of isotopic correction for M + 1 and M + 2 isotopic peaks (so called deisotoping).

| Lipid | m/z | Isotopic correction M + 2 | Isotopic correction M + 1 |
|---|---|---|---|
| PG P-40:5; PG 39:6 | 826.5593 | 14.80% | 0.00% |
| PG P-40:4; PG 39:5 | 828.5749 | 14.81% | 0.00% |
| PG P-40:3; PG 39:4 | 830.5905 | 14.82% | 0.00% |
| PG 40:10; PG P-40:2; PG 39:3 | 832.5123 | 14.84% | 0.00% |
| PG 40:9; PG P-40:1; PG 39:2 | 834.5280 | 14.98% | 0.00% |
| PG 40:8; PG P-40:0; PG 39:1 | 836.5436 | 14.99% | 0.00% |
| PG 40:7; PG O-40:0; PG 39:0 | 838.5592 | 15.00% | 0.00% |
| PG 40:6; PG P-41:5 | 840.5749 | 15.01% | 0.00% |
| PG 40:5; PG P-41:4 | 842.5906 | 15.03% | 0.00% |
| PG 40:4; PG P-42:10; PG P-41:3 | 844.6062 | 15.04% | 0.00% |
| PG 40:3; PG P-42:9; PG P-41:2 | 846.6219 | 15.05% | 0.00% |
| PG 40:2; PG P-42:8; PG P-41:1 | 848.6375 | 15.06% | 0.00% |
| PG 40:1; PG P-42:7; PG P-41:0 | 850.6531 | 15.07% | 0.00% |
| PG 40:0; PG P-42:6; PG O-41:0 | 852.6688 | 15.09% | 0.00% |
| PG P-42:5; PG 41:6 | 854.5905 | 15.96% | 0.00% |
| PG P-42:4; PG 41:5 | 856.6062 | 15.97% | 0.00% |
| PG P-42:3; PG 41:4 | 858.6218 | 15.99% | 0.00% |
| PG 42:10; PG P-42:2; PG 41:3 | 860.5436 | 16.00% | 0.00% |
| PG 42:9; PG P-42:1; PG 41:2 | 862.5593 | 16.14% | 0.00% |
| PG 42:8; PG P-42:0; PG 41:1 | 864.5749 | 16.15% | 0.00% |
| PG 42:7; PG O-42:0 | 866.5905 | 16.16% | 0.00% |
| PG 42:6; PG P-43:5 | 868.6062 | 16.17% | 0.00% |
| PG 42:5; PG P-43:4 | 870.6218 | 16.19% | 0.00% |
| PG 42:4; PG P-43:3 | 872.6375 | 16.20% | 0.00% |
| PG 42:3; PG P-43:2 | 874.6531 | 16.21% | 0.00% |
| PG 42:2; PG P-43:1 | 876.6688 | 16.23% | 0.00% |
| PG 42:1; PG P-43:0 | 878.6844 | 16.24% | 0.00% |
| PG 42:0; PG O-43:0 | 880.7001 | 16.25% | 0.00% |
| PG 44:0 | 908.7314 | 0.00% | 0.00% |

* mass-to-charge (m/z) of $[M + H]^+$; $[M + Na]^+$; $[M + NH_4]^+$; or $[M + NH_4-H_2O]^+$ depending on individual lipid (sub)class.

TABLE 20

Database of lipid species monitored during the identification step in the negative-ion mode together with the calculation of isotopic correction for M + 1 and M + 2 isotopic peaks (so called deisotoping).

| Lipid | m/z | Isotopic correction M + 2 | Isotopic correction M + 1 |
|---|---|---|---|
| SulfoHexCer 34:1 | 778.5145 | 0.00% | 0.00% |
| SulfoHexCer 34:2 (OH) | 792.4937 | 0.00% | 0.00% |
| SulfoHexCer 35:1 | 792.5301 | 0.00% | 0.00% |
| SulfoHexCer 34:1 (OH) | 794.5094 | 17.5% | 0.00% |
| SulfoHexCer 35:0 | 794.5458 | 17.5% | 0.00% |
| SulfoHexCer 34:0 (OH) | 796.5250 | 17.51% | 0.00% |
| SulfoHexCer 36:2 | 804.5301 | 0.00% | 0.00% |
| SulfoHexCer 36:1 | 806.5458 | 18% | 0.00% |
| SulfoHexCer 36:2 (OH) | 820.5250 | 0.00% | 0.00% |
| SulfoHexCer 37:1 | 820.5614 | 0.00% | 0.00% |
| SulfoHexCer 36:1 (OH) | 822.5407 | 18.55% | 0.00% |
| SulfoHexCer 38:2 | 832.5614 | 0.00% | 0.00% |
| SulfoHexCer 38:1 | 834.5771 | 19.01% | 0.00% |
| SulfoHexCer 39:1 | 848.5927 | 0.00% | 0.00% |
| SulfoHexCer 38:1 (OH) | 850.5720 | 19.65% | 0.00% |
| SulfoHexCer 40:2 | 860.5927 | 0.00% | 0.00% |
| SulfoHexCer 40:1 | 862.6084 | 20.19% | 0.00% |
| SulfoHexCer 39:1 (OH) | 864.5876 | 20.21% | 0.00% |
| SulfoHexCer 41:2 | 874.6084 | 0.00% | 0.00% |
| SulfoHexCer 40:2 (OH) | 876.5876 | 20.78% | 0.00% |
| SulfoHexCer 41:1 | 876.6240 | 20.78% | 0.00% |
| SulfoHexCer 40:1 (OH) | 878.6033 | 20.79% | 0.00% |
| SulfoHexCer 40:0 (OH) | 880.6189 | 20.44% | 0.00% |
| SulfoHexCer 42:4 | 884.5927 | 0.00% | 0.00% |
| SulfoHexCer 42:3 | 886.6084 | 21.34% | 0.00% |
| SulfoHexCer 42:2 | 888.6240 | 21.35% | 0.00% |
| SulfoHexCer 41:2 (OH) | 890.6033 | 21.36% | 0.00% |
| SulfoHexCer 42:1 | 890.6397 | 21.36% | 0.00% |
| SulfoHexCer 41:1 (OH) | 892.6189 | 21.37% | 0.00% |
| SulfoHexCer 41:0 (OH) | 894.6346 | 21.02% | 0.00% |
| SulfoHexCer 40:0 (2OH) | 896.6138 | 21.03% | 0.00% |
| SulfoHexCer 42:3 (OH) | 902.6033 | 0.00% | 0.00% |
| SulfoHexCer 43:2 | 902.6397 | 0.00% | 0.00% |
| SulfoHexCer 42:2 (OH) | 904.6189 | 21.97% | 0.00% |
| SulfoHexCer 43:1 | 904.6553 | 21.97% | 0.00% |
| SulfoHexCer 42:1 (OH) | 906.6346 | 21.98% | 0.00% |
| SulfoHexCer 42:0 (OH) | 908.6502 | 21.61% | 0.00% |
| SulfoHexCer 41:0 (2OH) | 910.6295 | 21.62% | 0.00% |
| SulfoHexCer 44:3 | 914.6397 | 0.00% | 0.00% |
| SulfoHexCer 44:2 | 916.6553 | 22.57% | 0.00% |
| SulfoHexCer 43:2 (OH) | 918.6346 | 22.58% | 0.00% |
| SulfoHexCer 44:1 | 918.6710 | 22.58% | 0.00% |
| SulfoHexCer 43:1 (OH) | 920.6502 | 22.59% | 0.00% |
| SulfoHexCer 42:1 (2OH) | 922.6295 | 22.21% | 0.00% |
| SulfoHexCer 43:0 (OH) | 922.6659 | 22.21% | 0.00% |
| SulfoHexCer 42:0 (2OH) | 924.6451 | 22.22% | 0.00% |
| SulfoHexCer 44:2(OH) | 932.6502 | 0.00% | 0.00% |
| SulfoHexCer 44:1(OH) | 934.6659 | 22.81% | 0.00% |
| SulfoHexCer 43:1 (2OH) | 936.6451 | 22.82% | 0.00% |
| SulfoHexCer 44:0 (OH) | 936.6815 | 22.82% | 0.00% |
| SulfoHexCer 43:0 (2OH) | 938.6608 | 22.83% | 0.00% |
| SulfoHex$_2$Cer 32:1 | 912.5360 | 0.00% | 0.00% |
| SulfoHex$_2$Cer 33:1 | 926.5516 | 0.00% | 0.00% |
| SulfoHex$_2$Cer 34:2 | 938.5516 | 0.00% | 0.00% |
| SulfoHex$_2$Cer 34:1 | 940.5673 | 21.31% | 0.00% |
| SulfoHex$_2$Cer 35:1 | 954.5829 | 0.00% | 0.00% |

TABLE 20-continued

Database of lipid species monitored during the identification step in the negative-ion mode together with the calculation of isotopic correction for M + 1 and M + 2 isotopic peaks (so called deisotoping).

| Lipid | m/z | M + 2 | M + 1 |
|---|---|---|---|
| SulfoHex$_2$Cer 34:1 (OH) | 956.5622 | 21.9% | 0.00% |
| SulfoHex$_2$Cer 36:2 | 966.5829 | 21.9% | 0.00% |
| SulfoHex$_2$Cer 36:1 | 968.5986 | 22% | 0.00% |
| SulfoHex$_2$Cer 37:1 | 982.6142 | 0.00% | 0.00% |
| SulfoHex$_2$Cer 36:1 (OH) | 984.5935 | 23.1% | 0.00% |
| SulfoHex$_2$Cer 38:2 | 994.6142 | 0.00% | 0.00% |
| SSulfoHex$_2$Cer 38:1 | 996.6299 | 23.71% | 0.00% |
| SulfoHex$_2$Cer 39:1 | 1010.6455 | 0.00% | 0.00% |
| SulfoHex$_2$Cer 38:1 (OH) | 1012.6248 | 24.35% | 0.00% |
| SulfoHex$_2$Cer 40:3 | 1020.6299 | 0.00% | 0.00% |
| SulfoHex$_2$Cer 40:2 | 1022.6455 | 24.96% | 0.00% |
| SulfoHex$_2$Cer 40:1 | 1024.6612 | 24.97% | 0.00% |
| SulfoHex$_2$Cer 41:3 | 1034.6455 | 24.97% | 0.00% |
| SulfoHex$_2$Cer 41:2 | 1036.6612 | 24.98% | 0.00% |
| SulfoHex$_2$Cer 40:2 (OH) | 1038.6404 | 24.99% | 0.00% |
| SulfoHex$_2$Cer 41:1 | 1038.6768 | 24.99% | 0.00% |
| SulfoHex$_2$Cer 40:1 (OH) | 1040.6561 | 25% | 0.00% |
| SulfoHex$_2$Cer 40:0 (OH) | 1042.6717 | 25.1% | 0.00% |
| SulfoHex$_2$Cer 42:4 | 1046.6455 | 0.00% | 0.00% |
| SulfoHex$_2$Cer 42:3 | 1048.6612 | 26.27% | 0.00% |
| SulfoHex$_2$Cer 42:2 | 1050.6768 | 26.28% | 0.00% |
| SulfoHex$_2$Cer 42:1 | 1052.6925 | 26.28% | 0.00% |
| SulfoHex$_2$Cer 42:3 (OH) | 1064.6561 | 0.00% | 0.00% |
| SulfoHex$_2$Cer 43:2 | 1064.6925 | 0.00% | 0.00% |
| SulfoHex$_2$Cer 42:2 (OH) | 1066.6717 | 26.98% | 0.00% |
| SulfoHex$_2$Cer 43:1 | 1066.7081 | 26.98% | 0.00% |
| SulfoHex$_2$Cer 42:1 (OH) | 1068.6874 | 26.99% | 0.00% |
| SulfoHex$_2$Cer 42:0 (OH) | 1070.7030 | 27% | 0.00% |
| SulfoHex$_2$Cer 44:4 | 1074.6770 | 0.00% | 0.00% |
| SulfoHex$_2$Cer 44:3 | 1076.6925 | 27.63% | 0.00% |
| SulfoHex$_2$Cer 44:2 | 1078.7081 | 27.64% | 0.00% |
| SulfoHex$_2$Cer 43:2 (OH) | 1080.6874 | 27.65% | 0.00% |
| SulfoHex$_2$Cer 44:1 | 1080.7238 | 27.65% | 0.00% |
| SulfoHex$_2$Cer 42:1 (2*OH) | 1084.6823 | 0.00% | 0.00% |
| SulfoHex$_2$Cer 44:2 (OH) | 1094.7030 | 0.00% | 0.00% |
| SulfoHexNAcHex2Cer 34:1 | 1143.6467 | 0.00% | 0.00% |
| SulfoHexNAcHex2Cer 38:1 | 1199.7093 | 0.00% | 0.00% |
| SulfoHexNAcHex2Cer 40:2 | 1225.7249 | 0.00% | 0.00% |
| SulfoHexNAcHex2Cer 40:1 | 1227.7406 | 31.93% | 0.00% |
| SulfoHexNAcHex2Cer 41:2 | 1239.7406 | 0.00% | 0.00% |
| SulfoHexNAcHex2Cer 41:1 | 1241.7562 | 32.69% | 0.00% |
| SulfoHexNAcHex2Cer 42:4 | 1249.7249 | 0.00% | 0.00% |
| SulfoHexNAcHex2Cer 42:3 | 1251.7406 | 33.43% | 0.00% |
| SulfoHexNAcHex2Cer 42:2 | 1253.7562 | 33.44% | 0.00% |
| SulfoHexNAcHex2Cer 42:1 | 1255.7719 | 33.45% | 0.00% |
| SulfoHexNAcHex2Cer 44:3 | 1279.7719 | 0.00% | 0.00% |
| SulfoHexNAcHex2Cer 44:2 | 1281.7875 | 0.00% | 0.00% |
| SulfoHexNAcHex4Cer 38:1 | 1523.8149 | 0.00% | 0.00% |
| SulfoHexNAcHex4Cer 40:2 | 1549.8306 | 0.00% | 0.00% |
| SulfoHexNAcHex4Cer 40:1 | 1551.8462 | 44.15% | 0.00% |
| SulfoHexNAcHex4Cer 41:2 | 1563.8462 | 0.00% | 0.00% |
| SulfoHexNAcHex4Cer 41:1 | 1565.8619 | 45.05% | 0.00% |
| SulfoHexNAcHex4Cer 42:3 | 1575.8462 | 0.00% | 0.00% |
| SulfoHexNAcHex4Cer 42:2 | 1577.8618 | 45.95% | 0.00% |
| SulfoHexNAcHex4Cer 42:1 | 1579.8775 | 45.97% | 0.00% |
| SulfoHexNAcHex4Cer 42:2 (OH) | 1593.8568 | 0.00% | 0.00% |
| SulfoHexNAcHex4Cer 42:1 (OH) | 1595.8724 | 46.2% | 0.00% |
| SulfoHexNAcHex3Cer 40:1 | 1389.7934 | 0.00% | 0.00% |
| SulfoHexNAcHex3Cer 42:2 | 1415.8090 | 0.00% | 0.00% |
| SulfoHexNAcHex3Cer 42:1 | 1417.8246 | 39.48% | 0.00% |
| SulfoHexNAcHex3Cer 42:2 (OH) | 1431.8039 | 0.00% | 0.00% |
| SulfoHexNAcHex3Cer 42:1 (OH) | 1433.8196 | 39.72% | 0.00% |
| GM3 32:1 | 1123.6746 | 0.00% | 0.00% |
| GM3 34:2 | 1149.6902 | 0.00% | 0.00% |
| GM3 34:1 | 1151.7059 | 24.68% | 0.00% |
| GM3 34:1 (OH) | 1167.7008 | 0.00% | 0.00% |
| GM3 36:2 | 1177.7215 | 0.00% | 0.00% |
| GM3 36:1 | 1179.7372 | 26.1% | 0.00% |
| GM3 36:1 (OH) | 1195.7321 | 0.00% | 0.00% |
| GM3 38:2 | 1205.7528 | 0.00% | 0.00% |
| GM3 38:1 | 1207.7685 | 27.6% | 0.00% |
| GM3 38:1 (OH) | 1223.7634 | 0.00% | 0.00% |
| GM3 40:2 | 1233.7841 | 0.00% | 0.00% |
| GM3 40:1 | 1235.7998 | 29.13% | 0.00% |
| GM3 41:2 | 1247.7998 | 0.00% | 0.00% |
| GM3 41:1 | 1249.8154 | 29.91% | 0.00% |
| GM3 40:1 (OH) | 1251.7947 | 29.93% | 0.00% |
| GM3 40:0 (OH) | 1253.8104 | 29.38% | 0.00% |
| GM3 42:3 | 1259.7998 | 0.00% | 0.00% |
| GM3 42:2 | 1261.8154 | 30.7% | 0.00% |
| GM3 42:1 | 1263.8311 | 30.71% | 0.00% |
| GM3 42:3 (OH) | 1275.7947 | 0.00% | 0.00% |
| GM3 42:2 (OH) | 1277.8103 | 30.9% | 0.00% |
| GM3 42:1 (OH) | 1279.8260 | 30.95% | 0.00% |
| PS 34:2 | 758.4977 | 0.00% | 0.00% |
| PS 34:1 | 760.5134 | 11.88% | 0.00% |
| PS 36:4 | 782.4977 | 0.00% | 0.00% |
| PS 36:2 | 786.5290 | 0.00% | 0.00% |
| PS 36:1 | 788.5447 | 12.88% | 0.00% |
| PS 38:4 | 810.5290 | 0.00% | 0.00% |
| PS 38:3 | 812.5447 | 13.91% | 0.00% |
| LPI 16:0 (IS) | 571.2889 | 0.00% | 0.00% |
| LPI 18:1 | 597.3045 | 0.00% | 0.00% |
| LPI 18:0 | 599.3202 | 6.87% | 0.00% |
| LPI 20:4 | 619.2889 | 0.00% | 0.00% |
| PI 32:1 (IS) | 807.5029 | 0.00% | 0.00% |
| PI 32:0 | 809.5185 | 12.88% | 0.00% |
| PI 34:2 | 833.5185 | 0.00% | 0.00% |
| PI 34:1 | 835.5342 | 13.89% | 0.00% |
| PI 34:0 | 837.5498 | 13.9% | 0.00% |
| PI 35:2 | 847.5342 | 0.00% | 0.00% |
| PI 35:1 | 849.5498 | 14.42% | 0.00% |
| PI 36:4 | 857.5185 | 0.00% | 0.00% |
| PI 36:3 | 859.5342 | 14.94% | 0.00% |
| PI 36:2 | 861.5498 | 14.95% | 0.00% |
| PI 36:1 | 863.5655 | 14.96% | 0.00% |
| PI 37:4 | 871.5342 | 0.00% | 0.00% |
| PI 37:3 | 873.5498 | 15.49% | 0.00% |
| PI 38:6 | 881.5185 | 0.00% | 0.00% |
| PI 38:5 | 883.5342 | 16.03% | 0.00% |
| PI 38:4 | 885.5498 | 16.05% | 0.00% |
| PI 38:3 | 887.5655 | 16.06% | 0.00% |
| PI 40:6 | 909.5498 | 0.00% | 0.00% |
| PI 40:5 | 911.5655 | 17.2% | 0.00% |
| PI 40:4 | 913.5811 | 17.21% | 0.00% |
| PG 32:0 (IS) | 721.5025 | 0.00% | 0.00% |
| PG 34:4 | 741.4712 | 0.00% | 0.00% |
| PG 34:3 | 743.4869 | 11.7% | 0.00% |
| PG 34:2 | 745.5025 | 11.71% | 0.00% |
| PG 34:1 | 747.5181 | 11.72% | 0.00% |
| PG 35:1 | 761.5338 | 0.00% | 0.00% |
| PG 36:4 | 769.5025 | 0.00% | 0.00% |
| PG 36:3 | 771.5181 | 12.69% | 0.00% |
| PG 36:2 | 773.5338 | 11.7% | 0.00% |
| PG 36:1 | 775.5494 | 11.71% | 0.00% |
| PG 38:5 | 795.5181 | 0.00% | 0.00% |
| PG 38:4 | 797.5338 | 13.73% | 0.00% |

*mass-to-charge (m/z) of [M − H]⁻.

Statistical Evaluation

Measured concentrations of individual lipids of all measured subjects are imported into a statistical software (e.g., SIMCA from Umetrics, Sweden). Proper transformation and scaling are chosen, typically logarithmic transformation and Pareto or UV scaling. The scaling and transformation are based on PCA analysis, where normal distribution of healthy and pancreatic cancer patients is desirable. PCA analysis is also used to find potential outliers, if so, the influence of the outlier on the model is tested (remove the outlier and check the model) and measurement methods are questioned. If a technical problem in case of outlier measurement is identified, then this measurement is removed from the data set. PCA method is used for finding other influential factors, such as gender or age. QC samples should cluster closely together in PCA analysis, typically close to the middle of the PCA graph.

The next step is the use of discrimination analysis (OPLS-DA) for the group separation of pancreatic cancer patients and healthy volunteers separately for males and females. The scaling and transformation is based on PCA results, but the final model has to be found. Models are fitted on all data together and also on separate strata for influential covariates. Different groups of lipids are used to build the model and to explore the influence on the healthy vs. cancer separation. The final model is chosen based on multiple factors as good fit (all known samples are correctly classified), on the model stability (no too influential observations), good prediction ability (by cross-validation performed automatically and then manually with random groups of observations) and biological reasoning and resistance to removing unimportant lipids. The final models are used to identify unknown samples, and the sensitivity and specificity are estimated based on these predictions. For this purpose, the receiver operating characteristic (ROC) curves are plotted, and the area under curve (AUC) is calculated. The model is again tested for good prediction ability via the final classification. After this last validation of the model, the most dysregulated lipids are identified using the S-plot or the loading plot. The limits to identify the lipid as dysregulated may be, for example, the ones from the S-plot with p bigger than 0.1 and pcorr bigger than 0.4. For these most dysregulated lipids, the box-plots comparing the average values in the group of pancreatic cancer and healthy volunteers for different strata are used to find exact biological interpretation.

Results of Experiments:

The present invention allows to determine whether the tested patient suffers from cancer, i.e., to distinguish between a healthy person and a person suffering from a cancer. Furthermore, the present invention also allows to determine the specific type of the cancer (also referred to herein as a localization of the cancer). The determination of the specific type (or localization) of the cancer is typically done as a second step, after determination that the tested patient suffers from cancer.

Typically, the distinction between a healthy person and a person suffering from a cancer has a high sensitivity and a high specificity (above 80%, or even above 90%). The distinction between specific types of cancer usually has a lower sensitivity and specificity.

Example A: UHPSFC/MS Lipidomic Analysis of Human Plasma of Cancer Patients and Healthy Volunteers Body fluid samples of various patients suffering from various types of cancer (kidney, prostate, and breast) and healthy volunteers were analyzed for their lipid profile using UHPSFC/MS. Generally, absolute and relative concentrations of the lipid species can be used to determine differences in samples of different health state. In the following, absolute concentrations were used for statistical analysis in order to visualize differences between sample groups and errors in sample preparation or measurements. After centering, transformation and Pareto scaling, PCA of all samples were performed in order to identify outliers and measurement errors.

FIG. 1 shows the results of the PCA analysis of 170 samples of healthy volunteers, 282 samples of patients suffering from cancer and 38 samples of unknown classification.

If unsupervised PCA does not show any significant clustering according to undesirable parameters (e.g., day of analysis) and unexplained outliers, then supervised OPLS-DA analysis is performed to improve the statistical model applicable also for predictions. If unwanted clustering or outliers are identified, then further investigations are necessary to identify the reason of those.

For OPLS-DA analysis, samples have to be defined according to their classification, i.e., groups of non-cancerous and cancerous samples. OPLS-DA analysis allows the visualization of differences between sample groups. It is preferred to have a clear differentiation, which means a gap between both groups. However, it may happen that there is a small overlay of both groups, as differences in the lipid pattern in biological fluids are not large enough due to the biological variability of samples or the investigated cancer type does not show a sufficiently large difference in the lipid profile measured in the biological fluid. Generally, it is expected that depending on the cancer type as well as cancer stage, the extent of differences in the lipid profile is altered.

Figure 2:
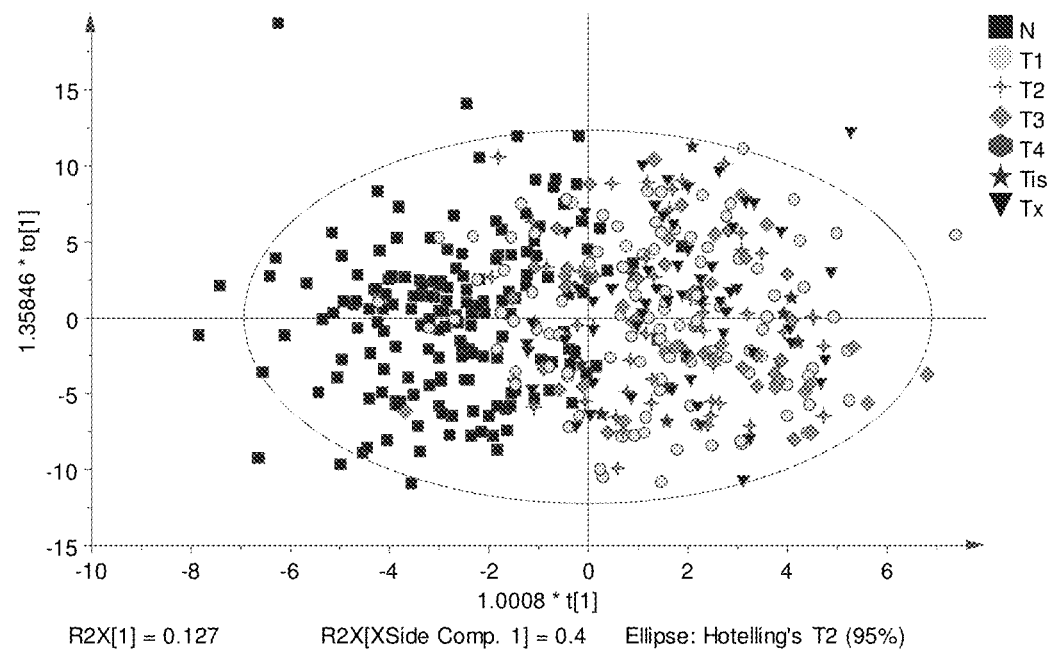
FIG. 2: OPLS-DA statistical model of healthy control (N) and cancerous plasma samples (tumor stages T1, T2, T3, T4, Tis, and Tx) for both genders (generated from UHPSFC/MS data).

FIG. 2 shows the OPLS-DA analysis of healthy (N, blue) and cancer samples (T) for both genders.

Figure 3:
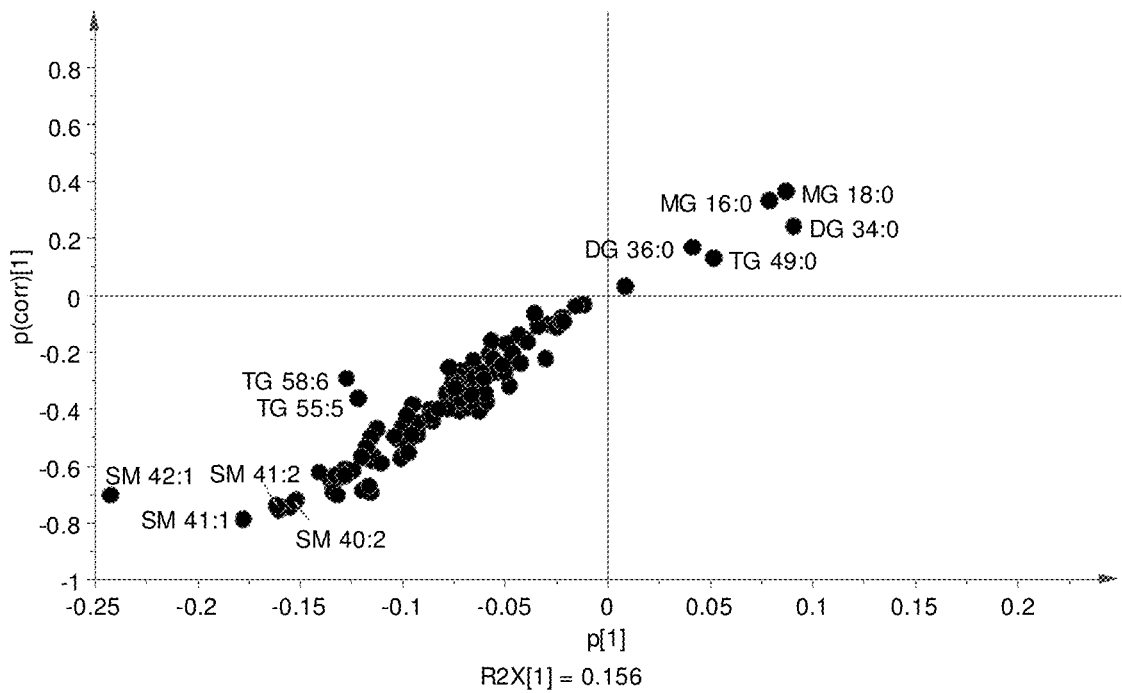
FIG. 3: S-plot representing the most up and down regulated lipid species for comparison of non-cancerous and cancerous plasma samples.

FIG. 2 shows that non-cancerous and cancerous samples can be differentiated. However, there is a certain region of overlap of both sample types with false positives and false negatives, which must be always expected in the analysis of real-life biological samples. In order to see the lipid species responsible for differentiation, an S-plot is prepared (FIG. 3). The S-plot allows the visualization of the most up-(upper right corner of the graph) and down-(bottom left corner) regulated lipid species for all investigated samples.

The prediction of the model encounts all components building up the model not only the most abundant once shown in the OPLS-DA plot.

Figure 4:
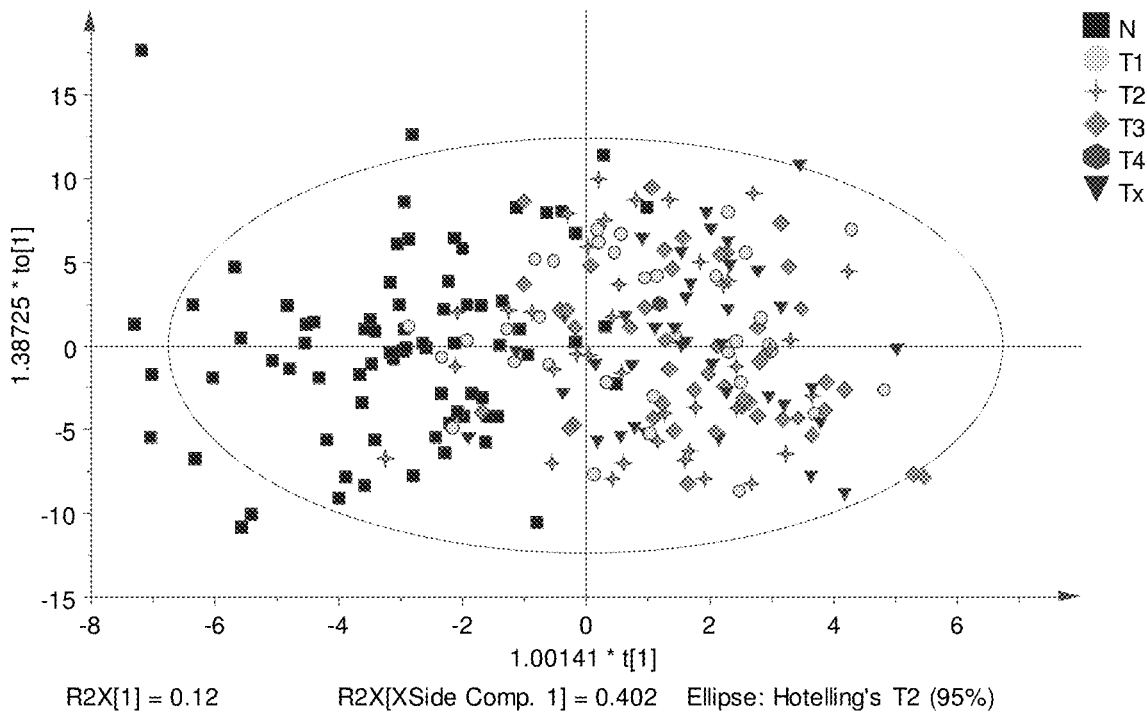
FIG. 4: OPLS-DA statistical model of plasma samples of healthy controls (N) and patients suffering from breast, kidney, and prostate cancers (tumor stages T1, T2, T3, T4, and Tx) for males (generated from UHPSFC/MS data).

The sensitivity describes the prediction power of the model to correctly predict samples as cancerous samples, whereby the specificity describes the correctly healthy predicted samples. For instance for the OPLS-DA model including healthy and cancer samples for all genders: in total 282 cancer samples are included and from those 252 samples were predicted as cancer samples whereas 30 samples were predicted as healthy samples, which leads to a sensitivity of 89.4%. 170 healthy samples are included in the model, and 137 samples were predicted as healthy, whereby 33 samples as cancer samples, which corresponds to a specificity of 80.6%. The sensitivity as well as the specificity may improve, when the statistical analysis is performed for both genders separately and for each cancer type separately. FIG. 4 shows the OPLS-DA plot for non-cancerous and cancerous samples for males and various cancer types The statistical analysis of male samples for various cancer types gives the sensitivity of 93.0% and the specificity of 81.3%.

Compared to results for both genders, the sensitivity increases from 89.4 to 93.0% and specificity increases from 80.6 to 81.3%.

Figure 5:
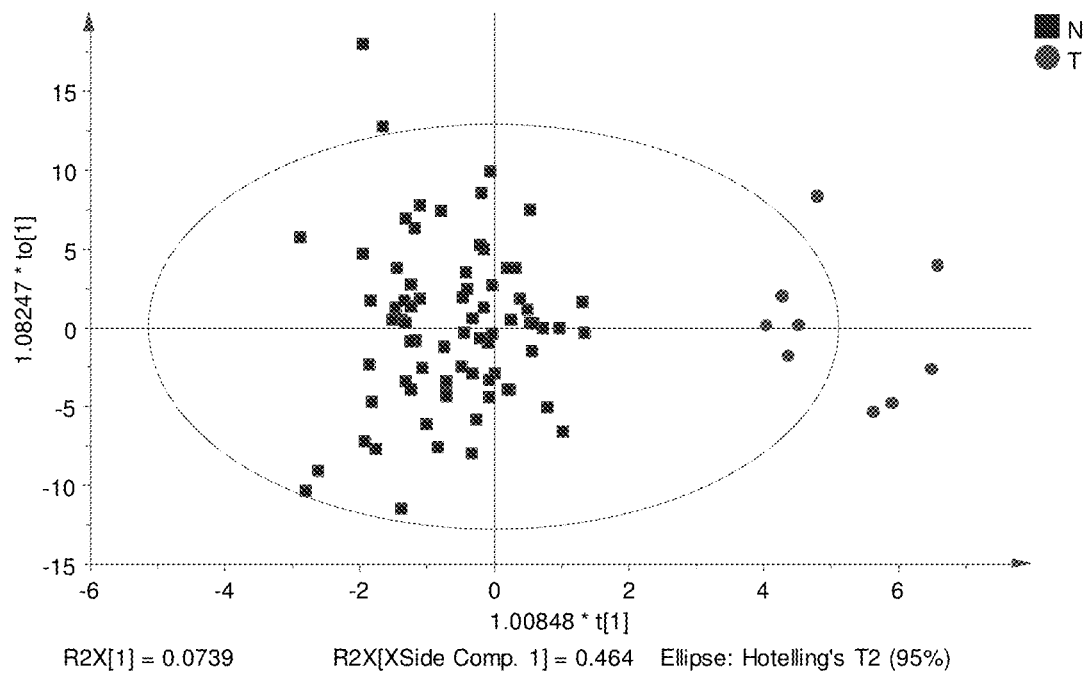
FIG. 5: OPLS-DA statistical model of plasma samples of healthy controls (N) and patients suffering from breast cancer (T) for males (generated from UHPSFC/MS data).

The statistical analysis of each cancer type separately in comparison to healthy samples may improve the sensitivity and specificity. For example, FIG. 5 shows the OPLS-DA plot for the analysis of samples of non-cancerous and cancerous samples suffering from breast cancer for males.

The differentiation of non-cancerous and cancerous subjects suffering from breast cancer for males is pronounced.

However, one has to keep in mind that just a very small amount of breast cancer samples for males are included in the model, as we did not get more samples provided from the hospital. The sensitivity and specificity is 100%.

Figure 6:
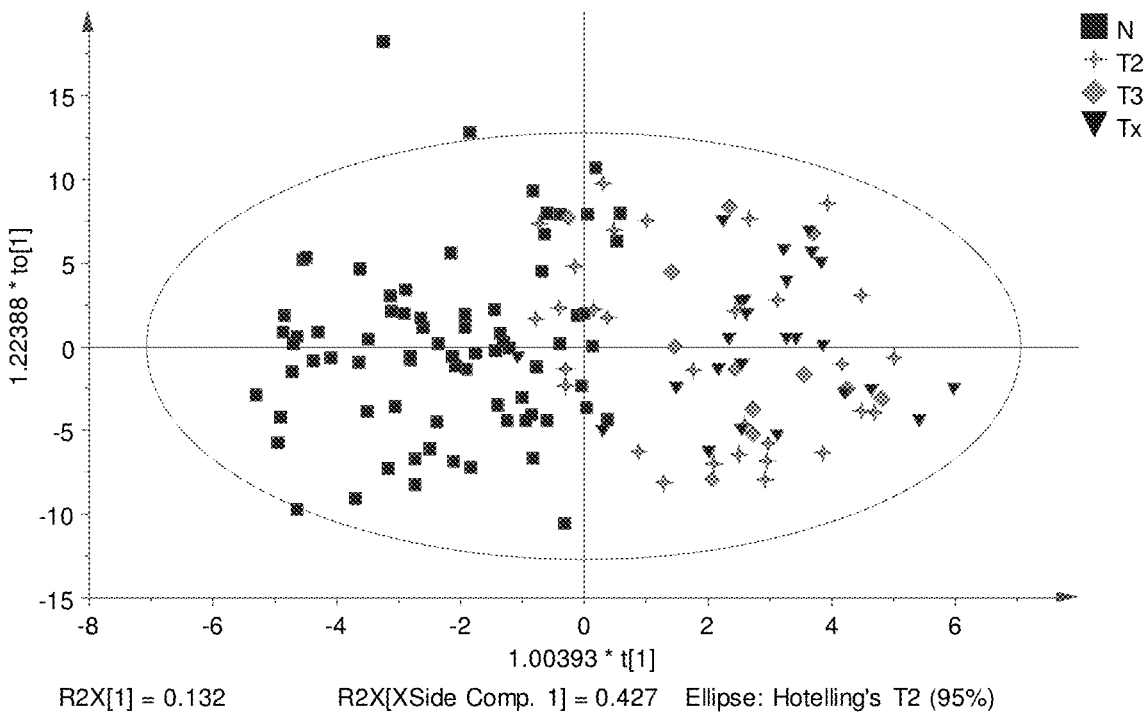
FIG. 6: OPLS-DA statistical model of plasma samples of healthy controls (N) and patients suffering from prostate cancer (tumor stages T2, T3, Tx) for males (generated from UHPSFC data).

FIG. 6 shows the OPLS-DA plot for the analysis of non-cancerous and cancerous samples suffering from prostate cancer for males. The sensitivity for the analysis of prostate cancer is 86.6% and the specificity is 94.7%.

Figure 7:
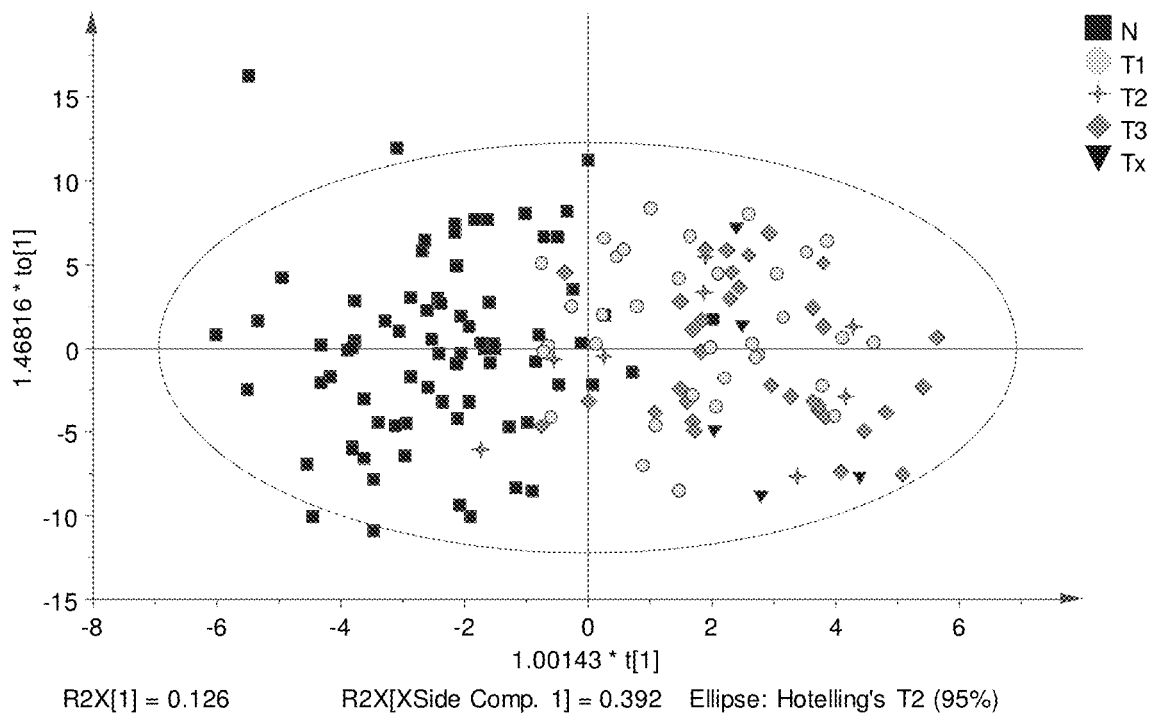
FIG. 7: OPLS-DA statistical model of plasma samples of healthy controls (N) and patients suffering from kidney cancer (tumor stages T1, T2, T3, and Tx) for males (generated from UHPSFC data).

FIG. 7 shows the OPLS-DA plot for the analysis of non-cancerous and cancerous samples suffering from kidney cancer for males. The sensitivity for the analysis of kidney cancer samples from males is 90.1% and the specificity is 90.7%.

Figure 8:
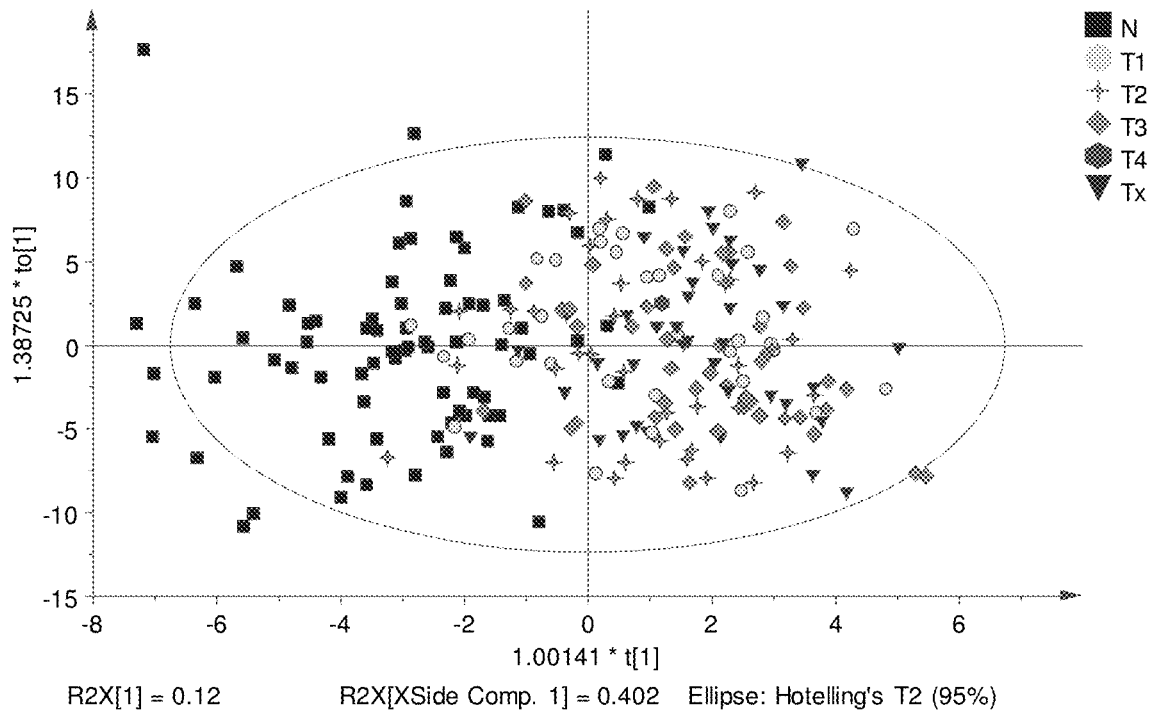
FIG. 8: OPLS-DA statistical model of plasma samples of healthy controls (N) and patients suffering from breast and kidney cancer types (tumor stages T1, T2, T3, T4, and Tx) for females (generated from UHPSFC/MS data).

FIG. 8 shows the OPLS-DA plot for the analysis of non-cancerous and cancerous samples for females. The sensitivity for the analysis of healthy and cancer samples from females is 88.0% and the specificity is 87.4%.

Figure 9:
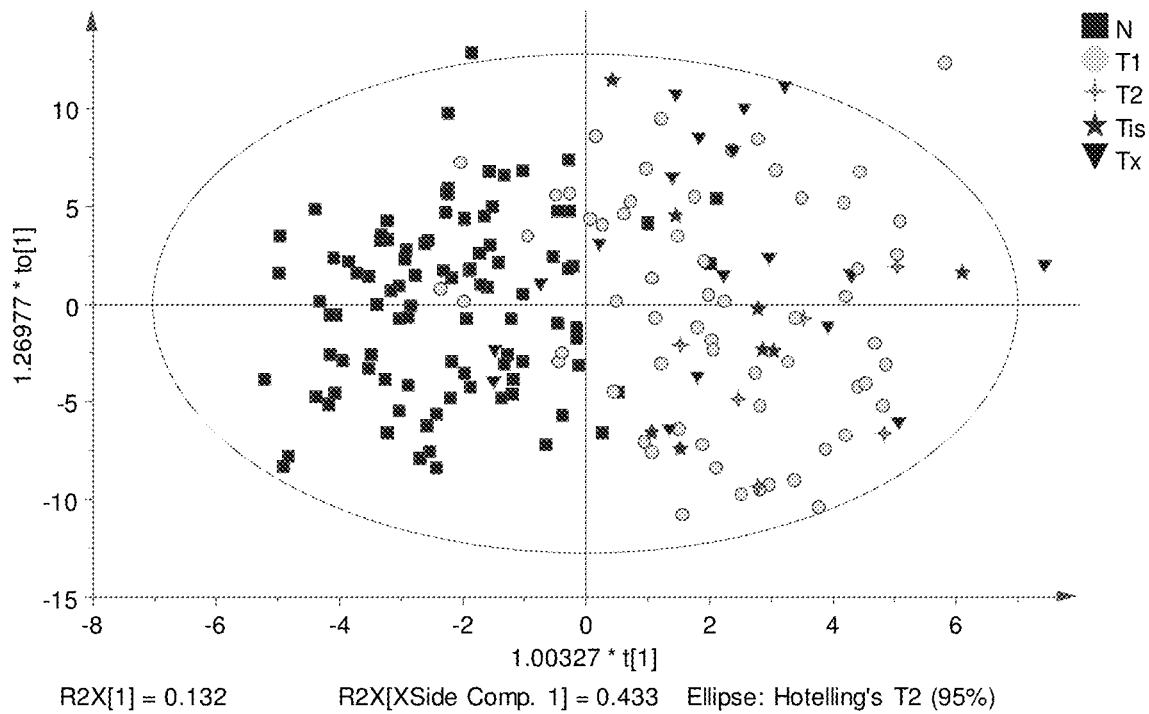
FIG. 9: OPLS-DA statistical model of plasma samples of healthy controls (N) and patients suffering from breast cancer (tumor stages T1, T2, Tis, and Tx) for females (generated from UHPSFC/MS data).

FIG. 9 represents the OPLS-DA plot for the analysis of non-cancerous and cancerous samples suffering from breast cancer samples for females. The sensitivity is 87.2% and the specificity is 93.7% for the analysis of breast cancer samples from females.

Figure 10:
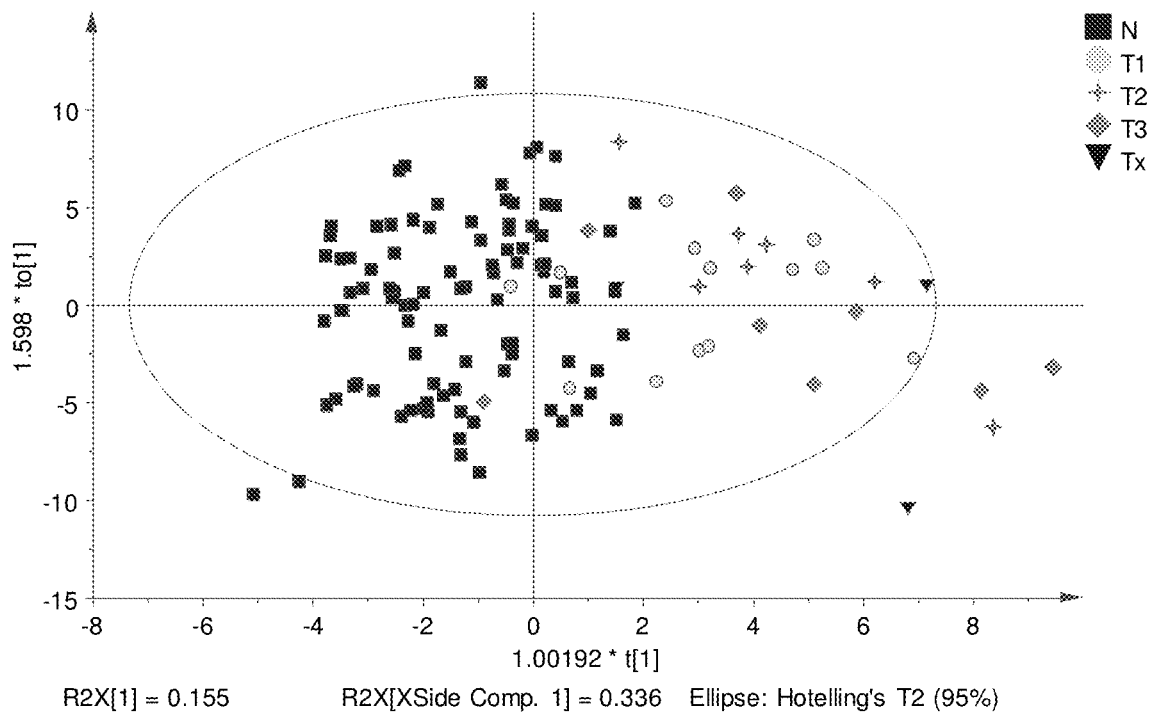
FIG. 10: OPLS-DA statistical model of plasma samples of healthy controls (N) and patients suffering from kidney cancer (tumor stages T1, T2, T3, and Tx) for females (generated from UHPSFC data).

FIG. 10 represents the OPLS-DA plot for the analysis of non-cancerous and cancerous samples suffering from kidney cancer for females. The sensitivity is 74.2% and the specificity is 100% for the analysis of kidney cancer samples from females.

Example B: Maldi-Ms Lipidomic Analysis of Body Fluids (Plasma, Urine) of Kidney Cancer Patients and Healthy Volunteers In this example, body fluid samples (plasma, urine) of various patients suffering from kidney cancer and healthy volunteers were analyzed for their lipid profile using MALDI-MS. In case of plasma samples, absolute concentrations (normalization to internal standard) were used for the statistical analysis in order to visualize differences between sample groups and errors in sample preparation or measurements. On the contrary, relative concentrations were used for this purpose in case of urine samples. Illustrated statistical models for plasma samples include following 74 variables: SM 32:1, SM 33:1, SM 34:2, SM 34:1, SM 34:0, SM 35:1, SM 36:2, SM 36:1, SM 36:0, SM 37:1, SM 38:2, SM 38:1, SM 39:2, SM 39:1, SM 40:3, SM 40:2, SM 40:1, SM 41:3, SM 41:2, SM 41:1, SM 42:3, SM 42:2, SM 42:1, SM 43:3, SM 43:2, SM 43:1, Sul 32:1 (OH), Sul 34:2, Sul 34:1, Sul 34:2 (OH), Sul 34:1 (OH), Sul 34:0 (OH), Sul 36:1, Sul 36:1 (OH), Sul 38:2, Sul 38:1, Sul 38:2 (OH), Sul 38:1 (OH), Sul 40:2, Sul 40:1, Sul 41:2, Sul 40:2 (OH), Sul 41:1, Su 140:1 (OH), Sul 40:0 (OH), Sul 42:3, Sul 42:2, Sul 41:2 (OH), Sul 42:1, Sul 41:1 (OH), Sul 40:0 (2OH), Sul 42:3 (OH), Sul 42:2 (OH), Sul 42:1 (OH), Sul 42:2 (2OH), Sul 42:1 (2OH), Sul 42:0 (2OH), SulfoHex2Cer 42:2, PI 32:1, PI 32:0, PI 34:2, PI 34:1, PI 36:4, PI 36:3, PI 36:2, PI 36:1, PI 38:6, PI 38:5, PI 38:4, PI 38:3, PI 38:2, PI 40:6, PI 40:5, PI 40:4). Illustrated statistical models for urine samples include following 46 variables: hydroxypregnenolone sulfate, C21H34O7S sulfate, C21H34O8S sulfate, cortisol sulfate, lithocholic acid sulfate, cholesterol sulfate, glycochenodeoxycholic acid sulfate, taurolithocholic acid, taurodeoxycholic acid, sulfoglycolithocholic acid, taurocholic acid, glycochenodeoxycholic acid sulfate, Sul 34:1, Sul 34:1 (OH), Sul 36:1 (OH), Sul 38:1, Sul 38:1 (OH), Sul 40:2, Sul 40:1, Sul 40:2 (OH), Sul 41:1, Sul 40:1 (OH), Sul 40:0 (OH), Sul 42:2, Sul 41:2 (OH), Sul 42:1, Sul 41:1 (OH), Sul 41:0 (OH), Sul 40:0 (2OH), Sul 42:2 (OH), Sul 42:1 (OH), Sul 42:0 (OH), Sul 41:0 (2OH), Sul 43:1 (OH), Sul 42:1 (2OH), Sul 42:0 (2OH), Sul 43:0 (2OH), SulfoHex2Cer 34:1, SulfoHex2Cer 38:1, SulfoHex2Cer 40:1, SulfoHex2Cer 40:1 (OH), SulfoHex2Cer 42:2, SulfoHex2Cer 42:1, SulfoHex2Cer 40:0 (2OH), SulfoHex2Cer 42:1 (OH), SulfoHex2Cer 42:0 (2OH).

Figure 11:
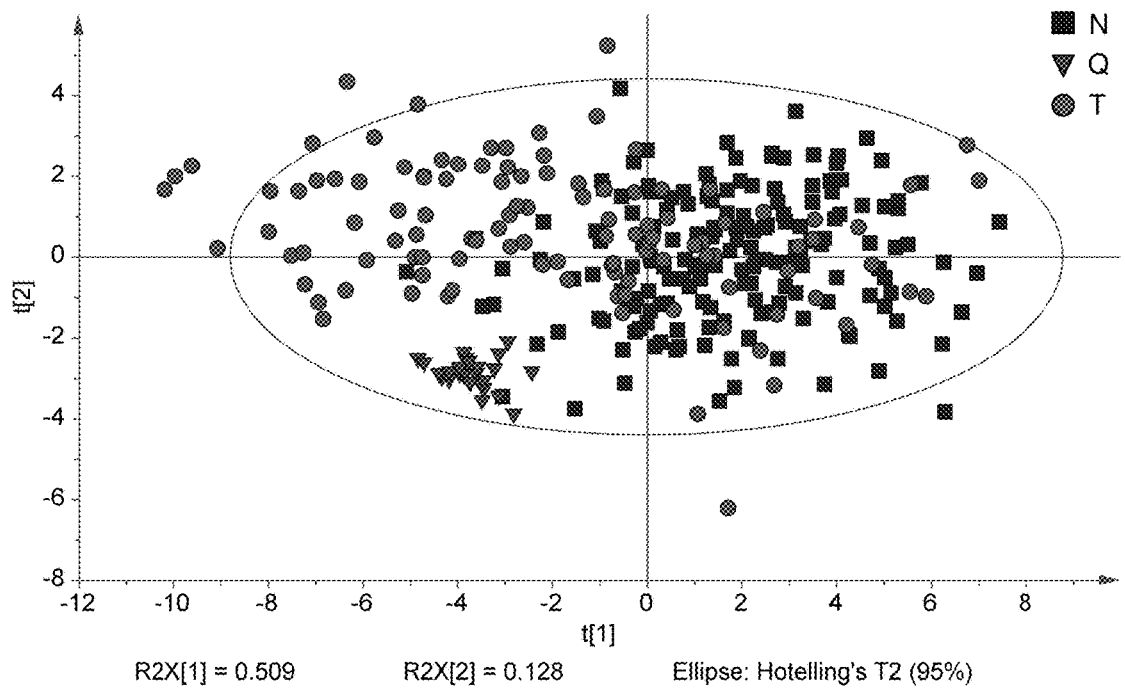
FIG. 11: PCA statistical model of 170 samples of healthy controls (N), 111 samples of patients suffering from kidney cancer (T) and 24 samples of quality control pooled samples (Q) for both genders (generated from MALDI-MS data).
Figure 12:
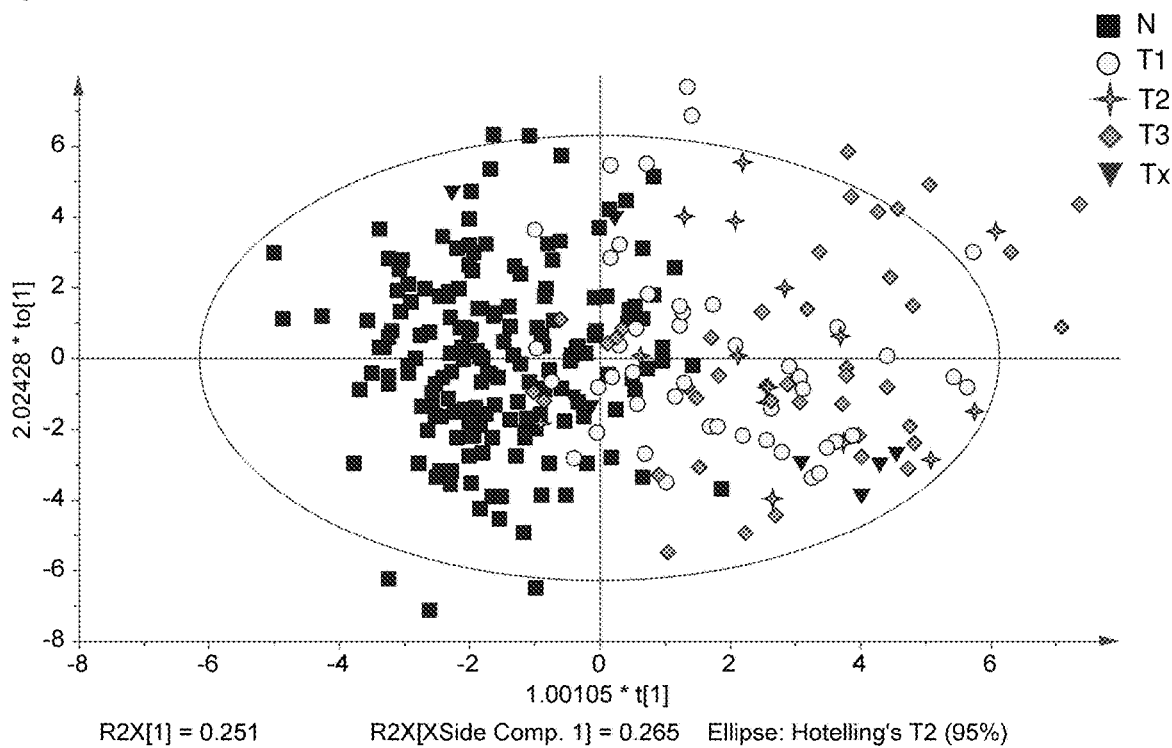
FIG. 12: OPLS-DA statistical model of 170 samples of healthy controls (N), 111 samples of patients suffering from kidney cancer (tumor stages T1, T2, T3, and Tx) for both genders (generated from MALDI-MS data).
Figure 13:
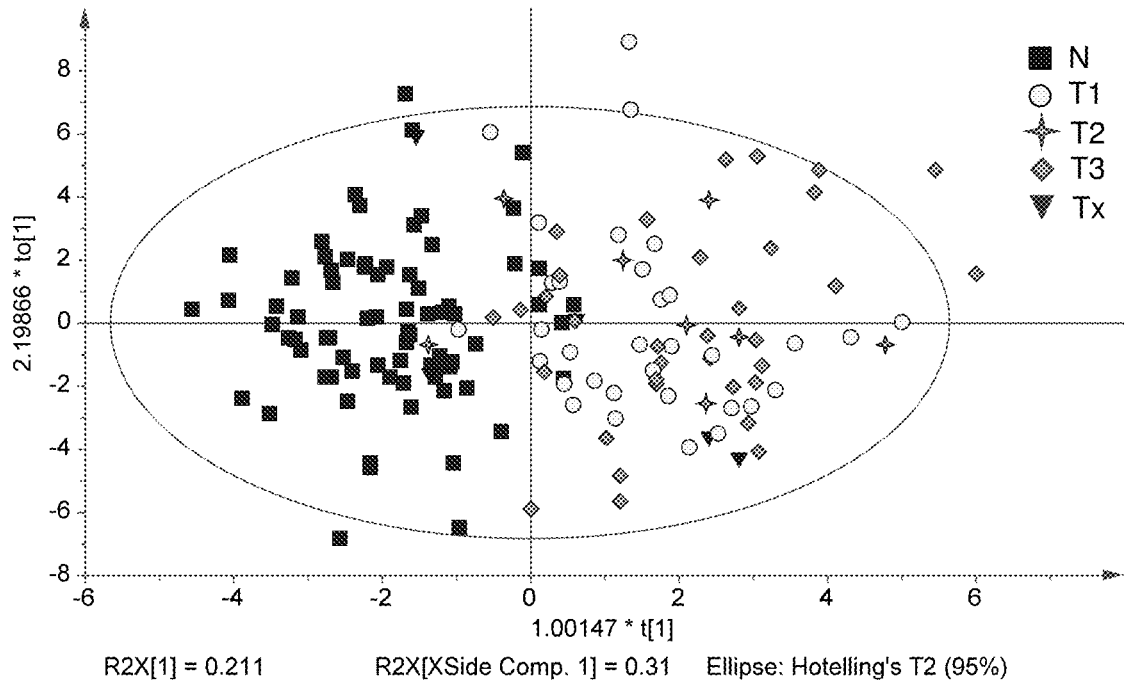
FIG. 13: OPLS-DA analysis of 75 samples of healthy controls (N), 80 samples of patients suffering from kidney cancer (tumor stages T1, T2, T3, and Tx) for males (generated from MALDI-MS data).
Figure 14:
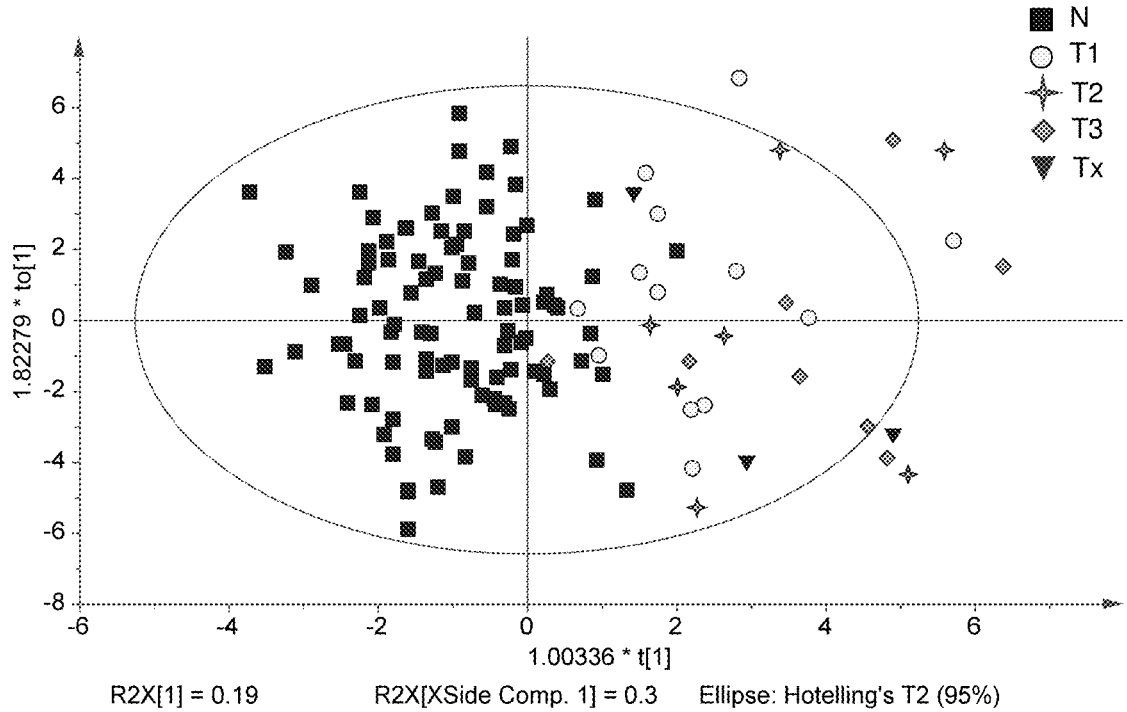
FIG. 14: OPLS-DA analysis of 95 samples of healthy controls (N), 32 samples of patients suffering from kidney cancer (tumor stages T1, T2, T3, and Tx) for females (generated from MALDI-MS data).
Figure 15:
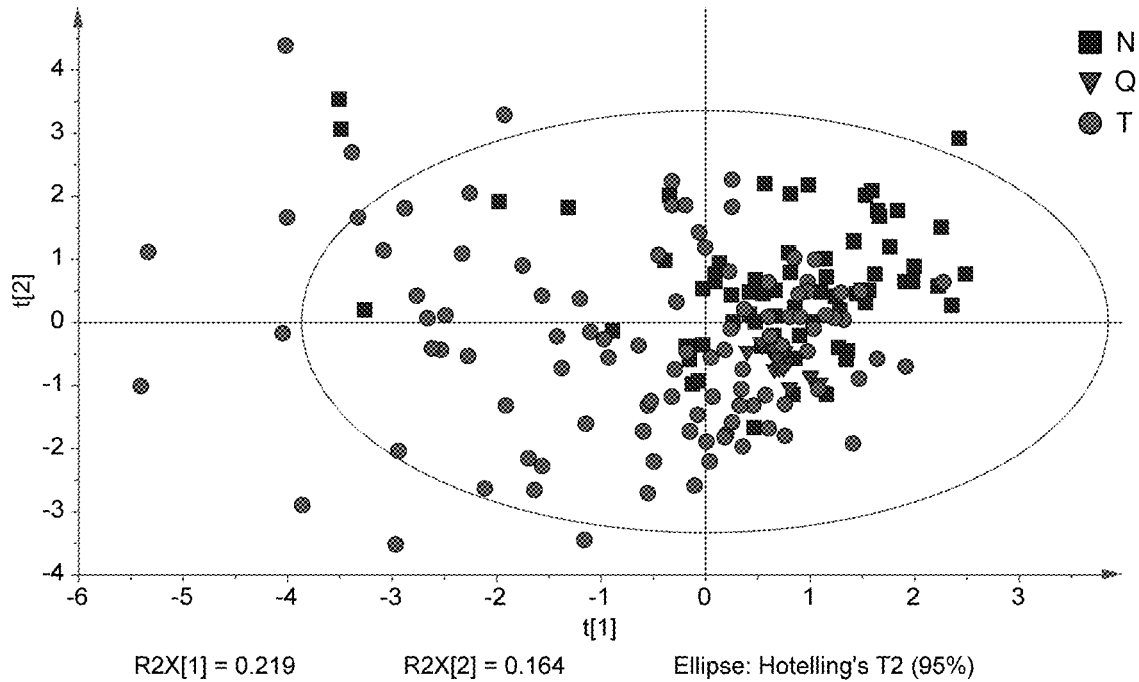
FIG. 15: PCA analysis of 70 samples of healthy controls (N), 101 samples of patients suffering from kidney cancer (T) and 24 samples of quality control pooled samples (Q) for both genders (generated from MALDI-MS data).
Figure 16:
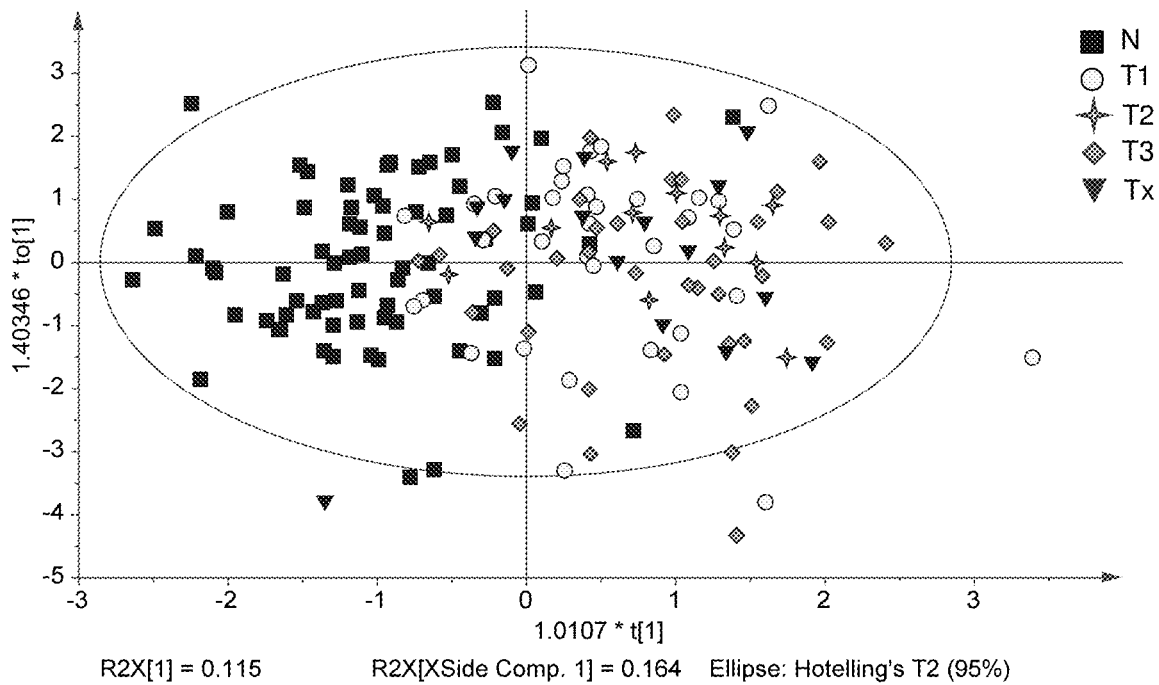
FIG. 16: OPLS-DA analysis of 70 samples of healthy controls (N), 101 samples of patients suffering from kidney cancer (tumor stages T1, T2, T3, and Tx) for both genders (generated from MALDI-MS data).
Figure 17:
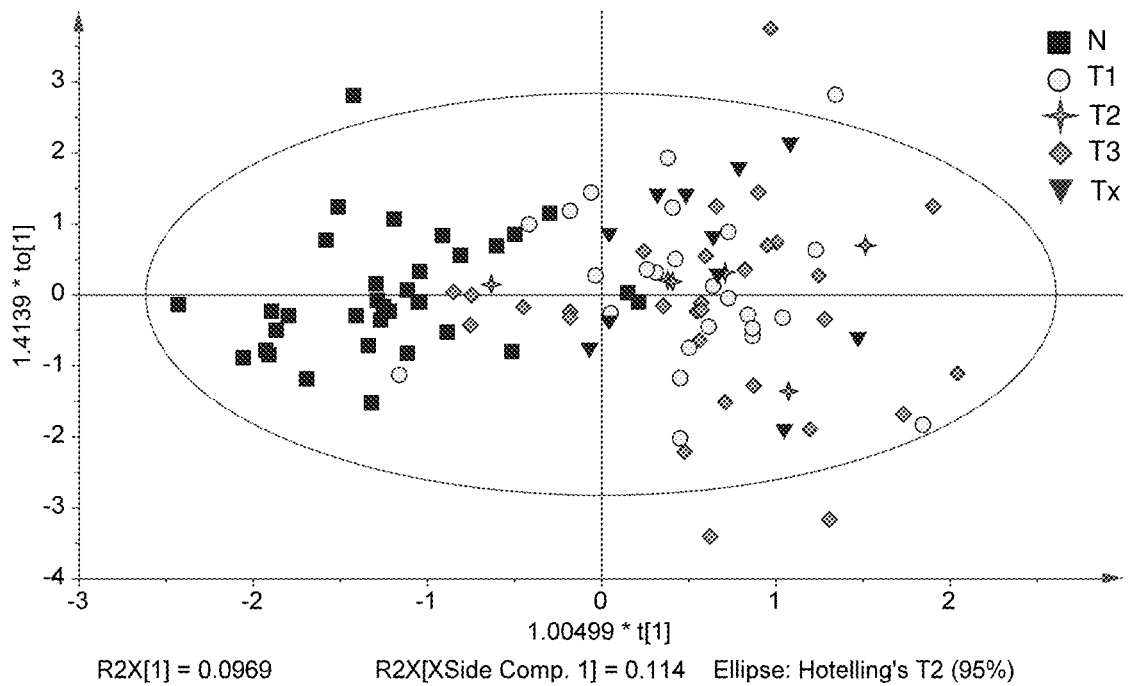
FIG. 17: OPLS-DA analysis of 34 samples of healthy controls (N), 72 samples of patients suffering from kidney cancer (tumor stages T1, T2, T3, and Tx) for males (generated from MALDI-MS data).
Figure 18:
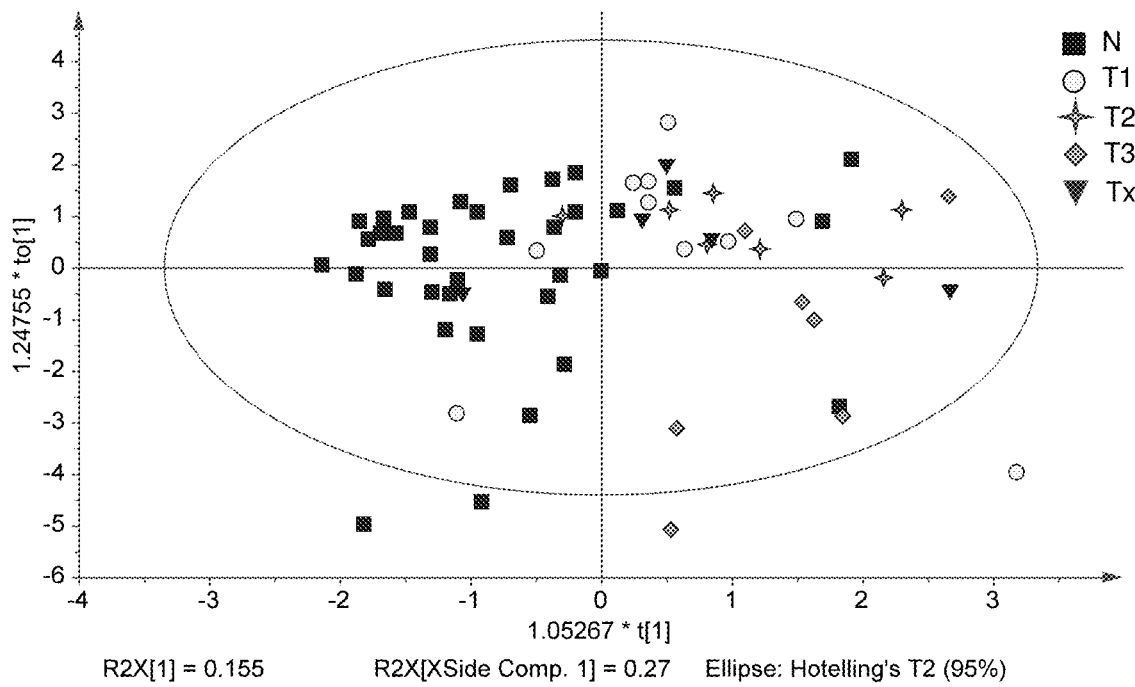
FIG. 18: OPLS-DA analysis of 36 samples of healthy controls (N), 29 samples of patients suffering from kidney cancer (tumor stages T1, T2, T3, and Tx) for females (generated from MALDI-MS data).

FIG. 11 shows the results of the PCA of 170 plasma samples of healthy volunteers (N), 111 plasma samples of patients suffering from kidney cancer (T) and 24 plasma samples of quality control pooled samples (Q) for both genders. Group separation between cancerous and healthy samples is evident even from unsupervised PCA model, but much better group separation is achieved using supervised OPLS-DA model illustrated in FIG. 12, which provides sensitivity 76.6%, specificity 95.3% and accuracy 87.9%. The sensitivity as well as the specificity is further improved, when the statistical analysis is performed for particular genders separately as illustrated in FIGS. 13 and 14. The statistical analysis of plasma samples of 80 patients suffering from kidney cancer and 75 healthy volunteers (control) gives the sensitivity 90%, specificity 93.3% (accuracy 91.6%) in case of males. The statistical analysis of plasma samples of 32 patients suffering from kidney cancer and 95 healthy volunteers gives the sensitivity 83.9%, specificity 98.9% (accuracy 95.2%) for females. Improvement of cancer prediction ability after gender separation is also observed for urine samples. FIG. 15 shows the results of the PCA analysis of 70 urine samples of healthy volunteers (34 of males and 36 females), 101 urine samples of patients suffering from kidney cancer (72 of males and 29 of females) and 16 urine samples of quality control pooled samples (Q) for both genders. Corresponding OPLS-DA model for both genders is illustrated in FIG. 16 and this model provides sensitivity 87.1%, specificity 82.9% (accuracy 85.4%). Subsequent separation to models for individual genders results in sensitivity 93.1%, specificity 91.2% (accuracy 92.5%) for males (FIG. 17) and sensitivity 86.2%, specificity 88.9% (accuracy 87.7%) for females (FIG. 18).

TABLE 21

Statistical parameters for UHPSFC/MS analysis of non-cancerous plasma samples and cancerous plasma samples of males (M) and females (F) for breast cancer.

| Species | Fold change | | P-value | | T-value | |
| --- | --- | --- | --- | --- | --- | --- |
|  | F | M | F | M | F | M |
| TG 48:2 | 0.9 | 0.5 | 2.4E−01 | 3.2E−02 | 0.7 | 2.1 |
| TG 50:3 | 0.9 | 0.7 | 2.0E−01 | 2.6E−02 | 0.8 | 2.2 |
| TG 50:2 | 0.9 | 0.8 | 2.4E−01 | 9.1E−02 | 0.7 | 1.5 |
| TG 51:4 | 0.8 | 0.7 | 6.5E−02 | 1.3E−01 | 1.5 | 1.3 |
| TG 51:3 | 0.7 | 0.8 | 1.1E−03 | 1.1E−01 | 3.1 | 1.4 |
| TG 51:2 | 0.7 | 0.8 | 4.6E−04 | 1.7E−01 | 3.4 | 1.0 |
| TG 52:3 | 0.9 | 0.9 | 2.1E−01 | 1.7E−01 | 0.8 | 1.0 |
| TG 53:4 | 0.8 | 0.8 | 1.5E−02 | 1.6E−01 | 2.2 | 1.1 |
| TG 53:3 | 0.7 | 0.9 | 2.6E−04 | 3.8E−01 | 3.5 | 0.3 |
| Cer40:1 | 0.5 | 0.5 | 1.0E−08 | 2.9E−04 | 5.9 | 4.3 |
| Cer42:1 | 0.5 | 0.4 | 1.4E−10 | 2.5E−08 | 6.7 | 7.0 |
| PC 32:2 | 0.5 | 0.3 | 6.3E−06 | 4.5E−08 | 4.5 | 6.8 |
| PC 34:2 | 0.6 | 0.6 | 4.2E−10 | 1.5E−06 | 6.5 | 6.7 |
| PC 34:1 | 0.6 | 0.7 | 9.8E−10 | 4.6E−03 | 6.3 | 3.2 |
| PC O-36:4 | 0.5 | 0.3 | 7.6E−11 | 3.5E−09 | 6.8 | 8.2 |
| PC O-36:3 | 0.5 | 0.4 | 1.6E−09 | 1.2E−11 | 6.3 | 8.6 |
| PC 36:4 | 0.6 | 0.5 | 1.8E−10 | 1.3E−06 | 6.7 | 6.6 |
| PC 36:3 | 0.6 | 0.5 | 1.6E−11 | 3.9E−11 | 7.1 | 9.4 |
| PC 36:2 | 0.6 | 0.5 | 1.5E−09 | 4.2E−06 | 6.3 | 6.3 |
| PC 38:6 | 0.6 | 0.5 | 3.0E−06 | 1.1E−04 | 4.7 | 4.5 |
| PC 38:5 | 0.6 | 0.4 | 1.4E−07 | 6.6E−08 | 5.4 | 7.0 |
| PC 38:4 | 0.7 | 0.6 | 1.6E−07 | 1.2E−03 | 5.3 | 4.0 |

TABLE 21-continued

Statistical parameters for UHPSFC/MS analysis of non-cancerous plasma samples and cancerous plasma samples of males (M) and females (F) for breast cancer.

| Species | Fold change F | Fold change M | P-value F | P-value M | T-value F | T-value M |
|---|---|---|---|---|---|---|
| PC 38:3 | 0.6 | 0.5 | 3.9E−05 | 1.2E−03 | 4.1 | 3.9 |
| SM 34:2 | 0.6 | 0.5 | 1.6E−10 | 5.9E−05 | 6.7 | 5.4 |
| SM 34:1 | 0.6 | 0.5 | 1.2E−09 | 3.0E−04 | 6.3 | 4.6 |
| SM 36:2 | 0.6 | 0.6 | 5.0E−09 | 2.3E−03 | 6.0 | 3.6 |
| SM 36:1 | 0.6 | 0.6 | 2.9E−08 | 6.4E−03 | 5.7 | 3.1 |
| SM 38:2 | 0.6 | 0.6 | 2.1E−09 | 4.6E−04 | 6.2 | 4.1 |
| SM 38:1 | 0.5 | 0.4 | 8.0E−13 | 9.9E−10 | 7.6 | 8.8 |
| SM 40:2 | 0.5 | 0.4 | 1.1E−11 | 1.0E−07 | 7.2 | 7.6 |
| SM 40:1 | 0.5 | 0.4 | 3.2E−12 | 8.8E−08 | 7.4 | 7.9 |
| SM 41:2 | 0.5 | 0.4 | 2.6E−13 | 8.1E−06 | 7.8 | 6.0 |
| SM 41:1 | 0.5 | 0.3 | 5.2E−14 | 3.6E−08 | 8.1 | 7.8 |
| SM 42:3 | 0.6 | 0.6 | 2.1E−08 | 1.2E−03 | 5.8 | 3.9 |
| SM 42:2 | 0.6 | 0.5 | 9.6E−08 | 3.2E−04 | 5.5 | 4.6 |
| SM 42:1 | 0.3 | 0.1 | 1.2E−09 | 7.3E−15 | 6.4 | 9.5 |
| LPC 16:0 | 0.6 | 0.3 | 1.3E−06 | 6.3E−12 | 6.3 | 12.1 |
| LPC 18:2 | 0.5 | 0.2 | 3.9E−08 | 8.8E−18 | 5.6 | 12.2 |
| LPC 18:1 | 0.5 | 0.2 | 3.0E−10 | 1.2E−18 | 6.6 | 12.3 |
| LPC 18:0 | 0.5 | 0.2 | 3.1E−11 | 8.6E−16 | 7.0 | 14.1 |

TABLE 22

Statistical parameters for UHPSFC/MS analysis of non-cancerous plasma samples and cancerous plasma samples of males (M) and females (F) for kidney cancer.

| Species | Fold change F | Fold change M | P-value F | P-value M | T-value F | T-value M |
|---|---|---|---|---|---|---|
| TG 48:2 | 0.4 | 0.5 | 1.0E−07 | 7.7E−04 | 5.5 | 3.3 |
| TG 50:3 | 0.6 | 0.6 | 2.2E−07 | 4.9E−06 | 5.5 | 4.6 |
| TG 50:2 | 0.6 | 0.6 | 1.0E−07 | 1.2E−04 | 5.6 | 3.8 |
| TG 51:4 | 0.5 | 0.6 | 1.3E−05 | 1.6E−05 | 4.5 | 4.3 |
| TG 51:3 | 0.6 | 0.6 | 9.4E−08 | 8.6E−07 | 5.8 | 5.1 |
| TG 51:2 | 0.5 | 0.5 | 1.2E−08 | 1.0E−05 | 6.1 | 4.5 |
| TG 52:3 | 0.7 | 0.7 | 1.3E−04 | 2.4E−06 | 3.9 | 4.8 |
| TG 53:4 | 0.6 | 0.6 | 4.5E−05 | 2.3E−05 | 4.2 | 4.3 |
| TG 53:3 | 0.6 | 0.6 | 9.8E−06 | 2.9E−05 | 4.6 | 4.2 |
| Cer40:1 | 0.6 | 0.7 | 2.8E−04 | 3.4E−03 | 3.7 | 2.8 |
| Cer42:1 | 0.5 | 0.6 | 1.0E−06 | 1.8E−04 | 5.3 | 3.7 |
| PC 32:2 | 0.4 | 0.7 | 8.3E−07 | 1.1E−02 | 5.1 | 2.3 |
| PC 34:2 | 0.6 | 0.7 | 7.6E−09 | 6.6E−07 | 6.7 | 5.1 |
| PC 34:1 | 0.6 | 0.7 | 1.9E−06 | 4.0E−03 | 5.2 | 2.7 |
| PC O-36:4 | 0.7 | 0.8 | 2.4E−03 | 2.0E−02 | 3.0 | 2.1 |
| PC O-36:3 | 0.6 | 0.8 | 8.1E−06 | 6.4E−02 | 4.6 | 1.5 |
| PC 36:4 | 0.7 | 0.7 | 1.6E−04 | 5.9E−04 | 3.9 | 3.3 |
| PC 36:3 | 0.6 | 0.7 | 8.9E−08 | 3.3E−06 | 6.0 | 4.7 |
| PC 36:2 | 0.6 | 0.6 | 6.7E−08 | 1.6E−07 | 6.1 | 5.4 |
| PC 38:6 | 0.7 | 0.8 | 2.3E−02 | 7.4E−02 | 2.1 | 1.5 |
| PC 38:5 | 0.7 | 0.7 | 1.2E−02 | 8.1E−03 | 2.4 | 2.4 |
| PC 38:4 | 0.8 | 0.7 | 1.1E−02 | 3.0E−05 | 2.4 | 4.2 |
| PC 38:3 | 0.7 | 0.7 | 4.7E−03 | 9.2E−05 | 2.7 | 3.9 |
| SM 34:2 | 0.7 | 0.7 | 3.3E−03 | 1.3E−04 | 2.9 | 3.8 |
| SM 34:1 | 0.6 | 0.6 | 2.6E−06 | 4.8E−09 | 5.1 | 6.1 |
| SM 36:2 | 0.8 | 0.7 | 3.0E−02 | 1.9E−03 | 2.0 | 3.0 |
| SM 36:1 | 0.8 | 0.7 | 6.9E−02 | 1.9E−03 | 1.5 | 3.0 |
| SM 38:2 | 0.7 | 0.8 | 1.1E−02 | 1.8E−02 | 2.4 | 2.1 |
| SM 38:1 | 0.6 | 0.6 | 4.7E−05 | 7.2E−06 | 4.3 | 4.5 |
| SM 40:2 | 0.6 | 0.6 | 2.3E−04 | 1.2E−05 | 3.8 | 4.4 |
| SM 40:1 | 0.6 | 0.6 | 1.0E−04 | 4.7E−07 | 4.1 | 5.2 |
| SM 41:2 | 0.5 | 0.6 | 4.9E−06 | 4.6E−06 | 5.0 | 4.6 |
| SM 41:1 | 0.5 | 0.5 | 3.5E−07 | 3.0E−08 | 5.6 | 5.7 |
| SM 42:3 | 0.8 | 0.7 | 4.2E−02 | 4.3E−03 | 1.8 | 2.7 |
| SM 42:2 | 0.7 | 0.6 | 3.7E−03 | 1.7E−05 | 2.9 | 4.3 |
| SM 42:1 | 0.4 | 0.5 | 4.7E−05 | 2.3E−03 | 4.2 | 2.9 |

TABLE 22-continued

Statistical parameters for UHPSFC/MS analysis of non-cancerous plasma samples and cancerous plasma samples of males (M) and females (F) for kidney cancer.

| Species | Fold change F | Fold change M | P-value F | P-value M | T-value F | T-value M |
|---|---|---|---|---|---|---|
| LPC 16:0 | 0.7 | 0.7 | 8.9E−03 | 4.9E−04 | 2.5 | 3.4 |
| LPC 18:2 | 0.4 | 0.5 | 1.2E−08 | 8.7E−07 | 6.1 | 5.0 |
| LPC 18:1 | 0.6 | 0.8 | 7.1E−04 | 2.3E−02 | 3.4 | 2.0 |
| LPC 18:0 | 0.7 | 0.7 | 2.5E−02 | 3.4E−04 | 2.0 | 3.5 |

TABLE 23

Statistical parameters for UHPSFC/MS analysis of non-cancerous plasma samples and cancerous plasma samples of males (M) and females (F) for prostate cancer.

| Species | Fold change M | P-value M | T-value M |
|---|---|---|---|
| TG 48:2 | 0.6 | 7.6E−03 | 2.5 |
| TG 50:3 | 0.7 | 3.0E−04 | 3.5 |
| TG 50:2 | 0.7 | 1.2E−03 | 3.1 |
| TG 51:4 | 0.7 | 3.3E−03 | 2.8 |
| TG 51:3 | 0.7 | 1.4E−03 | 3.1 |
| TG 51:2 | 0.7 | 3.6E−03 | 2.7 |
| TG 52:3 | 0.7 | 4.5E−05 | 4.1 |
| TG 53:4 | 0.7 | 4.3E−03 | 2.7 |
| TG 53:3 | 0.7 | 3.4E−03 | 2.8 |
| Cer40:1 | 0.5 | 3.6E−07 | 5.2 |
| Cer42:1 | 0.5 | 2.0E−08 | 5.9 |
| PC 32:2 | 0.6 | 1.2E−05 | 4.4 |
| PC 34:2 | 0.6 | 1.3E−13 | 8.2 |
| PC 34:1 | 0.6 | 1.1E−06 | 5.0 |
| PC O-36:4 | 0.5 | 1.7E−08 | 5.9 |
| PC O-36:3 | 0.6 | 6.2E−06 | 4.6 |
| PC 36:4 | 0.6 | 8.5E−09 | 6.0 |
| PC 36:3 | 0.6 | 7.3E−12 | 7.4 |
| PC 36:2 | 0.6 | 1.1E−11 | 7.3 |
| PC 38:6 | 0.7 | 1.5E−04 | 3.7 |
| PC 38:5 | 0.7 | 1.3E−05 | 4.4 |
| PC 38:4 | 0.6 | 1.9E−08 | 5.9 |
| PC 38:3 | 0.6 | 8.7E−06 | 4.5 |
| SM 34:2 | 0.5 | 4.5E−10 | 6.6 |
| SM 34:1 | 0.5 | 1.3E−13 | 8.2 |
| SM 36:2 | 0.6 | 1.5E−06 | 4.9 |
| SM 36:1 | 0.6 | 2.4E−07 | 5.3 |
| SM 38:2 | 0.6 | 2.5E−04 | 3.6 |
| SM 38:1 | 0.5 | 5.2E−11 | 7.0 |
| SM 40:2 | 0.5 | 1.4E−11 | 7.3 |
| SM 40:1 | 0.4 | 5.4E−14 | 8.3 |
| SM 41:2 | 0.4 | 6.7E−12 | 7.4 |
| SM 41:1 | 0.4 | 1.0E−13 | 8.2 |
| SM 42:3 | 0.5 | 6.4E−10 | 6.6 |
| SM 42:2 | 0.5 | 2.1E−12 | 7.7 |
| SM 42:1 | 0.3 | 1.2E−07 | 5.5 |
| LPC 16:0 | 0.5 | 1.0E−15 | 9.0 |
| LPC 18:2 | 0.4 | 1.6E−13 | 8.2 |
| LPC 18:1 | 0.5 | 5.7E−11 | 7.0 |
| LPC 18:0 | 0.5 | 3.2E−15 | 8.8 |

TABLE 24

Statistical parameters for MALDI-MS analysis of non-cancerous plasma samples and cancerous plasma samples of males (M) and females (F) for breast cancer.

| Species | Fold change F | Fold change M | P-value F | P-value M | T-value F | T-value M |
|---|---|---|---|---|---|---|
| cholesterol sulfate | 0.62 | 0.73 | 2.1E−09 | 6.8E−03 | 6.2 | 2.9 |
| SM 32:1 | 0.57 | 0.50 | 1.5E−16 | 1.9E−06 | 9.0 | 7.5 |
| SM 33:1 | 0.54 | 0.60 | 9.2E−18 | 1.3E−03 | 9.5 | 4.1 |
| SM 34:2 | 0.66 | 0.71 | 1.3E−10 | 2.4E−03 | 6.7 | 3.5 |
| SM 34:1 | 0.63 | 0.69 | 9.8E−15 | 6.9E−03 | 8.4 | 3.1 |
| SM 34:0 | 0.60 | 0.55 | 3.6E−15 | 4.5E−04 | 8.6 | 4.8 |
| SM 35:1 | 0.58 | 0.65 | 2.4E−14 | 3.0E−03 | 8.2 | 3.6 |
| SM 36:1 | 0.67 | 0.70 | 2.7E−11 | 1.7E−02 | 7.0 | 2.6 |
| SM 37:1 | 0.57 | 0.60 | 5.4E−15 | 2.9E−03 | 8.4 | 3.6 |
| SM 38:2 | 0.65 | 0.64 | 1.6E−10 | 2.3E−04 | 6.7 | 4.6 |
| SM 38:1 | 0.61 | 0.54 | 2.3E−16 | 4.4E−05 | 9.0 | 6.1 |
| SM 39:2 | 0.54 | 0.58 | 5.8E−08 | 4.7E−04 | 5.6 | 4.3 |
| SM 39:1 | 0.52 | 0.47 | 7.2E−18 | 3.0E−05 | 9.5 | 6.3 |
| SM 40:3 | 0.52 | 0.67 | 4.2E−10 | 1.6E−02 | 6.5 | 2.5 |
| SM 40:2 | 0.60 | 0.59 | 4.3E−15 | 4.1E−05 | 8.5 | 5.6 |
| SM 40:1 | 0.60 | 0.54 | 5.4E−16 | 5.2E−05 | 8.9 | 6.0 |
| SM 41:2 | 0.58 | 0.63 | 2.2E−15 | 1.1E−03 | 8.6 | 4.1 |
| SM 41:1 | 0.58 | 0.53 | 4.4E−16 | 1.4E−04 | 8.9 | 5.5 |
| SM 42:1 | 0.61 | 0.50 | 2.0E−14 | 7.5E−06 | 8.3 | 7.0 |
| SM 43:1 | 0.41 | 0.32 | 5.4E−12 | 2.0E−07 | 7.5 | 6.7 |
| Sul 34:2 (OH) | 0.57 | 0.36 | 9.7E−09 | 1.0E−08 | 5.9 | 7.4 |
| Sul 34:1 (OH) | 0.63 | 0.54 | 8.8E−11 | 1.4E−05 | 6.8 | 5.8 |
| Sul 34:0 (OH) | 0.44 | 0.26 | 2.7E−13 | 5.6E−10 | 7.8 | 8.5 |
| Sul 40:2 | 0.53 | 0.37 | 3.8E−08 | 4.2E−07 | 5.6 | 5.6 |
| Sul 40:1 | 0.54 | 0.25 | 4.4E−11 | 2.3E−09 | 6.9 | 9.3 |
| Sul 40:2 (OH) | 0.58 | 0.34 | 1.5E−06 | 1.2E−07 | 4.8 | 6.4 |
| Sul 41:1 | 0.48 | 0.34 | 3.3E−12 | 5.3E−13 | 7.4 | 8.6 |
| Sul 40:1 (OH) | 0.59 | 0.39 | 6.5E−11 | 3.8E−06 | 6.8 | 7.0 |
| Sul 42:3 | 0.58 | 0.43 | 2.9E−07 | 1.5E−05 | 5.2 | 4.8 |
| Sul 42:2 | 0.62 | 0.41 | 2.3E−10 | 1.1E−06 | 6.6 | 6.7 |
| Sul 42:1 | 0.52 | 0.25 | 3.1E−12 | 6.3E−13 | 7.4 | 10.1 |
| Sul 41:1 (OH) | 0.54 | 0.34 | 4.2E−12 | 3.1E−06 | 7.3 | 7.0 |
| Sul 42:1 (OH) | 0.63 | 0.39 | 7.9E−11 | 2.6E−07 | 6.8 | 8.3 |
| Sul 42:1 (2OH) | 0.54 | 0.44 | 2.9E−07 | 1.2E−03 | 5.2 | 3.9 |
| PI 34:1 | 0.61 | 0.62 | 1.9E−06 | 5.0E−03 | 4.8 | 3.2 |
| PI 36:4 | 0.63 | 0.54 | 3.4E−06 | 1.6E−03 | 4.7 | 3.7 |
| PI 36:3 | 0.64 | 0.51 | 2.0E−05 | 3.0E−05 | 4.2 | 5.0 |
| PI 36:1 | 0.58 | 0.59 | 9.4E−09 | 6.9E−03 | 5.9 | 3.1 |
| PI 38:5 | 0.58 | 0.51 | 9.1E−08 | 1.2E−03 | 5.5 | 3.9 |
| PI 38:3 | 0.65 | 0.40 | 7.0E−07 | 9.2E−09 | 5.0 | 8.8 |

TABLE 25

Statistical parameters for MALDI-MS analysis of non-cancerous plasma samples and cancerous plasma samples of males (M) and females (F) for kidney cancer.

| Species | Fold change F | Fold change M | P-value F | P-value M | T-value F | T-value M |
|---|---|---|---|---|---|---|
| cholesterol sulfate | 0.57 | 0.80 | 5.1E−09 | 1.6E−02 | 6.3 | 2.2 |
| SM 32:1 | 0.54 | 0.60 | 4.3E−10 | 1.4E−11 | 7.4 | 7.2 |
| SM 33:1 | 0.57 | 0.63 | 1.4E−08 | 4.4E−10 | 6.6 | 6.6 |
| SM 34:2 | 0.77 | 0.71 | 3.7E−03 | 6.7E−06 | 2.9 | 4.5 |
| SM 34:1 | 0.72 | 0.75 | 3.4E−04 | 3.0E−05 | 3.7 | 4.2 |
| SM 34:0 | 0.68 | 0.70 | 7.8E−05 | 1.2E−06 | 4.2 | 5.0 |
| SM 35:1 | 0.64 | 0.66 | 1.1E−05 | 4.1E−08 | 4.8 | 5.7 |
| SM 36:2 | 0.86 | 0.74 | 7.2E−02 | 1.8E−04 | 1.5 | 3.7 |
| SM 36:1 | 0.81 | 0.74 | 1.5E−02 | 2.5E−05 | 2.3 | 4.2 |
| SM 37:1 | 0.66 | 0.65 | 7.0E−05 | 1.1E−07 | 4.2 | 5.5 |
| SM 38:2 | 0.76 | 0.69 | 2.7E−03 | 4.0E−06 | 3.0 | 4.7 |
| SM 38:1 | 0.65 | 0.64 | 1.8E−05 | 9.9E−10 | 4.7 | 6.5 |
| SM 39:1 | 0.52 | 0.53 | 3.4E−08 | 2.1E−14 | 6.4 | 8.4 |
| SM 40:2 | 0.65 | 0.64 | 1.0E−05 | 2.2E−08 | 4.8 | 5.8 |
| SM 40:1 | 0.65 | 0.63 | 2.5E−05 | 6.1E−10 | 4.6 | 6.5 |
| SM 41:2 | 0.60 | 0.64 | 5.2E−07 | 1.3E−08 | 5.6 | 5.9 |
| SM 41:1 | 0.58 | 0.59 | 1.3E−06 | 2.8E−12 | 5.5 | 7.5 |
| SM 42:2 | 0.61 | 0.62 | 4.6E−06 | 9.0E−10 | 5.1 | 6.5 |
| SM 43:3 | 0.65 | 0.75 | 2.1E−06 | 3.4E−05 | 5.0 | 4.1 |
| SM 43:2 | 0.62 | 0.64 | 3.1E−05 | 2.9E−06 | 4.4 | 4.7 |
| SM 43:1 | 0.39 | 0.39 | 8.2E−10 | 1.8E−11 | 6.6 | 7.4 |
| Sul 32:1 (OH) | 0.63 | 0.81 | 6.0E−07 | 6.9E−04 | 5.2 | 3.3 |
| Sul 34:1 | 0.62 | 0.68 | 5.6E−05 | 2.0E−05 | 4.3 | 4.3 |
| Sul 34:1 (OH) | 0.61 | 0.68 | 1.6E−05 | 2.9E−05 | 4.7 | 4.2 |
| Sul 34:0 (OH) | 0.43 | 0.58 | 4.9E−08 | 3.5E−05 | 6.1 | 4.1 |
| Sul 40:1 | 0.62 | 0.60 | 4.6E−04 | 1.1E−05 | 3.6 | 4.4 |
| Sul 41:1 | 0.49 | 0.60 | 4.2E−07 | 2.7E−05 | 5.5 | 4.2 |
| Sul 40:1 (OH) | 0.57 | 0.58 | 9.1E−06 | 5.1E−08 | 4.8 | 5.6 |
| Sul 41:1 (OH) | 0.50 | 0.52 | 3.6E−07 | 6.4E−09 | 5.7 | 6.1 |
| Sul 40:0 (2OH) | 0.71 | 0.88 | 1.7E−05 | 3.4E−02 | 4.3 | 1.8 |
| Sul 42:1 (OH) | 0.58 | 0.61 | 8.5E−06 | 1.2E−07 | 4.9 | 5.5 |
| Sul 42:1 (2OH) | 0.55 | 0.60 | 8.8E−04 | 1.1E−04 | 3.3 | 3.8 |
| Sul 42:0 (2OH) | 0.72 | 0.85 | 8.2E−05 | 2.2E−02 | 3.9 | 2.0 |
| SulfoHex$_2$Cer 42:2 | 1.34 | 1.84 | 9.1E−02 | 2.7E−02 | −1.4 | −2.0 |
| PI 36:4 | 0.59 | 0.82 | 2.7E−05 | 4.9E−02 | 4.3 | 1.7 |
| PI 36:3 | 0.54 | 0.75 | 8.6E−06 | 1.3E−02 | 4.6 | 2.3 |
| PI 36:2 | 0.62 | 0.81 | 6.5E−06 | 1.2E−02 | 4.7 | 2.3 |
| PI 36:1 | 0.53 | 0.70 | 4.7E−07 | 5.0E−04 | 5.4 | 3.4 |
| PI 38:5 | 0.52 | 0.74 | 7.1E−07 | 1.1E−02 | 5.3 | 2.3 |
| PI 38:3 | 0.60 | 0.72 | 6.6E−06 | 7.3E−04 | 4.8 | 3.3 |

TABLE 26

Statistical parameters for MALDI-MS analysis of non-cancerous plasma samples and cancerous plasma samples of males (M) and females (F) for prostate cancer.

| Species | Fold change | P-value | T-value |
|---|---|---|---|
| cholesterol sulfate | 0.61 | 7.6E−09 | 6.1 |
| SM 32:1 | 0.60 | 8.9E−12 | 7.4 |
| SM 33:1 | 0.59 | 2.7E−11 | 7.2 |
| SM 34:2 | 0.60 | 1.6E−10 | 6.8 |
| SM 34:1 | 0.65 | 2.9E−10 | 6.7 |
| SM 36:2 | 0.61 | 1.2E−08 | 6.0 |
| SM 36:1 | 0.66 | 1.8E−08 | 5.9 |
| SM 37:1 | 0.59 | 3.6E−10 | 6.7 |
| SM 38:2 | 0.58 | 1.9E−10 | 6.8 |
| SM 38:1 | 0.62 | 2.9E−11 | 7.2 |
| SM 39:1 | 0.54 | 2.5E−13 | 8.0 |
| SM 40:3 | 0.46 | 6.2E−09 | 6.1 |
| SM 40:2 | 0.58 | 5.4E−12 | 7.5 |
| SM 40:1 | 0.59 | 6.8E−13 | 7.9 |
| SM 41:2 | 0.57 | 1.5E−12 | 7.7 |
| SM 41:1 | 0.58 | 2.1E−13 | 8.1 |
| SM 42:2 | 0.64 | 2.9E−09 | 6.3 |
| SM 42:1 | 0.59 | 1.6E−12 | 7.7 |
| SM 43:2 | 0.56 | 1.5E−08 | 5.9 |
| SM 43:1 | 0.46 | 4.0E−08 | 5.7 |
| Sul 34:1 | 0.62 | 4.0E−10 | 6.7 |
| Sul 34:2 (OH) | 0.52 | 1.9E−08 | 5.9 |
| Sul 34:1 (OH) | 0.61 | 2.4E−09 | 6.3 |
| Sul 34:0 (OH) | 0.45 | 3.7E−10 | 6.7 |
| Sul 40:2 | 0.47 | 1.5E−06 | 5.0 |
| Sul 40:1 | 0.47 | 4.0E−12 | 7.5 |
| Sul 40:2 (OH) | 0.49 | 9.0E−07 | 5.0 |
| Sul 41:1 | 0.51 | 2.6E−08 | 5.8 |
| Sul 40:1 (OH) | 0.56 | 2.6E−11 | 7.2 |
| Sul 42:2 | 0.57 | 1.8E−08 | 5.9 |
| Sul 42:1 | 0.51 | 2.1E−09 | 6.3 |
| Sul 41:1 (OH) | 0.53 | 6.7E−11 | 7.0 |
| Sul 42:2 (OH) | 0.64 | 3.8E−08 | 5.7 |

TABLE 26-continued

Statistical parameters for MALDI-MS analysis of non-cancerous plasma samples and cancerous plasma samples of males (M) and females (F) for prostate cancer.

| Species | Fold change | P-value | T-value |
|---|---|---|---|
| Sul 42:1 (OH) | 0.59 | 3.5E−11 | 7.1 |
| Sul 42:1 (2OH) | 0.55 | 1.0E−06 | 5.0 |
| PI 36:4 | 0.59 | 1.5E−06 | 4.9 |
| PI 36:3 | 0.57 | 3.0E−06 | 4.7 |
| PI 38:5 | 0.53 | 1.1E−07 | 5.5 |
| PI 38:4 | 0.60 | 1.8E−09 | 6.3 |
| PI 38:3 | 0.61 | 7.8E−09 | 6.0 |

Example C: UHPSFC/MS Lipidomic Analysis of Human Plasma of Cancer Patients for the Differentiation of Various Cancerous Samples The aim of the invention is not only to differentiate non-cancerous and cancerous samples from body fluids, but also the prediction of the localization of the cancer in the body. It was found that there is a difference of the lipid profile depending on the cancer type, which can be determined in the biological fluid. OPLS-DA could be again a tool to visualize the most probably minor differences of the lipid profile.

TABLE 27

Statistical parameters for the MALDI-MS analysis of non-cancerous urine samples and cancerous urine samples of males (M) and females (F) for kidney and prostate cancer.

| | Kidney | | | | | | Prostate | | |
|---|---|---|---|---|---|---|---|---|---|
| | Fold change | | P-value | | T-value | | Fold change | P-value | T-value |
| Species | F | M | F | M | F | M | M | M | M |
| cortisol sulfate | 1.9 | 3.8 | 5.2E−02 | 1.3E−03 | −1.7 | −3.1 | 1.5 | 5.2E−02 | −1.7 |
| lithocholic acid sulfate | 1.4 | 2.4 | 2.0E−01 | 4.4E−02 | −0.9 | −1.7 | 1.1 | 3.8E−01 | −0.3 |
| cholesterol sulfate | 1.1 | 1.7 | 3.8E−01 | 1.3E−02 | −0.3 | −2.3 | 1.5 | 1.0E−01 | −1.3 |
| taurolithocholic acid | 0.6 | 1.6 | 1.0E−01 | 9.7E−02 | 1.3 | −1.3 | 1.1 | 3.9E−01 | −0.3 |
| sulfocholic acid | 2.3 | 6.6 | 5.7E−02 | 5.7E−03 | −1.7 | −2.6 | 1.9 | 1.7E−02 | −2.2 |
| taurodeoxycholic acid | 0.8 | 2.8 | 3.3E−01 | 8.6E−03 | 0.5 | −2.4 | 1.5 | 8.9E−02 | −1.4 |
| sulfoglycolithocholic acid | 1.0 | 1.6 | 4.4E−01 | 2.9E−02 | 0.2 | −1.9 | 1.2 | 2.4E−01 | −0.7 |
| taurocholic acid | 0.6 | 2.0 | 8.6E−02 | 1.3E−02 | 1.4 | −2.3 | 1.6 | 8.6E−02 | −1.4 |
| glycochenodeoxycholic acid sulfate | 1.0 | 2.3 | 4.8E−01 | 1.5E−02 | 0.0 | −2.2 | 1.2 | 2.6E−01 | −0.7 |
| psychosine sulfate | 1.1 | 1.4 | 3.8E−01 | 5.2E−02 | −0.3 | −1.7 | 1.1 | 2.8E−01 | −0.6 |
| Sul 34:1 (OH) | 1.1 | 1.0 | 3.8E−01 | 4.4E−01 | −0.3 | −0.1 | 1.0 | 4.3E−01 | 0.2 |
| Sul 36:1 (OH) | 1.7 | 1.8 | 7.8E−02 | 3.9E−03 | −1.5 | −2.8 | 1.3 | 1.2E−01 | −1.2 |
| Sul 38:1 | 1.2 | 1.0 | 3.2E−01 | 4.9E−01 | −0.5 | 0.0 | 0.8 | 3.0E−01 | 0.5 |
| Sul 38:1 (OH) | 1.1 | 0.7 | 4.3E−01 | 1.3E−01 | −0.2 | 1.1 | 0.8 | 1.9E−01 | 0.9 |
| Sul 40:2 | 1.6 | 1.5 | 1.8E−01 | 8.2E−02 | −1.0 | −1.4 | 0.8 | 2.1E−01 | 0.8 |
| Sul 41:2 | 1.8 | 1.9 | 7.9E−02 | 1.8E−03 | −1.5 | −3.0 | 1.4 | 9.3E−02 | −1.3 |
| Sul 41:1 | 0.9 | 1.0 | 4.1E−01 | 4.5E−01 | 0.2 | 0.1 | 0.9 | 3.2E−01 | 0.5 |
| Sul 40:1 (OH) | 0.8 | 0.9 | 3.0E−01 | 3.4E−01 | 0.5 | 0.4 | 0.9 | 2.6E−01 | 0.7 |
| Sul 40:0 (OH) | 0.7 | 1.0 | 1.6E−01 | 4.5E−01 | 1.0 | 0.1 | 0.9 | 2.9E−01 | 0.6 |
| Sul 42:3 | 2.9 | 3.6 | 3.8E−02 | 3.3E−04 | −1.9 | −3.6 | 1.6 | 2.4E−02 | −2.0 |
| Sul 42:2 | 2.2 | 2.1 | 5.7E−02 | 5.1E−03 | −1.7 | −2.6 | 1.0 | 4.4E−01 | −0.1 |
| Sul 42:1 | 1.2 | 1.4 | 2.8E−01 | 8.3E−02 | −0.6 | −1.4 | 1.0 | 4.4E−01 | −0.1 |
| Sul 41:1 (OH) | 0.9 | 0.9 | 3.6E−01 | 3.6E−01 | 0.4 | 0.4 | 0.9 | 2.8E−01 | 0.6 |
| Sul 41:0 (OH) | 0.8 | 0.9 | 2.3E−01 | 3.3E−01 | 0.8 | 0.5 | 0.8 | 2.4E−01 | 0.7 |
| Sul 40:0 (2OH) | 0.7 | 0.9 | 1.7E−01 | 3.3E−01 | 1.0 | 0.5 | 0.8 | 2.1E−01 | 0.8 |
| Sul 42:3 (OH) | 1.6 | 2.0 | 8.5E−02 | 6.7E−04 | −1.4 | −3.3 | 1.5 | 5.6E−02 | −1.6 |
| Sul 41:0 (2OH) | 0.8 | 0.9 | 2.0E−01 | 3.9E−01 | 0.9 | 0.3 | 0.9 | 2.6E−01 | 0.6 |
| Sul 43:2 (OH) | 1.5 | 1.9 | 1.2E−01 | 1.0E−03 | −1.2 | −3.2 | 1.4 | 7.1E−02 | −1.5 |
| Sul 42:1 (2OH) | 0.8 | 1.1 | 2.0E−01 | 2.8E−01 | 0.9 | −0.6 | 0.9 | 3.2E−01 | 0.5 |
| Sul 42:0 (2OH) | 0.8 | 1.0 | 2.8E−01 | 4.5E−01 | 0.6 | −0.1 | 0.9 | 3.7E−01 | 0.3 |
| Sul 43:1 (2OH) | 1.7 | 2.1 | 7.7E−02 | 3.7E−04 | −1.5 | −3.5 | 1.6 | 3.3E−02 | −1.9 |
| Sul 43:0 (2OH) | 1.4 | 1.3 | 1.8E−01 | 8.7E−02 | −0.9 | −1.4 | 1.0 | 5.0E−01 | 0.0 |
| SulfoHex$_2$Cer 34:1 | 2.9 | 2.8 | 1.9E−02 | 2.6E−03 | −2.2 | −2.9 | 1.4 | 1.1E−01 | −1.3 |
| SulfoHex$_2$Cer 34:1 (OH) | 2.1 | 1.8 | 5.4E−02 | 6.3E−03 | −1.7 | −2.6 | 1.6 | 7.2E−02 | −1.5 |
| SulfoHex$_2$Cer 36:1 | 2.2 | 3.4 | 4.1E−02 | 1.8E−04 | −1.8 | −3.7 | 1.7 | 1.7E−02 | −2.2 |
| SulfoHex$_2$Cer 38:1 | 3.1 | 3.4 | 4.2E−02 | 2.1E−03 | −1.8 | −3.0 | 1.6 | 5.4E−02 | −1.6 |
| SulfoHex$_2$Cer 38:1 (OH) | 1.9 | 1.9 | 4.9E−02 | 5.5E−03 | −1.7 | −2.6 | 1.5 | 8.7E−02 | −1.4 |
| SulfoHex$_2$Cer 40:2 | 3.0 | 3.8 | 3.7E−02 | 1.2E−03 | −1.9 | −3.2 | 1.6 | 3.2E−02 | −1.9 |
| SulfoHex$_2$Cer 40:1 | 3.7 | 2.5 | 3.5E−02 | 2.4E−03 | −1.9 | −2.9 | 1.3 | 1.7E−01 | −1.0 |
| SulfoHex$_2$Cer 41:1 | 2.3 | 2.7 | 4.3E−02 | 6.3E−05 | −1.8 | −4.0 | 1.6 | 2.8E−02 | −2.0 |
| SulfoHex$_2$Cer 40:1 (OH) | 1.7 | 0.8 | 1.8E−01 | 2.0E−01 | −1.0 | 0.9 | 0.7 | 1.3E−01 | 1.2 |
| SulfoHex$_2$Cer 42:3 | 2.6 | 3.5 | 3.9E−02 | 1.3E−03 | −1.9 | −3.1 | 1.6 | 2.7E−02 | −2.0 |
| SulfoHex$_2$Cer 42:2 | 4.5 | 3.3 | 2.5E−02 | 1.1E−03 | −2.1 | −3.2 | 1.2 | 2.4E−01 | −0.7 |
| SulfoHex$_2$Cer 42:1 | 3.3 | 2.6 | 3.5E−02 | 1.1E−03 | −1.9 | −3.2 | 1.3 | 1.6E−01 | −1.0 |
| SulfoHex$_2$Cer 41:1 (OH) | 1.8 | 1.7 | 7.9E−02 | 1.0E−02 | −1.5 | −2.4 | 1.3 | 1.6E−01 | −1.0 |
| SulfoHex$_2$Cer 40:0 (2OH) | 1.2 | 0.8 | 3.1E−01 | 2.2E−01 | −0.5 | 0.8 | 0.7 | 7.4E−02 | 1.5 |

Figure 19:
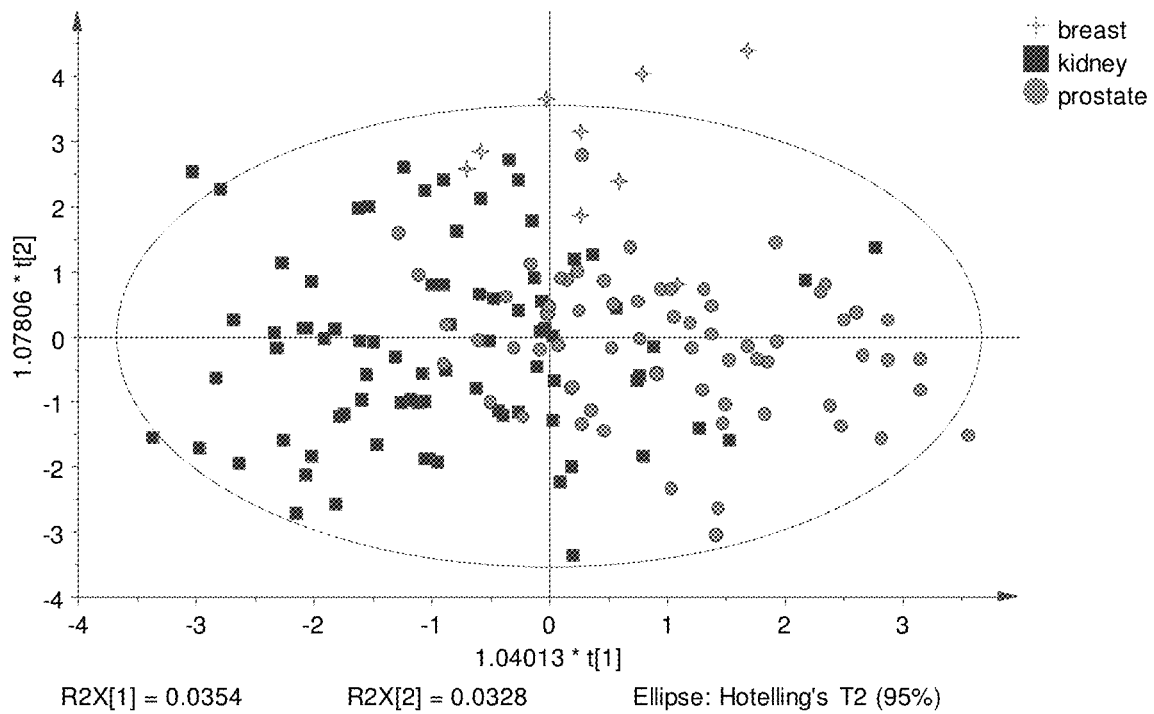
FIG. 19: OPLS-DA statistical model of breast, kidney, and prostate cancer plasma samples from males.

FIG. 19 represents the OPLS-DA plot of various cancer type samples (breast, kidney, prostate) from males. This figure confirms that there is a difference in the lipid profile of different cancer types.

Figure 20:
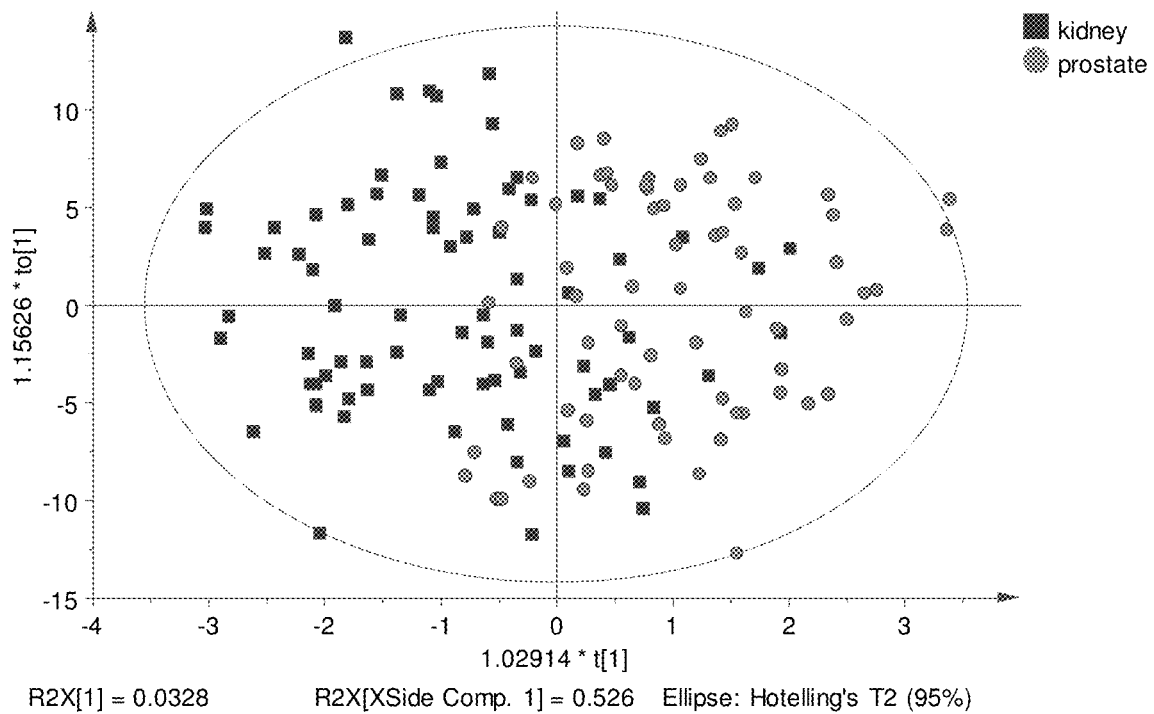
FIG. 20: OPLS-DA plot statistical model for the differentiation of prostate and kidney cancer plasma samples from males.

FIG. 20 shows the OPLS-DA plot for the differentiation of prostate and kidney cancer samples from males. The sensitivity is 76.1% and the specificity is 80.3% for males.

Figure 21:
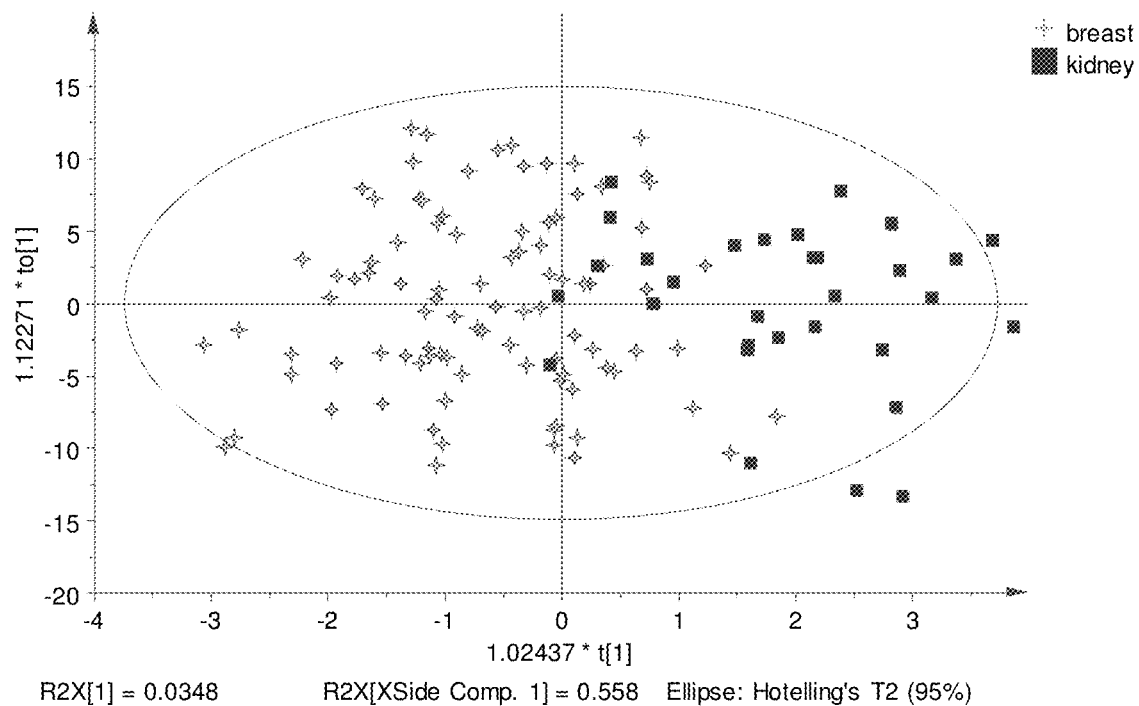
FIG. 21: OPLS-DA statistical model for the differentiation of breast and kidney cancer plasma samples from females.

FIG. 21 represents the OPLS-DA plot for the differentiation of breast and kidney cancer samples from females. The sensitivity is 74.2% and the specificity is 96.8% for females.

Example D—Experimental Results Relating to Diagnostics of Pancreatic Cancer

All quantified lipids in human serum of males (M) and females (F) for pancreatic cancer patients and healthy volunteers are summarized in Table 28 for shotgun measurements, in Table 29 for UHPSFC/MS measurements and in Table 30 for MALDI-MS measurements, together with fold changes, p-values, and T-values.

Figure 22:
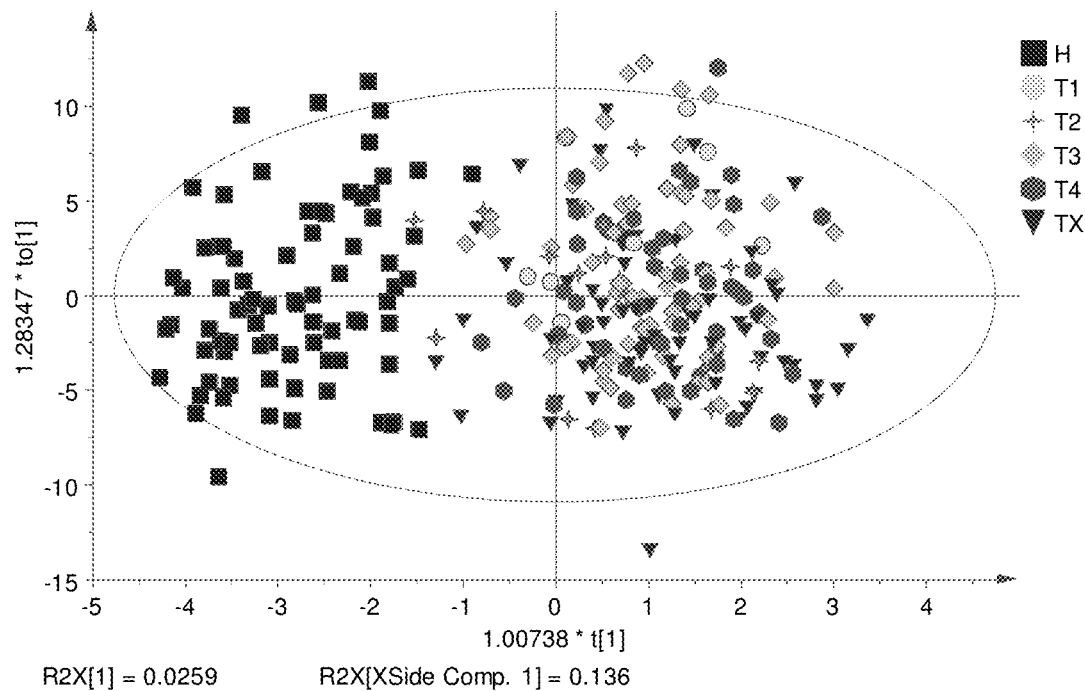
FIG. 22. OPLS-DA analysis of 79 samples of healthy controls (N), 213 samples of patients suffering from pancreatic cancer (tumor stages T1, T2, T3, T4, and Tx) for both genders (generated from UHPSFC/MS and shotgun data).
Figure 23:
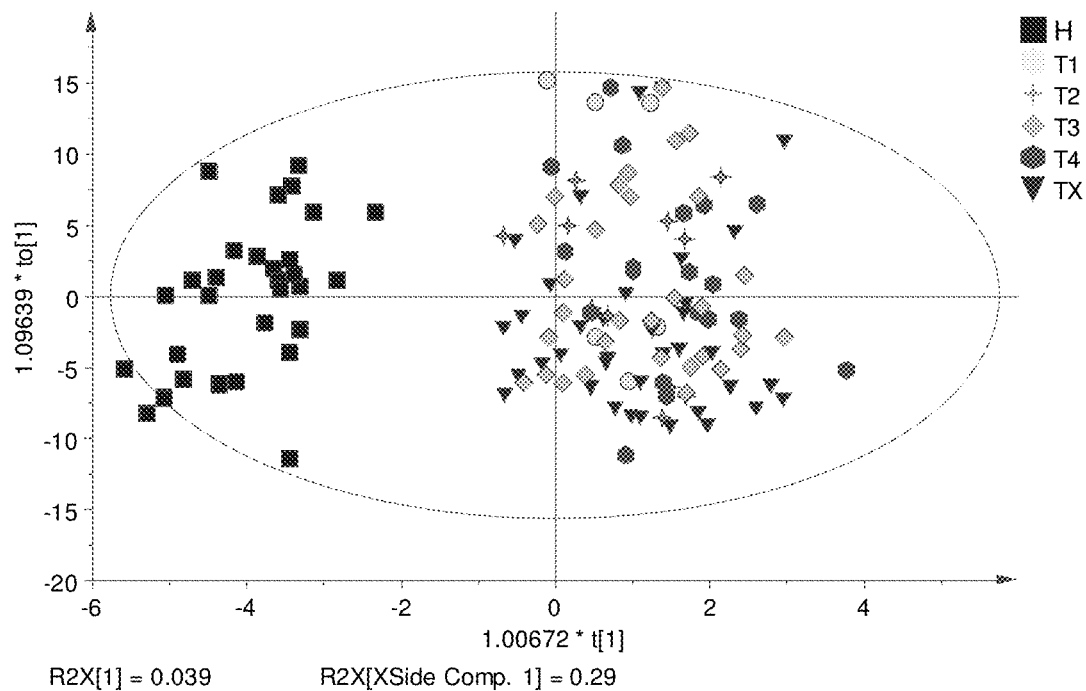
FIG. 23. OPLS-DA analysis of 49 samples of healthy controls (N), 109 samples of patients suffering from pancreatic cancer (tumor stages T1, T2, T3, T4, and Tx) for males (generated from UHPSFC/MS and shotgun data).
Figure 24:
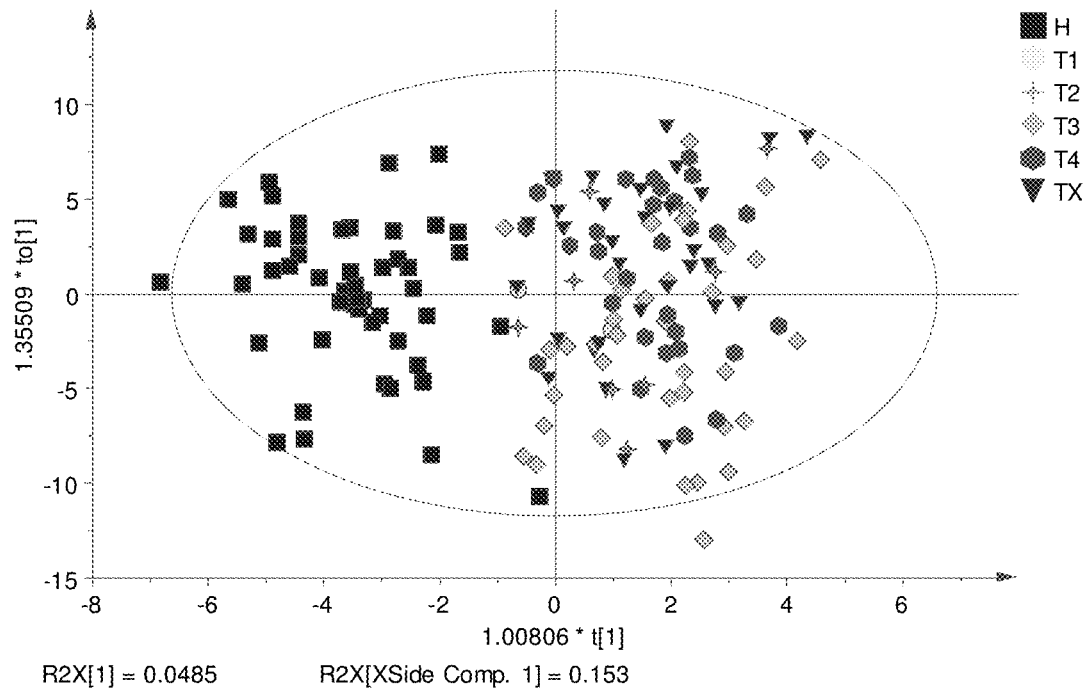
FIG. 24. OPLS-DA analysis of 30 samples of healthy controls (N), 104 samples of patients suffering from pancreatic cancer (tumor stages T1, T2, T3, T4, and Tx) for females (generated from UHPSFC/MS and shotgun data).

Pancreatic Cancer Model Based on Known Classification Using Shotgun and UHPSFC/MS Data:

These statistical models are built based on 292 known serum samples both for shotgun and UHPSFC/MS data sets. Absolute concentrations (normalization to internal standard) are used for these statistical analyses. First, the non-supervised PCA method is used to check the regular distribution of data, and it already shows partial separation of classes of cancer patients and healthy volunteers (controls). Then, supervised OPLS-DA model is prepared to improve class separation of non-cancerous and cancerous serum samples (FIG. 22). For this example of combination of data obtained using UHPSFC/MS and shotgun MS, specificitity 98.7% and sensitivity 98.6% (accuracy 98.6%) is obtained. These models include all lipids used (complete lipidome) and are automatically computed by SIMCA software. FIG. 23 (males) and FIG. 24 (females) show subsequently the OPLS-DA statistical models after gender separation. These models again illustrate another improvement of non-cancerous and cancerous samples differentiation, where sensitivity 100%, specificity 100% (accuracy 100%) is obtained in case of males and sensitivity 100%, specificity 95.9% (accuracy 98.7%) is obtained for females. It is worth noting that there is the gap between both groups, which visually highlights the reliability of the model for pancreatic cancer classification.

Figure 25:
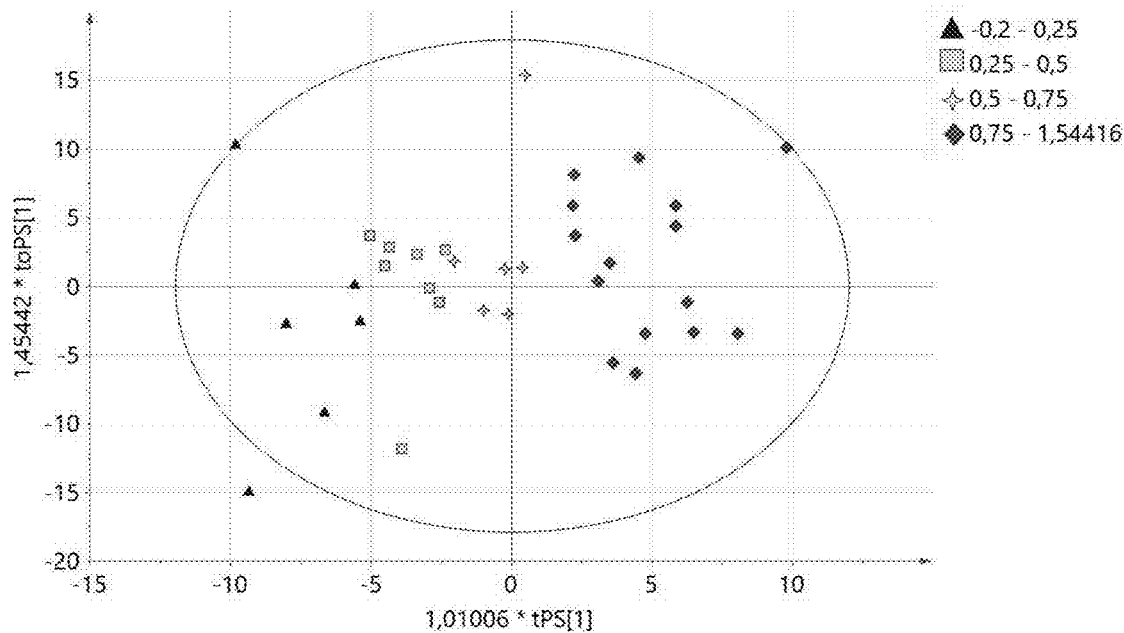
FIG. 25. OPLS-DA statistical model prediction of being pancreatic cancer patient for females from UHPSFC/MS and shotgun data for unknown samples.
Figure 26:
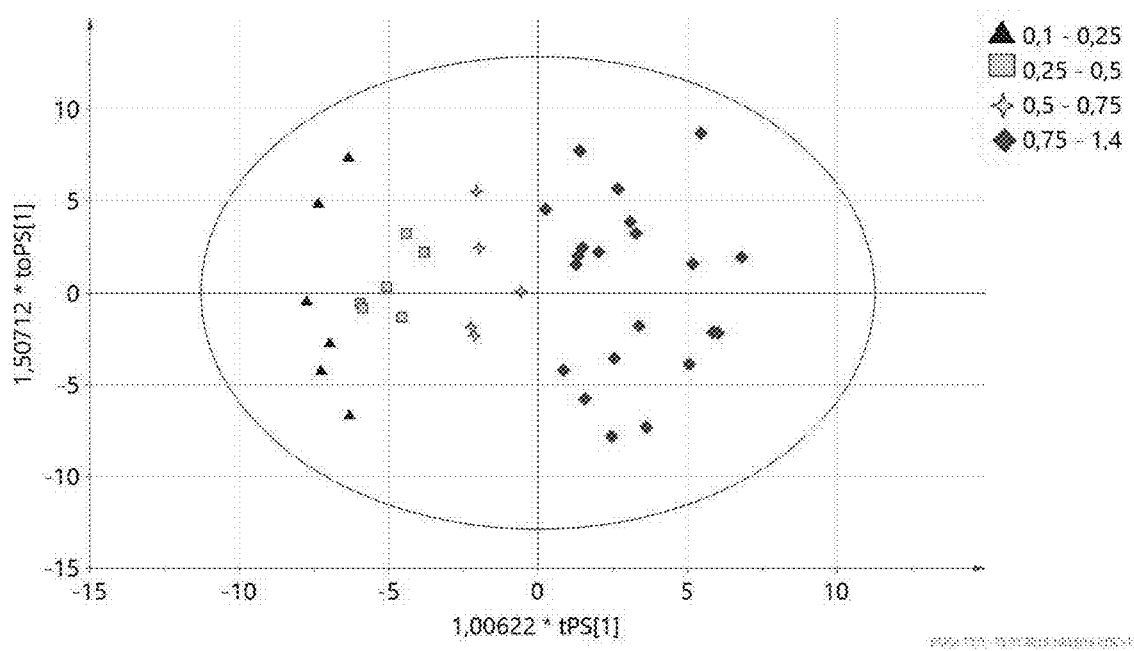
FIG. 26. OPLS-DA statistical model prediction of being pancreatic cancer patient for males from UHPSFC/MS and shotgun data for unknown samples.

Pancreatic Cancer Model Based on Unknown Classification Using Shotgun and UHPSFC/MS Data:

The next step is the verification of the quality of OPLS-DA model prepared for samples with known classification for blinded samples with unknown classification. The probability of being the cancer patient is estimated using 4 final models: #1/OPLS-DA of shotgun MS, #2/OPLS-DA of UHPSFC/MS, #3/OPLS-DA of all data, #4 Support vector machines (SVM) of all data, and finally the average of all models, which is used for the final assignment. The observation is classified as tumor if this estimate is bigger than 0.5 and as healthy volunteer if this probability is smaller than 0.5 (FIGS. 25 and 26). Triangle symbols shows observations "sure healthy", square symbols as "healthy", star symbols as "cancer" and diamond symbols as "sure cancer". The models resulted in very good prediction ability as was expected (4 wrongly classified from 73 unknown samples). Tables 31 and 32 show the resulting assignments of samples.

TABLE 28

List of all quantified lipids with shotgun measurement together with fold changes, p-values, and T-values.

| Lipid | Fold change | | p-value | | T-value | |
|---|---|---|---|---|---|---|
| | M | F | M | F | M | F |
| CE 14:0 | 0.88 | 0.73 | 9.7E−02 | 1.7E−04 | 1.3 | 3.8 |
| CE 16:0 | 1.02 | 0.96 | 3.5E−01 | 2.4E−01 | −0.4 | 0.7 |
| CE 16:1 | 1.35 | 0.83 | 2.7E−03 | 1.8E−02 | −2.8 | 2.1 |
| CE 18:1 | 1.15 | 0.94 | 1.2E−02 | 1.9E−01 | −2.3 | 0.9 |
| CE 18:2 | 0.90 | 0.80 | 2.9E−02 | 5.2E−04 | 2.0 | 3.4 |
| CE 18:3 | 0.87 | 0.70 | 4.6E−02 | 1.3E−04 | 1.7 | 3.9 |
| CE 20:4 | 0.94 | 1.00 | 1.9E−01 | 4.8E−01 | 0.9 | 0.1 |
| CE 20:5 | 0.65 | 0.77 | 1.0E−02 | 1.1E−02 | 2.5 | 2.4 |
| CE 22:4 | 1.09 | 0.90 | 7.5E−02 | 1.3E−01 | −1.5 | 1.1 |
| CE 22:5 | 2.68 | 0.83 | 1.5E−05 | 2.1E−01 | −4.4 | 0.8 |
| CE 22:6 | 0.95 | 1.01 | 2.4E−01 | 4.6E−01 | 0.7 | −0.1 |
| Cer d18:0/16:1; Cerd18:0/15:2(1OH) | 0.92 | 1.00 | 5.6E−02 | 5.0E−01 | 1.6 | 0.0 |
| Cer d18:0/16:2 | 0.96 | 0.96 | 2.1E−01 | 2.1E−01 | 0.8 | 0.8 |
| Cer d18:0/18:2 | 0.96 | 0.97 | 2.6E−01 | 2.3E−01 | 0.6 | 0.8 |
| Cer d18:0/24:0; Cer d18:0/23:1(1OH) | 0.94 | 0.75 | 2.9E−01 | 3.1E−03 | 0.6 | 2.8 |
| Cer d18:0/24:1; Cer d18:0/23:2(1OH) | 1.13 | 1.00 | 1.8E−02 | 4.6E−01 | −2.2 | −0.1 |
| Cer d18:1/16:0; Cer d18:1/15:1(1OH) | 1.64 | 1.29 | 1.8E−12 | 2.6E−03 | −8.1 | −2.9 |
| Cer d18:1/16:1; Cer d18:1/15:2(1OH) | 1.00 | 0.92 | 4.8E−01 | 4.9E−02 | −0.1 | 1.7 |
| Cer d18:1/16:2 | 1.08 | 0.89 | 9.4E−02 | 1.4E−02 | −1.4 | 2.3 |
| Cer d18:1/18:0; Cer d18:1/17:1(1OH) | 1.71 | 1.54 | 4.3E−13 | 6.2E−06 | −8.1 | −4.5 |
| Cer d18:1/18:2 | 1.07 | 0.89 | 1.2E−01 | 1.1E−02 | −1.2 | 2.4 |
| Cer d18:1/18:3 | 1.21 | 0.79 | 1.0E−03 | 1.7E−04 | −3.2 | 3.8 |
| Cer d18:1/20:0; Cer d18:1/19:1(1OH) | 1.23 | 1.28 | 5.9E−02 | 2.1E−02 | −1.6 | −2.1 |
| Cer d18:1/22:0; Cer d18:1/21:1(1OH) | 1.10 | 1.09 | 6.8E−02 | 1.0E−01 | −1.5 | −1.3 |
| Cer d18:1/23:0; Cer d18:1/22:1(1OH) | 0.85 | 0.77 | 1.5E−02 | 3.0E−04 | 2.3 | 3.6 |
| Cer d18:1/24:0; Cer d18:1/23:1(1OH) | 0.87 | 0.78 | 1.8E−02 | 4.9E−04 | 2.2 | 3.4 |
| Cer d18:1/24:1; Cer d18:1/23:2(1OH) | 1.53 | 1.36 | 6.2E−13 | 4.8E−05 | −8.3 | −4.1 |
| Cer d18:1/25:0; Cer d18:1/24:1(1OH) | 0.95 | 0.73 | 1.9E−01 | 2.5E−05 | 0.9 | 4.3 |
| DG 30:0 | 1.05 | 1.10 | 3.6E−01 | 1.7E−01 | −0.4 | −1.0 |
| DG 31:0 | 1.11 | 0.95 | 7.3E−02 | 2.5E−01 | −1.5 | 0.7 |
| DG 32:0 | 1.14 | 1.35 | 1.4E−01 | 3.4E−03 | −1.1 | −2.8 |

TABLE 28-continued

List of all quantified lipids with shotgun measurement
together with fold changes, p-values, and T-values.

| Lipid | Fold change M | Fold change F | p-value M | p-value F | T-value M | T-value F |
|---|---|---|---|---|---|---|
| DG 32:1 | 1.10 | 1.12 | 2.5E−01 | 1.2E−01 | −0.7 | −1.2 |
| DG 32:2 | 0.98 | 1.04 | 4.2E−01 | 3.1E−01 | 0.2 | −0.5 |
| DG 34:0 | 0.59 | 1.06 | 1.1E−03 | 2.1E−01 | 3.4 | −0.8 |
| DG 34:1 | 1.11 | 1.27 | 2.1E−01 | 1.1E−02 | −0.8 | −2.3 |
| DG 34:2 | 1.05 | 1.13 | 3.4E−01 | 9.1E−02 | −0.4 | −1.4 |
| DG 34:3 | 0.91 | 0.98 | 2.1E−01 | 4.3E−01 | 0.8 | 0.2 |
| DG 36:0 | 0.35 | 0.88 | 2.7E−03 | 1.0E−01 | 3.1 | 1.3 |
| DG 36:1 | 1.01 | 1.33 | 4.6E−01 | 2.1E−03 | −0.1 | −2.9 |
| DG 36:2 | 1.09 | 1.35 | 2.6E−01 | 1.1E−03 | −0.7 | −3.2 |
| DG 36:3 | 0.89 | 1.23 | 1.6E−01 | 1.7E−02 | 1.0 | −2.2 |
| DG 36:4 | 0.78 | 1.10 | 1.8E−02 | 1.8E−01 | 2.2 | −0.9 |
| DG 38:2 | 1.07 | 1.03 | 2.2E−01 | 3.3E−01 | −0.8 | −0.4 |
| DG 38:3 | 1.09 | 0.90 | 1.9E−01 | 9.9E−02 | −0.9 | 1.3 |
| DG 38:4 | 1.03 | 1.06 | 3.8E−01 | 2.3E−01 | −0.3 | −0.7 |
| DG 38:5 | 0.92 | 1.24 | 2.2E−01 | 2.2E−03 | 0.8 | −2.9 |
| DG 38:6 | 0.77 | 1.19 | 1.8E−02 | 8.9E−02 | 2.2 | −1.4 |
| Hex2Cer d18:1/16:0; Hex2Cer d18:1/15:1(1OH) | 1.25 | 1.08 | 8.2E−05 | 1.5E−01 | −3.9 | −1.1 |
| Hex2Cer d18:1/20:0; Hex2Cerd18:1/19:1(1OH) | 1.32 | 0.83 | 8.0E−02 | 1.3E−01 | −1.4 | 1.2 |
| Hex2Cer d18:1/21:0(1OH) | 1.12 | 0.95 | 1.8E−02 | 2.3E−01 | −2.1 | 0.8 |
| Hex2Cer d18:1/22:0; Hex2Cer d18:1/21:1(1OH) | 0.95 | 0.80 | 2.1E−01 | 1.0E−03 | 0.8 | 3.2 |
| Hex2Cer d18:1/24:1; Hex2Cer d18:1/23:2(1OH) | 1.34 | 1.19 | 6.6E−05 | 2.2E−02 | −4.1 | −2.1 |
| HexCer d18:1/16:0; HexCer d18:1/15:1(1OH) | 1.50 | 1.12 | 1.9E−13 | 7.8E−02 | −8.3 | −1.4 |
| HexCer d18:1/20:0; HexCer d18:1/19:1(1OH) | 1.19 | 1.10 | 3.3E−02 | 2.1E−01 | −1.9 | −0.8 |
| HexCer d18:1/22:0; HexCer d18:1/21:1(1OH) | 1.02 | 0.87 | 3.4E−01 | 1.7E−02 | −0.4 | 2.2 |
| HexCer d18:1/24:0; HexCer d18:1/23:1(1OH) | 0.96 | 0.79 | 2.6E−01 | 7.7E−04 | 0.7 | 3.3 |
| HexCer d18:1/24:1; HexCer d18:1/23:2(1OH) | 1.56 | 1.14 | 8.7E−13 | 5.1E−02 | −7.9 | −1.7 |
| HexCer d18:1/25:0; HexCer d18:1/24:1(1OH) | 0.91 | 1.10 | 2.2E−02 | 1.1E−02 | 2.1 | −2.3 |
| Chol | 1.12 | 0.95 | 8.3E−03 | 2.8E−01 | −2.5 | 0.6 |
| LPC 16:0 | 0.86 | 0.82 | 3.1E−03 | 1.1E−03 | 2.9 | 3.2 |
| LPC 16:1 | 0.97 | 0.75 | 3.5E−01 | 2.1E−04 | 0.4 | 3.7 |
| LPC 18:0 | 0.77 | 0.80 | 1.5E−04 | 1.9E−03 | 3.9 | 3.0 |
| LPC 18:1 | 0.92 | 0.85 | 8.7E−02 | 8.3E−03 | 1.4 | 2.5 |
| LPC 18:2 | 0.62 | 0.68 | 3.4E−07 | 3.0E−07 | 5.8 | 5.4 |
| LPC 20:1 | 1.13 | 0.74 | 1.7E−01 | 6.1E−04 | −1.0 | 3.4 |
| LPC 20:3 | 0.80 | 0.76 | 8.4E−04 | 5.8E−05 | 3.3 | 4.1 |
| LPC 20:4 | 0.75 | 0.87 | 2.0E−05 | 2.3E−02 | 4.5 | 2.0 |
| LPC 22:6 | 0.72 | 1.00 | 1.7E−06 | 4.8E−01 | 5.2 | 0.1 |
| LPE 16:0 | 1.12 | 0.94 | 1.2E−01 | 2.1E−01 | −1.2 | 0.8 |
| LPE 18:0 | 1.02 | 0.89 | 4.3E−01 | 6.9E−02 | −0.2 | 1.5 |
| LPE 18:1 | 0.92 | 0.84 | 2.5E−01 | 3.5E−02 | 0.7 | 1.8 |
| LPE 18:2 | 0.79 | 0.83 | 4.7E−02 | 2.2E−02 | 1.7 | 2.1 |
| LPE 20:4 | 0.78 | 1.25 | 2.1E−02 | 3.7E−02 | 2.1 | −1.8 |
| LPE 22:6 | 0.98 | 1.16 | 4.4E−01 | 6.2E−02 | 0.2 | −1.6 |
| LPG 20:0 | 0.87 | 0.89 | 2.8E−01 | 3.0E−01 | 0.6 | 0.5 |
| LPG O-18:0; LPG 17:0 | 0.85 | 1.16 | 2.0E−01 | 1.7E−01 | 0.8 | −1.0 |
| LPG O-20:0; LPG 19:0 | 0.93 | 1.21 | 3.3E−01 | 9.6E−02 | 0.4 | −1.3 |
| LPG O-22:0; LPG 21:0 | 0.91 | 1.32 | 2.4E−01 | 1.6E−02 | 0.7 | −2.2 |
| MG 16:0 | 0.89 | 1.13 | 4.3E−02 | 4.6E−02 | 1.8 | −1.7 |
| MG 17:0 | 0.67 | 1.54 | 5.6E−02 | 1.2E−02 | 1.7 | −2.3 |
| MG 18:0 | 0.67 | 1.07 | 2.3E−03 | 1.3E−01 | 3.1 | −1.1 |
| MG 18:1 | 1.35 | 1.72 | 3.3E−02 | 8.8E−03 | −1.9 | −2.4 |
| MG 22:0 | 1.19 | 1.04 | 1.3E−01 | 4.0E−01 | −1.1 | −0.3 |
| PA 38:4; PA P-40:10; PA P-29:3 | 0.79 | 2.08 | 5.4E−03 | 7.7E−07 | 2.7 | −5.1 |
| PC 30:0 | 1.21 | 0.92 | 6.8E−03 | 1.2E−01 | −2.6 | 1.2 |
| PC 32:0; PC O-33:0 | 1.55 | 1.10 | 2.5E−13 | 1.1E−01 | −8.1 | −1.2 |
| PC 32:1; PC P-33:0 | 1.90 | 0.93 | 6.1E−06 | 2.7E−01 | −4.6 | 0.6 |
| PC 32:2; PC P-33:1 | 0.67 | 0.53 | 1.4E−03 | 1.6E−06 | 3.1 | 5.0 |
| PC 34:1; PC P-35:0 | 1.46 | 1.02 | 1.2E−09 | 4.0E−01 | −6.5 | −0.3 |
| PC 34:2; PC P-35:1 | 1.10 | 0.86 | 2.4E−02 | 1.1E−02 | −2.0 | 2.4 |
| PC 34:3; PC P-35:2 | 1.06 | 0.76 | 1.9E−01 | 1.2E−04 | −0.9 | 3.9 |
| PC 34:4; PC P-35:3 | 0.79 | 0.70 | 2.7E−03 | 2.0E−05 | 2.9 | 4.4 |
| PC 36:0; PC P-38:6 | 0.43 | 0.50 | 3.2E−03 | 4.7E−04 | 2.9 | 3.5 |
| PC 36:1; PC P-37:0 | 1.30 | 0.95 | 2.4E−04 | 2.6E−01 | −3.6 | 0.7 |
| PC 36:2; PC P-37:1 | 1.02 | 0.86 | 3.3E−01 | 1.8E−02 | −0.4 | 2.2 |
| PC 36:3; PC P-37:2 | 1.16 | 0.85 | 3.1E−03 | 9.4E−03 | −2.8 | 2.4 |
| PC 36:4; PC P-37:3 | 1.04 | 0.95 | 2.4E−01 | 2.5E−01 | −0.7 | 0.7 |
| PC 36:5; PC P-37:4 | 0.72 | 0.81 | 2.5E−02 | 1.4E−02 | 2.1 | 2.3 |
| PC 38:2; PC P-40:8; PC P-39:1 | 1.10 | 0.47 | 3.7E−01 | 7.9E−04 | −0.3 | 3.3 |
| PC 38:3; PC P-40:9; PC P-39:2 | 1.12 | 0.94 | 2.2E−02 | 2.1E−01 | −2.1 | 0.8 |
| PC 38:4; PC P-40:10; PC P-29:3 | 1.00 | 1.01 | 4.8E−01 | 4.6E−01 | 0.0 | −0.1 |
| PC 38:5; PC P-39:4 | 0.93 | 0.92 | 1.8E−01 | 1.2E−01 | 0.9 | 1.2 |
| PC 38:6; PC P-39:5 | 0.94 | 1.02 | 1.9E−01 | 3.8E−01 | 0.9 | −0.3 |

TABLE 28-continued

List of all quantified lipids with shotgun measurement together with fold changes, p-values, and T-values.

| Lipid | Fold change | | p-value | | T-value | |
|---|---|---|---|---|---|---|
| | M | F | M | F | M | F |
| PC 40:4; PC P-42:10; PC P-41:3 | 1.17 | 0.89 | 7.4E−03 | 6.6E−02 | −2.5 | 1.5 |
| PC 40:5; PC P-41:4 | 1.06 | 1.03 | 2.4E−01 | 3.5E−01 | −0.7 | −0.4 |
| PC 40:6; PC P-41:5 | 0.98 | 1.17 | 4.1E−01 | 2.9E−02 | 0.2 | −1.9 |
| PC O-32:0; PC 31:0 | 1.36 | 0.91 | 3.6E−07 | 1.2E−01 | −5.4 | 1.2 |
| PC O-34:0; PC 33:0 | 1.16 | 0.92 | 3.8E−02 | 1.4E−01 | −1.8 | 1.1 |
| PC P-32:0; PC 31:1 | 1.43 | 0.82 | 6.2E−11 | 2.3E−03 | −7.1 | 3.0 |
| PC P-34:0; PC 33:1 | 1.44 | 0.96 | 1.6E−11 | 3.0E−01 | −7.5 | 0.5 |
| PC P-34:1; PC 33:2 | 1.04 | 0.71 | 2.7E−01 | 2.7E−06 | −0.6 | 4.9 |
| PC P-36:0; PC 35:1 | 1.05 | 0.71 | 3.0E−01 | 2.2E−04 | −0.5 | 3.7 |
| PC P-36:1; PC 35:2 | 1.04 | 0.79 | 2.8E−01 | 6.4E−04 | −0.6 | 3.4 |
| PC P-36:2; PC 35:3 | 1.07 | 0.74 | 1.3E−01 | 3.8E−05 | −1.1 | 4.2 |
| PC P-36:3; PC 35:4 | 1.06 | 0.83 | 1.4E−01 | 6.8E−03 | −1.1 | 2.5 |
| PC P-36:4; PC 35:5 | 0.99 | 0.84 | 4.5E−01 | 7.9E−03 | 0.1 | 2.5 |
| PC P-38:2; PC 37:3 | 0.91 | 0.69 | 1.8E−01 | 5.6E−05 | 0.9 | 4.1 |
| PC P-38:3; PC 37:4 | 1.08 | 0.87 | 5.8E−02 | 2.4E−02 | −1.6 | 2.0 |
| PC P-38:4; PC 37:5 | 1.13 | 0.96 | 4.1E−03 | 2.7E−01 | −2.7 | 0.6 |
| PC P-38:5; PC 37:6 | 0.96 | 0.88 | 2.3E−01 | 3.7E−02 | 0.8 | 1.8 |
| PC P-40:3; PC 39:4 | 0.96 | 0.72 | 2.8E−01 | 7.2E−05 | 0.6 | 4.0 |
| PC P-40:4; PC 39:5 | 1.01 | 0.81 | 4.6E−01 | 6.5E−03 | −0.1 | 2.6 |
| PC P-40:5; PC 39:6 | 1.00 | 0.97 | 4.8E−01 | 3.1E−01 | 0.0 | 0.5 |
| PE 32:0; PE O-33:0 | 1.47 | 1.27 | 2.0E−03 | 4.4E−02 | −3.0 | −1.7 |
| PE 32:1; PE P-33:0 | 2.48 | 1.19 | 1.4E−06 | 6.8E−02 | −4.9 | −1.5 |
| PE 34:0; PE P-36:6 | 1.07 | 0.76 | 2.8E−01 | 3.2E−03 | −0.6 | 2.8 |
| PE 34:1; PE P-35:0 | 1.98 | 1.20 | 1.5E−09 | 4.4E−02 | −6.4 | −1.7 |
| PE 34:2; PE P-35:1 | 1.78 | 1.11 | 1.2E−07 | 1.4E−01 | −5.5 | −1.1 |
| PE 34:3; PE P-35:2 | 1.55 | 0.96 | 1.9E−05 | 3.1E−01 | −4.3 | 0.5 |
| PE 36:0; PE P-38:6 | 0.77 | 0.84 | 1.5E−03 | 1.7E−02 | 3.2 | 2.2 |
| PE 36:1; PE P-37:0 | 1.18 | 1.06 | 8.1E−02 | 2.8E−01 | −1.4 | −0.6 |
| PE 36:2; PE P-37:1 | 1.33 | 1.04 | 4.8E−03 | 3.4E−01 | −2.7 | −0.4 |
| PE 36:3; PE P-37:2 | 1.43 | 0.97 | 3.1E−03 | 3.7E−01 | −2.8 | 0.3 |
| PE 36:4; PE P-37:3 | 1.70 | 1.15 | 2.1E−08 | 5.7E−02 | −5.9 | −1.6 |
| PE 36:5; PE P-37:4 | 1.26 | 0.93 | 1.8E−02 | 1.9E−01 | −2.2 | 0.9 |
| PE 38:0; PE P-40:6, PE O-39:0 | 0.77 | 0.81 | 1.8E−04 | 6.2E−03 | 3.8 | 2.6 |
| PE 38:1; PE P-40:7; PE P-39:0 | 0.94 | 0.83 | 1.5E−01 | 5.0E−03 | 1.1 | 2.7 |
| PE 38:2; PE P-40:8; PE P-39:1 | 1.05 | 1.51 | 2.4E−01 | 6.9E−04 | −0.7 | −3.3 |
| PE 38:3; PE P-40:9; PE P-39:2 | 1.67 | 0.90 | 4.6E−05 | 1.6E−01 | −4.1 | 1.0 |
| PE 38:4; PE P-40:10; PE P-29:3 | 1.41 | 1.14 | 3.8E−05 | 6.0E−02 | −4.2 | −1.6 |
| PE 38:5; PE P-39:4 | 1.49 | 1.02 | 2.3E−05 | 3.9E−01 | −4.3 | −0.3 |
| PE 38:6; PE P-39:5 | 1.65 | 1.19 | 1.3E−07 | 4.4E−02 | −5.6 | −1.7 |
| PE 38:7; PE O-38:0; PE 37:0 | 1.36 | 0.96 | 9.7E−06 | 3.0E−01 | −4.5 | 0.5 |
| PE 40:1; PE P-42:7; PE P-41:0 | 0.88 | 1.05 | 2.2E−01 | 3.7E−01 | 0.8 | −0.3 |
| PE 40:2; PE P-42:8; PE P-41:1 | 0.92 | 0.94 | 2.6E−01 | 3.4E−01 | 0.6 | 0.4 |
| PE 40:3; PE P-42:9; PE P-41:2 | 0.85 | 0.89 | 6.9E−02 | 1.7E−01 | 1.5 | 1.0 |
| PE 40:4; PE P-42:10; PE P-41:3 | 1.50 | 1.03 | 9.7E−05 | 3.3E−01 | −3.9 | −0.4 |
| PE 40:5; PE P-41:4 | 1.54 | 1.13 | 3.9E−05 | 9.2E−02 | −4.1 | −1.3 |
| PE 40:6; PE P-41:5 | 1.42 | 1.30 | 2.8E−04 | 3.3E−03 | −3.6 | −2.8 |
| PE 40:7; PE O-40:0; PE 39:0 | 1.51 | 1.03 | 1.9E−06 | 3.6E−01 | −4.9 | −0.4 |
| PE 40:8; PE P-40:0; PE 39:1 | 1.19 | 0.96 | 3.9E−03 | 3.0E−01 | −2.7 | 0.5 |
| PE 42:9; PE P-42:1; PE 41:2 | 0.97 | 1.09 | 4.1E−01 | 3.0E−01 | 0.2 | −0.5 |
| PE P-34:0; PE 33:1 | 1.03 | 0.66 | 3.5E−01 | 9.1E−08 | −0.4 | 5.8 |
| PE P-34:1; PE 33:2 | 0.86 | 0.67 | 6.1E−02 | 6.0E−06 | 1.6 | 4.7 |
| PE P-36:0; PE 35:1 | 1.31 | 0.89 | 4.1E−02 | 2.2E−01 | −1.8 | 0.8 |
| PE P-36:1; PE 35:2 | 1.12 | 0.80 | 6.7E−02 | 9.5E−04 | −1.5 | 3.2 |
| PE P-36:2; PE 35:3 | 0.89 | 0.69 | 8.8E−02 | 7.9E−06 | 1.4 | 4.6 |
| PE P-36:3; PE 35:4 | 0.72 | 0.56 | 8.8E−04 | 2.6E−06 | 3.3 | 5.0 |
| PE P-36:4; PE 35:5 | 0.76 | 0.79 | 5.3E−04 | 4.0E−03 | 3.5 | 2.7 |
| PE P-38:2; PE 37:3 | 1.39 | 0.57 | 4.9E−02 | 5.1E−06 | −1.7 | 4.8 |
| PE P-38:3; PE 37:4 | 0.87 | 0.69 | 4.8E−02 | 8.8E−05 | 1.7 | 4.0 |
| PE P-38:4; PE 37:5 | 0.74 | 0.68 | 1.9E−04 | 1.7E−05 | 3.8 | 4.4 |
| PE P-38:5; PE 37:6 | 0.73 | 0.71 | 3.6E−05 | 5.7E−05 | 4.3 | 4.1 |
| PE P-40:4; PE 39:5 | 0.91 | 0.80 | 9.6E−02 | 8.9E−04 | 1.3 | 3.3 |
| PE P-40:5; PE 39:6 | 0.83 | 0.78 | 8.9E−03 | 8.0E−04 | 2.5 | 3.3 |
| PG 32:0; PG O-33:0 | 0.84 | 1.35 | 2.6E−01 | 6.7E−02 | 0.7 | −1.5 |
| PG 32:1; PG P-33:0 | 0.90 | 1.32 | 3.6E−01 | 6.9E−02 | 0.4 | −1.5 |
| PG 34:0; PG P-36:6 | 0.61 | 0.96 | 5.7E−02 | 4.2E−01 | 1.6 | 0.2 |
| PG 34:1; PG P-35:0 | 0.86 | 1.24 | 2.5E−01 | 6.5E−02 | 0.7 | −1.5 |
| PG 34:2; PG P-35:1 | 0.76 | 1.09 | 1.1E−01 | 2.8E−01 | 1.3 | −0.6 |
| PG 36:1; PG P-37:0 | 0.86 | 1.13 | 1.7E−01 | 1.5E−01 | 1.0 | −1.0 |
| PG 36:2; PG P-37:1 | 0.83 | 1.14 | 1.8E−01 | 1.4E−01 | 1.0 | −1.1 |
| PG 36:3; PG P-37:2 | 0.64 | 0.67 | 1.7E−01 | 2.6E−02 | 1.0 | 2.0 |
| PG 36:4; PG P-37:3 | 0.70 | 1.19 | 5.1E−02 | 1.8E−01 | 1.7 | −0.9 |
| PI 32:0; PI O-33:0 | 0.90 | 1.27 | 3.1E−01 | 1.2E−01 | 0.5 | −1.2 |

TABLE 28-continued

List of all quantified lipids with shotgun measurement
together with fold changes, p-values, and T-values.

| Lipid | Fold change M | Fold change F | p-value M | p-value F | T-value M | T-value F |
|---|---|---|---|---|---|---|
| PI 32:1; PI P-33:0 | 1.63 | 0.92 | 3.4E−03 | 2.7E−01 | −2.8 | 0.6 |
| PI 34:0; PI P-36:6 | 0.92 | 0.81 | 4.0E−01 | 1.5E−01 | 0.3 | 1.0 |
| PI 34:1; PI P-35:0 | 1.58 | 0.86 | 9.7E−06 | 6.3E−02 | −4.5 | 1.6 |
| PI 34:2; PI P-35:1 | 1.53 | 0.98 | 2.3E−06 | 4.1E−01 | −4.8 | 0.2 |
| PI 36:0; PI P-38:6 | 1.21 | 0.82 | 1.8E−01 | 1.7E−01 | −0.9 | 0.9 |
| PI 36:1; PI P-37:0 | 1.34 | 0.75 | 4.4E−03 | 2.8E−03 | −2.7 | 2.9 |
| PI 36:2; PI P-37:1 | 1.38 | 0.92 | 2.7E−04 | 1.7E−01 | −3.6 | 1.0 |
| PI 36:3; PI P-37:2 | 1.53 | 0.95 | 1.2E−05 | 2.9E−01 | −4.5 | 0.6 |
| PI 36:4; PI P-37:3 | 1.34 | 0.95 | 7.3E−04 | 3.1E−01 | −3.3 | 0.5 |
| PI 38:2; PI P-40:8; PI P-39:1 | 1.43 | 0.90 | 2.0E−04 | 1.4E−01 | −3.7 | 1.1 |
| PI 38:3; PI P-40:9; PI P-39:2 | 1.26 | 0.80 | 2.7E−02 | 2.8E−02 | −2.0 | 1.9 |
| PI 38:4; PI P-40:10; PI P-29:3 | 1.21 | 0.98 | 2.3E−02 | 4.0E−01 | −2.1 | 0.3 |
| PI 38:5; PI P-39:4 | 1.34 | 0.92 | 1.0E−03 | 2.0E−01 | −3.2 | 0.8 |
| PI 38:6; PI P-39:5 | 1.54 | 1.02 | 4.2E−04 | 4.4E−01 | −3.5 | −0.2 |
| PI 40:0; PI P-42:6, PI O-41:0 | 1.16 | 0.95 | 1.3E−01 | 2.9E−01 | −1.1 | 0.6 |
| PI 40:4; PI P-42:10; PI P-41:3 | 1.52 | 0.98 | 2.2E−04 | 4.4E−01 | −3.7 | 0.2 |
| PI 40:5; PI P-41:4 | 1.44 | 1.05 | 1.2E−04 | 2.9E−01 | −3.9 | −0.6 |
| PI 40:6; PI P-41:5 | 1.71 | 1.09 | 1.8E−06 | 2.1E−01 | −4.9 | −0.8 |
| PI 42:3; PI P-43:2 | 1.32 | 0.93 | 1.6E−02 | 2.8E−01 | −2.2 | 0.6 |
| PI P-36:0; PI 35:1 | 1.30 | 0.89 | 1.0E−01 | 2.9E−01 | −1.3 | 0.6 |
| PI P-36:1; PI 35:2 | 1.07 | 1.01 | 3.4E−01 | 4.8E−01 | −0.4 | −0.1 |
| PI P-38:3; PI 37:4 | 1.22 | 0.92 | 4.3E−02 | 2.7E−01 | −1.8 | 0.6 |
| PS 34:0; PS P-36:6 | 1.36 | 1.12 | 5.4E−03 | 2.2E−01 | −2.6 | −0.8 |
| PS 34:2; PS P-35:1 | 1.03 | 1.13 | 3.4E−01 | 1.1E−01 | −0.4 | −1.2 |
| PS 36:1; PS P-37:0 | 1.46 | 1.07 | 1.1E−02 | 3.3E−01 | −2.4 | −0.5 |
| PS 38:4; PS P-40:10; PS P-29:3 | 1.29 | 1.48 | 7.9E−03 | 2.1E−04 | −2.5 | −3.6 |
| PS 38:6; PS P-39:5 | 0.88 | 1.40 | 7.0E−02 | 3.9E−03 | 1.5 | −2.7 |
| PS 42:1; PS P-43:0 | 0.82 | 1.34 | 8.1E−02 | 2.0E−02 | 1.4 | −2.1 |
| PS P-32:0; PS 31:1 | 1.23 | 0.98 | 7.5E−04 | 4.3E−01 | −3.3 | 0.2 |
| SM 32:1 | 0.93 | 0.84 | 1.1E−01 | 7.9E−03 | 1.2 | 2.5 |
| SM 33:1 | 1.03 | 0.94 | 3.0E−01 | 2.2E−01 | −0.5 | 0.8 |
| SM 34:0 | 1.38 | 1.09 | 2.6E−06 | 1.1E−01 | −4.8 | −1.2 |
| SM 34:1 | 1.28 | 1.06 | 2.7E−09 | 1.6E−01 | −6.5 | −1.0 |
| SM 34:2 | 1.07 | 0.97 | 6.2E−02 | 3.1E−01 | −1.6 | 0.5 |
| SM 35:1 | 0.77 | 1.65 | 1.3E−03 | 1.2E−03 | 3.1 | −3.2 |
| SM 36:0 | 2.02 | 1.94 | 5.5E−03 | 3.0E−03 | −2.6 | −2.8 |
| SM 36:1 | 1.16 | 1.28 | 1.7E−02 | 1.3E−03 | −2.2 | −3.1 |
| SM 36:2 | 1.10 | 1.11 | 3.0E−02 | 6.5E−02 | −1.9 | −1.5 |
| SM 37:0 | 0.83 | 0.76 | 2.6E−01 | 1.5E−01 | 0.7 | 1.1 |
| SM 39:1 | 0.71 | 0.65 | 1.9E−05 | 2.4E−05 | 4.6 | 4.4 |
| SM 40:0 | 0.96 | 0.84 | 2.8E−01 | 1.4E−02 | 0.6 | 2.3 |
| SM 40:1 | 0.90 | 0.84 | 6.0E−02 | 2.1E−02 | 1.6 | 2.1 |
| SM 41:1 | 0.78 | 0.70 | 6.5E−05 | 5.6E−06 | 4.2 | 4.7 |
| SM 41:2 | 0.91 | 0.80 | 4.8E−02 | 1.5E−03 | 1.7 | 3.1 |
| SM 42:2 | 1.31 | 1.10 | 1.1E−09 | 9.3E−02 | −6.6 | −1.3 |
| SM 43:1 | 1.45 | 0.60 | 3.8E−02 | 1.6E−05 | −1.8 | 4.4 |
| SM 44:2 | 1.65 | 0.93 | 6.2E−03 | 2.6E−01 | −2.6 | 0.6 |
| SulfoHexCer 41:0; SulfoHexCer 40:1(1OH) | 1.06 | 1.14 | 2.1E−01 | 7.7E−02 | −0.8 | −1.5 |
| SulfoHexCer 41:1; SulfoHexCer 40:2(1OH) | 0.92 | 0.83 | 1.4E−01 | 3.3E−02 | 1.1 | 1.9 |
| SulfoHexCer 43:0; SulfoHexCer 42:1(1OH) | 1.20 | 0.86 | 2.7E−02 | 6.5E−02 | −2.0 | 1.5 |
| SulfoHexCer 43:1; SulfoHexCer 42:2(1OH) | 0.72 | 1.07 | 2.7E−04 | 2.9E−01 | 3.7 | −0.5 |
| SulfoHexCer 43:2; SulfoHexCer 42:3(1OH) | 1.45 | 0.98 | 7.8E−03 | 4.6E−01 | −2.5 | 0.1 |
| TG 56:3 | 0.80 | 1.75 | 3.1E−02 | 6.5E−06 | 1.9 | −4.6 |
| TG 56:4 | 1.02 | 1.22 | 4.2E−01 | 7.5E−03 | −0.2 | −2.5 |
| TG 56:5 | 1.26 | 1.26 | 5.5E−03 | 3.6E−03 | −2.6 | −2.7 |
| TG 56:6 | 0.71 | 1.81 | 3.9E−03 | 2.0E−04 | 2.8 | −3.7 |
| TG 58:6 | 0.89 | 1.55 | 1.6E−01 | 2.5E−03 | 1.0 | −2.9 |

TABLE 29

List of all quantified lipids with UHPSFC/MS measurement together with fold changes, p-values, and T-values.

| Lipid | Fold change M | Fold change F | p-value M | p-value F | T-value M | T-value F |
|---|---|---|---|---|---|---|
| CE 16:1 | 1.52 | 0.85 | 2.6E-03 | 7.2E-02 | -2.9 | 1.5 |
| CE 16:0 | 1.02 | 1.07 | 3.9E-01 | 2.5E-01 | -0.3 | -0.7 |
| CE 18:3 | 0.78 | 0.68 | 8.2E-03 | 2.7E-04 | 2.5 | 3.6 |
| CE 18:2 | 0.93 | 0.86 | 3.3E-02 | 3.5E-03 | 1.9 | 2.8 |
| CE 18:1 | 1.19 | 0.98 | 7.9E-03 | 4.1E-01 | -2.5 | 0.2 |
| CE 18:0 | 0.50 | 0.87 | 8.3E-05 | 2.3E-01 | 4.3 | 0.7 |
| CE 20:5 | 0.60 | 0.71 | 3.5E-02 | 1.5E-02 | 1.9 | 2.2 |
| CE 20:4 | 0.97 | 0.97 | 3.3E-01 | 3.8E-01 | 0.5 | 0.3 |
| CE 20:3 | 0.97 | 0.83 | 3.9E-01 | 9.0E-02 | 0.3 | 1.4 |
| CE 20:2 | 0.77 | 0.86 | 3.9E-03 | 9.1E-02 | 2.8 | 1.4 |
| CE 22:6 | 0.91 | 1.11 | 1.7E-01 | 1.7E-01 | 1.0 | -1.0 |
| CE 22:5 | 1.45 | 0.88 | 1.9E-03 | 2.0E-01 | -3.0 | 0.9 |
| TG 44:2 | 1.09 | 1.40 | 4.3E-01 | 1.2E-01 | -0.2 | -1.2 |
| TG 44:1 | 1.22 | 1.39 | 3.5E-01 | 2.8E-01 | -0.4 | -0.6 |
| TG 44:0 | 0.34 | 1.41 | 2.3E-01 | 3.7E-01 | 0.8 | -0.3 |
| TG 46:3 | 0.71 | 1.31 | 2.3E-01 | 1.6E-01 | 0.8 | -1.0 |
| TG 46:2 | 0.94 | 1.16 | 4.4E-01 | 2.5E-01 | 0.2 | -0.7 |
| TG 46:1 | 1.19 | 1.20 | 3.2E-01 | 1.9E-01 | -0.5 | -0.9 |
| TG 46:0 | 1.27 | 1.27 | 2.6E-01 | 1.7E-01 | -0.6 | -1.0 |
| TG 47:2 | 0.80 | 1.16 | 2.5E-01 | 2.4E-01 | 0.7 | -0.7 |
| TG 47:1 | 0.98 | 1.23 | 4.8E-01 | 1.2E-01 | 0.1 | -1.2 |
| TG 47:0 | 1.08 | 1.30 | 4.2E-01 | 9.5E-02 | -0.2 | -1.3 |
| TG 48:4 | 0.58 | 1.17 | 4.9E-02 | 2.0E-01 | 1.7 | -0.9 |
| TG 48:3 | 0.70 | 1.02 | 9.8E-02 | 4.6E-01 | 1.3 | -0.1 |
| TG 48:2 | 1.03 | 1.02 | 4.5E-01 | 4.4E-01 | -0.1 | -0.1 |
| TG 48:1 | 1.20 | 1.11 | 2.3E-01 | 3.0E-01 | -0.7 | -0.5 |
| TG 48:0 | 1.29 | 1.24 | 1.7E-01 | 1.7E-01 | -1.0 | -1.0 |
| TG 49:3 | 0.76 | 1.15 | 1.3E-01 | 1.7E-01 | 1.2 | -1.0 |
| TG 49:2 | 0.90 | 1.14 | 3.3E-01 | 1.8E-01 | 0.5 | -0.9 |
| TG 49:1 | 1.01 | 1.25 | 4.9E-01 | 9.4E-02 | 0.0 | -1.3 |
| TG 50:5 | 0.52 | 1.14 | 1.2E-02 | 1.9E-01 | 2.4 | -0.9 |
| TG 50:4 | 0.66 | 1.01 | 1.9E-02 | 4.8E-01 | 2.2 | 0.0 |
| TG 50:3 | 0.89 | 1.04 | 2.3E-01 | 3.5E-01 | 0.8 | -0.4 |
| TG 50:2 | 1.29 | 1.18 | 4.5E-02 | 6.5E-02 | -1.7 | -1.5 |
| TG 50:1 | 1.42 | 1.36 | 1.2E-02 | 9.7E-03 | -2.3 | -2.4 |
| TG 51:6 | 1.20 | 1.11 | 3.9E-02 | 1.0E-01 | -1.8 | -1.3 |
| TG 51:5 | 1.18 | 1.37 | 5.4E-02 | 7.9E-04 | -1.7 | -3.3 |
| TG 51:4 | 0.65 | 1.32 | 9.0E-03 | 1.2E-02 | 2.5 | -2.3 |
| TG 51:3 | 0.87 | 1.21 | 2.0E-01 | 3.2E-02 | 0.9 | -1.9 |
| TG 51:2 | 1.10 | 1.29 | 2.9E-01 | 1.2E-02 | -0.6 | -2.3 |
| TG 51:1 | 1.05 | 1.45 | 4.2E-01 | 9.3E-03 | -0.2 | -2.4 |
| TG 52:7 | 0.44 | 1.30 | 1.6E-02 | 9.7E-02 | 2.3 | -1.3 |
| TG 52:6 | 0.51 | 1.16 | 7.3E-03 | 1.6E-01 | 2.6 | -1.0 |
| TG 52:5 | 0.65 | 1.08 | 9.1E-03 | 2.9E-01 | 2.5 | -0.6 |
| TG 52:4 | 0.83 | 1.16 | 7.8E-02 | 7.4E-02 | 1.5 | -1.5 |
| TG 52:3 | 1.05 | 1.26 | 3.0E-01 | 5.6E-03 | -0.5 | -2.6 |
| TG 52:2 | 1.31 | 1.33 | 3.9E-03 | 9.6E-04 | -2.8 | -3.2 |
| TG 52:1 | 1.07 | 1.52 | 3.7E-01 | 9.6E-03 | -0.3 | -2.4 |
| TG 52:0 | 1.00 | 1.35 | 5.0E-01 | 4.1E-03 | 0.0 | -2.7 |
| TG 53:5 | 0.91 | 1.46 | 2.4E-01 | 1.6E-04 | 0.7 | -3.7 |
| TG 53:4 | 0.79 | 1.32 | 8.7E-02 | 1.1E-02 | 1.4 | -2.3 |
| TG 53:3 | 0.99 | 1.34 | 4.6E-01 | 2.2E-03 | 0.1 | -2.9 |
| TG 53:2 | 1.11 | 1.41 | 2.4E-01 | 4.5E-04 | -0.7 | -3.4 |
| TG 54:8 | 0.39 | 1.23 | 4.3E-03 | 1.9E-01 | 2.8 | -0.9 |
| TG 54:7 | 0.54 | 1.24 | 7.6E-03 | 1.0E-01 | 2.6 | -1.3 |
| TG 54:6 | 0.72 | 1.35 | 2.4E-01 | 1.4E-02 | 2.1 | -2.2 |
| TG 54:5 | 0.88 | 1.32 | 1.9E-01 | 9.4E-03 | 0.9 | -2.4 |
| TG 54:4 | 0.99 | 1.34 | 4.8E-01 | 5.6E-03 | 0.0 | -2.6 |
| TG 54:3 | 1.23 | 1.45 | 8.1E-02 | 4.2E-04 | -1.4 | -3.5 |
| TG 54:2 | 1.23 | 1.56 | 9.7E-03 | 5.5E-04 | -1.3 | -3.4 |
| TG 54:1 | 0.73 | 1.58 | 1.3E-01 | 3.2E-02 | 1.2 | -1.9 |
| TG 54:0 | 0.93 | 1.66 | 3.0E-01 | 3.2E-06 | 0.5 | -4.8 |
| TG 55:6 | 1.15 | 1.62 | 1.4E-01 | 1.5E-06 | -1.1 | -4.9 |
| TG 55:4 | 0.95 | 1.61 | 3.6E-01 | 5.3E-05 | 0.4 | -4.0 |
| TG 55:3 | 1.08 | 1.61 | 2.9E-01 | 8.2E-06 | -0.6 | -4.5 |
| TG 56:9 | 0.46 | 1.35 | 2.6E-03 | 5.0E-02 | 3.0 | -1.7 |
| TG 56:8 | 0.62 | 1.53 | 1.3E-02 | 2.4E-03 | 2.4 | -2.9 |
| TG 56:7 | 0.79 | 1.52 | 7.6E-02 | 7.0E-04 | 1.5 | -3.3 |
| TG 56:6 | 1.04 | 1.51 | 3.7E-01 | 2.2E-04 | -0.3 | -3.6 |
| TG 56:5 | 1.38 | 1.68 | 3.4E-03 | 1.3E-05 | -2.8 | -4.4 |
| TG 56:4 | 1.14 | 1.30 | 1.7E-01 | 9.7E-03 | -1.0 | -2.4 |
| TG 56:3 | 1.08 | 1.39 | 3.1E-01 | 7.3E-03 | -0.5 | -2.5 |
| TG 56:2 | 0.76 | 1.19 | 1.1E-01 | 1.4E-01 | 1.3 | -1.1 |
| TG 56:1 | 0.62 | 1.38 | 5.6E-02 | 1.1E-01 | 1.6 | -1.2 |
| TG 58:10 | 0.58 | 1.62 | 1.4E-02 | 1.4E-03 | 2.3 | -3.1 |
| TG 58:9 | 0.78 | 1.64 | 7.5E-02 | 1.5E-04 | 1.5 | -3.7 |
| TG 58:8 | 0.95 | 1.72 | 3.7E-01 | 2.1E-05 | 0.3 | -4.3 |
| TG 58:7 | 1.11 | 1.37 | 1.6E-01 | 7.7E-05 | -1.0 | -3.9 |
| TG 58:6 | 1.35 | 1.79 | 2.4E-02 | 7.2E-06 | -2.0 | -4.5 |
| TG 58:5 | 1.33 | 1.79 | 2.8E-02 | 5.7E-06 | -2.0 | -4.6 |
| DG 34:2 | 1.06 | 1.28 | 3.5E-01 | 4.1E-02 | -0.4 | -1.8 |
| DG 34:1 | 1.23 | 1.23 | 8.5E-02 | 8.1E-02 | -1.4 | -1.4 |
| DG 34:0 | 0.67 | 2.27 | 4.6E-03 | 2.5E-08 | 2.7 | -5.8 |
| DG 36:4 | 0.65 | 1.38 | 7.6E-03 | 3.9E-02 | 2.6 | -1.8 |
| DG 36:3 | 0.89 | 1.26 | 1.6E-01 | 6.2E-02 | 1.0 | -1.6 |
| DG 36:2 | 1.20 | 1.34 | 9.2E-02 | 2.6E-02 | -1.4 | -2.0 |
| Coenzyme Q10 | 0.70 | 0.92 | 1.1E-02 | 3.2E-01 | 2.4 | 0.5 |
| MG 16:0 | 0.95 | 1.29 | 3.0E-01 | 1.2E-03 | 0.5 | -3.1 |
| MG 18:0 | 0.88 | 1.22 | 2.8E-02 | 3.6E-04 | 2.0 | -3.5 |
| Cer d40:1 | 1.07 | 0.96 | 2.4E-01 | 3.5E-01 | -0.7 | 0.4 |
| Cer d42:2 | 1.63 | 1.21 | 5.1E-11 | 2.3E-02 | -7.3 | -2.0 |
| Cer d42:1 | 0.96 | 0.68 | 3.0E-01 | 3.4E-04 | 0.5 | 3.6 |
| PC 30:0 | 1.48 | 0.79 | 1.7E-02 | 4.1E-02 | -2.2 | 1.8 |
| PC O-32:1/P-32:0 | 1.89 | 0.88 | 5.5E-07 | 1.5E-01 | -5.3 | 1.0 |
| PC 32:2 | 0.85 | 0.60 | 1.5E-01 | 2.1E-05 | 1.0 | 4.4 |
| PC 32:1 | 2.10 | 0.98 | 2.0E-06 | 4.0E-01 | -4.8 | 0.3 |
| PC 32:0 | 1.99 | 1.12 | 7.7E-13 | 5.8E-02 | -7.9 | -1.6 |
| PC O-34:3/P-34:2 | 1.02 | 0.62 | 4.1E-01 | 7.4E-07 | -0.2 | 5.3 |
| PC O-34:2/P-34:1 | 1.14 | 0.67 | 8.5E-02 | 4.8E-06 | -1.4 | 4.8 |
| PC 34:3 | 1.12 | 0.71 | 1.0E-01 | 6.7E-05 | -1.3 | 4.0 |
| PC 34:2 | 1.28 | 0.75 | 1.1E-03 | 5.2E-05 | -3.2 | 4.1 |
| PC 34:1 | 1.88 | 0.96 | 1.2E-11 | 2.9E-01 | -7.4 | 0.6 |
| PC O-36:5/P-36:4 | 1.04 | 0.83 | 3.1E-01 | 2.2E-02 | -0.4 | 2.1 |
| PC O-36:4/P-36:3 | 1.14 | 0.78 | 4.2E-02 | 2.2E-03 | -1.8 | 3.0 |
| PC O-36:3/P-36:2 | 1.10 | 0.61 | 1.9E-01 | 3.7E-06 | -0.9 | 4.9 |
| PC 35:2 | 1.19 | 0.75 | 2.3E-02 | 1.1E-03 | -2.0 | 3.2 |
| PC 35:1 | 2.05 | 1.09 | 3.6E-07 | 2.2E-01 | -5.4 | -0.8 |
| PC 36:5 | 0.97 | 0.73 | 4.1E-01 | 8.0E-04 | 0.2 | 3.3 |
| PC 36:4 | 1.19 | 0.86 | 1.9E-02 | 4.5E-02 | -2.1 | 1.7 |
| PC 36:3 | 1.34 | 0.73 | 2.2E-04 | 9.5E-05 | -3.7 | 4.0 |
| PC 36:2 | 1.23 | 0.76 | 9.0E-03 | 3.5E-04 | -2.4 | 3.6 |
| PC 36:1 | 2.10 | 1.06 | 3.6E-06 | 3.3E-01 | -4.7 | -0.4 |
| PC O-38:6/P-38:5 | 1.00 | 0.82 | 4.9E-01 | 8.0E-02 | 0.0 | 1.4 |
| PC O-38:5/P-38:4 | 1.28 | 0.93 | 6.0E-04 | 2.0E-01 | -3.4 | 0.9 |
| PC O-38:4/P-38:3 | 1.30 | 0.88 | 1.6E-04 | 6.9E-02 | -3.8 | 1.5 |
| PC 37:3 | 1.29 | 0.78 | 9.5E-03 | 2.1E-02 | -2.4 | 2.1 |
| PC 38:7 | 1.13 | 0.89 | 1.3E-01 | 1.2E-01 | -1.2 | 1.2 |
| PC 38:6 | 1.08 | 0.91 | 2.5E-01 | 2.0E-01 | -0.7 | 0.8 |
| PC 38:5 | 1.04 | 0.80 | 3.6E-01 | 7.1E-03 | -0.4 | 2.5 |
| PC 38:4 | 1.12 | 0.94 | 1.1E-01 | 2.3E-01 | -1.3 | 0.8 |
| PC 38:3 | 1.25 | 0.83 | 2.4E-02 | 3.2E-02 | -2.0 | 1.9 |
| PC 38:2 | 1.68 | 1.73 | 1.0E-03 | 8.4E-04 | -3.2 | -3.2 |
| PC 40:7 | 1.11 | 0.97 | 1.6E-01 | 3.8E-01 | -1.0 | 0.3 |
| PC 40:6 | 1.10 | 1.13 | 2.3E-01 | 1.2E-01 | -0.8 | -1.2 |
| PC 40:5 | 1.16 | 1.05 | 1.1E-01 | 2.9E-01 | -1.3 | -0.6 |
| PC 40:4 | 1.82 | 1.18 | 1.0E-03 | 1.3E-01 | -3.2 | -1.2 |
| SM d32:1 | 1.06 | 0.74 | 3.1E-01 | 8.8E-03 | -0.5 | 2.5 |
| SM d34:2 | 1.17 | 0.91 | 5.0E-03 | 1.4E-01 | -2.7 | 1.1 |
| SM d34:1 | 1.55 | 0.93 | 9.9E-10 | 1.9E-01 | -6.5 | 0.9 |
| SM d36:2 | 1.30 | 1.15 | 2.7E-03 | 1.0E-01 | -2.9 | -1.3 |
| SM d36:1 | 1.49 | 1.16 | 1.2E-07 | 5.7E-02 | -5.5 | -1.6 |
| SM d38:1 | 0.96 | 0.74 | 2.9E-01 | 2.0E-03 | 0.6 | 3.0 |
| SM d40:2 | 0.96 | 0.73 | 2.7E-01 | 6.9E-04 | 0.6 | 3.4 |
| SM d40:1 | 0.90 | 0.70 | 6.7E-02 | 7.1E-05 | 1.5 | 4.1 |
| SM d41:2 | 0.92 | 0.69 | 2.0E-01 | 1.1E-03 | 0.9 | 3.2 |
| SM d41:1 | 0.70 | 0.55 | 9.2E-05 | 1.6E-06 | 4.1 | 5.1 |
| SM d42:3 | 1.35 | 0.96 | 5.3E-06 | 3.2E-01 | -4.7 | 0.5 |
| SM d42:2 | 1.50 | 0.98 | 1.0E-08 | 3.9E-01 | -6.1 | 0.3 |
| SM d42:1 | 0.77 | 0.61 | 8.3E-04 | 2.6E-07 | 3.4 | 5.6 |

TABLE 30

List of all quantified lipids with MALDI-MS measurement together with fold changes, p-values, and T-values.

| Lipid | Fold change M | Fold change F | p-value M | p-value F | t-value M | t-value F |
|---|---|---|---|---|---|---|
| cholesterol sulfate | 1.02 | 1.21 | 4.5E−01 | 1.6E−01 | −0.1 | −1 |
| cholesterol sulfate (OH) | 1.06 | 1.69 | 4.3E−01 | 6.0E−02 | −0.2 | −1.6 |
| SM 32:1 | 0.86 | 1.01 | 1.9E−01 | 4.7E−01 | 0.9 | −0.1 |
| SM 33:2 | 1.45 | 1.31 | 1.3E−01 | 1.7E−01 | −1.2 | −1 |
| SM 33:1 | 1.04 | 1.24 | 4.2E−01 | 1.7E−01 | −0.2 | −1 |
| SM 34:2 | 1.12 | 1.06 | 2.6E−01 | 3.6E−01 | −0.7 | −0.4 |
| SM 34:1 | 1.19 | 1.26 | 1.7E−01 | 8.0E−02 | −1 | −1.5 |
| SM 34:0 | 1.13 | 1.23 | 2.7E−01 | 1.5E−01 | −0.7 | −1.1 |
| SM 35:1 | 1.15 | 1.3 | 2.8E−01 | 1.0E−01 | −0.6 | −1.4 |
| SM 36:2 | 1.19 | 1.16 | 1.8E−01 | 2.3E−01 | −1 | −0.8 |
| SM 36:1 | 1.24 | 1.35 | 1.3E−01 | 6.0E−02 | −1.2 | −1.6 |
| SM 36:0 | 1.42 | 2 | 4.8E−02 | 4.0E−02 | −1.8 | −1.9 |
| SM 37:1 | 1.08 | 1.37 | 3.9E−01 | 1.6E−01 | −0.3 | −1 |
| SM 38:1 | 0.9 | 1.03 | 2.9E−01 | 4.4E−01 | 0.6 | −0.2 |
| SM 39:1 | 0.57 | 0.81 | 1.7E−02 | 2.6E−01 | 2.3 | 0.7 |
| SM 40:3 | 1.19 | 1.43 | 2.8E−01 | 9.5E−02 | −0.6 | −1.4 |
| SM 40:2 | 0.94 | 1.02 | 3.7E−01 | 4.7E−01 | 0.4 | −0.1 |
| SM 40:1 | 0.86 | 0.98 | 2.1E−01 | 4.6E−01 | 0.9 | 0.1 |
| SM 41:3 | 1.42 | 1.26 | 1.2E−01 | 1.9E−01 | −1.3 | −0.9 |
| SM 41:2 | 0.84 | 0.99 | 2.2E−01 | 4.8E−01 | 0.8 | 0.1 |
| SM 41:1 | 0.68 | 0.85 | 2.8E−02 | 2.6E−01 | 2.1 | 0.7 |
| SM 42:4 | 1.16 | 1.17 | 2.7E−01 | 2.7E−01 | −0.6 | −0.6 |
| SM 42:3 | 1.19 | 1.19 | 2.1E−01 | 1.8E−01 | −0.9 | −1 |
| SM 42:2 | 1.19 | 1.28 | 2.1E−01 | 9.0E−02 | −0.9 | −1.4 |
| SM 42:1 | 0.83 | 0.92 | 1.7E−01 | 3.3E−01 | 1 | 0.5 |
| SM 43:2 | 1.27 | 1.56 | 2.5E−01 | 1.0E−01 | −0.7 | −1.4 |
| SM 43:1 | 1.05 | 0.96 | 2.5E−01 | 3.7E−01 | −0.7 | 0.4 |
| SulfoHexCer 34:2 | 1.43 | 0.9 | 2.5E−01 | 3.9E−01 | −0.7 | 0.3 |
| SulfoHexCer 34:1 | 0.81 | 0.92 | 1.8E−01 | 3.7E−01 | 1 | 0.3 |
| SulfoHexCer 34:2 (OH) | 0.86 | 0.87 | 3.7E−01 | 3.7E−01 | 0.4 | 0.4 |
| SulfoHexCer 35:1 | 0.63 | 1.02 | 2.8E−03 | 4.7E−01 | 3.1 | −0.1 |
| SulfoHexCer 34:1 (OH) | 0.76 | 0.93 | 9.0E−02 | 3.7E−01 | 1.4 | 0.3 |
| SulfoHexCer 35:0 | 0.78 | 1.23 | 1.9E−01 | 2.5E−01 | 0.9 | −0.7 |
| SulfoHexCer 34:0 (OH) | 0.58 | 0.93 | 4.1E−02 | 4.3E−01 | 1.9 | 0.2 |
| SulfoHexCer 37:2 | 0.96 | 0.96 | 3.5E−01 | 3.3E−01 | 0.4 | 0.5 |
| SulfoHexCer 37:1 | 0.62 | 1.1 | 4.2E−03 | 3.6E−01 | 2.9 | −0.4 |
| SulfoHexCer 38:1 | 1.04 | 1.13 | 4.0E−01 | 2.3E−01 | −0.3 | −0.8 |
| SulfoHexCer 38:1 (OH) | 0.94 | 1.11 | 3.3E−01 | 3.5E−01 | 0.5 | −0.4 |
| SulfoHexCer 40:2 | 0.79 | 0.86 | 1.6E−01 | 3.3E−01 | 1.1 | 0.5 |
| SulfoHexCer 40:1 | 0.47 | 0.79 | 1.0E−02 | 2.6E−01 | 2.6 | 0.7 |
| SulfoHexCer 40:2 (OH) | 0.75 | 0.94 | 1.6E−01 | 4.4E−01 | 1.1 | 0.2 |
| SulfoHexCer 41:1 | 0.73 | 0.76 | 6.5E−02 | 1.9E−01 | 1.6 | 0.9 |
| SulfoHexCer 40:1 (OH) | 0.47 | 0.74 | 4.8E−03 | 1.6E−01 | 2.9 | 1 |
| SulfoHexCer 42:3 | 1.03 | 1.11 | 4.7E−01 | 4.0E−01 | −0.1 | −0.3 |
| SulfoHexCer 42:2 | 0.8 | 0.96 | 2.1E−01 | 4.5E−01 | 0.9 | 0.1 |
| SulfoHexCer 41:2 (OH) | 0.8 | 1.08 | 1.7E−01 | 4.3E−01 | 1 | −0.2 |
| SulfoHexCer 42:1 | 0.63 | 0.74 | 6.5E−02 | 2.1E−01 | 1.6 | 0.8 |
| SulfoHexCer 41:1 (OH) | 0.38 | 0.74 | 2.7E−03 | 2.2E−01 | 3.2 | 0.8 |
| SulfoHexCer 42:3 (OH) | 1.02 | 0.98 | 4.8E−01 | 4.8E−01 | 0 | 0.1 |
| SulfoHexCer 42:2 (OH) | 0.69 | 0.89 | 3.5E−02 | 3.0E−01 | 1.9 | 0.5 |
| SulfoHexCer 42:1 (OH) | 0.56 | 0.76 | 1.0E−02 | 1.7E−01 | 2.5 | 1 |
| SulfoHexCer 42:1 (2OH) | 0.75 | 1.17 | 2.0E−01 | 3.5E−01 | 0.9 | −0.4 |
| PI 34:2 | 0.9 | 2.78 | 4.0E−01 | 3.2E−02 | 0.3 | −2 |
| PI 34:1 | 0.82 | 2.25 | 2.8E−01 | 5.0E−02 | 0.6 | −1.8 |
| PI 36:4 | 0.81 | 2.61 | 2.4E−01 | 4.5E−02 | 0.7 | −1.8 |
| PI 36:3 | 0.89 | 2.2 | 2.9E−01 | 5.5E−02 | 0.6 | −1.8 |
| PI 36:2 | 1.02 | 1.84 | 4.8E−01 | 4.9E−02 | −0.1 | −1.8 |
| PI 36:1 | 0.56 | 1.89 | 5.0E−02 | 8.5E−02 | 1.8 | −1.5 |
| PI 38:5 | 0.79 | 2.11 | 4.2E−02 | 4.4E−02 | 1.9 | −1.9 |
| PI 38:4 | 1.09 | 1.9 | 3.7E−01 | 4.0E−02 | −0.4 | −1.9 |
| PI 38:3 | 1.16 | 1.98 | 3.1E−01 | 6.0E−02 | −0.5 | −1.7 |
| GM3 34:1 | 1.35 | 2.04 | 1.7E−01 | 1.2E−04 | −1 | −4.7 |
| GM3 40:1 | 1.07 | 1.35 | 3.3E−01 | 1.4E−01 | −0.5 | −1.1 |
| GM3 42:2 | 1.55 | 2.26 | 9.5E−02 | 7.5E−03 | −1.4 | −2.7 |

TABLE 31

Assignment of human male subjects with unknown classification based on 4 statistical models (#1 OPLS-DA of shotgun MS, #2 OPLS-DA of UHPSFC/MS, #3 OPLS-DA of all data, and #4 SVM of all data) and the average of all 4 models used for the final assignment (N = normal, T = tumor, T1, T2, T3, T4 = tumor stages (T1, T2 are early tumor stages), Tx = tumor but stage is not reported). Real state = health state/diagnosis confirmed by standard examination methods (imaging and/or biopsy).

| Sample No. | Final prediction | Real state | Model 1 | Model 2 | Model 3 | Model 4 | Average of 4 models |
|---|---|---|---|---|---|---|---|
| 21 | T | Tx | 1.00 | 1.00 | 1.00 | 0.99 | 1.00 |
| 29 | T | T4 | 0.99 | 1.00 | 1.00 | 1.00 | 1.00 |
| 40 | N | N | 0.19 | 0.23 | 0.23 | 0.08 | 0.18 |
| 44 | N | N | 0.15 | 0.36 | 0.18 | 0.12 | 0.20 |
| 46 | N | N | 0.26 | 0.22 | 0.26 | 0.13 | 0.22 |
| 50 | N | N | 0.33 | 0.15 | 0.27 | 0.61 | 0.34 |
| 64 | (T) | T4 | 0.31 | 0.89 | 0.40 | 0.66 | 0.57 |
| 89 | T | Tx | 0.76 | 0.70 | 0.80 | 0.89 | 0.79 |
| 106 | T | T3 | 1.00 | 1.00 | 0.99 | 1.00 | 1.00 |
| 110 | T | T3 | 0.66 | 0.44 | 0.58 | 0.96 | 0.66 |
| 115 | N | N | 0.14 | 0.48 | 0.14 | 0.32 | 0.27 |
| 118 | N | N | 0.37 | 0.36 | 0.34 | 0.09 | 0.29 |
| 120 | N | N | 0.11 | 0.42 | 0.11 | 0.08 | 0.18 |
| 133 | T | Tx | 0.95 | 0.73 | 0.91 | 1.00 | 0.90 |
| 142 | T | T3 | 0.97 | 0.81 | 0.95 | 1.00 | 0.93 |
| 149 | N | T2 | 0.37 | 0.39 | 0.38 | 0.27 | 0.35 |
| 166 | N | N | 0.44 | 0.30 | 0.45 | 0.43 | 0.41 |
| 168 | N | N | 0.21 | 0.48 | 0.23 | 0.19 | 0.28 |
| 173 | N | N | 0.09 | 0.46 | 0.15 | 0.03 | 0.18 |
| 177 | (N) | N | 0.54 | 0.38 | 0.59 | 0.28 | 0.45 |
| 184 | T | T1 | 0.87 | 0.93 | 0.90 | 0.95 | 0.91 |
| 194 | T | Tx | 0.82 | 1.00 | 0.89 | 0.99 | 0.93 |
| 203 | T | T3 | 1.00 | 0.83 | 1.00 | 1.00 | 0.96 |
| 247 | T | Tx | 0.62 | 0.92 | 0.61 | 0.73 | 0.72 |
| 251 | T | T3 | 1.00 | 0.65 | 1.00 | 0.99 | 0.91 |
| 255 | T | T4 | 0.81 | 0.97 | 0.89 | 0.98 | 0.91 |
| 258 | T | Tx | 1.00 | 1.00 | 1.00 | 1.00 | 1.00 |
| 264 | T | T2 | 0.68 | 0.69 | 0.60 | 0.84 | 0.70 |
| 267 | T | Tx | 1.00 | 1.00 | 1.00 | 1.00 | 1.00 |
| 271 | T | T4 | 1.00 | 1.00 | 1.00 | 1.00 | 1.00 |
| 275 | T | T3 | 0.98 | 1.00 | 1.00 | 1.00 | 1.00 |
| 305 | T | T4 | 0.92 | 0.96 | 1.00 | 1.00 | 0.97 |
| 310 | T | Tx | 0.83 | 0.81 | 0.85 | 1.00 | 0.87 |
| 317 | T | Tx | 1.00 | 1.00 | 1.00 | 1.00 | 1.00 |
| 322 | T | T3 | 1.00 | 1.00 | 1.00 | 1.00 | 1.00 |
| 347 | T | T3 | 1.00 | 0.71 | 1.00 | 0.97 | 0.92 |
| 351 | T | T3 | 0.85 | 0.74 | 0.90 | 0.95 | 0.86 |
| 355 | T | Tx | 0.94 |  | 0.73 |  | 0.84 |

TABLE 32

Assignment of human female subjects with unknown classification based on 4 statistical models (#1 OPLS-DA of shotgun MS, #2 OPLS-DA of UHPSFC/MS, #3 OPLS-DA of all data, and #4 SVM of all data) and the average of all 4 models used for the final assignment (N = normal, T = tumor, T1, T2, T3, T4 = tumor stages, Tx = tumor but stage is not reported). Real state = health state/diagnosis confirmed by standard examination methods (imaging and/or biopsy).

| Sample No. | Final prediction | Real state | Model | Model 2 | Model 3 | Model 4 | Average of 4 models |
|---|---|---|---|---|---|---|---|
| 17 | T | T1 | 0.89 | 1.00 | 0.88 | 1.00 | 0.94 |
| 25 | T | T4 | 1.00 | 1.00 | 1.00 | 1.00 | 1.00 |
| 34 | T | T3 | 1.00 | 0.98 | 1.00 | 0.99 | 0.99 |
| 55 | T | T4 | 1.00 | 0.90 | 1.00 | 1.00 | 0.97 |
| 68 | T | Tx | 0.92 | 1.00 | 1.00 | 1.00 | 0.98 |
| 73 | T | T3 | 0.85 | 1.00 | 0.89 | 0.99 | 0.93 |
| 78 | T | Tx | 0.82 | 0.71 | 0.68 | 0.95 | 0.79 |
| 83 | T | T3 | 1.00 | 1.00 | 1.00 | 1.00 | 1.00 |
| 93 | T | T4 | 1.00 | 1.00 | 1.00 | 1.00 | 1.00 |
| 98 | T | T3 | 1.00 | 1.00 | 1.00 | 1.00 | 1.00 |
| 104 | N | Tx | 0.16 | 0.52 | 0.40 | 0.23 | 0.33 |
| 125 | T | T3 | 1.00 | 0.75 | 1.00 | 1.00 | 0.94 |
| 130 | T | T3 | 0.94 | 1.00 | 1.00 | 0.86 | 0.95 |
| 157 | T | T4 | 0.61 | 0.49 | 0.51 | 0.96 | 0.64 |
| 161 | T | Tx | 0.92 | 0.68 | 0.72 | 0.88 | 0.80 |
| 181 | T | Tx | 0.96 | 1.00 | 1.00 | 0.96 | 0.98 |
| 190 | T | T3 | 0.65 | 0.97 | 0.67 | 0.56 | 0.71 |
| 199 | N | T2 | 0.47 | 0.52 | 0.44 | 0.11 | 0.38 |
| 208 | T | T4 | 0.76 | 0.73 | 0.96 | 0.97 | 0.85 |
| 218 | T | T2 | 0.98 | 0.87 | 0.89 | 1.00 | 0.93 |
| 226 | N | N | 0.13 | 0.32 | 0.22 | 0.21 | 0.22 |
| 230 | N | N | 0.25 | 0.36 | 0.25 | 0.02 | 0.22 |
| 235 | N | N | 0.36 | 0.00 | 0.31 | 0.07 | 0.19 |
| 239 | (N) | N | 0.64 | 0.30 | 0.48 | 0.40 | 0.46 |
| 280 | (T) | T3 | 0.33 | 0.70 | 0.47 | 0.56 | 0.51 |
| 283 | N | N | 0.41 | 0.19 | 0.30 | 0.59 | 0.37 |
| 288 | N | N | 0.16 | 0.55 | 0.35 | 0.22 | 0.32 |
| 292 | N | N | 0.15 | 0.00 | 0.00 | 0.03 | 0.04 |
| 293 | N | N | 0.00 | 0.02 | 0.00 | 0.01 | 0.01 |
| 296 | N | N | 0.27 | 0.19 | 0.20 | 0.13 | 0.20 |
| 327 | N | N | 0.13 | 0.08 | 0.11 | 0.21 | 0.13 |
| 331 | T | N | 0.76 | 0.33 | 0.73 | 0.82 | 0.66 |
| 335 | N | N | 0.00 | 0.00 | 0.00 | 0.00 | 0.00 |
| 344 | T | Tx | 1.00 | 1.00 | 1.00 | 0.99 | 1.00 |
| 359 | T | Tx | 0.59 | 0.64 | 0.61 | 0.54 | 0.59 |

Calculation of Sample Throughput for Early Screening and Monitoring of Therapy of Pancreatic Cancer Patients Based on the Lipidomic Analysis of Human Serum, Plasma, Urine or Other Body Fluids Calculation for 100 samples of human serum (plasma, urine, or other type of body fluid)

Instrumentation:

1 MS system (shotgun MS, UHPSFC/MS, or MALDI-MS)

laboratory for sample preparation in Biological Safety Level (BSL) 2 regime

TABLE 33

Time calculation of individual steps in our methodology for high-throughput lipidomic quantitation

| Step | Time [days] | Comments |
|---|---|---|
| Sample preparation (liquid/liquid extraction) | 1.5 | 10-12 hours for 1 person |
| Analysis (including continuous measurement control) | 2.5 | 2 injections = 40 samples/24 hours, 1 injection = 80 (possible 2. injection incase of positive results or ambiguity) |
| Data processing (noise reduction and data conversion) | 1 | In fact, it is 2.5 days, but it runs in parallel with the analysis |
| Quantitation using Microsoft Excel script | 0.75 | |
| Multivariate data analysis (MDA) | 0.25 | |
| Spare time for unexpected circumstances | 1 | |
| TOTAL | 7 | |

Calculation for 1000 samples of human plasma:

7*10=70 working days—reduction due to some multiplexing and possible over weekend automated operation=ca. 3 months How many samples per year for 1 MS system:

1000 (per 3 months)*4=ca. 4000 samples/year

Further automation of sample preparation, data processing, multiplexing of tasks, and shortening the analysis time could further increase the sample throughput at least two times.

INDUSTRIAL APPLICABILITY

The method of the invention can be used for population screening of the whole population or selected population groups based on risk factors such as age, gender, body-mass-index, genetic predispositions, risk behavior, etc. The subjects having the positive output from population screening above a pre-determined threshold can then be subjected to further examinations and tests (e.g., computer tomography or other advanced imaging methods). As the present screening method is non-invasive, can be performed in a high-throughput mode, and can detect early stages of cancers, it is the first known method suitable for routine screening of various cancer types including the early stages. The analytical methodology is fully validated in line with recommendations of authoritative organizations, such Food and Drug Administration or European Medicines Agency (EMEA).

The invention claimed is:

1. A method of diagnosing cancer, selected from the group consisting of kidney, breast, and pancreatic cancer, based on lipidomic analysis of a first sample of a body fluid selected from serum, plasma, blood, urine, said first sample of the body fluid being taken from the body of a patient, characterized in that said method comprises the steps of:

spiking of the first sample with a set of internal standards comprising

| | |
|---|---|
| D7-CE 16:0 | MG 19:1 |
| Cer d18:1/12:0 | PA 14:0/14:0 |
| DG 12:1/12:1 | PC 14:0/14:0 |
| Hex2Cer d18:1/12:0 | PE 14:0/14:0 |
| HexCer d18:1/12:0 | PG 14:0/14:0 |
| D7-Chol | PS 14:0/14:0 |

-continued

| | |
|---|---|
| LPC 17:0 | SM d18:1/12:0 |
| LPE 14:0 | SulfoHexCer d18:1/12:0 |
| LPG 14:0 | TG 19:1/19:1/19:1 |
| LPA 14:0 | LPS 17:1 | subsequently processing the first sample by liquid-liquid lipidomic extraction or by solid phase lipidomic extraction, measurement of the processed first sample by a mass spectrometry method, determining concentrations for all lipids present at a level above a detection threshold of the mass spectrometry method, using the internal standards for the corresponding lipid classes, to which a corresponding one of the internal standards belong, for quantitation, or using relative concentrations of lipids, or using ratios of concentrations and/or signal intensities, computer-implemented statistical evaluation of the determined concentrations of the lipids, wherein the statistical evaluation involves principal component analysis (PCA) and/or by orthogonal partial least squares-discriminant analysis (OPLS-DA), said statistical evaluation determining the level of probability of the patient suffering from kidney, breast or pancreatic cancer based on the determined lipid concentrations compared to a kidney, breast or pancreatic cancerous pattern, and a non-cancerous pattern, wherein the kidney, breast or pancreatic cancerous pattern and the non-cancerous pattern are determined by statistical analysis of the lipid concentrations for a group of known cancer samples and non-cancer samples, and wherein the statistical evaluation is done separately for males and females.

2. The method according to claim 1, wherein the lipids include the following lipids:

| Sphingolipids | | | | | |
|---|---|---|---|---|---|
| Cer 34:1 | SM 34:2 | SM 40:1 | SM 42:2 | Sul 40:1 | Sul 42:1 |
| Cer 42:1 | SM 36:1 | SM 40:2 | SM 42:3 | Sul 40:1(OH) | Sul 42:1(2OH) |
| Cer 40:1 | SM 36:2 | SM 41:1 | SM 43:1 | Sul 40:2(OH) | Sul 42:1(OH) |
| Cer 42:2 | SM 38:1 | SM 41:2 | Sul 34:0(OH) | Sul 41:1 | |
| SM 34:1 | SM 39:1 | SM 42:1 | Sul 34:2(OH) | Sul 41:1(OH) | |
| Glycerophospholipids | | | | | |
| LPC 16:0 | LPC 18:2 | PC 34:1 | PC 36:3 | PCO-34:2/P-34:1 | PCO-36:5/P-36:4 |
| LPC 18:0 | PC 32:0 | PC 34:2 | PC 36:4 | PCO-34:3/P-34:2 | PE 34:1 |
| LPC 18:1 | PC 32:2 | PC 36:2 | PC 38:4 | PCO-36:3/P-36:2 | |
| Glycerolipids | | | | | |
| TG 49:1 | TG 50:4 | TG 50:5 | TG 51:4 | TG 53:4 | TG 55:5 |

3. A method of diagnosing pancreatic cancer based on lipidomic analysis of a first sample of a body fluid selected from serum, plasma, blood, urine, said sample of the body fluid being taken from the body of a patient, characterized in that it comprises the steps of:

spiking of the first sample with a set of internal standards comprising:

| | |
|---|---|
| D7-CE 16:0 | MG 19:1 |
| Cer d18:1/12:0 | PA 14:0/14:0 |
| DG 12:1/12:1 | PC 14:0/14:0 |
| Hex2Cer d18:1/12:0 | PE 14:0/14:0 |
| HexCer d18:1/12:0 | PG 14:0/14:0 |
| D7-Chol | PS 14:0/14:0 |
| LPC 17:0 | SM d18:1/12:0 |
| LPE 14:0 | SulfoHexCer d18:1/12:0 |
| LPG 14:0 | TG 19:1/19:1/19:1 |
| LPA 14:0 | LPS 17:1, | subsequently processing the first sample by liquid-liquid lipidomic extraction, measurement of the processed first sample by a mass spectrometry method, determining concentrations for all lipids present at a level above a detection threshold of the mass spectrometry method, using the internal standards for the corresponding lipid classes, to which a corresponding one of the internal standards belong, for quantitation, or using relative concentrations of lipids, or using ratios of concentrations and/or signal intensities, computer-implemented statistical evaluation of the determined concentrations of the lipids, wherein the statistical evaluation involves principal component analysis (PCA) and/or by orthogonal partial least squares-discriminant analysis (OPLS-DA), said statistical evaluation determining the level of probability of the patient suffering from pancreatic cancer based on the determined lipid concentrations compared to a pancreatic cancerous pattern and a non-cancerous pattern, wherein the pancreatic cancerous pattern and the non-cancerous pattern are determined by statistical analysis of the lipid concentrations for a group of known pancreatic cancer samples and non-cancer samples, and wherein the statistical evaluation is done separately for males and females.

4. The method according to claim 3, wherein the lipids include:

| Lipid |
|---|
| HexCer d18:1/16:0; HexCer d18:1/15:1 (1OH) |
| SM 34:1 |
| HexCer d18:1/24:1; HexCer d18:1/23:2 (1OH) |
| PE 34:1; PE P-35:0 |
| PC 32:0; PC O-33:0 |
| PE 36:4; PE P-37:3 |
| PC 34:1; PC P-35:0 |
| PE 34:2; PE P-35:1 |
| PC P-34:0; PC 33:1 |
| DG 36:2 |
| Cer d18:1/24:1; Cer d18:1/23:2 (1OH) |
| CE 16:0 |
| SM 41:1 |
| SM 41:2 |

-continued

| Lipid |
|---|
| PC 34:4; PC P-35:3 |
| HexCer d18:1/24:0; HexCer d18:1/23:1 (1OH) |
| PE P-36:3; PE 35:4 |
| PE P-38:4; PE 37:5 |
| PE P-38:5; PE 37:6 |
| PE P-36:2; PE 35:3 |
| SM 32:1 |
| HexCer d18:1/22:0; HexCer d18:1/21:1 (1OH) |
| PE P-38:3; PE 37:4 |
| PC P-38:2; PC 37:3 |
| PE P-40:5; PE 39:6 |
| PE 36:0; PE P-38:6 |
| PE 38:0; PE P-40:6, PE 0-39:0 |
| PE P-36:3; PE 35:4 |
| PC P-34:1; PC 33:2 |
| PC P-36:2; PC 35:3 |
| DG 34:3 |

5. The method according to claim 1, wherein the patient is a mammal.

6. The method according to claim 1, wherein the mass spectrometry method is selected from shotgun mass spectrometry, ultrahigh-performance liquid chromatography—mass spectrometry, ultrahigh-performance supercritical fluid chromatography—mass spectrometry, and matrix-assisted laser desorption/ionization mass spectrometry.

7. The method according to claim 1, wherein a pooled sample is prepared by mixing identical volumes of several samples and processed in the same way as the first sample, wherein the pooled sample includes samples from pancreatic cancer patients and healthy volunteers, and wherein the pooled sample is used for observing intra-day accuracy and intra-day precision, and/or for inter-day accuracy and inter-day precision, and/or for determining the lower limit of quantitation and the upper limit of quantitation, and/or for quality control during measurements of sample set.

8. The method according to claim 1, wherein an order of samples is randomized in sample measurement sequences.

9. The method according to claim 1, wherein the step of determining concentrations for all lipids present at a level above a detection threshold of the mass spectrometry method, using the internal standards for the corresponding lipid classes for the quantitation, comprises one or more of the following procedures and corrections:
   isotopic correction,
   zero filling procedure in which the signals of lipid species which are not detected for particular sample are replaced by 50 to 100%, or by 70 to 100%, or by 80%, of the minimum concentration observed for said lipid species in the sample.

10. The method according to claim 1, wherein the statistical evaluation involves
   data pre-processing by centering, scaling, and/or transformation;
   PCA analysis for identification of influential factors including outliers and/or measurement failures,
   discrimination analysis by OPLS-DA for group separation of pancreatic, kidney or breast cancer patients and healthy volunteers performed for males and females separately,
   assignment of the statistical parameters as well as the evaluation of the prediction power.

11. The method according to claim 3, wherein the patient is a mammal.

12. The method according to claim 3, wherein the mass spectrometry method is selected from shotgun mass spectrometry, ultrahigh-performance liquid chromatography—mass spectrometry, ultrahigh-performance supercritical fluid chromatography—mass spectrometry, and matrix-assisted laser desorption/ionization mass spectrometry.

13. The method according to claim 3, wherein a pooled sample is prepared by mixing identical volumes of several samples and processed in the same way as the first sample, wherein the pooled sample includes samples from pancreatic cancer patients and healthy volunteers, and wherein the pooled sample is used for observing intra-day accuracy and intra-day precision, and/or for inter-day accuracy and inter-day precision, and/or for determining the lower limit of quantitation and the upper limit of quantitation, and/or for quality control during measurements of sample set.

14. The method according to claim 3, wherein an order of samples is randomized in sample measurement sequences.

15. The method according to claim 3, wherein the step of determining concentrations for all lipids present at a level above a detection threshold of the mass spectrometry method, using the internal standards for the corresponding lipid classes for the quantitation, comprises one or more of the following procedures and corrections:
   isotopic correction,
   zero filling procedure in which the signals of lipid species which are not detected for particular sample are replaced by 50 to 100%, or by 70 to 100%, or by 80%, of the minimum concentration observed for said lipid species in several samples.

16. The method according to claim 3, wherein the statistical evaluation involves
   data pre-processing by centering, scaling, and/or transformation;
   PCA analysis for identification of influential factors including outliers and/or measurement failures,
   discrimination analysis by OPLS-DA for group separation of pancreatic cancer patients and healthy volunteers performed for males and females separately,
   assignment of the statistical parameters as well as the evaluation of the prediction power.

* * * * *